(12) United States Patent
Puckette et al.

(10) Patent No.: US 10,829,770 B2
(45) Date of Patent: *Nov. 10, 2020

(54) FUSION PROTEINS CONTAINING LUCIFERASE AND A POLYPEPTIDE OF INTEREST

(71) Applicant: The Government of the United States of America, as represented by the Secretary of Homeland Security, Washington, DC (US)

(72) Inventors: Michael Puckette, Waterford, CT (US); Max V. Rasmussen, Guilford, CT (US)

(73) Assignee: The Government of the United States of America, as represented by the Secretary of Homeland Security, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/571,616

(22) Filed: Sep. 16, 2019

(65) Prior Publication Data
US 2020/0002707 A1 Jan. 2, 2020

Related U.S. Application Data

(63) Continuation of application No. 15/583,459, filed on May 1, 2017, now Pat. No. 10,435,695, which is a (Continued)

(51) Int. Cl.
*C12N 15/63* (2006.01)
*A61K 38/21* (2006.01)
(Continued)

(52) U.S. Cl.
CPC ............ *C12N 15/63* (2013.01); *A61K 38/21* (2013.01); *C07K 14/56* (2013.01); *C07K 14/705* (2013.01);
(Continued)

(58) Field of Classification Search
None
See application file for complete search history.

(56) References Cited

U.S. PATENT DOCUMENTS 6,232,107 B1 * 5/2001 Bryan ................ A61K 49/0013
435/183
8,236,548 B2 8/2012 Zhi-Ying Chen
(Continued)

FOREIGN PATENT DOCUMENTS

| GB | 2 463 783 A | 3/2010 |
| WO | 2011/048353 A2 | 4/2011 |
| WO | 2011/048353 A3 | 4/2011 |

OTHER PUBLICATIONS

Luke et al. (Journal of General Virology. 2008; 89: 1036-1042).*
(Continued)

*Primary Examiner* — Shanon A. Foley
(74) *Attorney, Agent, or Firm* — Lavanya Ratnam; Kelly G. Hyndman

(57) ABSTRACT

Polynucleotides encoding fusion proteins contain a secretable luciferase fused to a modified polypeptide of interest are disclosed. The polypeptide of interest has been modified to remove a native N-terminal secretion sequence and has been replaced by the secretable luciferase. One example of a modified polypeptide of interest is interferon. The polynucleotides and fusion proteins have biotherapeutic, diagnostic, and quality control applications in biotechnological, medical, and veterinary fields. Methods for producing the secretable fusion protein are also disclosed.

19 Claims, 10 Drawing Sheets

Specification includes a Sequence Listing.

Luciferase readings of constructs separated by the Δ1D2A translational interrupter and corresponding controls.

Related U.S. Application Data continuation-in-part of application No. 15/259,409, filed on Sep. 8, 2016, now Pat. No. 10,385,319.

(51) Int. Cl.

| | |
|---|---|
| *C07K 14/705* | (2006.01) |
| *C12Q 1/66* | (2006.01) |
| *C07K 14/56* | (2006.01) |
| *C12N 9/02* | (2006.01) |
| *C07K 14/00* | (2006.01) |
| *C12N 15/00* | (2006.01) |
| *A61K 38/00* | (2006.01) |

(52) U.S. Cl.
CPC ............ *C12N 9/0069* (2013.01); *C12Q 1/66* (2013.01); *A61K 38/00* (2013.01); *C07K 14/00* (2013.01); *C07K 2319/00* (2013.01); *C12N 15/00* (2013.01)

(56) References Cited

U.S. PATENT DOCUMENTS

| | | | |
|---|---|---|---|
| 10,435,695 | B2* | 10/2019 | Puckette .............. C07K 14/705 |
| 2004/0101513 | A1* | 5/2004 | Zuckermann .......... A61K 39/12 424/93.2 |
| 2009/0263880 | A1* | 10/2009 | Kawasaki ............ C12N 9/0069 435/188 |
| 2011/0143362 | A1 | 6/2011 | Oyler et al. |
| 2011/0236416 | A1 | 9/2011 | Audonnet et al. |
| 2012/0122182 | A1 | 5/2012 | Tannous et al. |
| 2012/0258133 | A1 | 10/2012 | Bryan Charleston |
| 2012/0315295 | A1 | 12/2012 | Rieder et al. |
| 2013/0243809 | A1 | 9/2013 | Liao et al. |
| 2014/0186959 | A1 | 7/2014 | Slater et al. |
| 2018/0066235 | A1 | 3/2018 | Puckette et al. |
| 2018/0066267 | A1 | 3/2018 | Puckette et al. |

OTHER PUBLICATIONS

Minskaia et al. "Protein coexpression using FMDV 2A: effect of "linker" residues." BioMed research international 2013 (2013).*
Torres et al. (Journal of Biotechnology. 2010; 146: 138-142).*
Luker et al. (Nature Medicine. Jan. 2012; 18 (1): 172-177).*
G. R. Stark, I. M. Kerr, B. R. Williams, R. H. Silverman, R. D. Schreiber, How cells respond to interferons. Annual review of biochemistry 67, 227-264 (1998).
K. Schroder, P. J. Hertzog, T. Ravasi, D. A. Hume, Interferon-gamma: an overview of signals, mechanisms and functions. Journal of leukocyte biology 75, 163-189 (2004).
H. M. Lazear, T. J. Nice, M. S. Diamond, Interferon-lambda: Immune Functions at Barrier Surfaces and Beyond. Immunity 43, 15-28 (2015).
J. Chinsangaram, M. Koster, M. J. Grubman, Inhibition of L-deleted foot-and-mouth disease virus replication by alpha/beta interferon involves double-stranded RNA-dependent protein kinase. Journal of virology 75, 5498-5503 (2001).
J. Chinsangaram, M. P. Moraes, M. Koster, M. J. Grubman, Novel viral disease control strategy: adenovirus expressing alpha interferon rapidly protects swine from foot-and-mouth disease. Journal of virology 77, 1621-1625 (2003).

H. Yin et al., Antitumor potential of a synthetic interferon-alpha/PLGF-2 positive charge peptide hybrid molecule in pancreatic cancer cells. Scientific reports 5, 16975 (2015).

M. Nakamura et al., Expression and visualization of a human interferon-beta-enhanced green fluorescent protein chimeric molecule in cultured cells. Biological & pharmaceutical bulletin 27, 411-414 (2004).

M. Maruyama et al., Simultaneous detection of DsRed2-tagged and EGFP-tagged human beta-interferons in the same single cells. Journal of cellular biochemistry 93, 497-502 (2004).

M. M. Mizokami, P. Hu, L. A. Khawli, J. Li, A. L. Epstein, Chimeric TNT-3 antibody/murine interferon-gamma fusion protein for the immunotherapy of solid malignancies. Hybridoma and hybridomics 22, 197-207 (2003).

M. Verhaegen, T. K. Christopoulos, Recombinant Gaussia luciferase. Overexpression, purification, and analytical application of a bioluminescent reporter for DNA hybridization. Analytical chemistry 74, 4378-4385 (2002).

B. A. Tannous, D. E. Kim, J. L. Fernandez, R. Weissleder, X. O. Breakefield, Codon-optimized Gaussia luciferase cDNA for mammalian gene expression in culture and in vivo. Molecular therapy : the journal of the American Society of Gene Therapy 11, 435-443 (2005).

S. B. Kim, H. Suzuki, M. Sato, H. Tao, Superluminescent variants of marine luciferases for bioassays. Analytical chemistry 83, 8732-8740 (2011).

Díaz-San Segundo F, et al. Antiviral activity of bovine type III interferon against foot-and-mouth disease virus. Virology. May 10, 2011;413(2):283-92.

Perez-Martin E, et al. Bovine type III interferon significantly delays and reduces the severity of foot-and-mouth disease in cattle. J Virol. Apr. 2012;86(8):4477-87.

Shao L, Feng W, Sun Y, Bai H, Liu J, Currie C, et al. Generation of iPS cells using defined factors linked via the self-cleaving 2A sequences in a single open reading frame. Cell research. 2009;19:296-306.

Mir FA, Kaufmann SH, Eddine AN. A multicistronic DNA vaccine induces significant protection against tuberculosis in mice and offers flexibility in the expressed antigen repertoire. Clinical and vaccine immunology : CVI. 2009;16:1467-75.

Rothwell DG, Crossley R, Bridgeman JS, Sheard V, Zhang Y, Sharp TV, et al. Functional expression of secreted proteins from a bicistronic retroviral cassette based on foot-and-mouth disease virus 2A can be position dependent. Human gene therapy. 2010;21:1631-7.

Breese SS, Jr., Graves JH. Electron microscopic observation of crystalline arrays of foot-and-mouth disease virus. Journal of bacteriology. 1966;92:1835-7.

Breese SS. Reactions of intracellular crystals of foot-and-mouth disease virus with ferritin-tagged antibody. J Gen Virol. 1969;4:343-6.

Kay MA, He CY, Chen ZY. A robust system for production of minicircle DNA vectors, Nature Biotechnology. 2010;28:1287-89.

Yang et al., "Crystal structure of the 3C protease from Southern African Territories type 2 foot-and-mouth disease virus", (Peer J. DOI 10.7717/peerj.1964) dated Apr. 26, 2016.

Veerapen et al., "Novel expression of immunogenic foot-and-mouth disease virus-like particles in Nicotiana benthamiana", (Virus Research, 2018; 244: 213-217).

Zunszain et al., "Insights into Cleavage Specificity from the Crystal Structure of Foot-and-Mouth Disease Virus 3C Protease Complexed with a Peptide Substrate", Journal of Molecular Biology, 395 pp. 375-389, 2010.

Sweeney et al., "Structural and Mutagenic Analysis of Foot-and-Mouth Disease Virus 3C Protease Reveals the Role of the β-Ribbon in Proteolysis", Journal of Virology, vol. 81, No. 1, pp. 115-124, Jan. 2007.

International Search Report and the Written Opinion of the International Searching Authority for PCT/US2017/048828 dated Jan. 29, 2018.

Birtley JR, Curry S. Crystallization of foot-and-mouth disease virus 3C protease: surface mutagenesis and a novel crystal-optimization strategy. Acta Crystallographica Section D Biological Crystallography. 2005;61:646-650.

Birtley JR, Knox SR, Jaulent AM, Brick, P, Leatherbarrow RJ, et al. Crystal structure of foot-and-mouth disease virus 3C protease. 2005;280:11520-527.

Sweeney, TR, Roqué-Rosell N, Birtley JR, Leatherbarrow RJ, Curry S. Structural and mutagenic analysis of foot-and-mouth disease virus 3C protease reveals the role of the □-ribbon in proteolysis. J Virol. Jan. 2007;81(1):115-24. Epub Oct. 25, 2006.

Vakharia VN, Devaney MA, Moore DM, Dunn JJ, Grubman MJ. Proteolytic processing of foot-and-mouth disease virus polyproteins

(56) References Cited

OTHER PUBLICATIONS expressed in a cell-free system from clone-derived transcripts. Journal of virology. 1987;61:3199-207.

Mayr GA, Chinsangaram J, Grubman MJ. Development of replication-defective adenovirus serotype 5 containing the capsid and 3C protease coding regions of foot-and-mouth disease virus as a vaccine candidate. Virology. 1999;263:496-506.

Mayr GA, O'Donnell V, Chinsangaram J, Mason PW, Grubman MJ. Immune responses and protection against foot-and-mouth disease virus (FMDV) challenge in swine vaccinated with adenovirus-FMDV constructs. Vaccine. 2001;19:2152-62.

Moraes MP, Mayr GA, Mason PW, Grubman MJ. Early protection against homologous challenge after a single dose of replication-defective human adenovirus type 5 expressing capsid proteins of foot-and-mouth disease virus (FMDV) strain A24. Vaccine. 2002;20:1631-9.

Gullberg M, Muszynski B, Organtini LJ, Ashley RE, Hafenstein SL, Belsham GJ, et al. Assembly and characterization of foot-and-mouth disease virus empty capsid particles expressed within mammalian cells. The Journal of general virology. 2013;94:1769-79.
Porta C, Xu X, Loureiro S, Paramasivam S, Ren J, Al-Khalil T, et al. Efficient production of foot-and-mouth disease virus empty capsids in insect cells following down regulation of 3C protease activity. Journal of virological methods. 2013;187:406-12.
Porta C, Kotecha A, Burman A, Jackson T, Ren J, Loureiro S, et al. Rational engineering of recombinant Picornavirus capsids to produce safe, protective vaccine antigen. PLOS Pathogens. 2013;9:e1003255.
Dus Santos MJ, Carrillo C, Ardila F, Rios RD, Franzone P, Piccone ME, et al. Development of transgenic alfalfa plants containing the foot and mouth disease virus structural polyprotein gene P1 and its utilization as an experimental immunogen. Vaccine. 2005;23:1838-43.
Grubman MJ, Zellner M, Bablanian G, Mason PW, Piccone ME. Identification of the active-site residues of the 3C proteinase of foot-and-mouth disease virus. Virology. 1995;213:581-9.
Falk MM, Grigera PR, Bergmann IE, Zibert A, Multhaup G, Beck E. Foot-and-mouth disease virus protease 3C induces specific proteolytic cleavage of host cell histone H3. Journal of virology. 1990;64:748-56.
Belsham GJ, McInerney GM, Ross-Smith N. Foot-and-mouth disease virus 3C protease induces cleavage of translation initiation factors eIF4A and eIF4G within infected cells. Journal of virology. 2000;74:272-80.
Li W, Ross-Smith N, Proud CG, Belsham GJ. Cleavage of translation initiation factor 4AI (eIF4AI) but not eIF4AII by foot-and-mouth disease virus 3C protease: identification of the eIF4AI cleavage site. FEBS letters. 2001;507:1-5.
Lawrence P, Schafer EA, Rieder E. The nuclear protein Sam68 is cleaved by the FMDV 3C protease redistributing Sam68 to the cytoplasm during FMDV infection of host cells. Virology. 2012;425:40-52.
Wang D, Fang L, Li K, Zhong H, Fan J, Ouyang C, et al. Foot-and-mouth disease virus 3C protease cleaves NEMO to impair innate immune signaling. Journal of virology. 2012;86:9311-22.
Zhou Z, Mogensen MM, Powell PP, Curry S, Wileman T. Foot-and-mouth disease virus 3C protease induces fragmentation of the Golgi compartment and blocks intra-Golgi transport. Journal of virology. 2013;87:11721-9.
Zunszain PA, Knox SR, Sweeney TR, Yang J, Roque-Rosell N, Belsham GJ, et al. Insights into cleavage specificity from the crystal structure of foot-and-mouth disease virus 3C protease complexed with a peptide substrate. Journal of molecular biology. 2010;395:375-89.
Tannous BA, Kim DE, Fernandez JL, Weissleder R, Breakefield XO. Codon-optimized Gaussia luciferase cDNA for mammalian gene expression in culture and in vivo. Mol Ther 2005;11:435-43.
Verhaegent M, Christopoulos TK. Recombinant Gaussia luciferase. Overexpression, purification, and analytical application of a bioluminescent reporter for DNA hybridization. Anal Chem. 2002;74:4378-85.
Chung E, Yamashita H, Au P, Tannous BA, Fukumura D, Jain RK. Secreted Gaussia luciferase as a biomarker for monitoring tumor progression and treatment response of systemic metastases. PLoS One. 2009;4:e8316.
Tannous BA. Gaussia luciferase reporter assay for monitoring biological processes in culture and in vivo. Nat Protoc. 2009;4:582-91.
Wurdinger T, Badr C, Pike L, de Kleine R, Weissleder R, Breakefield XO, et al. A secreted luciferase for ex vivo monitoring of in vivo processes. Nat Methods. 2008;5:171-3.
Inoue Y, Sheng F, Kiryu S, Watanabe M, Ratanakanit H, Izawa K, et al. Gaussia luciferase for bioluminescence tumor monitoring in comparison with firefly luciferase. Mol Imaging. 2011;10:377-85.
El-Amaud SS, Cao P, Miao C, Pan D. Secreted luciferase for in vivo evaluation of systemic protein delivery in mice. Mol Biotechnol. 2012;53:63-73.
Griesenbach U, Vicente CC, Roberts MJ, Meng C, Soussi S, Xenariou S, et al. Secreted Gaussia luciferase as a sensitive reporter gene for in vivo and ex vivo studies of airway gene transfer Biomaterials. 2011;32:2614-24.
Kim SB, Suzuki H, Sato M, Tao H. Superluminescent variants of marine luciferases for bioassays. Anal Chem. 2011;83:8732-40.
De Felipe P. Polycistronic viral vectors. Current gene therapy. 2002;2:355-78.
Ryan MD, Drew J. Foot-and-mouth disease virus 2A oligopeptide mediated cleavage of an artificial polyprotein. The EMBO journal. 1994;13:928-33.
Donnelly ML, Luke G, Mehrotra A, Li X, Hughes LE, Gani D, et al. Analysis of the aphthovirus 2A/2B polyprotein cleavage' mechanism indicates not a proteolytic reaction, but a novel translational effect: a putative ribosomal 'skip'. The Journal of general virology. 2001;82:1013-25.
Minskaia E, Ryan MD. Protein coexpression using FMDV 2A: effect of "linker" residues. BioMed research international. 2013;2013:291730.
Donnelly ML, Gani D, Flint M, Monaghan S, Ryan MD. The cleavage activities of aphthovirus and cardiovirus 2A proteins. J Gen Virol. 1997;78 ( Pt 1):13-21.
Luke GA, de Felipe P, Lukashev A, Kallioinen SE, Bruno EA, Ryan MD. Occurrence, function and evolutionary origins of '2A-like' sequences in virus genomes. J Gen Virol. 2008;89:1036-42.
Kim JH, Lee SR, Li LH, Park HJ, Park JH, Lee KY, et al. High cleavage efficiency of a 2A peptide derived from porcine teschovirus-1 in human cell lines, zebrafish and mice. PLoS One. 2011;6:e18556.
Torres V, Barra L, Garces F, Ordenes K, Leal-Ortiz S, Garner CC, et al. A bicistronic lentiviral vector based on the 1D/2A sequence of foot-and-mouth disease virus expresses proteins stoichiometrically. Journal of biotechnology. 2010;146:138-42.
Ahier A, Jarriault S. Simultaneous expression of multiple proteins under a single promoter in Caenorhabditis elegans via a versatile 2A-based toolkit. Genetics. 2014;196:605-13.
Daniels RW, Rossano AJ, Macleod GT, Ganetzky B. Expression of multiple transgenes from a single construct using viral 2A peptides in *Drosophila*. PLoS One. 2014;9:e100637.
Unkles SE, Valiante V, Mattern DJ, Brakhage AA. Synthetic biology tools for bioprospecting of natural products in eukaryotes. Chemistry & biology. 2014;21:502-8.
Heinonen AM, Rahman M, Dogbevia G, Jakobi H, Wolfl S, Sprengel R, et al. Neuroprotection by rAAV-mediated gene transfer of bone morphogenic protein 7. BMC neuroscience. 2014;15:38.
Jung L, Tropel P, Moal Y, Teletin M, Jeandidier E, Gayon R, et al. ONSL and OSKM cocktails act synergistically in reprogramming human somatic cells into induced pluripotent stem cells. Molecular human reproduction. 2014;20:538-49.
Beekwilder J, van Rossum HM, Koopman F, Sonntag F, Buchhaupt M, Schrader J, et al. Polycistronic expression of a beta-carotene biosynthetic pathway in *Saccharomyces cerevisiae* coupled to beta-ionone production. Journal of biotechnology. 2014.

(56) References Cited

OTHER PUBLICATIONS

De Felipe P, Martin V, Cortes ML, Ryan M, Izquierdo M. Use of the 2A sequence from foot-and-mouth disease virus in the generation of retroviral vectors for gene therapy. Gene Ther. 1999;6:198-208.

Geu-Flores F, Olsen CE, Halkier BA. Towards engineering glucosinolates into non-cruciferous plants. Planta. 2009;229:261-70.

Carey BW, Markoulaki S, Hanna J, Saha K, Gao Q, Mitalipova M, et al. Reprogramming of murine and human somatic cells using a single polycistronic vector. Proceedings of the National Academy of Sciences of the United States of America. 2009;106:157-62.

Wu et al. (Biochemica et Biophysica Acta. 2015; 1854: 1392-1399).

Alignment of SEQ ID 24 with Genseq access No. ABB81097 Jun. 2007 Zuckermann in WO20260921.

Cheng et al. (Gene. 2006; 382: 28-38).

Alignment of SEQ ID 4 with Genseq db access AYL 17606 Dec. 2010 Sungbae et al. in WO2010119721.

Polacek, C. et al., "Low Levels of foot-and-mouth disease virus 3C protease expression are required to achieve optimal capsid protein expression and processing in mammalian cells", Journal of General Virology, Society for General Microbiology, Spencers Wood, GB, vol. 94, No. Part 6, Jun. 1, 2013, pp. 1249-1258, XP-002754915.
Database Geneseq [Online], "Foot-and-mouth disease virus P12A3C protein, Seq Id 2", Oct. 2, 2008, XP002796961, retrieved from EBI accession No. GSP:ARY99720.
Kopfleisch, Constanze et al., "Effect of foot-and-mouth disease virus capsid precursor protein and 3C protease expression on bovine herpesvirus 1 replication", Archives of Virology; Official Journal of the Virology Division of the International Union of Microbiological Societies, Springer-Verlag, VI, vol. 155, No. 5, Mar. 24, 2010, pp. 723-731, XP019805242, ISSN: 1432-8798.
Korean Notice of Preliminary Office Action for Korean Patent Application No. 10-2019-7004444 dated Dec. 29, 2019 with Partial Translated Summary.
European Search Report and Written Opinion for European Application EP17849320 dated Jan. 28, 2020.

* cited by examiner

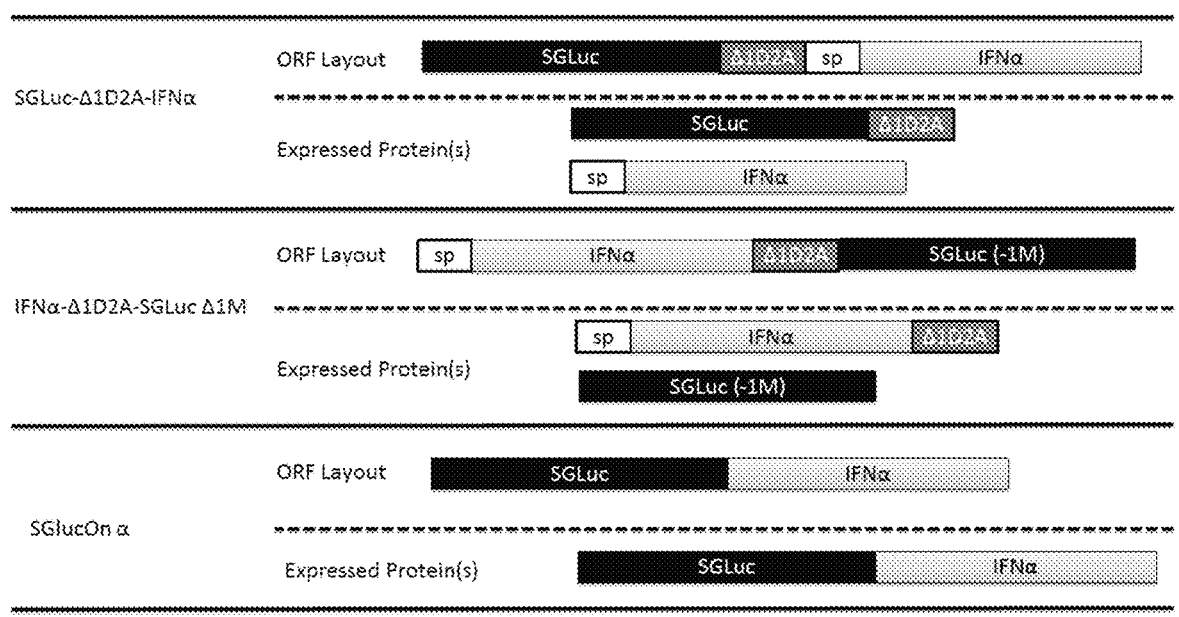
Figure 1: Layout of the three interferon α containing constructs created and evaluated. "sp" = secretion peptide sequence of interferon α.

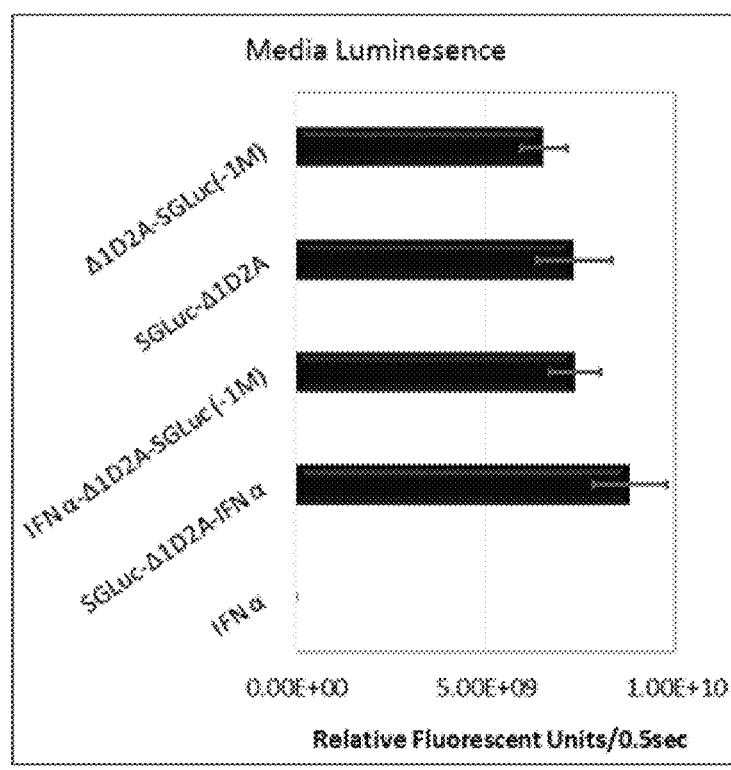
Figure 2A: Luciferase readings of constructs separated by the Δ1D2A translational interrupter and corresponding controls.

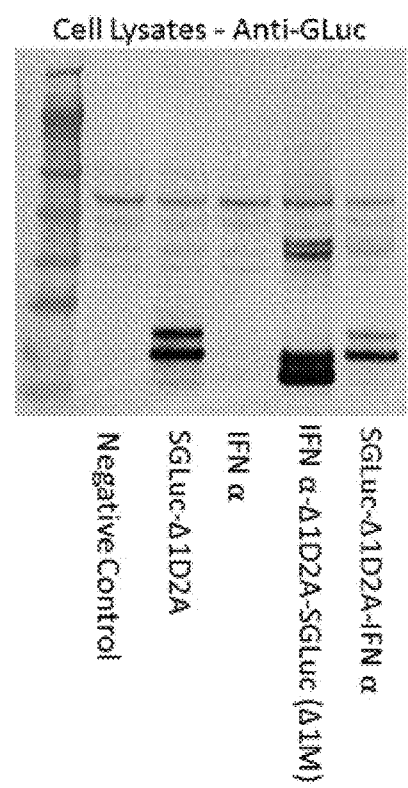
Figure 2B: Western blots of media harvested off of cells transfected with constructs separated by the Δ1D2A translational interrupter and corresponding controls.

| | |
|---|---|
| Porcine IFN α | <u>MAPTSAFLTALVLLSCNAICS</u>LGCDLPQTHSLAHTRALRLLAQMRRISPFSCLDHRRDFG SPHEAFGGNQVQKAQAMALVHEMLQQTFQLFSTEGSAAAWNESLLHQFCTGLDQQ LRDLEACVMQEAGLEGTPLLEEDSILAVRKYFHRLTLYLQEKSYSPCAWEIVRAEVMRSF SSSRNLQDRLRKKE |
| Porcine IFN β | <u>MANKCILQIALLMCFSTTALS</u>MSYDVLRYQQRSSNLACQKLLGQLPGTPQYCLEDRMN FEVPEEIMQPPQFQKEDAVLIIHEMLQQIFGILRRNFSSTGWNETVIKTILVELDGQMD DLETILEEIMEEENFPRGDMTILHLKKYYLSILQYLKSKEYRSCAWTVVQVEILRNFSFLN RLTDYLRN |
| Bovine IFN γ | <u>MKYTSYFLALLLCGLLGFSGSYG</u>QGQFFREIENLKEYFNASSPDVAKGGPLFSEILKNWK DESDKKIIQSQIVSFYFKLFENLKDNQVIQRSMDIIKQDMFQKFLNGSSEKLEDFKKLIQI PVDDLQIQRKAINELIKVMNDLSPKSNLRKRKRSQNLFRGRRAST |
| Bovine IFN λ | <u>MAPGCTLVLVLMLTTVALS</u>RTGAVPVPSAPRALPPARGCHVAQFKSLSPQELQAFKTA RDAFEDSFLPKDWDCSTHLFPRTRDLKHLQVWERPVALEAELALTLTVLEAMANSSLG HSLEQPLLTLQNIHSKLQACVPAQPTASSRPRGRLHHWLHRLQEARKESQDCLEASVM FNLLRLLTRDLKCVASGDQCV |

Figure 3: Amino acid sequences for Porcine Interferon α, Porcine Interferon β, Bovine Interferon γ, and Bovine Interferon λ. Underlined letters represent the secretion domains of each interferon sequence.

| | |
|---|---|
| SGlucON α | *MGVKVLFALICIAVAEAKPTENNEDFNIVAVASNFATTDLDADRGKLPGKKLPLEVLKEMEAN ARKAGCTRGCLICLSHIKCTPKMKKWLPGRCHTYEGDKESAQGGIGEAIVDIPEIPGFKDLEP MEQFIAQVDLCVDCTTGCLKGLANVQCSDLLKKWLPQRCATFASKIQGQVDKIKGAGGDGP* GCDLPQTHSLAHTRALRLLAQMRRISPFSCLDHRRDFGSPHEAFGGNQVQKAQAMALVHE MLQQTFQLFSTEGSAAAWNESLLHQFCTGLDQQLRDLEACVMQEAGLEGTPLLEEDSILAV RKYFHRLTLYLQEKSYSPCAWEIVRAEVMRSFSSSRNLQDRLRKKE |
| SGlucON β | *MGVKVLFALICIAVAEAKPTENNEDFNIVAVASNFATTDLDADRGKLPGKKLPLEVLKEMEAN ARKAGCTRGCLICLSHIKCTPKMKKWLPGRCHTYEGDKESAQGGIGEAIVDIPEIPGFKDLEP MEQFIAQVDLCVDCTTGCLKGLANVQCSDLLKKWLPQRCATFASKIQGQVDKIKGAGGDGP* MSYDVLRYQQRSSNLACQKLLGQLPGTPQYCLEDRMNFEVPEEIMQPPQFQKEDAVLIIHE MLQQIFGILRRNFSSTGWNETVIKTILVELDGQMDDLETILEEIMEEENFPRGDMTILHLKKY YLSILQYLKSKEYRSCAWTVVQVEILRNFSFLNRLTDYLRN |
| SGlucON γ | *MGVKVLFALICIAVAEAKPTENNEDFNIVAVASNFATTDLDADRGKLPGKKLPLEVLKEMEAN ARKAGCTRGCLICLSHIKCTPKMKKWLPGRCHTYEGDKESAQGGIGEAIVDIPEIPGFKDLEP MEQFIAQVDLCVDCTTGCLKGLANVQCSDLLKKWLPQRCATFASKIQGQVDKIKGAGGDGP* QGQFFREIENLKEYFNASSPDVAKGGPLFSEILKNWKDESDKKIIQSQIVSFYFKLFENLKDNQ VIQRSMDIIKQDMFQKFLNGSSEKLEDFKKLIQIPVDDLQIQRKAINELIKVMNDLSPKSNLRK RKRSQNLFRGRRAST |
| SGlucON λ | *MGVKVLFALICIAVAEAKPTENNEDFNIVAVASNFATTDLDADRGKLPGKKLPLEVLKEMEAN ARKAGCTRGCLICLSHIKCTPKMKKWLPGRCHTYEGDKESAQGGIGEAIVDIPEIPGFKDLEP MEQFIAQVDLCVDCTTGCLKGLANVQCSDLLKKWLPQRCATFASKIQGQVDKIKGAGGDGP* RTGAVPVPSAPRALPPARGCHVAQFKSLSPQELQAFKTARDAFEDSFLPKDWDCSTHLFPRT RDLKHLQVWERPVALEAELALTLTVLEAMANSSLGHSLEQPLLTLQNIHSKLQACVPAQPTAS SRPRGRLHHWLHRLQEARKESQDCLEASVMFNLLRLLTRDLKCVASGDQCV |

Figure 4: Amino acid sequences for SGLucON α, SGLucON β, SGLucON γ, and SGLucON λ. Italicized white letters with black background represent the *Gaussia* Luciferase amino acids.

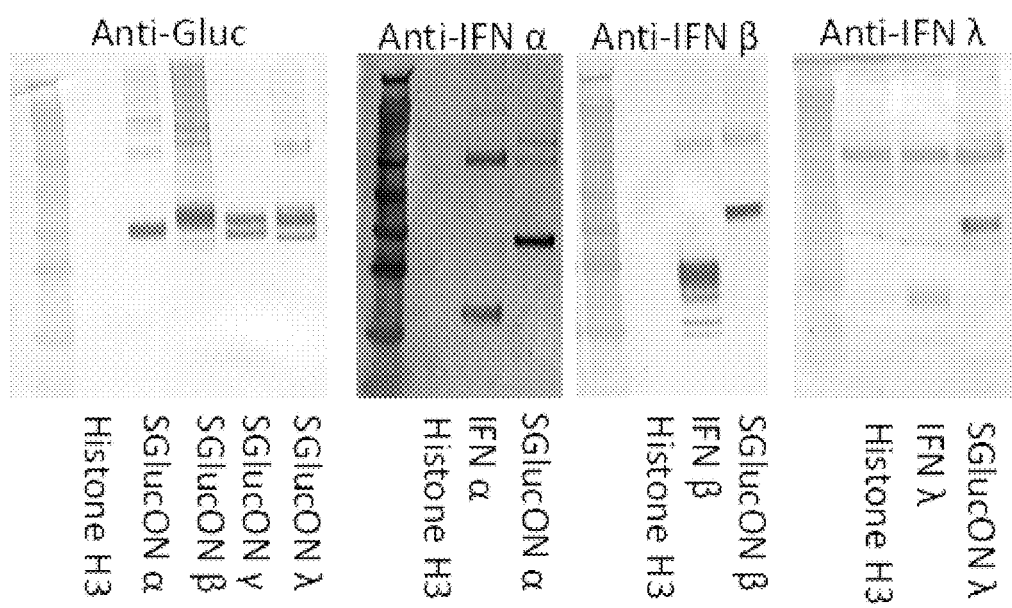
Figure 5A: Western blots of media harvested from transfected cells using anti-GLuc, Anti-IFN α, Anti-IFN β, and Anti-IFN λ antibodies.

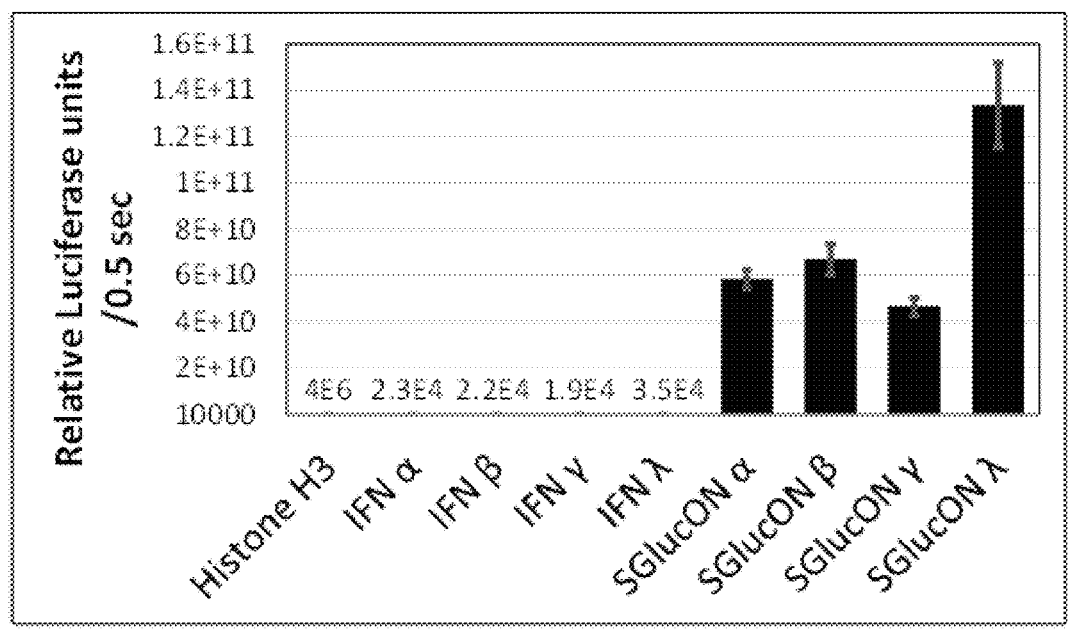
Figure 5B: Relative Luciferase Units per half second for IFN and SGLucON α, β, γ, and λ media samples.

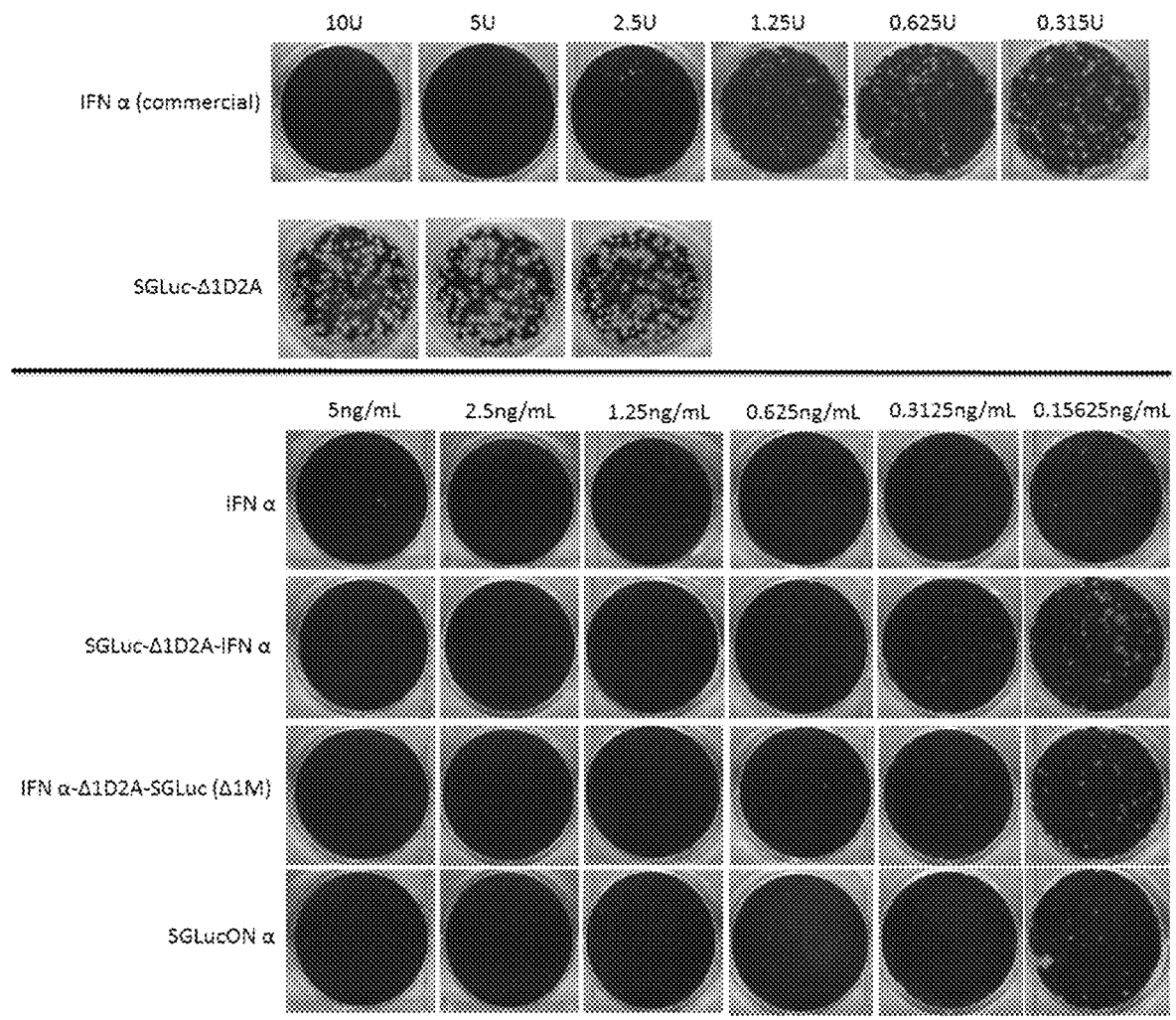
Figure 6: Plaque assay of IFN α, SGLuc-Δ1D2A-IFN α, IFN α-Δ1D2A-SGLuc (Δ1M), and SGLucON α activity against VSV-NJ.

| Sample | Concentration of IFNα ± standard deviation (ng/ml) |
|---|---|
| IFNα | 1239 ± 86 |
| SGLuc-Δ1D2A-IFNα | 921 ± 55 |
| IFNα-Δ1D2A-SGLucΔ1M | 528 ± 72 |
| Δ1D2A-SGLucΔ1M (IFNα negative control) | <18 (limit of detection at 1:500 dilution) |
| SGLuc-Δ1D2A (IFNα negative control) | <18 (limit of detection at 1:500 dilution) |

Figure 7: Concentration of IFNα in harvested media from cells transfected with pTarget IFNα, pTarget SGLuc-Δ1D2A-IFNα, pTarget IFNα-Δ1D2A-SGLucΔ1M, pTarget Δ1D2A-SGLucΔ1M, and pTarget SGLuc-Δ1D2A. There were 3 replicates per each of 4 dilutions for each sample.

| Sample | Concentration of IFNα in each sample (ng/ml) | | | | | |
|---|---|---|---|---|---|---|
| | 5 | 2.5 | 1.25 | 0.625 | 0.312 | 0.1525 |
| IFNα | 0 | 0 | 0 | 4.5 | 19 | 58 |
| SGLuc-Δ1D2A-IFNα | 0 | 0 | 2 | 17.5 | 53.5 | 116.5 |
| IFNα-Δ1D2A-SGLucΔ1M | 0 | 0 | 1 | 11.5 | 37 | 91.5 |
| SGLucONα | 0 | 0 | 0 | 1.5 | 9.5 | 25.5 |
| SGLuc-Δ1D2A (IFNα negative control) | 245 | 230 | 220.5 | ND | ND | ND |

Figure 8: Effects of IFNα on growth of Vesicular Stomatitis Virus-NJ (VSV-NJ). IFNα levels produced in growth media harvested from HEK293-T cells transfected with pTarget IFNα, pTarget SGLuc-Δ1D2A-IFNα, pTarget IFNα-Δ1D2A-SGLucΔ1M, mpTarget SGLucONα, or pTarget SGLuc-Δ1D2A (negative control) were measured and adjusted to concentrations listed before samples were exposed to MDBK cells. VSV-NJ was added to the MDBK cells and Plaque Forming Units (PFU) were counted after the growth period; average of 2 replicates are reported. ND, not determined.

SEQUENCE LISTING

<160> NUMBER OF SEQ ID NOS: 113

<210> SEQ ID NO 1
<211> LENGTH: 558
<212> TYPE: DNA
<213> ORGANISM: Gaussia princeps
<220> FEATURE:
<221> NAME/KEY: CDS
<222> LOCATION: (1)..(558)
<220> FEATURE:
<221> NAME/KEY: misc_feature
<222> LOCATION: (1)..(558)
<223> OTHER INFORMATION: GLuc polynucleotide

<400> SEQUENCE: 1

```
atg gga gtc aaa gtt ctg ttt gcc ctg atc tgc atc gct gtg gcc gag      48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc      96
Ala Lys Pro Thr Glu Asn Asn Glu Asp Phe Asn Ile Val Ala Val Ala
            20                  25                  30 agc aac ttc gcg acc acg gat ctc gat gct gac cgc ggg aag ttg ccc     144
Ser Asn Phe Ala Thr Thr Asp Leu Asp Ala Asp Arg Gly Lys Leu Pro
```

|  |  |  |  |  |  |  |  |  |  |  |  |  |  |  |  |
|---|---|---|---|---|---|---|---|---|---|---|---|---|---|---|---|

```
                  35                  40                  45
ggc aag aag ctg ccg ctg gag gtg ctc aaa gag atg gaa gcc aat gcc        192
Gly Lys Lys Leu Pro Leu Glu Val Leu Lys Glu Met Glu Ala Asn Ala
     50                  55                  60 cgg aaa gct ggc tgc acc agg ggc tgt ctg atc tgc ctg tcc cac atc        240
Arg Lys Ala Gly Cys Thr Arg Gly Cys Leu Ile Cys Leu Ser His Ile
 65                  70                  75                  80 aag tgc acg ccc aag atg aag aag ttc atc cca gga cgc tgc cac acc        288
Lys Cys Thr Pro Lys Met Lys Lys Phe Ile Pro Gly Arg Cys His Thr
                 85                  90                  95 tac gaa ggc gac aaa gag tcc gca cag ggc ggc ata ggc gag gcg atc        336
Tyr Glu Gly Asp Lys Glu Ser Ala Gln Gly Gly Ile Gly Glu Ala Ile
            100                 105                 110 gtc gac att cct gag att cct ggg ttc aag gac ttg gag ccc atg gag        384
Val Asp Ile Pro Glu Ile Pro Gly Phe Lys Asp Leu Glu Pro Met Glu
        115                 120                 125 cag ttc atc gca cag gtc gat ctg tgt gtg gac tgc aca act ggc tgc        432
Gln Phe Ile Ala Gln Val Asp Leu Cys Val Asp Cys Thr Thr Gly Cys
    130                 135                 140 ctc aaa ggg ctt gcc aac gtg cag tgt tct gac ctg ctc aag aag tgg        480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg        528
Leu Pro Gln Arg Cys Ala Thr Phe Ala Ser Lys Ile Gln Gly Gln Val
                165                 170                 175 gac aag atc aag ggg gcc ggt ggt gac taa                                558
Asp Lys Ile Lys Gly Ala Gly Gly Asp
            180             185

<210> SEQ ID NO 2
<211> LENGTH: 185
<212> TYPE: PRT
<213> ORGANISM: Gaussia princeps

<400> SEQUENCE: 2

Met Gly Val Lys Val Leu Phe Ala Leu Ile Cys Ile Ala Val Ala Glu
 1               5                  10                  15

Ala Lys Pro Thr Glu Asn Asn Glu Asp Phe Asn Ile Val Ala Val Ala
             20                  25                  30

Ser Asn Phe Ala Thr Thr Asp Leu Asp Ala Asp Arg Gly Lys Leu Pro
         35                  40                  45

Gly Lys Lys Leu Pro Leu Glu Val Leu Lys Glu Met Glu Ala Asn Ala
     50                  55                  60

Arg Lys Ala Gly Cys Thr Arg Gly Cys Leu Ile Cys Leu Ser His Ile
 65                  70                  75                  80

Lys Cys Thr Pro Lys Met Lys Lys Phe Ile Pro Gly Arg Cys His Thr
                 85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175
```

```
Asp Lys Ile Lys Gly Ala Gly Gly Asp
            180                 185

<210> SEQ ID NO 3
<211> LENGTH: 558
<212> TYPE: DNA
<213> ORGANISM: Gaussia princeps
<220> FEATURE:
<221> NAME/KEY: CDS
<222> LOCATION: (1)..(558)
<223> OTHER INFORMATION: SGLuc polynucleotide

<400> SEQUENCE: 3 atg gga gtc aaa gtt ctg ttt gcc ctg atc tgc atc gct gtg gcc gag    48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc    96
Ala Lys Pro Thr Glu Asn Asn Glu Asp Phe Asn Ile Val Ala Val Ala
                20                  25                  30 agc aac ttt gcg acc acg gat ctc gat gct gac cga ggg aag ttg ccc   144
Ser Asn Phe Ala Thr Thr Asp Leu Asp Ala Asp Arg Gly Lys Leu Pro
            35                  40                  45 ggc aag aag ctg ccg ctg gag gtg ctc aaa gag atg gaa gcc aat gcc   192
Gly Lys Lys Leu Pro Leu Glu Val Leu Lys Glu Met Glu Ala Asn Ala
    50                  55                  60 cgg aaa gct ggc tgc acc agg ggc tgt ctg atc tgc ctg tcc cac atc   240
Arg Lys Ala Gly Cys Thr Arg Gly Cys Leu Ile Cys Leu Ser His Ile
65                  70                  75                  80 aag tgc acg ccc aag atg aag aag tgg ctc cca gga cgc tgc cac acc   288
Lys Cys Thr Pro Lys Met Lys Lys Trp Leu Pro Gly Arg Cys His Thr
                85                  90                  95 tac gaa ggc gac aaa gag tcc gca cag ggc ggc ata ggc gag gcg atc   336
Tyr Glu Gly Asp Lys Glu Ser Ala Gln Gly Gly Ile Gly Glu Ala Ile
                100                 105                 110 gtc gat att cct gag att cct ggg ttc aag gac ttg gag cca atg gag   384
Val Asp Ile Pro Glu Ile Pro Gly Phe Lys Asp Leu Glu Pro Met Glu
            115                 120                 125 cag ttc atc gca cag gtc gat ctg tgt gtg gac tgc aca act ggc tgc   432
Gln Phe Ile Ala Gln Val Asp Leu Cys Val Asp Cys Thr Thr Gly Cys
        130                 135                 140 ctc aaa ggg ctt gcc aac gtg cag tgt tct gac ctg ctc aag aag tgg   480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg   528
Leu Pro Gln Arg Cys Ala Thr Phe Ala Ser Lys Ile Gln Gly Gln Val
                165                 170                 175 gac aag atc aag ggg gcc ggt ggt gac taa                           558
Asp Lys Ile Lys Gly Ala Gly Gly Asp
            180                 185

<210> SEQ ID NO 4
<211> LENGTH: 185
<212> TYPE: PRT
<213> ORGANISM: Gaussia princeps

<400> SEQUENCE: 4

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
                20                  25                  30

Ser Asn Phe Ala Thr Thr Asp Leu Asp Ala Asp Arg Gly Lys Leu Pro
            35                  40                  45
```

```
Gly Lys Lys Leu Pro Leu Glu Val Leu Lys Glu Met Glu Ala Asn Ala
 50                  55                  60
Arg Lys Ala Gly Cys Thr Arg Gly Cys Leu Ile Cys Leu Ser His Ile
 65                  70                  75                  80
Lys Cys Thr Pro Lys Met Lys Lys Trp Leu Pro Gly Arg Cys His Thr
                 85                  90                  95
Tyr Glu Gly Asp Lys Glu Ser Ala Gln Gly Gly Ile Gly Glu Ala Ile
                 100                 105                 110
Val Asp Ile Pro Glu Ile Pro Gly Phe Lys Asp Leu Glu Pro Met Glu
                 115                 120                 125
Gln Phe Ile Ala Gln Val Asp Leu Cys Val Asp Cys Thr Thr Gly Cys
    130                 135                 140
Leu Lys Gly Leu Ala Asn Val Gln Cys Ser Asp Leu Leu Lys Lys Trp
145                 150                 155                 160
Leu Pro Gln Arg Cys Ala Thr Phe Ala Ser Lys Ile Gln Gly Gln Val
                165                 170                 175
Asp Lys Ile Lys Gly Ala Gly Gly Asp
                180                 185

<210> SEQ ID NO 5
<211> LENGTH: 90
<212> TYPE: DNA
<213> ORGANISM: Artificial Sequence
<220> FEATURE:
<223> OTHER INFORMATION: Translation interrupter motif
<220> FEATURE:
<221> NAME/KEY: CDS
<222> LOCATION: (1)..(90)
<223> OTHER INFORMATION: Translation interrupter motif (TIM) DNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
```

```
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t

<400> SEQUENCE: 5 nrn mrn nhn vmn nyn ryn rvn syn ghn arr car vyn ykn ary tty gay      48
Xaa Xaa Xaa Xaa Xaa Xaa Xaa Xaa Xaa Xaa Gln Xaa Xaa Xaa Phe Asp
1               5                   10                  15 ytn ytn aar ytn gcn ggn gay gtn gar tcn aay ccn ggn ccn              90
Leu Leu Lys Leu Ala Gly Asp Val Gl or Phe.
<220> FEATURE:
<221> NAME/KEY: misc_feature
<222> LOCATION: (4)..(4)
<223> OTHER INFORMATION: The 'Xaa' at location 4 stands for Lys, Asn,
Thr, Glu, Asp, Ala, Gln, His, or Pro.
<220> FEATURE:
<221> NAME/KEY: misc_feature
<222> LOCATION: (5)..(5)
<223> OTHER INFORMATION: The 'Xaa' at location 5 stands for Thr, Ile,
Met, Ala, Val, Pro, Leu, Ser, or Phe.
<220> FEATURE:
<221> NAME/KEY: misc_feature
<222> LOCATION: (6)..(6)
<223> OTHER INFORMATION: The 'Xaa' at location 6 stands for Ala, Val,
Thr, Ile, or Met.
<220> FEATURE:
<221> NAME/KEY: misc_feature
<222> LOCATION: (7)..(7)
<223> OTHER INFORMATION: The 'Xaa' at location 7 stands for Glu, Asp,
Gly, Ala, Lys, Asn, Arg, Ser, or Thr.
<220> FEATURE:
<221> NAME/KEY: misc_feature
<222> LOCATION: (8)..(8)
<223> OTHER INFORMATION: The 'Xaa' at location 8 stands for Ala, Val,
Pro, or Leu.
<220> FEATURE:
<221> NAME/KEY: misc_feature
<222> LOCATION: (9)..(9)
<223> OTHER INFORMATION: The 'Xaa' at location 9 stands for Glu, Asp,
Ala, or Val.
<220> FEATURE:
<221> NAME/KEY: misc_feature
<222> LOCATION: (10)..(10)
<223> OTHER INFORMATION: The 'Xaa' at location 10 stands for Arg, or
Lys.
<220> FEATURE:
<221> NAME/KEY: misc_feature
<222> LOCATION: (12)..(12)
<223> OTHER INFORMATION: The 'Xaa' at location 12 stands for Thr, Ile,
Met, Ala, Val, Pro, or Leu.
<220> FEATURE:
<221> NAME/KEY: misc_feature
<222> LOCATION: (13)..(13)
<223> OTHER INFORMATION: The 'Xaa' at location 13 stands for Arg, Leu,
Trp, Cys, or Phe.
<220> FEATURE:
<221> NAME/KEY: misc_feature
<222> LOCATION: (14)..(14)
<223> OTHER INFORMATION: The 'Xaa' at location 14 stands for Ser, or
Asn.
<220> FEATURE:
<221> NAME/KEY: misc_feature
<222> LOCATION: (26)..(26)
<223> OTHER INFORMATION: The 'Xaa' at location 26 stands for Ser.
<220> FEATURE:
<223> OTHER INFORMATION: Synthetic Construct

<400> SEQUENCE: 6

Xaa Xaa Xaa Xaa Xaa Xaa Xaa Xaa Xaa Xaa Gln Xaa Xaa Xaa Phe Asp
1               5                   10                  15

Leu Leu Lys Leu Ala Gly Asp Val Glu Xaa Asn Pro Gly Pro
            20                  25                  30

<210> SEQ ID NO 7
<211> LENGTH: 57
<212> TYPE: DNA
<213> ORGANISM: Artificial Sequence
<220> FEATURE:
<223> OTHER INFORMATION: Translation interrupter motif 2
<220> FEATURE:
<221> NAME/KEY: CDS
<222> LOCATION: (1)..(57)
<220> FEATURE:
<221> NAME/KEY: misc_feature
<222> LOCATION: (3)..(3)

```
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t

<400> SEQUENCE: 7 ryn hbn ary wwn kmn ctn ctn mwn cdn gcn ggn gay rtn gar wsn aay      48
Xaa Xaa Xaa Xaa Xaa Xaa Xaa Xaa Xaa Ala Gly Asp Xaa Glu Ser Asn
1               5                   10                  15 ccn ggn ccn                                                          57
Pro Gly Pro <210> SEQ ID NO 8
<211> LENGTH: 19
<212> TYPE: PRT
<213> ORGANISM: Artificial Sequence
<220> FEATURE:
<221> NAME/KEY: misc_feature
<222> LOCATION: (1)..(1)
<223> OTHER INFORMATION: The 'Xaa' at location 1 stands for Ala, Val,
      Thr, Ile, or Met.
<220> FEATURE:
<221> NAME/KEY: misc_feature
```

```
<222> LOCATION: (2)..(2)
<223> OTHER INFORMATION: The 'Xaa' at location 2 stands for Arg, Ser,
      Thr, Ile, Met, Pro, Leu, Trp, Cys, or Phe.
<220> FEATURE:
<221> NAME/KEY: misc_feature
<222> LOCATION: (3)..(3)
<223> OTHER INFORMATION: The 'Xaa' at location 3 stands for Ser, or Asn.
<220> FEATURE:
<221> NAME/KEY: misc_feature
<222> LOCATION: (4)..(4)
<223> OTHER INFORMATION: The 'Xaa' at location 4 stands for Lys, Asn,
      Ile, Met, Tyr, Leu, or Phe.
<220> FEATURE:
<221> NAME/KEY: misc_feature
<222> LOCATION: (5)..(5)
<223> OTHER INFORMATION: The 'Xaa' at location 5 stands for Glu, Asp,
      Ala, Tyr, or Ser.
<220> FEATURE:
<221> NAME/KEY: misc_feature
<222> LOCATION: (6)..(6)
<223> OTHER INFORMATION: The 'Xaa' at location 6 stands for Leu.
<220> FEATURE:
<221> NAME/KEY: misc_feature
<222> LOCATION: (7)..(7)
<223> OTHER INFORMATION: The 'Xaa' at location 7 stands for Leu.
<220> FEATURE:
<221> NAME/KEY: misc_feature
<222> LOCATION: (8)..(8)
<223> OTHER INFORMATION: The 'Xaa' at location 8 stands for Lys, Asn,
      Ile, Met, Gln, His, or Leu.
<220> FEATURE:
<221> NAME/KEY: misc_feature
<222> LOCATION: (9)..(9)
<223> OTHER INFORMATION: The 'Xaa' at location 9 stands for Gln, His,
      Arg, or Leu.
<220> FEATURE:
<221> NAME/KEY: misc_feature
<222> LOCATION: (13)..(13)
<223> OTHER INFORMATION: The 'Xaa' at location 13 stands for Val, Ile,
      or Met.
<220> FEATURE:
<223> OTHER INFORMATION: Synthetic Construct

<400> SEQUENCE: 8

Xaa Xaa Xaa Xaa Xaa Xaa Xaa Xaa Xaa Ala Gly Asp Xaa Glu Ser Asn
1               5                   10                  15

Pro Gly Pro

<210> SEQ ID NO 9
<211> LENGTH: 30
<212> TYPE: DNA
<213> ORGANISM: Artificial Sequence
<220> FEATURE:
<223> OTHER INFORMATION: Translation interruptor motif 3
<220> FEATURE:
<221> NAME/KEY: CDS
<222> LOCATION: (1)..(30)
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
```

```
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t

<400> SEQUENCE: 9 gcn ggn gay rtn gar wsn aay ccn ggn ccn                              30
Ala Gly Asp Xaa Glu Ser Asn Pro Gly Pro
1               5                   10

<210> SEQ ID NO 10
<211> LENGTH: 10
<212> TYPE: PRT
<213> ORGANISM: Artificial Sequence
<220> FEATURE:
<221> NAME/KEY: misc_feature
<222> LOCATION: (4)..(4)
<223> OTHER INFORMATION: The 'Xaa' at location 4 stands for Val, Ile, or
      Met.
<220> FEATURE:
<223> OTHER INFORMATION: Synthetic Construct

<400> SEQUENCE: 10

Ala Gly Asp Xaa Glu Ser Asn Pro Gly Pro
1               5                   10

<210> SEQ ID NO 11
<211> LENGTH: 42
<212> TYPE: DNA
<213> ORGANISM: Artificial Sequence
<220> FEATURE:
<223> OTHER INFORMATION: Translation interruptor 4
<220> FEATURE:
<221> NAME/KEY: CDS
<222> LOCATION: (1)..(42)
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (22)..(24)
<223> OTHER INFORMATION: n is a, c, g, or t
<220> FEATURE:
<221> NAME/KEY: misc_feature
<222> LOCATION: (28)..(30)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
```

<223> OTHER INFORMATION: n is a, c, g, or t

<400> SEQUENCE: 11

```
ctn ctn nnn nnn gcn ggn gay nnn gar nnn aay ccn ggn ccn        42
Xaa Xaa Xaa Xaa Ala Gly Asp Xaa Glu Xaa Asn Pro Gly Pro
1               5                   10
```

<210> SEQ ID NO 12
<211> LENGTH: 14
<212> TYPE: PRT
<213> ORGANISM: Artificial Sequence
<220> FEATURE:
<221> NAME/KEY: misc_feature
<222> LOCATION: (1)..(1)
<223> OTHER INFORMATION: The 'Xaa' at location 1 stands for Leu.
<220> FEATURE:
<221> NAME/KEY: misc_feature
<222> LOCATION: (2)..(2)
<223> OTHER INFORMATION: The 'Xaa' at location 2 stands for Leu.
<220> FEATURE:
<221> NAME/KEY: misc_feature
<222> LOCATION: (3)..(3)
<223> OTHER INFORMATION: The 'Xaa' at location 3 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (4)..(4)
<223> OTHER INFORMATION: The 'Xaa' at location 4 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (8)..(8)
<223> OTHER INFORMATION: The 'Xaa' at location 8 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (10)..(10)
<223> OTHER INFORMATION: The 'Xaa' at location 10 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 12

```
Xaa Xaa Xaa Xaa Ala Gly Asp Xaa Glu Xaa Asn Pro Gly Pro
1               5                   10
```

<210> SEQ ID NO 13
<211> LENGTH: 24
<212> TYPE: DNA
<213> ORGANISM: Artificial Sequence
<220> FEATURE:
<223> OTHER INFORMATION: Translation interruptor sequence 5
<220> FEATURE:
<221> NAME/KEY: CDS
<222> LOCATION: (1)..(24)
<220> FEATURE:
<221> NAME/KEY: misc_feature
<222> LOCATION: (4)..(6)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t -continued

```
<220> FEATURE:
<221> NAME/KEY: misc_feature
<222> LOCATION: (24)..(24)
<223> OTHER INFORMATION: n is a, c, g, or t

<400> SEQUENCE: 13 gay nnn gar nnn aay ccn ggn ccn                              24
Asp Xaa Glu Xaa Asn Pro Gly Pro
1               5

<210> SEQ ID NO 14
<211> LENGTH: 8
<212> TYPE: PRT
<213> ORGANISM: Artificial Sequence
<220> FEATURE:
<221> NAME/KEY: misc_feature
<222> LOCATION: (2)..(2)
<223> OTHER INFORMATION: The 'Xaa' at location 2 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (4)..(4)
<223> OTHER INFORMATION: The 'Xaa' at location 4 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 14

Asp Xaa Glu Xaa Asn Pro Gly Pro
1               5

<210> SEQ ID NO 15
<211> LENGTH: 90
<212> TYPE: DNA
<213> ORGANISM: Foot-and-mouth disease virus
<220> FEATURE:
<221> NAME/KEY: CDS
<222> LOCATION: (1)..(90)
<223> OTHER INFORMATION: Delta-2A

<400> SEQUENCE: 15 cac aag caa aag atc att gca cca gca aag cag ctt ctg aat ttt gac    48
His Lys Gln Lys Ile Ile Ala Pro Ala Lys Gln Leu Leu Asn Phe Asp
1               5                   10                  15 ctg ctc aag ttg gcc gga gac gtt gag tcc aac cct gga ccc              90
Leu Leu Lys Leu Ala Gly Asp Val Glu Ser Asn Pro Gly Pro
            20                  25                  30

<210> SEQ ID NO 16
<211> LENGTH: 30
<212> TYPE: PRT
<213> ORGANISM: Foot-and-mouth disease virus

<400> SEQUENCE: 16

His Lys Gln Lys Ile Ile Ala Pro Ala Lys Gln Leu Leu Asn Phe Asp
1               5                   10                  15

Leu Leu Lys Leu Ala Gly Asp Val Glu Ser Asn Pro Gly Pro
            20                  25                  30

<210> SEQ ID NO 17
<211> LENGTH: 60
<212> TYPE: DNA
<213> ORGANISM: Foot-and-mouth disease virus
<220> FEATURE:
<221> NAME/KEY: CDS
<222> LOCATION: (1)..(60)
<223> OTHER INFORMATION: FMDV 2A polynucleotide
```

<400> SEQUENCE: 17

```
cag ctt ctg aat ttt gac ctg ctc aag ttg gcc gga gac gtt gag tcc      48
Gln Leu Leu Asn Phe Asp Leu Leu Lys Leu Ala Gly Asp Val Glu Ser
1               5                   10                  15 aac cct ggg ccc                                                      60
Asn Pro Gly Pro
            20
```

<210> SEQ ID NO 18
<211> LENGTH: 20
<212> TYPE: PRT
<213> ORGANISM: Foot-and-mouth disease virus

<400> SEQUENCE: 18

```
Gln Leu Leu Asn Phe Asp Leu Leu Lys Leu Ala Gly Asp Val Glu Ser
1               5                   10                  15

Asn Pro Gly Pro
            20
```

<210> SEQ ID NO 19
<211> LENGTH: 63
<212> TYPE: DNA
<213> ORGANISM: Bovine rhinitis virus A
<220> FEATURE:
<221> NAME/KEY: CDS
<222> LOCATION: (1)..(63)
<223> OTHER INFORMATION: Bovine rhinitis A 2A

<400> SEQUENCE: 19

```
tct ggt ata agc aac aag gac ctg cta ttg cag gcc ggt gat gtt gag      48
Ser Gly Ile Ser Asn Lys Asp Leu Leu Leu Gln Ala Gly Asp Val Glu
1               5                   10                  15 aca aac cct ggt ccc                                                  63
Thr Asn Pro Gly Pro
            20
```

<210> SEQ ID NO 20
<211> LENGTH: 21
<212> TYPE: PRT
<213> ORGANISM: Bovine rhinitis virus A

<400> SEQUENCE: 20

```
Ser Gly Ile Ser Asn Lys Asp Leu Leu Leu Gln Ala Gly Asp Val Glu
1               5                   10                  15

Thr Asn Pro Gly Pro
            20
```

<210> SEQ ID NO 21
<211> LENGTH: 51
<212> TYPE: DNA
<213> ORGANISM: Equine rhinitis B
<220> FEATURE:
<221> NAME/KEY: CDS
<222> LOCATION: (1)..(51)
<223> OTHER INFORMATION: Equine rhinitis B 2A

<400> SEQUENCE: 21

```
aac ttt gac ctg ctc aaa ctg gca ggc gat gtg gaa tca aac cca ggc      48
Asn Phe Asp Leu Leu Lys Leu Ala Gly Asp Val Glu Ser Asn Pro Gly
1               5                   10                  15 ccc                                                                  51
Pro
```

<210> SEQ ID NO 22
<211> LENGTH: 17
<212> TYPE: PRT
<213> ORGANISM: Equine rhinitis B

<400> SEQUENCE: 22

Asn Phe Asp Leu Leu Lys Leu Ala Gly Asp Val Glu Ser Asn Pro Gly
1               5                   10                  15

Pro

<210> SEQ ID NO 23
<211> LENGTH: 570
<212> TYPE: DNA
<213> ORGANISM: Sus scrofa
<220> FEATURE:
<221> NAME/KEY: CDS
<222> LOCATION: (1)..(570)
<223> OTHER INFORMATION: Porcine Interferon Alpha

<400> SEQUENCE: 23

```
atg gcc cca acc tca gcc ttc ctc acg gcc ctg gtg cta ctc agc tgc         48
Met Ala Pro Thr Ser Ala Phe Leu Thr Ala Leu Val Leu Leu Ser Cys
1               5                   10                  15 aat gcc atc tgc tct ctg ggc tgt gac ctg cct cag acc cac agc ctg         96
Asn Ala Ile Cys Ser Leu Gly Cys Asp Leu Pro Gln Thr His Ser Leu
                20                  25                  30 gct cac acc aga gcc ctg agg ctc ctg gca caa atg agg aga atc tct        144
Ala His Thr Arg Ala Leu Arg Leu Leu Ala Gln Met Arg Arg Ile Ser
            35                  40                  45 ccc ttc tcc tgc ctg gac cac aga agg gac ttt ggt tcc cct cat gag        192
Pro Phe Ser Cys Leu Asp His Arg Arg Asp Phe Gly Ser Pro His Glu
        50                  55                  60 gct ttt ggg ggc aac cag gtc cag aag gct caa gcc atg gct ctg gtg        240
Ala Phe Gly Gly Asn Gln Val Gln Lys Ala Gln Ala Met Ala Leu Val
65                  70                  75                  80 cat gag atg ctc cag cag acc ttc cag ctc ttc agc aca gag ggc tcg        288
His Glu Met Leu Gln Gln Thr Phe Gln Leu Phe Ser Thr Glu Gly Ser
                85                  90                  95 gct gct gcc tgg aat gag agc ctc ctg cac cag ttc tgc act gga ctg        336
Ala Ala Ala Trp Asn Glu Ser Leu Leu His Gln Phe Cys Thr Gly Leu
            100                 105                 110 gat cag cag ctc agg gac ctg gaa gcc tgt gtc atg cag gag gcg ggg        384
Asp Gln Gln Leu Arg Asp Leu Glu Ala Cys Val Met Gln Glu Ala Gly
        115                 120                 125 ctg gaa ggg acc ccc ctg ctg gag gag gac tcc atc ctg gct gtg agg        432
Leu Glu Gly Thr Pro Leu Leu Glu Glu Asp Ser Ile Leu Ala Val Arg
130                 135                 140 aaa tac ttc cac aga ctc acc ctc tat ctg caa gag aag agc tac agc        480
Lys Tyr Phe His Arg Leu Thr Leu Tyr Leu Gln Glu Lys Ser Tyr Ser
145                 150                 155                 160 ccc tgt gcc tgg gag atc gtc agg gca gaa gtc atg aga tcc ttc tct        528
Pro Cys Ala Trp Glu Ile Val Arg Ala Glu Val Met Arg Ser Phe Ser
                165                 170                 175 tcc tcc aga aac ctg caa gac aga ctc agg aag aag gag tga                570
Ser Ser Arg Asn Leu Gln Asp Arg Leu Arg Lys Lys Glu
            180                 185
```

<210> SEQ ID NO 24
<211> LENGTH: 189
<212> TYPE: PRT
<213> ORGANISM: Sus scrofa

<400> SEQUENCE: 24

Met Ala Pro Thr Ser Ala Phe Leu Thr Ala Leu Val Leu Leu Ser Cys
1               5                   10                  15

Asn Ala Ile Cys Ser Leu Gly Cys Asp Leu Pro Gln Thr His Ser Leu
            20                  25                  30

Ala His Thr Arg Ala Leu Arg Leu Leu Ala Gln Met Arg Arg Ile Ser
        35                  40                  45

Pro Phe Ser Cys Leu Asp His Arg Arg Asp Phe Gly Ser Pro His Glu
    50                  55                  60

Ala Phe Gly Gly Asn Gln Val Gln Lys Ala Gln Ala Met Ala Leu Val
65                  70                  75                  80

His Glu Met Leu Gln Gln Thr Phe Gln Leu Phe Ser Thr Glu Gly Ser
                85                  90                  95

Ala Ala Ala Trp Asn Glu Ser Leu Leu His Gln Phe Cys Thr Gly Leu
            100                 105                 110

Asp Gln Gln Leu Arg Asp Leu Glu Ala Cys Val Met Gln Glu Ala Gly
        115                 120                 125

Leu Glu Gly Thr Pro Leu Leu Glu Glu Asp Ser Ile Leu Ala Val Arg
130                 135                 140

Lys Tyr Phe His Arg Leu Thr Leu Tyr Leu Gln Glu Lys Ser Tyr Ser
145                 150                 155                 160

Pro Cys Ala Trp Glu Ile Val Arg Ala Glu Val Met Arg Ser Phe Ser
                165                 170                 175

Ser Ser Arg Asn Leu Gln Asp Arg Leu Arg Lys Lys Glu
            180                 185

<210> SEQ ID NO 25
<211> LENGTH: 66
<212> TYPE: DNA
<213> ORGANISM: Sus scrofa
<220> FEATURE:
<221> NAME/KEY: CDS
<222> LOCATION: (1)..(66)
<223> OTHER INFORMATION: Porcine Interferon Alpha Secretion Peptide

<400> SEQUENCE: 25 atg gcc cca acc tca gcc ttc ctc acg gcc ctg gtg cta ctc agc tgc      48
Met Ala Pro Thr Ser Ala Phe Leu Thr Ala Leu Val Leu Leu Ser Cys
1               5                   10                  15 aat gcc atc tgc tct ctg                                               66
Asn Ala Ile Cys Ser Leu
            20

<210> SEQ ID NO 26
<211> LENGTH: 22
<212> TYPE: PRT
<213> ORGANISM: Sus scrofa

<400> SEQUENCE: 26

Met Ala Pro Thr Ser Ala Phe Leu Thr Ala Leu Val Leu Leu Ser Cys
1               5                   10                  15

Asn Ala Ile Cys Ser Leu
            20

<210> SEQ ID NO 27
<211> LENGTH: 69
<212> TYPE: DNA
<213> ORGANISM: Homo sapiens
<220> FEATURE:
<221> NAME/KEY: CDS
<222> LOCATION: (1)..(69)

<223> OTHER INFORMATION: Human Interferon Alpha Secretion peptide

<400> SEQUENCE: 27

```
atg gcc tcg ccc ttt gct tta ctg atg gtc ctg gtg gtg ctc agc tgc        48
Met Ala Ser Pro Phe Ala Leu Leu Met Val Leu Val Val Leu Ser Cys
1               5                   10                  15 aag tca agc tgc tct ccg ggc                                             69
Lys Ser Ser Cys Ser Pro Gly
            20
```

<210> SEQ ID NO 28
<211> LENGTH: 23
<212> TYPE: PRT
<213> ORGANISM: Homo sapiens

<400> SEQUENCE: 28

```
Met Ala Ser Pro Phe Ala Leu Leu Met Val Leu Val Val Leu Ser Cys
1               5                   10                  15

Lys Ser Ser Cys Ser Pro Gly
            20
```

<210> SEQ ID NO 29
<211> LENGTH: 63
<212> TYPE: DNA
<213> ORGANISM: Bos taurus
<220> FEATURE:
<221> NAME/KEY: CDS
<222> LOCATION: (1)..(63)
<223> OTHER INFORMATION: Bovine Interferon Beta Secretion Peptide

<400> SEQUENCE: 29

```
atg acc tac cgg tgc ctc ctc cag atg gtt ctc ctg ctg tgt ttc tcc        48
Met Thr Tyr Arg Cys Leu Leu Gln Met Val Leu Leu Leu Cys Phe Ser
1               5                   10                  15 acc aca gct ctt tcc                                                     63
Thr Thr Ala Leu Ser
            20
```

<210> SEQ ID NO 30
<211> LENGTH: 21
<212> TYPE: PRT
<213> ORGANISM: Bos taurus

<400> SEQUENCE: 30

```
Met Thr Tyr Arg Cys Leu Leu Gln Met Val Leu Leu Leu Cys Phe Ser
1               5                   10                  15

Thr Thr Ala Leu Ser
            20
```

<210> SEQ ID NO 31
<211> LENGTH: 63
<212> TYPE: DNA
<213> ORGANISM: Sus scrofa
<220> FEATURE:
<221> NAME/KEY: CDS
<222> LOCATION: (1)..(63)
<223> OTHER INFORMATION: Porcine Interferon Beta Secretion Peptide

<400> SEQUENCE: 31

```
atg gct aac aag tgc atc ctc caa atc gct ctc ctg atg tgt ttc tcc        48
Met Ala Asn Lys Cys Ile Leu Gln Ile Ala Leu Leu Met Cys Phe Ser
1               5                   10                  15 acc aca gct ctt tcc                                                     63
Thr Thr Ala Leu Ser
            20
```

<210> SEQ ID NO 32
<211> LENGTH: 21
<212> TYPE: PRT
<213> ORGANISM: Sus scrofa

<400> SEQUENCE: 32

Met Ala Asn Lys Cys Ile Leu Gln Ile Ala Leu Leu Met Cys Phe Ser
1               5                   10                  15

Thr Thr Ala Leu Ser
            20

<210> SEQ ID NO 33
<211> LENGTH: 63
<212> TYPE: DNA
<213> ORGANISM: Homo sapiens
<220> FEATURE:
<221> NAME/KEY: CDS
<222> LOCATION: (1)..(63)
<223> OTHER INFORMATION: Human Interferon Beta Secretion peptide

<400> SEQUENCE: 33 atg acc aac aag tgt ctc ctc caa att gct ctc ctg ttg tgc ttc tcc      48
Met Thr Asn Lys Cys Leu Leu Gln Ile Ala Leu Leu Leu Cys Phe Ser
1               5                   10                  15 acg aca gct ctt tcc                                                   63
Thr Thr Ala Leu Ser
            20

<210> SEQ ID NO 34
<211> LENGTH: 21
<212> TYPE: PRT
<213> ORGANISM: Homo sapiens

<400> SEQUENCE: 34

Met Thr Asn Lys Cys Leu Leu Gln Ile Ala Leu Leu Leu Cys Phe Ser
1               5                   10                  15

Thr Thr Ala Leu Ser
            20

<210> SEQ ID NO 35
<211> LENGTH: 69
<212> TYPE: DNA
<213> ORGANISM: Bos taurus
<220> FEATURE:
<221> NAME/KEY: CDS
<222> LOCATION: (1)..(69)
<223> OTHER INFORMATION: Bovine Interferon Gamma Secretion peptide

<400> SEQUENCE: 35 atg aaa tat aca agc tat ttc tta gct tta ctg ctc tgt ggg ctt ttg      48
Met Lys Tyr Thr Ser Tyr Phe Leu Ala Leu Leu Leu Cys Gly Leu Leu
1               5                   10                  15 ggt ttt tct ggt tct tat ggc                                           69
Gly Phe Ser Gly Ser Tyr Gly
            20

<210> SEQ ID NO 36
<211> LENGTH: 23
<212> TYPE: PRT
<213> ORGANISM: Bos taurus

<400> SEQUENCE: 36

Met Lys Tyr Thr Ser Tyr Phe Leu Ala Leu Leu Leu Cys Gly Leu Leu
1               5                   10                  15

Gly Phe Ser Gly Ser Tyr Gly
            20

<210> SEQ ID NO 37
<211> LENGTH: 69
<212> TYPE: DNA
<213> ORGANISM: Sus scrofa
<220> FEATURE:
<221> NAME/KEY: CDS
<222> LOCATION: (1)..(69)
<223> OTHER INFORMATION: Porcine Interferon Gamma Secretion peptide

<400> SEQUENCE: 37

```
atg agt tat aca act tat ttc tta gct ttt cag ctt tgc gtg act ttg    48
Met Ser Tyr Thr Thr Tyr Phe Leu Ala Phe Gln Leu Cys Val Thr Leu
1               5                   10                  15 tgt ttt tct ggc tct tac tgc                                        69
Cys Phe Ser Gly Ser Tyr Cys
            20
```

<210> SEQ ID NO 38
<211> LENGTH: 23
<212> TYPE: PRT
<213> ORGANISM: Sus scrofa

<400> SEQUENCE: 38

Met Ser Tyr Thr Thr Tyr Phe Leu Ala Phe Gln Leu Cys Val Thr Leu
1               5                   10                  15

Cys Phe Ser Gly Ser Tyr Cys
            20

<210> SEQ ID NO 39
<211> LENGTH: 69
<212> TYPE: DNA
<213> ORGANISM: Homo sapiens
<220> FEATURE:
<221> NAME/KEY: CDS
<222> LOCATION: (1)..(69)
<223> OTHER INFORMATION: Human Interferon Gamma Secretion peptide

<400> SEQUENCE: 39

```
atg aaa tat aca agt tat atc ttg gct ttt cag ctc tgc atc gtt tgg    48
Met Lys Tyr Thr Ser Tyr Ile Leu Ala Phe Gln Leu Cys Ile Val Leu
1               5                   10                  15 ggt tct ctt ggc tgt tac tgc                                        69
Gly Ser Leu Gly Cys Tyr Cys
            20
```

<210> SEQ ID NO 40
<211> LENGTH: 23
<212> TYPE: PRT
<213> ORGANISM: Homo sapiens

<400> SEQUENCE: 40

Met Lys Tyr Thr Ser Tyr Ile Leu Ala Phe Gln Leu Cys Ile Val Leu
1               5                   10                  15

Gly Ser Leu Gly Cys Tyr Cys
            20

<210> SEQ ID NO 41
<211> LENGTH: 57
<212> TYPE: DNA
<213> ORGANISM: Bos taurus
<220> FEATURE:
<221> NAME/KEY: CDS -continued

```
<222> LOCATION: (1)..(57)
<223> OTHER INFORMATION: Bovine Interferon Lambda Secretion peptide

<400> SEQUENCE: 41 atg gcc ccg ggc tgc acg ctg gtg ctg gtg ctg atg ctg acg acc gtg        48
Met Ala Pro Gly Cys Thr Leu Val Leu Val Leu Met Leu Thr Thr Val
1               5                  10                  15 gcg ctg agc                                                             57
Ala Leu Ser <210> SEQ ID NO 42
<211> LENGTH: 19
<212> TYPE: PRT
<213> ORGANISM: Bos taurus

<400> SEQUENCE: 42

Met Ala Pro Gly Cys Thr Leu Val Leu Val Leu Met Leu Thr Thr Val
1               5                  10                  15

Ala Leu Ser

<210> SEQ ID NO 43
<211> LENGTH: 48
<212> TYPE: DNA
<213> ORGANISM: Sus scrofa
<220> FEATURE:
<221> NAME/KEY: CDS
<222> LOCATION: (1)..(48)
<223> OTHER INFORMATION: Porcine Interferon Lambda Secretion peptide

<400> SEQUENCE: 43 atg gct aca gct tgg atc gtg gtg ctg gcg act gtg atg ctg gac ttg        48
Met Ala Thr Ala Trp Ile Val Val Leu Ala Thr Val Met Leu Asp Leu
1               5                  10                  15

<210> SEQ ID NO 44
<211> LENGTH: 16
<212> TYPE: PRT
<213> ORGANISM: Sus scrofa

<400> SEQUENCE: 44

Met Ala Thr Ala Trp Ile Val Val Leu Ala Thr Val Met Leu Asp Leu
1               5                  10                  15

<210> SEQ ID NO 45
<211> LENGTH: 45
<212> TYPE: DNA
<213> ORGANISM: Homo sapiens
<220> FEATURE:
<221> NAME/KEY: CDS
<222> LOCATION: (1)..(45)
<223> OTHER INFORMATION: Human Interferon Lambda Secretion peptide

<400> SEQUENCE: 45 atg gct gca gct tgg acc gtg gtg ctg gtg act ttg gtg cta ggc            45
Met Ala Ala Ala Trp Thr Val Val Leu Val Thr Leu Val Leu Gly
1               5                  10                  15

<210> SEQ ID NO 46
<211> LENGTH: 15
<212> TYPE: PRT
<213> ORGANISM: Homo sapiens

<400> SEQUENCE: 46

Met Ala Ala Ala Trp Thr Val Val Leu Val Thr Leu Val Leu Gly
1               5                  10                  15
```

<210> SEQ ID NO 47
<211> LENGTH: 1065
<212> TYPE: DNA
<213> ORGANISM: Sus scrofa
<220> FEATURE:
<221> NAME/KEY: CDS
<222> LOCATION: (1)..(1065)
<223> OTHER INFORMATION: Porcine SGLucON Alpha

<400> SEQUENCE: 47

```
atg gga gtc aaa gtt ctg ttt gcc ctg atc tgc atc gct gtg gcc gag      48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc      96
Ala Lys Pro Thr Glu Asn Asn Glu Asp Phe Asn Ile Val Ala Val Ala
                20                  25                  30 agc aac ttt gcg acc acg gat ctc gat gct gac cga ggg aag ttg ccc     144
Ser Asn Phe Ala Thr Thr Asp Leu Asp Ala Asp Arg Gly Lys Leu Pro
            35                  40                  45 ggc aag aag ctg ccg ctg gag gtg ctc aaa gag atg gaa gcc aat gcc     192
Gly Lys Lys Leu Pro Leu Glu Val Leu Lys Glu Met Glu Ala Asn Ala
        50                  55                  60 cgg aaa gct ggc tgc acc agg ggc tgt ctg atc tgc ctg tcc cac atc     240
Arg Lys Ala Gly Cys Thr Arg Gly Cys Leu Ile Cys Leu Ser His Ile
65                  70                  75                  80 aag tgc acg ccc aag atg aag aag tgg ctc cca gga cgc tgt cac acc     288
Lys Cys Thr Pro Lys Met Lys Lys Trp Leu Pro Gly Arg Cys His Thr
                85                  90                  95 tac gaa ggc gac aaa gag tcc gca cag ggc ggc ata ggc gag gcg atc     336
Tyr Glu Gly Asp Lys Glu Ser Ala Gln Gly Gly Ile Gly Glu Ala Ile
                100                 105                 110 gtc gat att cct gag att cct ggg ttc aag gac ttg gag cca atg gag     384
Val Asp Ile Pro Glu Ile Pro Gly Phe Lys Asp Leu Glu Pro Met Glu
            115                 120                 125 cag ttc atc gca cag gtc gat ctg tgt gtg gac tgc aca act ggc tgc     432
Gln Phe Ile Ala Gln Val Asp Leu Cys Val Asp Cys Thr Thr Gly Cys
        130                 135                 140 ctc aaa ggg ctt gcc aac gtg cag tgt tct gac ctg ctc aag aag tgg     480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg     528
Leu Pro Gln Arg Cys Ala Thr Phe Ala Ser Lys Ile Gln Gly Gln Val
                165                 170                 175 gac aag atc aag ggg gcc ggt ggt gac ggg ccc ggg tgt gac ctg cct     576
Asp Lys Ile Lys Gly Ala Gly Gly Asp Gly Pro Gly Cys Asp Leu Pro
            180                 185                 190 cag acc cac agc ctg gct cac acc aga gcc ctg agg ctc ctg gca caa     624
Gln Thr His Ser Leu Ala His Thr Arg Ala Leu Arg Leu Leu Ala Gln
        195                 200                 205 atg agg aga atc tct ccc ttc tcc tgc ctg gac cac aga agg gac ttt     672
Met Arg Arg Ile Ser Pro Phe Ser Cys Leu Asp His Arg Arg Asp Phe
    210                 215                 220 ggt tcc cct cat gag gct ttt ggg ggc aac cag gtc cag aag gct caa     720
Gly Ser Pro His Glu Ala Phe Gly Gly Asn Gln Val Gln Lys Ala Gln
225                 230                 235                 240 gcc atg gct ctg gtg cat gag atg ctc cag cag acc ttc cag ctc ttc     768
Ala Met Ala Leu Val His Glu Met Leu Gln Gln Thr Phe Gln Leu Phe
                245                 250                 255 agc aca gag ggc tcg gct gct gcc tgg aat gag agc ctc ctg cac cag     816
Ser Thr Glu Gly Ser Ala Ala Ala Trp Asn Glu Ser Leu Leu His Gln
            260                 265                 270
```

```
ttc tgc act gga ctg gat cag cag ctc agg gac ctg gaa gcc tgt gtc      864
Phe Cys Thr Gly Leu Asp Gln Gln Leu Arg Asp Leu Glu Ala Cys Val
            275                 280                 285 atg cag gag gcg ggg ctg gaa ggg acc ccc ctg ctg gag gag gac tcc      912
Met Gln Glu Ala Gly Leu Glu Gly Thr Pro Leu Leu Glu Glu Asp Ser
        290                 295                 300 atc ctg gct gtg agg aaa tac ttc cac aga ctc acc ctc tat ctg caa      960
Ile Leu Ala Val Arg Lys Tyr Phe His Arg Leu Thr Leu Tyr Leu Gln
305                 310                 315                 320 gag aag agc tac agc ccc tgt gcc tgg gag atc gtc agg gca gaa gtc     1008
Glu Lys Ser Tyr Ser Pro Cys Ala Trp Glu Ile Val Arg Ala Glu Val
                325                 330                 335 atg aga tcc ttc tct tcc tcc aga aac ctg caa gac aga ctc agg aag     1056
Met Arg Ser Phe Ser Ser Ser Arg Asn Leu Gln Asp Arg Leu Arg Lys
            340                 345                 350 aag gag tga                                                          1065
Lys Glu <210> SEQ ID NO 48
<211> LENGTH: 354
<212> TYPE: PRT
<213> ORGANISM: Sus scrofa

<400> SEQUENCE: 48

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Trp Leu Pro Gly Arg Cys His Thr
                85                  90                  95

Tyr Glu Gly Asp Lys Glu Ser Ala Gln Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp Gly Pro Gly Cys Asp Leu Pro
            180                 185                 190

Gln Thr His Ser Leu Ala His Thr Arg Ala Leu Arg Leu Leu Ala Gln
        195                 200                 205

Met Arg Arg Ile Ser Pro Phe Ser Cys Leu Asp His Arg Arg Asp Phe
    210                 215                 220

Gly Ser Pro His Glu Ala Phe Gly Gly Asn Gln Val Gln Lys Ala Gln
225                 230                 235                 240

Ala Met Ala Leu Val His Glu Met Leu Gln Gln Thr Phe Gln Leu Phe
                245                 250                 255
```

```
Ser Thr Glu Gly Ser Ala Ala Ala Trp Asn Glu Ser Leu Leu His Gln
            260                 265                 270

Phe Cys Thr Gly Leu Asp Gln Gln Leu Arg Asp Leu Glu Ala Cys Val
        275                 280                 285

Met Gln Ala Gly Leu Glu Gly Thr Pro Leu Leu Glu Glu Asp Ser
    290                 295                 300

Ile Leu Ala Val Arg Lys Tyr Phe His Arg Leu Thr Leu Tyr Leu Gln
305                 310                 315                 320

Glu Lys Ser Tyr Ser Pro Cys Ala Trp Glu Ile Val Arg Ala Glu Val
                325                 330                 335

Met Arg Ser Phe Ser Ser Ser Arg Asn Leu Gln Asp Arg Leu Arg Lys
            340                 345                 350

Lys Glu

<210> SEQ ID NO 49
<211> LENGTH: 570
<212> TYPE: DNA
<213> ORGANISM: Homo sapiens
<220> FEATURE:
<221> NAME/KEY: CDS
<222> LOCATION: (1)..(570)
<223> OTHER INFORMATION: Human Interferon Alpha

<400> SEQUENCE: 49 atg gcc tcg ccc ttt gct tta ctg atg gtc ctg gtg gtg ctc agc tgc     48
Met Ala Ser Pro Phe Ala Leu Leu Met Val Leu Val Val Leu Ser Cys
1               5                   10                  15 aag tca agc tgc tct ccg ggc tgt gat ctc cct gag acc cac agc ctg     96
Lys Ser Ser Cys Ser Pro Gly Cys Asp Leu Pro Glu Thr His Ser Leu
            20                  25                  30 gat aac agg agg acc ttg atg ctc ctg gca caa atg agc aga atc tct    144
Asp Asn Arg Arg Thr Leu Met Leu Leu Ala Gln Met Ser Arg Ile Ser
        35                  40                  45 cct tcc tcc tgt ctg atg gac aga cat gac ttt gga ttt ccc cag gag    192
Pro Ser Ser Cys Leu Met Asp Arg His Asp Phe Gly Phe Pro Gln Glu
    50                  55                  60 gag ttt gat ggc aac cag ttc cag aag gct cca gcc atc tct gtc ctc    240
Glu Phe Asp Gly Asn Gln Phe Gln Lys Ala Pro Ala Ile Ser Val Leu
65                  70                  75                  80 caa gag ctg atc cag cag atc ttc aac ctc ttt acc aca aaa gat tca    288
Gln Glu Leu Ile Gln Gln Ile Phe Asn Leu Phe Thr Thr Lys Asp Ser
                85                  90                  95 tct gct gct tgg gat gag gac ctc cta gac aaa ttc tgc acc gaa ctc    336
Ser Ala Ala Trp Asp Glu Asp Leu Leu Asp Lys Phe Cys Thr Glu Leu
            100                 105                 110 tac cag cag ctg aat gac ttg gaa gcc tgt gtg atg cag gag gag agg    384
Tyr Gln Gln Leu Asn Asp Leu Glu Ala Cys Val Met Gln Glu Glu Arg
        115                 120                 125 gtg gga gaa act ccc ctg atg aat gcg gac tcc atc ttg gct gtg aag    432
Val Gly Glu Thr Pro Leu Met Asn Ala Asp Ser Ile Leu Ala Val Lys
    130                 135                 140 aaa tac ttc cga aga atc act ctc tat ctg acg gag aag aaa tac agc    480
Lys Tyr Phe Arg Arg Ile Thr Leu Tyr Leu Thr Glu Lys Lys Tyr Ser
145                 150                 155                 160 cct tgt gcc tgg gag gtt gtc aga gca gaa atc gtg aga tcc ctc tct    528
Pro Cys Ala Trp Glu Val Val Arg Ala Glu Ile Val Arg Ser Leu Ser
                165                 170                 175 tta tca aca aac ttg caa gaa aga tta agg agg aag gaa taa             570
Leu Ser Thr Asn Leu Gln Glu Arg Leu Arg Arg Lys Glu
```

<210> SEQ ID NO 50
<211> LENGTH: 189
<212> TYPE: PRT
<213> ORGANISM: Homo sapiens

<400> SEQUENCE: 50

Met Ala Ser Pro Phe Ala Leu Leu Met Val Leu Val Val Leu Ser Cys
1               5                   10                  15

Lys Ser Ser Cys Ser Pro Gly Cys Asp Leu Pro Glu Thr His Ser Leu
            20                  25                  30

Asp Asn Arg Arg Thr Leu Met Leu Leu Ala Gln Met Ser Arg Ile Ser
        35                  40                  45

Pro Ser Ser Cys Leu Met Asp Arg His Asp Phe Gly Phe Pro Gln Glu
    50                  55                  60

Glu Phe Asp Gly Asn Gln Phe Gln Lys Ala Pro Ala Ile Ser Val Leu
65                  70                  75                  80

Gln Glu Leu Ile Gln Gln Ile Phe Asn Leu Phe Thr Thr Lys Asp Ser
                85                  90                  95

Ser Ala Ala Trp Asp Glu Asp Leu Leu Asp Lys Phe Cys Thr Glu Leu
            100                 105                 110

Tyr Gln Gln Leu Asn Asp Leu Glu Ala Cys Val Met Gln Glu Glu Arg
        115                 120                 125

Val Gly Glu Thr Pro Leu Met Asn Ala Asp Ser Ile Leu Ala Val Lys
    130                 135                 140

Lys Tyr Phe Arg Arg Ile Thr Leu Tyr Leu Thr Glu Lys Lys Tyr Ser
145                 150                 155                 160

Pro Cys Ala Trp Glu Val Val Arg Ala Glu Ile Val Arg Ser Leu Ser
                165                 170                 175

Leu Ser Thr Asn Leu Gln Glu Arg Leu Arg Arg Lys Glu
            180                 185

<210> SEQ ID NO 51
<211> LENGTH: 1056
<212> TYPE: DNA
<213> ORGANISM: Homo sapiens
<220> FEATURE:
<221> NAME/KEY: CDS
<222> LOCATION: (1)..(1056)
<223> OTHER INFORMATION: Human GlucON Alpha

<400> SEQUENCE: 51 atg gga gtc aaa gtt ctg ttt gcc ctg atc tgc atc gct gtg gcc gag      48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc      96
Ala Lys Pro Thr Glu Asn Asn Glu Asp Phe Asn Ile Val Ala Val Ala
            20                  25                  30 agc aac ttc gcg acc acg gat ctc gat gct gac cgc ggg aag ttg ccc     144
Ser Asn Phe Ala Thr Thr Asp Leu Asp Ala Asp Arg Gly Lys Leu Pro
        35                  40                  45 ggc aag aag ctg ccg ctg gag gtg ctc aaa gag atg gaa gcc aat gcc     192
Gly Lys Lys Leu Pro Leu Glu Val Leu Lys Glu Met Glu Ala Asn Ala
    50                  55                  60 cgg aaa gct ggc tgc acc agg ggc tgt ctg atc tgc ctg tcc cac atc     240
Arg Lys Ala Gly Cys Thr Arg Gly Cys Leu Ile Cys Leu Ser His Ile
65                  70                  75                  80 aag tgc acg ccc aag atg aag aag ttc atc cca gga cgc tgc cac acc     288

```
Lys Cys Thr Pro Lys Met Lys Lys Phe Ile Pro Gly Arg Cys His Thr
            85                  90                  95 tac gaa ggc gac aaa gag tcc gca cag ggc ggc ata ggc gag gcg atc     336
Tyr Glu Gly Asp Lys Glu Ser Ala Gln Gly Gly Ile Gly Glu Ala Ile
            100                 105                 110 gtc gac att cct gag att cct ggg ttc aag gac ttg gag ccc atg gag     384
Val Asp Ile Pro Glu Ile Pro Gly Phe Lys Asp Leu Glu Pro Met Glu
            115                 120                 125 cag ttc atc gca cag gtc gat ctg tgt gtg gac tgc aca act ggc tgc     432
Gln Phe Ile Ala Gln Val Asp Leu Cys Val Asp Cys Thr Thr Gly Cys
    130                 135                 140 ctc aaa ggg ctt gcc aac gtg cag tgt tct gac ctg ctc aag aag tgg     480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg     528
Leu Pro Gln Arg Cys Ala Thr Phe Ala Ser Lys Ile Gln Gly Gln Val
                165                 170                 175 gac aag atc aag ggg gcc ggt ggt gac tgt gat ctc cct gag acc cac     576
Asp Lys Ile Lys Gly Ala Gly Gly Asp Cys Asp Leu Pro Glu Thr His
            180                 185                 190 agc ctg gat aac agg agg acc ttg atg ctc ctg gca caa atg agc aga     624
Ser Leu Asp Asn Arg Arg Thr Leu Met Leu Leu Ala Gln Met Ser Arg
            195                 200                 205 atc tct cct tcc tcc tgt ctg atg gac aga cat gac ttt gga ttt ccc     672
Ile Ser Pro Ser Ser Cys Leu Met Asp Arg His Asp Phe Gly Phe Pro
    210                 215                 220 cag gag gag ttt gat ggc aac cag ttc cag aag gct cca gcc atc tct     720
Gln Glu Glu Phe Asp Gly Asn Gln Phe Gln Lys Ala Pro Ala Ile Ser
225                 230                 235                 240 gtc ctc caa gag ctg atc cag cag atc ttc aac ctc ttt acc aca aaa     768
Val Leu Gln Glu Leu Ile Gln Gln Ile Phe Asn Leu Phe Thr Thr Lys
                245                 250                 255 gat tca tct gct gct tgg gat gag gac ctc cta gac aaa ttc tgc acc     816
Asp Ser Ser Ala Ala Trp Asp Glu Asp Leu Leu Asp Lys Phe Cys Thr
            260                 265                 270 gaa ctc tac cag cag ctg aat gac ttg gaa gcc tgt gtg atg cag gag     864
Glu Leu Tyr Gln Gln Leu Asn Asp Leu Glu Ala Cys Val Met Gln Glu
            275                 280                 285 gag agg gtg gga gaa act ccc ctg atg aat gcg gac tcc atc ttg gct     912
Glu Arg Val Gly Glu Thr Pro Leu Met Asn Ala Asp Ser Ile Leu Ala
    290                 295                 300 gtg aag aaa tac ttc cga aga atc act ctc tat ctg acg gag aag aaa     960
Val Lys Lys Tyr Phe Arg Arg Ile Thr Leu Tyr Leu Thr Glu Lys Lys
305                 310                 315                 320 tac agc cct tgt gcc tgg gag gtt gtc aga gca gaa atc gtg aga tcc    1008
Tyr Ser Pro Cys Ala Trp Glu Val Val Arg Ala Glu Ile Val Arg Ser
                325                 330                 335 ctc tct tta tca aca aac ttg caa gaa aga tta agg agg aag gaa taa    1056
Leu Ser Leu Ser Thr Asn Leu Gln Glu Arg Leu Arg Arg Lys Glu
            340                 345                 350
```

<210> SEQ ID NO 52
<211> LENGTH: 351
<212> TYPE: PRT
<213> ORGANISM: Homo sapiens

<400> SEQUENCE: 52

```
Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
```

```
                  20                  25                  30
Ser Asn Phe Ala Thr Thr Asp Leu Asp Ala Asp Arg Gly Lys Leu Pro
                35                  40                  45

Gly Lys Lys Leu Pro Leu Glu Val Leu Lys Glu Met Glu Ala Asn Ala
 50                  55                  60

Arg Lys Ala Gly Cys Thr Arg Gly Cys Leu Ile Cys Leu Ser His Ile
 65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
               100                 105                 110

Val Asp Ile Pro Glu Ile Pro Gly Phe Lys Asp Leu Glu Pro Met Glu
               115                 120                 125

Gln Phe Ile Ala Gln Val Asp Leu Cys Val Asp Cys Thr Thr Gly Cys
               130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
               165                 170                 175

Asp Lys Ile Lys Gly Ala Gly Gly Asp Cys Asp Leu Pro Glu Thr His
               180                 185                 190

Ser Leu Asp Asn Arg Arg Thr Leu Met Leu Leu Ala Gln Met Ser Arg
               195                 200                 205

Ile Ser Pro Ser Ser Cys Leu Met Asp Arg His Asp Phe Gly Phe Pro
               210                 215                 220

Gln Glu Glu Phe Asp Gly Asn Gln Phe Gln Lys Ala Pro Ala Ile Ser
225                 230                 235                 240

Val Leu Gln Glu Leu Ile Gln Gln Ile Phe Asn Leu Phe Thr Thr Lys
               245                 250                 255

Asp Ser Ser Ala Ala Trp Asp Glu Asp Leu Leu Asp Lys Phe Cys Thr
               260                 265                 270

Glu Leu Tyr Gln Gln Leu Asn Asp Leu Glu Ala Cys Val Met Gln Glu
               275                 280                 285

Glu Arg Val Gly Glu Thr Pro Leu Met Asn Ala Asp Ser Ile Leu Ala
               290                 295                 300

Val Lys Lys Tyr Phe Arg Arg Ile Thr Leu Tyr Leu Thr Glu Lys Lys
305                 310                 315                 320

Tyr Ser Pro Cys Ala Trp Glu Val Val Arg Ala Glu Ile Val Arg Ser
               325                 330                 335

Leu Ser Leu Ser Thr Asn Leu Gln Glu Arg Leu Arg Arg Lys Glu
               340                 345                 350

<210> SEQ ID NO 53
<211> LENGTH: 570
<212> TYPE: DNA
<213> ORGANISM: Bos taurus
<220> FEATURE:
<221> NAME/KEY: CDS
<222> LOCATION: (1)..(570)
<223> OTHER INFORMATION: Bovine Interferon Alpha

<400> SEQUENCE: 53 atg gcc cca gcc tgg tcc ttc ctg cta tcc ctg ttg ctg ctc agc tgc     48
Met Ala Pro Ala Trp Ser Phe Leu Leu Ser Leu Leu Leu Leu Ser Cys
1               5                   10                  15 aac gcc atc tgc tct ctg ggt tgc cac ctg cct cac acc cac agc ctg     96
```

|     |     |     |     |     |     |     |     |     |     |     |     |     |     |     |     |     |
|---|---|---|---|---|---|---|---|---|---|---|---|---|---|---|---|---|
| Asn | Ala | Ile | Cys | Ser | Leu | Gly | Cys | His | Leu | Pro | His | Thr | His | Ser | Leu | |
|     |     |     | 20  |     |     |     |     | 25  |     |     |     |     | 30  |     |     | |

```
gcc aac agg agg gtc ctg atg ctc ctg caa caa ctg aga agg gtc tcc        144
Ala Asn Arg Arg Val Leu Met Leu Leu Gln Gln Leu Arg Arg Val Ser
 35                  40                  45 cct tcc tcc tgc ctg cag gac aga aat gac ttc gaa ttc ctc cag gag        192
Pro Ser Ser Cys Leu Gln Asp Arg Asn Asp Phe Glu Phe Leu Gln Glu
 50                  55                  60 gct ctg ggt ggc agc cag ttg cag aag gct caa gcc atc tct gtg ctc        240
Ala Leu Gly Gly Ser Gln Leu Gln Lys Ala Gln Ala Ile Ser Val Leu
65                  70                  75                  80 cac gag gtg acc cag cac acc ttc cag ctc ttc agc aca gag ggc tcg        288
His Glu Val Thr Gln His Thr Phe Gln Leu Phe Ser Thr Glu Gly Ser
                 85                  90                  95 ccc gcc acg tgg gac aag agc ctc ctg gac aag cta cgc gct gcg ctg        336
Pro Ala Thr Trp Asp Lys Ser Leu Leu Asp Lys Leu Arg Ala Ala Leu
             100                 105                 110 gat cag cag ctc act gac ctg caa gcc tgt ctg acg cag gag gag ggg        384
Asp Gln Gln Leu Thr Asp Leu Gln Ala Cys Leu Thr Gln Glu Glu Gly
         115                 120                 125 ctg cga ggg gct ccc ctc ctc aag gag gac tcc agc ctg gct gtg agg        432
Leu Arg Gly Ala Pro Leu Leu Lys Glu Asp Ser Ser Leu Ala Val Arg
     130                 135                 140 aaa tac ttc cac aga ctc act ctc tat ctg caa gag aag aga cac agc        480
Lys Tyr Phe His Arg Leu Thr Leu Tyr Leu Gln Glu Lys Arg His Ser
145                 150                 155                 160 cct tgt gcc tgg gag gtt gtc aga gca gaa gtc atg aga gcc ttc tct        528
Pro Cys Ala Trp Glu Val Val Arg Ala Glu Val Met Arg Ala Phe Ser
                 165                 170                 175 tcc tca aca aac ttg cag gag agt ttc agg aga aag gac tga                570
Ser Ser Thr Asn Leu Gln Glu Ser Phe Arg Arg Lys Asp
             180                 185
```

<210> SEQ ID NO 54
<211> LENGTH: 189
<212> TYPE: PRT
<213> ORGANISM: Bos taurus

<400> SEQUENCE: 54

|     |     |     |     |     |     |     |     |     |     |     |     |     |     |     |     |
|---|---|---|---|---|---|---|---|---|---|---|---|---|---|---|---|
| Met | Ala | Pro | Ala | Trp | Ser | Phe | Leu | Leu | Ser | Leu | Leu | Leu | Leu | Ser | Cys |
| 1   |     |     |     | 5   |     |     |     |     | 10  |     |     |     |     | 15  |     |
| Asn | Ala | Ile | Cys | Ser | Leu | Gly | Cys | His | Leu | Pro | His | Thr | His | Ser | Leu |
|     |     |     | 20  |     |     |     |     | 25  |     |     |     |     | 30  |     |     |
| Ala | Asn | Arg | Arg | Val | Leu | Met | Leu | Leu | Gln | Gln | Leu | Arg | Arg | Val | Ser |
|     |     |     | 35  |     |     |     |     | 40  |     |     |     |     | 45  |     |     |
| Pro | Ser | Ser | Cys | Leu | Gln | Asp | Arg | Asn | Asp | Phe | Glu | Phe | Leu | Gln | Glu |
|     |     |     | 50  |     |     |     |     | 55  |     |     |     |     | 60  |     |     |
| Ala | Leu | Gly | Gly | Ser | Gln | Leu | Gln | Lys | Ala | Gln | Ala | Ile | Ser | Val | Leu |
| 65  |     |     |     |     | 70  |     |     |     |     | 75  |     |     |     |     | 80  |
| His | Glu | Val | Thr | Gln | His | Thr | Phe | Gln | Leu | Phe | Ser | Thr | Glu | Gly | Ser |
|     |     |     |     | 85  |     |     |     |     | 90  |     |     |     |     | 95  |     |
| Pro | Ala | Thr | Trp | Asp | Lys | Ser | Leu | Leu | Asp | Lys | Leu | Arg | Ala | Ala | Leu |
|     |     |     |     | 100 |     |     |     |     | 105 |     |     |     |     | 110 |     |
| Asp | Gln | Gln | Leu | Thr | Asp | Leu | Gln | Ala | Cys | Leu | Thr | Gln | Glu | Glu | Gly |
|     |     |     |     | 115 |     |     |     |     | 120 |     |     |     |     | 125 |     |
| Leu | Arg | Gly | Ala | Pro | Leu | Leu | Lys | Glu | Asp | Ser | Ser | Leu | Ala | Val | Arg |
|     |     |     |     | 130 |     |     |     |     | 135 |     |     |     |     | 140 |     |
| Lys | Tyr | Phe | His | Arg | Leu | Thr | Leu | Tyr | Leu | Gln | Glu | Lys | Arg | His | Ser |

```
145                 150                 155                 160
Pro Cys Ala Trp Glu Val Val Arg Ala Glu Val Met Arg Ala Phe Ser
                165                 170                 175
Ser Ser Thr Asn Leu Gln Glu Ser Phe Arg Arg Lys Asp
            180                 185

<210> SEQ ID NO 55
<211> LENGTH: 1056
<212> TYPE: DNA
<213> ORGANISM: Bos taurus
<220> FEATURE:
<221> NAME/KEY: CDS
<222> LOCATION: (1)..(1056)
<223> OTHER INFORMATION: Bovine GlucON Alpha

<400> SEQUENCE: 55 atg gga gtc aaa gtt ctg ttt gcc ctg atc tgc atc gct gtg gcc gag      48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc      96
Ala Lys Pro Thr Glu Asn Asn Glu Asp Phe Asn Ile Val Ala Val Ala
                20                  25                  30 agc aac ttc gcg acc acg gat ctc gat gct gac cgc ggg aag ttg ccc     144
Ser Asn Phe Ala Thr Thr Asp Leu Asp Ala Asp Arg Gly Lys Leu Pro
            35                  40                  45 ggc aag aag ctg ccg ctg gag gtg ctc aaa gag atg gaa gcc aat gcc     192
Gly Lys Lys Leu Pro Leu Glu Val Leu Lys Glu Met Glu Ala Asn Ala
        50                  55                  60 cgg aaa gct ggc tgc acc agg ggc tgt ctg atc tgc ctg tcc cac atc     240
Arg Lys Ala Gly Cys Thr Arg Gly Cys Leu Ile Cys Leu Ser His Ile
65                  70                  75                  80 aag tgc acg ccc aag atg aag aag ttc atc cca gga cgc tgc cac acc     288
Lys Cys Thr Pro Lys Met Lys Lys Phe Ile Pro Gly Arg Cys His Thr
                85                  90                  95 tac gaa ggc gac aaa gag tcc gca cag ggc ggc ata ggc gag gcg atc     336
Tyr Glu Gly Asp Lys Glu Ser Ala Gln Gly Gly Ile Gly Glu Ala Ile
            100                 105                 110 gtc gac att cct gag att cct ggg ttc aag gac ttg gag ccc atg gag     384
Val Asp Ile Pro Glu Ile Pro Gly Phe Lys Asp Leu Glu Pro Met Glu
        115                 120                 125 cag ttc atc gca cag gtc gat ctg tgt gtg gac tgc aca act ggc tgc     432
Gln Phe Ile Ala Gln Val Asp Leu Cys Val Asp Cys Thr Thr Gly Cys
130                 135                 140 ctc aaa ggg ctt gcc aac gtg cag tgt tct gac ctg ctc aag aag tgg     480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg     528
Leu Pro Gln Arg Cys Ala Thr Phe Ala Ser Lys Ile Gln Gly Gln Val
                165                 170                 175 gac aag atc aag ggg gcc ggt ggt gac tgc cac ctg cct cac acc cac     576
Asp Lys Ile Lys Gly Ala Gly Gly Asp Cys His Leu Pro His Thr His
            180                 185                 190 agc ctg gcc aac agg agg gtc ctg atg ctc ctg caa caa ctg aga agg     624
Ser Leu Ala Asn Arg Arg Val Leu Met Leu Leu Gln Gln Leu Arg Arg
        195                 200                 205 gtc tcc cct tcc tcc tgc ctg cag gac aga aat gac ttc gaa ttc ctc     672
Val Ser Pro Ser Ser Cys Leu Gln Asp Arg Asn Asp Phe Glu Phe Leu
210                 215                 220 cag gag gct ctg ggt ggc agc cag ttg cag aag gct caa gcc atc tct     720
Gln Glu Ala Leu Gly Gly Ser Gln Leu Gln Lys Ala Gln Ala Ile Ser
225                 230                 235                 240
```

```
gtg ctc cac gag gtg acc cag cac acc ttc cag ctc ttc agc aca gag      768
Val Leu His Glu Val Thr Gln His Thr Phe Gln Leu Phe Ser Thr Glu
            245                 250                 255 ggc tcg ccc gcc acg tgg gac aag agc ctc ctg gac aag cta cgc gct      816
Gly Ser Pro Ala Thr Trp Asp Lys Ser Leu Leu Asp Lys Leu Arg Ala
        260                 265                 270 gcg ctg gat cag cag ctc act gac ctg caa gcc tgt ctg acg cag gag      864
Ala Leu Asp Gln Gln Leu Thr Asp Leu Gln Ala Cys Leu Thr Gln Glu
    275                 280                 285 gag ggg ctg cga ggg gct ccc ctc aag gag gac tcc agc ctg gct          912
Glu Gly Leu Arg Gly Ala Pro Leu Leu Lys Glu Asp Ser Ser Leu Ala
290                 295                 300 gtg agg aaa tac ttc cac aga ctc act ctc tat ctg caa gag aag aga      960
Val Arg Lys Tyr Phe His Arg Leu Thr Leu Tyr Leu Gln Glu Lys Arg
305                 310                 315                 320 cac agc cct tgt gcc tgg gag gtt gtc aga gca gaa gtc atg aga gcc     1008
His Ser Pro Cys Ala Trp Glu Val Val Arg Ala Glu Val Met Arg Ala
                325                 330                 335 ttc tct tcc tca aca aac ttg cag gag agt ttc agg aga aag gac tga     1056
Phe Ser Ser Ser Thr Asn Leu Gln Glu Ser Phe Arg Arg Lys Asp
            340                 345                 350

<210> SEQ ID NO 56
<211> LENGTH: 351
<212> TYPE: PRT
<213> ORGANISM: Bos taurus

<400> SEQUENCE: 56

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp Cys His Leu Pro His Thr His
            180                 185                 190

Ser Leu Ala Asn Arg Arg Val Leu Met Leu Leu Gln Gln Leu Arg Arg
        195                 200                 205

Val Ser Pro Ser Ser Cys Leu Gln Asp Arg Asn Asp Phe Glu Phe Leu
    210                 215                 220
```

```
Gln Glu Ala Leu Gly Gly Ser Gln Leu Gln Lys Ala Gln Ala Ile Ser
225                 230                 235                 240

Val Leu His Glu Val Thr Gln His Thr Phe Gln Leu Phe Ser Thr Glu
            245                 250                 255

Gly Ser Pro Ala Thr Trp Asp Lys Ser Leu Leu Asp Lys Leu Arg Ala
        260                 265                 270

Ala Leu Asp Gln Gln Leu Thr Asp Leu Gln Ala Cys Leu Thr Gln Glu
    275                 280                 285

Glu Gly Leu Arg Gly Ala Pro Leu Leu Lys Glu Asp Ser Ser Leu Ala
    290                 295                 300

Val Arg Lys Tyr Phe His Arg Leu Thr Leu Tyr Leu Gln Glu Lys Arg
305                 310                 315                 320

His Ser Pro Cys Ala Trp Glu Val Val Arg Ala Glu Val Met Arg Ala
            325                 330                 335

Phe Ser Ser Ser Thr Asn Leu Gln Glu Ser Phe Arg Arg Lys Asp
            340                 345                 350

<210> SEQ ID NO 57
<211> LENGTH: 564
<212> TYPE: DNA
<213> ORGANISM: Homo sapiens
<220> FEATURE:
<221> NAME/KEY: CDS
<222> LOCATION: (1)..(564)
<223> OTHER INFORMATION: Human Interferon Beta

<400> SEQUENCE: 57 atg acc aac aag tgt ctc ctc caa att gct ctc ctg ttg tgc ttc tcc      48
Met Thr Asn Lys Cys Leu Leu Gln Ile Ala Leu Leu Leu Cys Phe Ser
1               5                   10                  15 acg aca gct ctt tcc atg agc tac aac ttg ctt gga ttc cta caa aga      96
Thr Thr Ala Leu Ser Met Ser Tyr Asn Leu Leu Gly Phe Leu Gln Arg
            20                  25                  30 agc agc aat tgt cag tgt cag aag ctc ctg tgg caa ttg aat ggg agg     144
Ser Ser Asn Cys Gln Cys Gln Lys Leu Leu Trp Gln Leu Asn Gly Arg
        35                  40                  45 ctt gaa tac tgc ctc aag gac agg agg aac ttt gac atc cct gag gag     192
Leu Glu Tyr Cys Leu Lys Asp Arg Arg Asn Phe Asp Ile Pro Glu Glu
    50                  55                  60 att aag cag ctg cag cag ttc cag aag gag gac gcc gca gtg acc atc     240
Ile Lys Gln Leu Gln Gln Phe Gln Lys Glu Asp Ala Ala Val Thr Ile
65                  70                  75                  80 tat gag atg ctc cag aac atc ttt gct att ttc aga caa gat tca tcg     288
Tyr Glu Met Leu Gln Asn Ile Phe Ala Ile Phe Arg Gln Asp Ser Ser
                85                  90                  95 agc act ggc tgg aat gag act att gtt gag aac ctc ctg gct aat gtc     336
Ser Thr Gly Trp Asn Glu Thr Ile Val Glu Asn Leu Leu Ala Asn Val
            100                 105                 110 tat cat cag aga aac cat ctg aag aca gtc ctg gaa gaa aaa ctg gag     384
Tyr His Gln Arg Asn His Leu Lys Thr Val Leu Glu Glu Lys Leu Glu
        115                 120                 125 aaa gaa gat ttc acc agg gga aaa cgc atg agc agt ctg cac ctg aaa     432
Lys Glu Asp Phe Thr Arg Gly Lys Arg Met Ser Ser Leu His Leu Lys
    130                 135                 140 aga tat tat ggg agg att ctg cat tac ctg aag gcc aag gag gac agt     480
Arg Tyr Tyr Gly Arg Ile Leu His Tyr Leu Lys Ala Lys Glu Asp Ser
145                 150                 155                 160 cac tgt gcc tgg acc ata gtc aga gtg gaa atc cta agg aac ttt tac     528
His Cys Ala Trp Thr Ile Val Arg Val Glu Ile Leu Arg Asn Phe Tyr
                165                 170                 175
```

```
gtc att aac aga ctt aca ggt tac ctc cga aac tga                    564
Val Ile Asn Arg Leu Thr Gly Tyr Leu Arg Asn
        180                     185

<210> SEQ ID NO 58
<211> LENGTH: 187
<212> TYPE: PRT
<213> ORGANISM: Homo sapiens

<400> SEQUENCE: 58

Met Thr Asn Lys Cys Leu Leu Gln Ile Ala Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Cys Gln Cys Gln Lys Leu Leu Trp Gln Leu Asn Gly Arg
        35                  40                  45

Leu Glu Tyr Cys Leu Lys Asp Arg Arg Asn Phe Asp Ile Pro Glu Glu
    50                  55                  60

Ile Lys Gln Leu Gln Gln Phe Gln Lys Glu Asp Ala Ala Val Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Arg Asn His Leu Lys Thr Val Leu Glu Glu Lys Leu Glu
        115                 120                 125

Lys Glu Asp Phe Thr Arg Gly Lys Arg Met Ser Ser Leu His Leu Lys
    130                 135                 140

Arg Tyr Tyr Gly Arg Ile Leu His Tyr Leu Lys Ala Lys Glu Asp Ser
145                 150                 155                 160

His Cys Ala Trp Thr Ile Val Arg Val Glu Ile Leu Arg Asn Phe Tyr
                165                 170                 175

Val Ile Asn Arg Leu Thr Gly Tyr Leu Arg Asn
            180                 185

<210> SEQ ID NO 59
<211> LENGTH: 1056
<212> TYPE: DNA
<213> ORGANISM: Homo sapiens
<220> FEATURE:
<221> NAME/KEY: CDS
<222> LOCATION: (1)..(1056)
<223> OTHER INFORMATION: Human GlucON Beta

<400> SEQUENCE: 59 atg gga gtc aaa gtt ctg ttt gcc ctg atc tgc atc gct gtg gcc gag    48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc    96
Ala Lys Pro Thr Glu Asn Asn Glu Asp Phe Asn Ile Val Ala Val Ala
            20                  25                  30 agc aac ttc gcg acc acg gat ctc gat gct gac cgc ggg aag ttg ccc   144
Ser Asn Phe Ala Thr Thr Asp Leu Asp Ala Asp Arg Gly Lys Leu Pro
        35                  40                  45 ggc aag aag ctg ccg ctg gag gtg ctc aaa gag atg gaa gcc aat gcc   192
Gly Lys Lys Leu Pro Leu Glu Val Leu Lys Glu Met Glu Ala Asn Ala
    50                  55                  60 cgg aaa gct ggc tgc acc agg ggc tgt ctg atc tgc ctg tcc cac atc   240
Arg Lys Ala Gly Cys Thr Arg Gly Cys Leu Ile Cys Leu Ser His Ile
65                  70                  75                  80
```

```
                65                  70                  75                  80
aag tgc acg ccc aag atg aag aag ttc atc cca gga cgc tgc cac acc         288
Lys Cys Thr Pro Lys Met Lys Lys Phe Ile Pro Gly Arg Cys His Thr
                    85                  90                  95 tac gaa ggc gac aaa gag tcc gca cag ggc ggc ata ggc gag gcg atc         336
Tyr Glu Gly Asp Lys Glu Ser Ala Gln Gly Gly Ile Gly Glu Ala Ile
                100                 105                 110 gtc gac att cct gag att cct ggg ttc aag gac ttg gag ccc atg gag         384
Val Asp Ile Pro Glu Ile Pro Gly Phe Lys Asp Leu Glu Pro Met Glu
                115                 120                 125 cag ttc atc gca cag gtc gat ctg tgt gtg gac tgc aca act ggc tgc         432
Gln Phe Ile Ala Gln Val Asp Leu Cys Val Asp Cys Thr Thr Gly Cys
            130                 135                 140 ctc aaa ggg ctt gcc aac gtg cag tgt tct gac ctg ctc aag aag tgg         480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg         528
Leu Pro Gln Arg Cys Ala Thr Phe Ala Ser Lys Ile Gln Gly Gln Val
                165                 170                 175 gac aag atc aag ggg gcc ggt ggt gac atg agc tac aac ttg ctt gga         576
Asp Lys Ile Lys Gly Ala Gly Gly Asp Met Ser Tyr Asn Leu Leu Gly
                180                 185                 190 ttc cta caa aga agc agc aat tgt cag tgt cag aag ctc ctg tgg caa         624
Phe Leu Gln Arg Ser Ser Asn Cys Gln Cys Gln Lys Leu Leu Trp Gln
                195                 200                 205 ttg aat ggg agg ctt gaa tac tgc ctc aag gac agg agg aac ttt gac         672
Leu Asn Gly Arg Leu Glu Tyr Cys Leu Lys Asp Arg Arg Asn Phe Asp
        210                 215                 220 atc cct gag gag att aag cag ctg cag cag ttc cag aag gag gac gcc         720
Ile Pro Glu Glu Ile Lys Gln Leu Gln Gln Phe Gln Lys Glu Asp Ala
225                 230                 235                 240 gca gtg acc atc tat gag atg ctc cag aac atc ttt gct att ttc aga         768
Ala Val Thr Ile Tyr Glu Met Leu Gln Asn Ile Phe Ala Ile Phe Arg
                245                 250                 255 caa gat tca tcg agc act ggc tgg aat gag act att gtt gag aac ctc         816
Gln Asp Ser Ser Ser Thr Gly Trp Asn Glu Thr Ile Val Glu Asn Leu
                260                 265                 270 ctg gct aat gtc tat cat cag aga aac cat ctg aag aca gtc ctg gaa         864
Leu Ala Asn Val Tyr His Gln Arg Asn His Leu Lys Thr Val Leu Glu
                275                 280                 285 gaa aaa ctg gag aaa gaa gat ttc acc agg gga aaa cgc atg agc agt         912
Glu Lys Leu Glu Lys Glu Asp Phe Thr Arg Gly Lys Arg Met Ser Ser
        290                 295                 300 ctg cac ctg aaa aga tat tat ggg agg att ctg cat tac ctg aag gcc         960
Leu His Leu Lys Arg Tyr Tyr Gly Arg Ile Leu His Tyr Leu Lys Ala
305                 310                 315                 320 aag gag gac agt cac tgt gcc tgg acc ata gtc aga gtg gaa atc cta        1008
Lys Glu Asp Ser His Cys Ala Trp Thr Ile Val Arg Val Glu Ile Leu
                325                 330                 335 agg aac ttt tac gtc att aac aga ctt aca ggt tac ctc cga aac tga        1056
Arg Asn Phe Tyr Val Ile Asn Arg Leu Thr Gly Tyr Leu Arg Asn
                340                 345                 350

<210> SEQ ID NO 60
<211> LENGTH: 351
<212> TYPE: PRT
<213> ORGANISM: Homo sapiens

<400> SEQUENCE: 60

Met Gly Val Lys Val Leu Phe Ala Leu Ile Cys Ile Ala Val Ala Glu
```

```
1               5                   10                  15
Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
            35                  40                  45

Gly Lys Lys Leu Pro Leu Glu Val Leu Lys Glu Met Glu Ala Asn Ala
        50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
                100                 105                 110

Val Asp Ile Pro Glu Ile Pro Gly Phe Lys Asp Leu Glu Pro Met Glu
            115                 120                 125

Gln Phe Ile Ala Gln Val Asp Leu Cys Val Asp Cys Thr Thr Gly Cys
130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Asp Met Ser Tyr Asn Leu Leu Gly
                180                 185                 190

Phe Leu Gln Arg Ser Ser Asn Cys Gln Cys Gln Lys Leu Leu Trp Gln
                195                 200                 205

Leu Asn Gly Arg Leu Glu Tyr Cys Leu Lys Asp Arg Arg Asn Phe Asp
    210                 215                 220

Ile Pro Glu Glu Ile Lys Gln Leu Gln Gln Phe Gln Lys Glu Asp Ala
225                 230                 235                 240

Ala Val Thr Ile Tyr Glu Met Leu Gln Asn Ile Phe Ala Ile Phe Arg
                245                 250                 255

Gln Asp Ser Ser Ser Thr Gly Trp Asn Glu Thr Ile Val Glu Asn Leu
                260                 265                 270

Leu Ala Asn Val Tyr His Gln Arg Asn His Leu Lys Thr Val Leu Glu
            275                 280                 285

Glu Lys Leu Glu Lys Glu Asp Phe Thr Arg Gly Lys Arg Met Ser Ser
        290                 295                 300

Leu His Leu Lys Arg Tyr Tyr Gly Arg Ile Leu His Tyr Leu Lys Ala
305                 310                 315                 320

Lys Glu Asp Ser His Cys Ala Trp Thr Ile Val Arg Val Glu Ile Leu
                325                 330                 335

Arg Asn Phe Tyr Val Ile Asn Arg Leu Thr Gly Tyr Leu Arg Asn
                340                 345                 350
```

<210> SEQ ID NO 61
<211> LENGTH: 561
<212> TYPE: DNA
<213> ORGANISM: Bos taurus
<220> FEATURE:
<221> NAME/KEY: CDS
<222> LOCATION: (1)..(561)
<223> OTHER INFORMATION: Bovine Interferon Beta

<400> SEQUENCE: 61

```
atg acc tac cgg tgc ctc ctc cag atg gtt ctc ctg ctg tgt ttc tcc    48
Met Thr Tyr Arg Cys Leu Leu Gln Met Val Leu Leu Leu Cys Phe Ser
```

```
               1               5                   10                  15
acc aca gct ctt tcc agg agc tac agc ttg ctt cga ttc caa caa cgt      96
Thr Thr Ala Leu Ser Arg Ser Tyr Ser Leu Leu Arg Phe Gln Gln Arg
            20                  25                  30 cag agc ctt aaa gag tgt cag aaa ctc ctg ggg cag tta cct tca act     144
Gln Ser Leu Lys Glu Cys Gln Lys Leu Leu Gly Gln Leu Pro Ser Thr
        35                  40                  45 cct caa cat tgc ctc gag gcc agg atg gac ttc cag atg cct gag gag     192
Pro Gln His Cys Leu Glu Ala Arg Met Asp Phe Gln Met Pro Glu Glu
50                  55                  60 atg aag caa gaa cag cag ttc cag aag gaa gat gcc ata ttg gtc atg     240
Met Lys Gln Glu Gln Gln Phe Gln Lys Glu Asp Ala Ile Leu Val Met
65                  70                  75                  80 tat gag gtg ctc cag cac atc ttc ggc att ctc acc aga gac ttc tcc     288
Tyr Glu Val Leu Gln His Ile Phe Gly Ile Leu Thr Arg Asp Phe Ser
                85                  90                  95 agc act ggc tgg tct gag acc atc atc gag gac ctc ctt gag gaa ctc     336
Ser Thr Gly Trp Ser Glu Thr Ile Ile Glu Asp Leu Leu Glu Glu Leu
            100                 105                 110 tat ggg cag atg aat cgt ctg cag cca atc cag aag gaa ata atg cag     384
Tyr Gly Gln Met Asn Arg Leu Gln Pro Ile Gln Lys Glu Ile Met Gln
        115                 120                 125 aag caa aac acc aca gcg gga gac acg atc gtt ccc cac cta ggg aaa     432
Lys Gln Asn Thr Thr Ala Gly Asp Thr Ile Val Pro His Leu Gly Lys
130                 135                 140 tat tac ttc aac ctc atg cag tac ctg gag tcc aag gag tac gac agg     480
Tyr Tyr Phe Asn Leu Met Gln Tyr Leu Glu Ser Lys Glu Tyr Asp Arg
145                 150                 155                 160 tgt gcc tgg aca gtc gtg caa gtg caa ata ctc acg aac gtt tct ttc     528
Cys Ala Trp Thr Val Val Gln Val Gln Ile Leu Thr Asn Val Ser Phe
                165                 170                 175 ctg atg aga cta aca ggt tac gtc cgt gac tga                         561
Leu Met Arg Leu Thr Gly Tyr Val Arg Asp
            180                 185
```

<210> SEQ ID NO 62
<211> LENGTH: 186
<212> TYPE: PRT
<213> ORGANISM: Bos taurus

<400> SEQUENCE: 62

```
Met Thr Tyr Arg Cys Leu Leu Gln Met Val Leu Leu Cys Phe Ser
1               5                   10                  15

Thr Thr Ala Leu Ser Arg Ser Tyr Ser Leu Leu Arg Phe Gln Gln Arg
            20                  25                  30

Gln Ser Leu Lys Glu Cys Gln Lys Leu Leu Gly Gln Leu Pro Ser Thr
        35                  40                  45

Pro Gln His Cys Leu Glu Ala Arg Met Asp Phe Gln Met Pro Glu Glu
50                  55                  60

Met Lys Gln Glu Gln Gln Phe Gln Lys Glu Asp Ala Ile Leu Val Met
65                  70                  75                  80

Tyr Glu Val Leu Gln His Ile Phe Gly Ile Leu Thr Arg Asp Phe Ser
                85                  90                  95

Ser Thr Gly Trp Ser Glu Thr Ile Ile Glu Asp Leu Leu Glu Glu Leu
            100                 105                 110

Tyr Gly Gln Met Asn Arg Leu Gln Pro Ile Gln Lys Glu Ile Met Gln
        115                 120                 125

Lys Gln Asn Thr Thr Ala Gly Asp Thr Ile Val Pro His Leu Gly Lys
```

```
                    130                 135                 140
Tyr Tyr Phe Asn Leu Met Gln Tyr Leu Glu Ser Lys Glu Tyr Asp Arg
145                 150                 155                 160

Cys Ala Trp Thr Val Val Gln Val Gln Ile Leu Thr Asn Val Ser Phe
                165                 170                 175

Leu Met Arg Leu Thr Gly Tyr Val Arg Asp
            180                 185

<210> SEQ ID NO 63
<211> LENGTH: 1053
<212> TYPE: DNA
<213> ORGANISM: Bos taurus
<220> FEATURE:
<221> NAME/KEY: CDS
<222> LOCATION: (1)..(1053)
<223> OTHER INFORMATION: GlucON Beta Bovine

<400> SEQUENCE: 63
```

| | | | | | | | | | | | | | | | | |
|---|---|---|---|---|---|---|---|---|---|---|---|---|---|---|---|---|
| atg | gga | gtc | aaa | gtt | ctg | ttt | gcc | ctg | atc | tgc | atc | gct | gtg | gcc | gag | 48 |
| Met | Gly | Val | Lys | Val | Leu | Phe | Ala | Leu | Ile | Cys | Ile | Ala | Val | Ala | Glu | |
| 1 | | | | 5 | | | | | 10 | | | | | 15 | | |
| gcc | aag | ccc | acc | gag | aac | aac | gaa | gac | ttc | aac | atc | gtg | gcc | gtg | gcc | 96 |
| Ala | Lys | Pro | Thr | Glu | Asn | Asn | Glu | Asp | Phe | Asn | Ile | Val | Ala | Val | Ala | |
| | | | 20 | | | | | 25 | | | | | 30 | | | |
| agc | aac | ttc | gcg | acc | acg | gat | ctc | gat | gct | gac | cgc | ggg | aag | ttg | ccc | 144 |
| Ser | Asn | Phe | Ala | Thr | Thr | Asp | Leu | Asp | Ala | Asp | Arg | Gly | Lys | Leu | Pro | |
| | | 35 | | | | | 40 | | | | | 45 | | | | |
| ggc | aag | aag | ctg | ccg | ctg | gag | gtg | ctc | aaa | gag | atg | gaa | gcc | aat | gcc | 192 |
| Gly | Lys | Lys | Leu | Pro | Leu | Glu | Val | Leu | Lys | Glu | Met | Glu | Ala | Asn | Ala | |
| 50 | | | | | 55 | | | | | 60 | | | | | | |
| cgg | aaa | gct | ggc | tgc | acc | agg | ggc | tgt | ctg | atc | tgc | ctg | tcc | cac | atc | 240 |
| Arg | Lys | Ala | Gly | Cys | Thr | Arg | Gly | Cys | Leu | Ile | Cys | Leu | Ser | His | Ile | |
| 65 | | | | 70 | | | | | 75 | | | | | 80 | | |
| aag | tgc | acg | ccc | aag | atg | aag | aag | ttc | atc | cca | gga | cgc | tgc | cac | acc | 288 |
| Lys | Cys | Thr | Pro | Lys | Met | Lys | Lys | Phe | Ile | Pro | Gly | Arg | Cys | His | Thr | |
| | | | | 85 | | | | | 90 | | | | | 95 | | |
| tac | gaa | ggc | gac | aaa | gag | tcc | gca | cag | ggc | ggc | ata | ggc | gag | gcg | atc | 336 |
| Tyr | Glu | Gly | Asp | Lys | Glu | Ser | Ala | Gln | Gly | Gly | Ile | Gly | Glu | Ala | Ile | |
| | | | 100 | | | | | 105 | | | | | 110 | | | |
| gtc | gac | att | cct | gag | att | cct | ggg | ttc | aag | gac | ttg | gag | ccc | atg | gag | 384 |
| Val | Asp | Ile | Pro | Glu | Ile | Pro | Gly | Phe | Lys | Asp | Leu | Glu | Pro | Met | Glu | |
| | | 115 | | | | | 120 | | | | | 125 | | | | |
| cag | ttc | atc | gca | cag | gtc | gat | ctg | tgt | gtg | gac | tgc | aca | act | ggc | tgc | 432 |
| Gln | Phe | Ile | Ala | Gln | Val | Asp | Leu | Cys | Val | Asp | Cys | Thr | Thr | Gly | Cys | |
| 130 | | | | | 135 | | | | | 140 | | | | | | |
| ctc | aaa | ggg | ctt | gcc | aac | gtg | cag | tgt | tct | gac | ctg | ctc | aag | aag | tgg | 480 |
| Leu | Lys | Gly | Leu | Ala | Asn | Val | Gln | Cys | Ser | Asp | Leu | Leu | Lys | Lys | Trp | |
| 145 | | | | 150 | | | | | 155 | | | | | 160 | | |
| ctg | ccg | caa | cgc | tgt | gcg | acc | ttt | gcc | agc | aag | atc | cag | ggc | cag | gtg | 528 |
| Leu | Pro | Gln | Arg | Cys | Ala | Thr | Phe | Ala | Ser | Lys | Ile | Gln | Gly | Gln | Val | |
| | | | | 165 | | | | | 170 | | | | | 175 | | |
| gac | aag | atc | aag | ggg | gcc | ggt | ggt | gac | agg | agc | tac | agc | ttg | ctt | cga | 576 |
| Asp | Lys | Ile | Lys | Gly | Ala | Gly | Gly | Asp | Arg | Ser | Tyr | Ser | Leu | Leu | Arg | |
| | | | 180 | | | | | 185 | | | | | 190 | | | |
| ttc | caa | caa | cgt | cag | agc | ctt | aaa | gag | tgt | cag | aaa | ctc | ctg | ggg | cag | 624 |
| Phe | Gln | Gln | Arg | Gln | Ser | Leu | Lys | Glu | Cys | Gln | Lys | Leu | Leu | Gly | Gln | |
| | | 195 | | | | | 200 | | | | | 205 | | | | |
| tta | cct | tca | act | cct | caa | cat | tgc | ctc | gag | gcc | agg | atg | gac | ttc | cag | 672 |
| Leu | Pro | Ser | Thr | Pro | Gln | His | Cys | Leu | Glu | Ala | Arg | Met | Asp | Phe | Gln | |
| 210 | | | | | 215 | | | | | 220 | | | | | | |

```
atg cct gag gag atg aag caa gaa cag cag ttc cag aag gaa gat gcc      720
Met Pro Glu Glu Met Lys Gln Glu Gln Gln Phe Gln Lys Glu Asp Ala
225                 230                 235                 240 ata ttg gtc atg tat gag gtg ctc cag cac atc ttc ggc att ctc acc      768
Ile Leu Val Met Tyr Glu Val Leu Gln His Ile Phe Gly Ile Leu Thr
                245                 250                 255 aga gac ttc tcc agc act ggc tgg tct gag acc atc atc gag gac ctc      816
Arg Asp Phe Ser Ser Thr Gly Trp Ser Glu Thr Ile Ile Glu Asp Leu
            260                 265                 270 ctt gag gaa ctc tat ggg cag atg aat cgt ctg cag cca atc cag aag      864
Leu Glu Glu Leu Tyr Gly Gln Met Asn Arg Leu Gln Pro Ile Gln Lys
        275                 280                 285 gaa ata atg cag aag caa aac acc aca gcg gga gac acg atc gtt ccc      912
Glu Ile Met Gln Lys Gln Asn Thr Thr Ala Gly Asp Thr Ile Val Pro
    290                 295                 300 cac cta ggg aaa tat tac ttc aac ctc atg cag tac ctg gag tcc aag      960
His Leu Gly Lys Tyr Tyr Phe Asn Leu Met Gln Tyr Leu Glu Ser Lys
305                 310                 315                 320 gag tac gac agg tgt gcc tgg aca gtc gtg caa gtg caa ata ctc acg     1008
Glu Tyr Asp Arg Cys Ala Trp Thr Val Val Gln Val Gln Ile Leu Thr
                325                 330                 335 aac gtt tct ttc ctg atg aga cta aca ggt tac gtc cgt gac tga         1053
Asn Val Ser Phe Leu Met Arg Leu Thr Gly Tyr Val Arg Asp
            340                 345                 350

<210> SEQ ID NO 64
<211> LENGTH: 350
<212> TYPE: PRT
<213> ORGANISM: Bos taurus

<400> SEQUENCE: 64

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Asp Arg Ser Tyr Ser Leu Leu Arg
            180                 185                 190

Phe Gln Gln Arg Gln Ser Leu Lys Glu Cys Gln Lys Leu Leu Gly Gln
        195                 200                 205
```

```
Leu Pro Ser Thr Pro Gln His Cys Leu Glu Ala Arg Met Asp Phe Gln
    210                 215                 220

Met Pro Glu Glu Met Lys Gln Glu Gln Gln Phe Gln Lys Glu Asp Ala
225                 230                 235                 240

Ile Leu Val Met Tyr Glu Val Leu Gln His Ile Phe Gly Ile Leu Thr
                245                 250                 255

Arg Asp Phe Ser Ser Thr Gly Trp Ser Glu Thr Ile Ile Glu Asp Leu
                260                 265                 270

Leu Glu Glu Leu Tyr Gly Gln Met Asn Arg Leu Gln Pro Ile Gln Lys
            275                 280                 285

Glu Ile Met Gln Lys Gln Asn Thr Thr Ala Gly Asp Thr Ile Val Pro
290                 295                 300

His Leu Gly Lys Tyr Tyr Phe Asn Leu Met Gln Tyr Leu Glu Ser Lys
305                 310                 315                 320

Glu Tyr Asp Arg Cys Ala Trp Thr Val Val Gln Val Gln Ile Leu Thr
                325                 330                 335

Asn Val Ser Phe Leu Met Arg Leu Thr Gly Tyr Val Arg Asp
                340                 345                 350

<210> SEQ ID NO 65
<211> LENGTH: 561
<212> TYPE: DNA
<213> ORGANISM: Sus scrofa
<220> FEATURE:
<221> NAME/KEY: CDS
<222> LOCATION: (1)..(561)
<223> OTHER INFORMATION: Porcine Interferon Beta

<400> SEQUENCE: 65 atg gct aac aag tgc atc ctc caa atc gct ctc ctg atg tgt ttc tcc    48
Met Ala Asn Lys Cys Ile Leu Gln Ile Ala Leu Leu Met Cys Phe Ser
1               5                  10                  15 acc aca gct ctt tcc atg agc tat gat gtg ctt cga tac caa caa agg    96
Thr Thr Ala Leu Ser Met Ser Tyr Asp Val Leu Arg Tyr Gln Gln Arg
            20                  25                  30 agc agc aat ttg gca tgt cag aag ctc ctg gga cag ttg cct ggg act   144
Ser Ser Asn Leu Ala Cys Gln Lys Leu Leu Gly Gln Leu Pro Gly Thr
        35                  40                  45 cct caa tat tgc ctc gaa gat agg atg aac ttt gag gtc cct gag gag   192
Pro Gln Tyr Cys Leu Glu Asp Arg Met Asn Phe Glu Val Pro Glu Glu
    50                  55                  60 att atg caa cca cca caa ttc cag aag gaa gat gca gta ttg att atc   240
Ile Met Gln Pro Pro Gln Phe Gln Lys Glu Asp Ala Val Leu Ile Ile
65                  70                  75                  80 cac gag atg ctc cag cag atc ttc ggc att ctc aga aga aat ttc tct   288
His Glu Met Leu Gln Gln Ile Phe Gly Ile Leu Arg Arg Asn Phe Ser
                85                  90                  95 agc act ggc tgg aat gaa acc gtc att aag act atc ctt gtg gaa ctt   336
Ser Thr Gly Trp Asn Glu Thr Val Ile Lys Thr Ile Leu Val Glu Leu
            100                 105                 110 gat ggg cag atg gat gac ctg gag aca atc ctg gag gaa atc atg gag   384
Asp Gly Gln Met Asp Asp Leu Glu Thr Ile Leu Glu Glu Ile Met Glu
        115                 120                 125 gag gaa aat ttc ccc agg gga gac atg acc att ctt cac ctg aag aaa   432
Glu Glu Asn Phe Pro Arg Gly Asp Met Thr Ile Leu His Leu Lys Lys
    130                 135                 140 tat tac ttg agc att ctg cag tac ctg aag tcc aag gag tac aga agc   480
Tyr Tyr Leu Ser Ile Leu Gln Tyr Leu Lys Ser Lys Glu Tyr Arg Ser
145                 150                 155                 160
```

```
tgt gcc tgg aca gtc gtc caa gtg gaa atc ctc agg aac ttt tct ttc    528
Cys Ala Trp Thr Val Val Gln Val Glu Ile Leu Arg Asn Phe Ser Phe
            165                 170                 175 ctt aac aga ctt aca gat tac ctc cgg aac tga                        561
Leu Asn Arg Leu Thr Asp Tyr Leu Arg Asn
        180                 185
```

<210> SEQ ID NO 66
<211> LENGTH: 186
<212> TYPE: PRT
<213> ORGANISM: Sus scrofa

<400> SEQUENCE: 66

Met Ala Asn Lys Cys Ile Leu Gln Ile Ala Leu Leu Met Cys Phe Ser
1               5                   10                  15

Thr Thr Ala Leu Ser Met Ser Tyr Asp Val Leu Arg Tyr Gln Gln Arg
            20                  25                  30

Ser Ser Asn Leu Ala Cys Gln Lys Leu Leu Gly Gln Leu Pro Gly Thr
        35                  40                  45

Pro Gln Tyr Cys Leu Glu Asp Arg Met Asn Phe Glu Val Pro Glu Glu
    50                  55                  60

Ile Met Gln Pro Pro Gln Phe Gln Lys Glu Asp Ala Val Leu Ile Ile
65                  70                  75                  80

His Glu Met Leu Gln Gln Ile Phe Gly Ile Leu Arg Arg Asn Phe Ser
                85                  90                  95

Ser Thr Gly Trp Asn Glu Thr Val Ile Lys Thr Ile Leu Val Glu Leu
            100                 105                 110

Asp Gly Gln Met Asp Asp Leu Glu Thr Ile Leu Glu Glu Ile Met Glu
        115                 120                 125

Glu Glu Asn Phe Pro Arg Gly Asp Met Thr Ile Leu His Leu Lys Lys
    130                 135                 140

Tyr Tyr Leu Ser Ile Leu Gln Tyr Leu Lys Ser Lys Glu Tyr Arg Ser
145                 150                 155                 160

Cys Ala Trp Thr Val Val Gln Val Glu Ile Leu Arg Asn Phe Ser Phe
                165                 170                 175

Leu Asn Arg Leu Thr Asp Tyr Leu Arg Asn
            180                 185

<210> SEQ ID NO 67
<211> LENGTH: 1059
<212> TYPE: DNA
<213> ORGANISM: Sus scrofa
<220> FEATURE:
<221> NAME/KEY: CDS
<222> LOCATION: (1)..(1059)
<223> OTHER INFORMATION: GLucON Beta porcine

<400> SEQUENCE: 67

```
atg gga gtc aaa gtt ctg ttt gcc ctg atc tgc atc gct gtg gcc gag    48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc    96
Ala Lys Pro Thr Glu Asn Asn Glu Asp Phe Asn Ile Val Ala Val Ala
            20                  25                  30 agc aac ttc gcg acc acg gat ctc gat gct gac cgc ggg aag ttg ccc    144
Ser Asn Phe Ala Thr Thr Asp Leu Asp Ala Asp Arg Gly Lys Leu Pro
        35                  40                  45 ggc aag aag ctg ccg ctg gag gtg ctc aaa gag atg gaa gcc aat gcc    192
Gly Lys Lys Leu Pro Leu Glu Val Leu Lys Glu Met Glu Ala Asn Ala
    50                  55                  60
```

```
cgg aaa gct ggc tgc acc agg ggc tgt ctg atc tgc ctg tcc cac atc    240
Arg Lys Ala Gly Cys Thr Arg Gly Cys Leu Ile Cys Leu Ser His Ile
 65                  70                  75                  80 aag tgc acg ccc aag atg aag aag ttc atc cca gga cgc tgc cac acc    288
Lys Cys Thr Pro Lys Met Lys Lys Phe Ile Pro Gly Arg Cys His Thr
                 85                  90                  95 tac gaa ggc gac aaa gag tcc gca cag ggc ggc ata ggc gag gcg atc    336
Tyr Glu Gly Asp Lys Glu Ser Ala Gln Gly Gly Ile Gly Glu Ala Ile
            100                 105                 110 gtc gac att cct gag att cct ggg ttc aag gac ttg gag ccc atg gag    384
Val Asp Ile Pro Glu Ile Pro Gly Phe Lys Asp Leu Glu Pro Met Glu
        115                 120                 125 cag ttc atc gca cag gtc gat ctg tgt gtg gac tgc aca act ggc tgc    432
Gln Phe Ile Ala Gln Val Asp Leu Cys Val Asp Cys Thr Thr Gly Cys
    130                 135                 140 ctc aaa ggg ctt gcc aac gtg cag tgt tct gac ctc ctc aag aag tgg    480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg    528
Leu Pro Gln Arg Cys Ala Thr Phe Ala Ser Lys Ile Gln Gly Gln Val
                165                 170                 175 gac aag atc aag ggg gcc ggt ggt gac ggg ccc atg agc tat gat gtg    576
Asp Lys Ile Lys Gly Ala Gly Gly Asp Gly Pro Met Ser Tyr Asp Val
            180                 185                 190 ctt cga tac caa caa agg agc agc aat ttg gca tgt cag aag ctc ctg    624
Leu Arg Tyr Gln Gln Arg Ser Ser Asn Leu Ala Cys Gln Lys Leu Leu
        195                 200                 205 gga cag ttg cct ggg act cct caa tat tgc ctc gaa gat agg atg aac    672
Gly Gln Leu Pro Gly Thr Pro Gln Tyr Cys Leu Glu Asp Arg Met Asn
    210                 215                 220 ttt gag gtc cct gag gag att atg caa cca cca caa ttc cag aag gaa    720
Phe Glu Val Pro Glu Glu Ile Met Gln Pro Pro Gln Phe Gln Lys Glu
225                 230                 235                 240 gat gca gta ttg att atc cac gag atg ctc cag cag atc ttc ggc att    768
Asp Ala Val Leu Ile Ile His Glu Met Leu Gln Gln Ile Phe Gly Ile
                245                 250                 255 ctc aga aga aat ttc tct agc act ggc tgg aat gaa acc gtc att aag    816
Leu Arg Arg Asn Phe Ser Ser Thr Gly Trp Asn Glu Thr Val Ile Lys
            260                 265                 270 act atc ctt gtg gaa ctt gat ggg cag atg gat gac ctg gag aca atc    864
Thr Ile Leu Val Glu Leu Asp Gly Gln Met Asp Asp Leu Glu Thr Ile
        275                 280                 285 ctg gag gaa atc atg gag gag gaa aat ttc ccc agg gga gac atg acc    912
Leu Glu Glu Ile Met Glu Glu Glu Asn Phe Pro Arg Gly Asp Met Thr
    290                 295                 300 att ctt cac ctg aag aaa tat tac ttg agc att ctg cag tac ctg aag    960
Ile Leu His Leu Lys Lys Tyr Tyr Leu Ser Ile Leu Gln Tyr Leu Lys
305                 310                 315                 320 tcc aag gag tac aga agc tgt gcc tgg aca gtc gtc caa gtg gaa atc   1008
Ser Lys Glu Tyr Arg Ser Cys Ala Trp Thr Val Val Gln Val Glu Ile
                325                 330                 335 ctc agg aac ttt tct ttc ctt aac aga ctt aca gat tac ctc cgg aac   1056
Leu Arg Asn Phe Ser Phe Leu Asn Arg Leu Thr Asp Tyr Leu Arg Asn
            340                 345                 350 tga                                                                1059

<210> SEQ ID NO 68
<211> LENGTH: 352
<212> TYPE: PRT
```

<213> ORGANISM: Sus scrofa

<400> SEQUENCE: 68

```
Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp Gly Pro Met Ser Tyr Asp Val
            180                 185                 190

Leu Arg Tyr Gln Gln Arg Ser Ser Asn Leu Ala Cys Gln Lys Leu Leu
        195                 200                 205

Gly Gln Leu Pro Gly Thr Pro Gln Tyr Cys Leu Glu Asp Arg Met Asn
    210                 215                 220

Phe Glu Val Pro Glu Glu Ile Met Gln Pro Gln Phe Gln Lys Glu
225                 230                 235                 240

Asp Ala Val Leu Ile Ile His Glu Met Leu Gln Gln Ile Phe Gly Ile
                245                 250                 255

Leu Arg Arg Asn Phe Ser Ser Thr Gly Trp Asn Glu Thr Val Ile Lys
            260                 265                 270

Thr Ile Leu Val Glu Leu Asp Gly Gln Met Asp Leu Glu Thr Ile
        275                 280                 285

Leu Glu Glu Ile Met Glu Glu Asn Phe Pro Arg Gly Asp Met Thr
    290                 295                 300

Ile Leu His Leu Lys Lys Tyr Tyr Leu Ser Ile Leu Gln Tyr Leu Lys
305                 310                 315                 320

Ser Lys Glu Tyr Arg Ser Cys Ala Trp Thr Val Val Gln Val Glu Ile
                325                 330                 335

Leu Arg Asn Phe Ser Phe Leu Asn Arg Leu Thr Asp Tyr Leu Arg Asn
            340                 345                 350
```

<210> SEQ ID NO 69
<211> LENGTH: 1062
<212> TYPE: DNA
<213> ORGANISM: Sus scrofa
<220> FEATURE:
<221> NAME/KEY: CDS
<222> LOCATION: (1)..(1062)
<223> OTHER INFORMATION: SGLucON Beta porcine

<400> SEQUENCE: 69

```
atg gga gtc aaa gtt ctg ttt gcc ctg atc tgc atc gct gtg gcc gag      48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc      96
Ala Lys Pro Thr Glu Asn Asn Glu Asp Phe Asn Ile Val Ala Val Ala
                20                  25                  30 agc aac ttt gcg acc acg gat ctc gat gct gac cga ggg aag ttg ccc     144
Ser Asn Phe Ala Thr Thr Asp Leu Asp Ala Asp Arg Gly Lys Leu Pro
            35                  40                  45 ggc aag aag ctg ccg ctg gag gtg ctc aaa gag atg gaa gcc aat gcc     192
Gly Lys Lys Leu Pro Leu Glu Val Leu Lys Glu Met Glu Ala Asn Ala
        50                  55                  60 cgg aaa gct ggc tgc acc agg ggc tgt ctg atc tgc ctg tcc cac atc     240
Arg Lys Ala Gly Cys Thr Arg Gly Cys Leu Ile Cys Leu Ser His Ile
65                  70                  75                  80 aag tgc acg ccc aag atg aag aag tgg ctc cca gga cgc tgc cac acc     288
Lys Cys Thr Pro Lys Met Lys Lys Trp Leu Pro Gly Arg Cys His Thr
                85                  90                  95 tac gaa ggc gac aaa gag tcc gca cag ggc ggc ata ggc gag gcg atc     336
Tyr Glu Gly Asp Lys Glu Ser Ala Gln Gly Gly Ile Gly Glu Ala Ile
                100                 105                 110 gtc gat att cct gag att cct ggg ttc aag gac ttg gag cca atg gag     384
Val Asp Ile Pro Glu Ile Pro Gly Phe Lys Asp Leu Glu Pro Met Glu
            115                 120                 125 cag ttc atc gca cag gtc gat ctg tgt gtg gac tgc aca act ggc tgc     432
Gln Phe Ile Ala Gln Val Asp Leu Cys Val Asp Cys Thr Thr Gly Cys
        130                 135                 140 ctc aaa ggg ctt gcc aac gtg cag tgt tct gac ctg ctc aag aag tgg     480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg     528
Leu Pro Gln Arg Cys Ala Thr Phe Ala Ser Lys Ile Gln Gly Gln Val
                165                 170                 175 gac aag atc aag ggg gcc ggt ggt gac ggg ccc ggg atg agc tat gat     576
Asp Lys Ile Lys Gly Ala Gly Gly Asp Gly Pro Gly Met Ser Tyr Asp
                180                 185                 190 gtg ctt cga tac caa caa agg agc agc aat ttg gca tgt cag aag ctc     624
Val Leu Arg Tyr Gln Gln Arg Ser Ser Asn Leu Ala Cys Gln Lys Leu
            195                 200                 205 ctg gga cag ttg cct ggg act cct caa tat tgc ctc gaa gat agg atg     672
Leu Gly Gln Leu Pro Gly Thr Pro Gln Tyr Cys Leu Glu Asp Arg Met
        210                 215                 220 aac ttt gag gtc cct gag gag att atg caa cca cca caa ttc cag aag     720
Asn Phe Glu Val Pro Glu Glu Ile Met Gln Pro Pro Gln Phe Gln Lys
225                 230                 235                 240 gaa gat gca gta ttg att atc cac gag atg ctc cag cag atc ttc ggc     768
Glu Asp Ala Val Leu Ile Ile His Glu Met Leu Gln Gln Ile Phe Gly
                245                 250                 255 att ctc aga aga aat ttc tct agc act ggc tgg aat gaa acc gtc att     816
Ile Leu Arg Arg Asn Phe Ser Ser Thr Gly Trp Asn Glu Thr Val Ile
                260                 265                 270 aag act atc ctt gtg gaa ctt gat ggg cag atg gat gac ctg gag aca     864
Lys Thr Ile Leu Val Glu Leu Asp Gly Gln Met Asp Asp Leu Glu Thr
            275                 280                 285 atc ctg gag gaa atc atg gag gag gaa aat ttc ccc agg gga gac atg     912
Ile Leu Glu Glu Ile Met Glu Glu Glu Asn Phe Pro Arg Gly Asp Met
        290                 295                 300
```

```
acc att ctt cac ctg aag aaa tat tac ttg agc att ctg cag tac ctg    960
Thr Ile Leu His Leu Lys Lys Tyr Tyr Leu Ser Ile Leu Gln Tyr Leu
305                 310                 315                 320 aag tcc aag gag tac aga agc tgt gcc tgg aca gtc gtc caa gtg gaa    1008
Lys Ser Lys Glu Tyr Arg Ser Cys Ala Trp Thr Val Val Gln Val Glu
                325                 330                 335 atc ctc agg aac ttt tct ttc ctt aac aga ctt aca gat tac ctc cgg    1056
Ile Leu Arg Asn Phe Ser Phe Leu Asn Arg Leu Thr Asp Tyr Leu Arg
            340                 345                 350 aac tga                                                             1062
Asn

<210> SEQ ID NO 70
<211> LENGTH: 353
<212> TYPE: PRT
<213> ORGANISM: Sus scrofa

<400> SEQUENCE: 70

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Trp Leu Pro Gly Arg Cys His Thr
                85                  90                  95

Tyr Glu Gly Asp Lys Glu Ser Ala Gln Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp Gly Pro Gly Met Ser Tyr Asp
            180                 185                 190

Val Leu Arg Tyr Gln Gln Arg Ser Ser Asn Leu Ala Cys Gln Lys Leu
        195                 200                 205

Leu Gly Gln Leu Pro Gly Thr Pro Gln Tyr Cys Leu Glu Asp Arg Met
210                 215                 220

Asn Phe Glu Val Pro Glu Glu Ile Met Gln Pro Gln Phe Gln Lys
225                 230                 235                 240

Glu Asp Ala Val Leu Ile Ile His Glu Met Leu Gln Gln Ile Phe Gly
                245                 250                 255

Ile Leu Arg Arg Asn Phe Ser Ser Thr Gly Trp Asn Glu Thr Val Ile
            260                 265                 270

Lys Thr Ile Leu Val Glu Leu Asp Gly Gln Met Asp Asp Leu Glu Thr
        275                 280                 285

Ile Leu Glu Glu Ile Met Glu Glu Asn Phe Pro Arg Gly Asp Met
290                 295                 300
```

```
Thr Ile Leu His Leu Lys Lys Tyr Tyr Leu Ser Ile Leu Gln Tyr Leu
305                 310                 315                 320

Lys Ser Lys Glu Tyr Arg Ser Cys Ala Trp Thr Val Val Gln Val Glu
            325                 330                 335

Ile Leu Arg Asn Phe Ser Phe Leu Asn Arg Leu Thr Asp Tyr Leu Arg
        340                 345                 350

Asn

<210> SEQ ID NO 71
<211> LENGTH: 501
<212> TYPE: DNA
<213> ORGANISM: Homo sapiens
<220> FEATURE:
<221> NAME/KEY: CDS
<222> LOCATION: (1)..(501)
<223> OTHER INFORMATION: Human Interferon Gamma

<400> SEQUENCE: 71 atg aaa tat aca agt tat atc ttg gct ttt cag ctc tgc atc gtt ttg      48
Met Lys Tyr Thr Ser Tyr Ile Leu Ala Phe Gln Leu Cys Ile Val Leu
1               5                   10                  15 ggt tct ctt ggc tgt tac tgc cag gac cca tat gta aaa gaa gca gaa      96
Gly Ser Leu Gly Cys Tyr Cys Gln Asp Pro Tyr Val Lys Glu Ala Glu
            20                  25                  30 aac ctt aag aaa tat ttt aat gca ggt cat tca gat gta gcg gat aat     144
Asn Leu Lys Lys Tyr Phe Asn Ala Gly His Ser Asp Val Ala Asp Asn
        35                  40                  45 gga act ctt ttc tta ggc att ttg aag aat tgg aaa gag gag agt gac     192
Gly Thr Leu Phe Leu Gly Ile Leu Lys Asn Trp Lys Glu Glu Ser Asp
    50                  55                  60 aga aaa ata atg cag agc caa att gtc tcc ttt tac ttc aaa ctt ttt     240
Arg Lys Ile Met Gln Ser Gln Ile Val Ser Phe Tyr Phe Lys Leu Phe
65                  70                  75                  80 aaa aac ttt aaa gat gac cag agc atc caa aag agt gtg gag acc atc     288
Lys Asn Phe Lys Asp Asp Gln Ser Ile Gln Lys Ser Val Glu Thr Ile
                85                  90                  95 aag gaa gac atg aat gtc aag ttt ttc aat agc aac aaa aag aaa cga     336
Lys Glu Asp Met Asn Val Lys Phe Phe Asn Ser Asn Lys Lys Lys Arg
            100                 105                 110 gat gac ttc gaa aag ctg act aat tat tcg gta act gac ttg aat gtc     384
Asp Asp Phe Glu Lys Leu Thr Asn Tyr Ser Val Thr Asp Leu Asn Val
        115                 120                 125 caa cgc aaa gca ata cat gaa ctc atc caa gtg atg gct gaa ctg tcg     432
Gln Arg Lys Ala Ile His Glu Leu Ile Gln Val Met Ala Glu Leu Ser
    130                 135                 140 cca gca gct aaa aca ggg aag cga aaa agg agt cag atg ctg ttt cga     480
Pro Ala Ala Lys Thr Gly Lys Arg Lys Arg Ser Gln Met Leu Phe Arg
145                 150                 155                 160 ggt cga aga gca tcc cag taa                                          501
Gly Arg Arg Ala Ser Gln
                165

<210> SEQ ID NO 72
<211> LENGTH: 166
<212> TYPE: PRT
<213> ORGANISM: Homo sapiens

<400> SEQUENCE: 72

Met Lys Tyr Thr Ser Tyr Ile Leu Ala Phe Gln Leu Cys Ile Val Leu
1               5                   10                  15
```

```
Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Ser Asp
50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 73
<211> LENGTH: 987
<212> TYPE: DNA
<213> ORGANISM: Homo sapiens
<220> FEATURE:
<221> NAME/KEY: CDS
<222> LOCATION: (1)..(987)
<223> OTHER INFORMATION: Human GlucON Gamma

<400> SEQUENCE: 73 atg gga gtc aaa gtt ctg ttt gcc ctg atc tgc atc gct gtg gcc gag      48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc      96
Ala Lys Pro Thr Glu Asn Asn Glu Asp Phe Asn Ile Val Ala Val Ala
            20                  25                  30 agc aac ttc gcg acc acg gat ctc gat gct gac cgc ggg aag ttg ccc     144
Ser Asn Phe Ala Thr Thr Asp Leu Asp Ala Asp Arg Gly Lys Leu Pro
        35                  40                  45 ggc aag aag ctg ccg ctg gag gtg ctc aaa gag atg gaa gcc aat gcc     192
Gly Lys Lys Leu Pro Leu Glu Val Leu Lys Glu Met Glu Ala Asn Ala
    50                  55                  60 cgg aaa gct ggc tgc acc agg ggc tgt ctg atc tgc ctg tcc cac atc     240
Arg Lys Ala Gly Cys Thr Arg Gly Cys Leu Ile Cys Leu Ser His Ile
65                  70                  75                  80 aag tgc acg ccc aag atg aag aag ttc atc cca gga cgc tgc cac acc     288
Lys Cys Thr Pro Lys Met Lys Lys Phe Ile Pro Gly Arg Cys His Thr
                85                  90                  95 tac gaa ggc gac aaa gag tcc gca cag ggc ggc ata ggc gag gcg atc     336
Tyr Glu Gly Asp Lys Glu Ser Ala Gln Gly Gly Ile Gly Glu Ala Ile
            100                 105                 110 gtc gac att cct gag att cct ggg ttc aag gac ttg gag ccc atg gag     384
Val Asp Ile Pro Glu Ile Pro Gly Phe Lys Asp Leu Glu Pro Met Glu
        115                 120                 125 cag ttc atc gca cag gtc gat ctg tgt gtg gac tgc aca act ggc tgc     432
Gln Phe Ile Ala Gln Val Asp Leu Cys Val Asp Cys Thr Thr Gly Cys
    130                 135                 140 ctc aaa ggg ctt gcc aac gtg cag tgt tct gac ctg ctc aag aag tgg     480
```

```
                                       Leu Lys Gly Leu Ala Asn Val Gln Cys Ser Asp Leu Leu Lys Lys Trp
                                       145                 150                 155                 160 ctg ccg caa cgc tgt gcg acc ttt gcc agc aag atc cag ggc cag gtg                528
Leu Pro Gln Arg Cys Ala Thr Phe Ala Ser Lys Ile Gln Gly Gln Val
                165                 170                 175 gac aag atc aag ggg gcc ggt ggt gac cag gac cca tat gta aaa gaa                576
Asp Lys Ile Lys Gly Ala Gly Gly Asp Gln Asp Pro Tyr Val Lys Glu
        180                 185                 190 gca gaa aac ctt aag aaa tat ttt aat gca ggt cat tca gat gta gcg                624
Ala Glu Asn Leu Lys Lys Tyr Phe Asn Ala Gly His Ser Asp Val Ala
                195                 200                 205 gat aat gga act ctt ttc tta ggc att ttg aag aat tgg aaa gag gag                672
Asp Asn Gly Thr Leu Phe Leu Gly Ile Leu Lys Asn Trp Lys Glu Glu
        210                 215                 220 agt gac aga aaa ata atg cag agc caa att gtc tcc ttt tac ttc aaa                720
Ser Asp Arg Lys Ile Met Gln Ser Gln Ile Val Ser Phe Tyr Phe Lys
225                 230                 235                 240 ctt ttt aaa aac ttt aaa gat gac cag agc atc caa aag agt gtg gag                768
Leu Phe Lys Asn Phe Lys Asp Asp Gln Ser Ile Gln Lys Ser Val Glu
                245                 250                 255 acc atc aag gaa gac atg aat gtc aag ttt ttc aat agc aac aaa aag                816
Thr Ile Lys Glu Asp Met Asn Val Lys Phe Phe Asn Ser Asn Lys Lys
        260                 265                 270 aaa cga gat gac ttc gaa aag ctg act aat tat tcg gta act gac ttg                864
Lys Arg Asp Asp Phe Glu Lys Leu Thr Asn Tyr Ser Val Thr Asp Leu
                275                 280                 285 aat gtc caa cgc aaa gca ata cat gaa ctc atc caa gtg atg gct gaa                912
Asn Val Gln Arg Lys Ala Ile His Glu Leu Ile Gln Val Met Ala Glu
290                 295                 300 ctg tcg cca gca gct aaa aca ggg aag cga aaa agg agt cag atg ctg                960
Leu Ser Pro Ala Ala Lys Thr Gly Lys Arg Lys Arg Ser Gln Met Leu
305                 310                 315                 320 ttt cga ggt cga aga gca tcc cag taa                                            987
Phe Arg Gly Arg Arg Ala Ser Gln
                325

<210> SEQ ID NO 74
<211> LENGTH: 328
<212> TYPE: PRT
<213> ORGANISM: Homo sapiens

<400> SEQUENCE: 74

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
                20                  25                  30

Ser Asn Phe Ala Thr Thr Asp Leu Asp Ala Asp Arg Gly Lys Leu Pro
            35                  40                  45

Gly Lys Lys Leu Pro Leu Glu Val Leu Lys Glu Met Glu Ala Asn Ala
        50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
                100                 105                 110

Val Asp Ile Pro Glu Ile Pro Gly Phe Lys Asp Leu Glu Pro Met Glu
            115                 120                 125
```

```
Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp Gln Asp Pro Tyr Val Lys Glu
            180                 185                 190

Ala Glu Asn Leu Lys Lys Tyr Phe Asn Ala Gly His Ser Asp Val Ala
                195                 200                 205

Asp Asn Gly Thr Leu Phe Leu Gly Ile Leu Lys Asn Trp Lys Glu Glu
    210                 215                 220

Ser Asp Arg Lys Ile Met Gln Ser Gln Ile Val Ser Phe Tyr Phe Lys
225                 230                 235                 240

Leu Phe Lys Asn Phe Lys Asp Asp Gln Ser Ile Gln Lys Ser Val Glu
                245                 250                 255

Thr Ile Lys Glu Asp Met Asn Val Lys Phe Phe Asn Ser Asn Lys Lys
            260                 265                 270

Lys Arg Asp Asp Phe Glu Lys Leu Thr Asn Tyr Ser Val Thr Asp Leu
    275                 280                 285

Asn Val Gln Arg Lys Ala Ile His Glu Leu Ile Gln Val Met Ala Glu
    290                 295                 300

Leu Ser Pro Ala Ala Lys Thr Gly Lys Arg Lys Arg Ser Gln Met Leu
305                 310                 315                 320

Phe Arg Gly Arg Arg Ala Ser Gln
                325

<210> SEQ ID NO 75
<211> LENGTH: 501
<212> TYPE: DNA
<213> ORGANISM: Bos taurus
<220> FEATURE:
<221> NAME/KEY: CDS
<222> LOCATION: (1)..(501)
<223> OTHER INFORMATION: 75)Bovine Interferon Gamma

<400> SEQUENCE: 75 atg aaa tat aca agc tat ttc tta gct tta ctg ctc tgt ggg ctt ttg      48
Met Lys Tyr Thr Ser Tyr Phe Leu Ala Leu Leu Leu Cys Gly Leu Leu
1               5                   10                  15 ggt ttt tct ggt tct tat ggc cag ggc caa ttt ttt aga gaa ata gaa      96
Gly Phe Ser Gly Ser Tyr Gly Gln Gly Gln Phe Phe Arg Glu Ile Glu
                20                  25                  30 aac tta aag gag tat ttt aat gca agc agc cca gat gta gct aag ggt     144
Asn Leu Lys Glu Tyr Phe Asn Ala Ser Ser Pro Asp Val Ala Lys Gly
            35                  40                  45 ggg cct ctc ttc tca gaa att ttg aag aat tgg aaa gat gaa agt gac     192
Gly Pro Leu Phe Ser Glu Ile Leu Lys Asn Trp Lys Asp Glu Ser Asp
    50                  55                  60 aaa aaa att att cag agc caa att gtc tcc ttc tac ttc aaa ctc ttt     240
Lys Lys Ile Ile Gln Ser Gln Ile Val Ser Phe Tyr Phe Lys Leu Phe
65                  70                  75                  80 gaa aac ctc aaa gat aac cag gtc att caa agg agc atg gat atc atc     288
Glu Asn Leu Lys Asp Asn Gln Val Ile Gln Arg Ser Met Asp Ile Ile
                85                  90                  95 aag caa gac atg ttt cag aag ttc ttg aat ggc agc tct gag aaa ctg     336
Lys Gln Asp Met Phe Gln Lys Phe Leu Asn Gly Ser Ser Glu Lys Leu
            100                 105                 110
```

```
gag gac ttc aaa aag ctg att caa att ccg gtg gat gat ctg cag atc      384
Glu Asp Phe Lys Lys Leu Ile Gln Ile Pro Val Asp Asp Leu Gln Ile
        115                 120                 125 cag cgc aaa gcc ata aat gaa ctc atc aaa gtg atg aat gac ctg tca      432
Gln Arg Lys Ala Ile Asn Glu Leu Ile Lys Val Met Asn Asp Leu Ser
    130                 135                 140 cca aaa tct aac ctc aga aag cgg aag aga agt cag aat ctc ttt cga      480
Pro Lys Ser Asn Leu Arg Lys Arg Lys Arg Ser Gln Asn Leu Phe Arg
145                 150                 155                 160 ggc cgg aga gca tca acg taa                                          501
Gly Arg Arg Ala Ser Thr
                165

<210> SEQ ID NO 76
<211> LENGTH: 166
<212> TYPE: PRT
<213> ORGANISM: Bos taurus

<400> SEQUENCE: 76

Met Lys Tyr Thr Ser Tyr Phe Leu Ala Leu Leu Leu Cys Gly Leu Leu
1               5                   10                  15

Gly Phe Ser Gly Ser Tyr Gly Gln Gly Gln Phe Phe Arg Glu Ile Glu
            20                  25                  30

Asn Leu Lys Glu Tyr Phe Asn Ala Ser Ser Pro Asp Val Ala Lys Gly
        35                  40                  45

Gly Pro Leu Phe Ser Glu Ile Leu Lys Asn Trp Lys Asp Glu Ser Asp
    50                  55                  60

Lys Lys Ile Ile Gln Ser Gln Ile Val Ser Phe Tyr Phe Lys Leu Phe
65                  70                  75                  80

Glu Asn Leu Lys Asp Asn Gln Val Ile Gln Arg Ser Met Asp Ile Ile
                85                  90                  95

Lys Gln Asp Met Phe Gln Lys Phe Leu Asn Gly Ser Ser Glu Lys Leu
            100                 105                 110

Glu Asp Phe Lys Lys Leu Ile Gln Ile Pro Val Asp Asp Leu Gln Ile
        115                 120                 125

Gln Arg Lys Ala Ile Asn Glu Leu Ile Lys Val Met Asn Asp Leu Ser
    130                 135                 140

Pro Lys Ser Asn Leu Arg Lys Arg Lys Arg Ser Gln Asn Leu Phe Arg
145                 150                 155                 160

Gly Arg Arg Ala Ser Thr
                165

<210> SEQ ID NO 77
<211> LENGTH: 993
<212> TYPE: DNA
<213> ORGANISM: Bos taurus
<220> FEATURE:
<221> NAME/KEY: CDS
<222> LOCATION: (1)..(993)
<223> OTHER INFORMATION: Bovine GlucON Gamma

<400> SEQUENCE: 77 atg gga gtc aaa gtt ctg ttt gcc ctg atc tgc atc gct gtg gcc gag      48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc      96
Ala Lys Pro Thr Glu Asn Asn Glu Asp Phe Asn Ile Val Ala Val Ala
            20                  25                  30 agc aac ttc gcg acc acg gat ctc gat gct gac cgc ggg aag ttg ccc     144
Ser Asn Phe Ala Thr Thr Asp Leu Asp Ala Asp Arg Gly Lys Leu Pro
```

|  |  |  |  |  |  |  | 35 |  |  |  |  | 40 |  |  |  |  | 45 |  |  |  |  |
|---|---|---|---|---|---|---|---|---|---|---|---|---|---|---|---|---|---|---|---|---|---|

```
ggc aag aag ctg ccg ctg gag gtg ctc aaa gag atg gaa gcc aat gcc      192
Gly Lys Lys Leu Pro Leu Glu Val Leu Lys Glu Met Glu Ala Asn Ala
 50                  55                  60 cgg aaa gct ggc tgc acc agg ggc tgt ctg atc tgc ctg tcc cac atc      240
Arg Lys Ala Gly Cys Thr Arg Gly Cys Leu Ile Cys Leu Ser His Ile
 65                  70                  75                  80 aag tgc acg ccc aag atg aag aag ttc atc cca gga cgc tgc cac acc      288
Lys Cys Thr Pro Lys Met Lys Lys Phe Ile Pro Gly Arg Cys His Thr
                 85                  90                  95 tac gaa ggc gac aaa gag tcc gca cag ggc ggc ata ggc gag gcg atc      336
Tyr Glu Gly Asp Lys Glu Ser Ala Gln Gly Gly Ile Gly Glu Ala Ile
            100                 105                 110 gtt gac att cct gag att cct ggg ttc aag gac ttg gag ccc atg gag      384
Val Asp Ile Pro Glu Ile Pro Gly Phe Lys Asp Leu Glu Pro Met Glu
        115                 120                 125 cag ttc atc gca cag gtc gat ctg tgt gtg gac tgc aca act ggc tgc      432
Gln Phe Ile Ala Gln Val Asp Leu Cys Val Asp Cys Thr Thr Gly Cys
130                 135                 140 ctc aaa ggg ctt gcc aac gtg cag tgt tct gac ctg ctc aag aag tgg      480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg      528
Leu Pro Gln Arg Cys Ala Thr Phe Ala Ser Lys Ile Gln Gly Gln Val
                165                 170                 175 gac aag atc aag ggg gcc ggt ggt gac ggg ccc cag ggc caa ttt ttt      576
Asp Lys Ile Lys Gly Ala Gly Gly Asp Gly Pro Gln Gly Gln Phe Phe
            180                 185                 190 aga gaa ata gaa aac tta aag gag tat ttt aat gca agt agc cca gat      624
Arg Glu Ile Glu Asn Leu Lys Glu Tyr Phe Asn Ala Ser Ser Pro Asp
        195                 200                 205 gta gct aag ggt ggg cct ctc ttc tca gaa att ttg aag aat tgg aaa      672
Val Ala Lys Gly Gly Pro Leu Phe Ser Glu Ile Leu Lys Asn Trp Lys
210                 215                 220 gat gaa agt gac aaa aaa att att cag agc caa att gtc tcc ttc tac      720
Asp Glu Ser Asp Lys Lys Ile Ile Gln Ser Gln Ile Val Ser Phe Tyr
225                 230                 235                 240 ttc aaa ctc ttt gaa aac ctc aaa gat aac cag gtc att caa agg agc      768
Phe Lys Leu Phe Glu Asn Leu Lys Asp Asn Gln Val Ile Gln Arg Ser
                245                 250                 255 atg gat ata atc aag caa gac atg ttt cag aag ttc ttg aat ggc agc      816
Met Asp Ile Ile Lys Gln Asp Met Phe Gln Lys Phe Leu Asn Gly Ser
            260                 265                 270 tct gag aaa ctg gag gac ttc aaa aag ctg att caa att ccg gtg gat      864
Ser Glu Lys Leu Glu Asp Phe Lys Lys Leu Ile Gln Ile Pro Val Asp
        275                 280                 285 gat ctc cag atc cag cgc aaa gcc ata aat gaa ctc atc aaa gtg atg      912
Asp Leu Gln Ile Gln Arg Lys Ala Ile Asn Glu Leu Ile Lys Val Met
290                 295                 300 aat gac ctg tca cca aaa tct aac ctc aga aag cgg aag aga agt cag      960
Asn Asp Leu Ser Pro Lys Ser Asn Leu Arg Lys Arg Lys Arg Ser Gln
305                 310                 315                 320 aat ctc ttt cga ggc cgg aga gca tca acg taa                         993
Asn Leu Phe Arg Gly Arg Arg Ala Ser Thr
                325                 330

<210> SEQ ID NO 78
<211> LENGTH: 330
<212> TYPE: PRT
<213> ORGANISM: Bos taurus
```

<400> SEQUENCE: 78

| Met | Gly | Val | Lys | Val | Leu | Phe | Ala | Leu | Ile | Cys | Ile | Ala | Val | Ala | Glu |
| 1 | | | | 5 | | | | | 10 | | | | | 15 | |

| Ala | Lys | Pro | Thr | Glu | Asn | Asn | Glu | Asp | Phe | Asn | Ile | Val | Ala | Val | Ala |
| | | | 20 | | | | | 25 | | | | | 30 | | |

| Ser | Asn | Phe | Ala | Thr | Thr | Asp | Leu | Asp | Ala | Asp | Arg | Gly | Lys | Leu | Pro |
| | | 35 | | | | | 40 | | | | | 45 | | | |

| Gly | Lys | Lys | Leu | Pro | Leu | Glu | Val | Leu | Lys | Glu | Met | Glu | Ala | Asn | Ala |
| | 50 | | | | | 55 | | | | | 60 | | | | |

| Arg | Lys | Ala | Gly | Cys | Thr | Arg | Gly | Cys | Leu | Ile | Cys | Leu | Ser | His | Ile |
| 65 | | | | | 70 | | | | | 75 | | | | | 80 |

| Lys | Cys | Thr | Pro | Lys | Met | Lys | Lys | Phe | Ile | Pro | Gly | Arg | Cys | His | Thr |
| | | | | 85 | | | | | 90 | | | | | 95 | |

| Tyr | Glu | Gly | Asp | Lys | Glu | Ser | Ala | Gln | Gly | Ile | Gly | Glu | Ala | Ile |
| | | | 100 | | | | | 105 | | | | | 110 | |

| Val | Asp | Ile | Pro | Glu | Ile | Pro | Gly | Phe | Lys | Asp | Leu | Glu | Pro | Met | Glu |
| | | | 115 | | | | | 120 | | | | | 125 | | |

| Gln | Phe | Ile | Ala | Gln | Val | Asp | Leu | Cys | Val | Asp | Cys | Thr | Thr | Gly | Cys |
| | 130 | | | | | 135 | | | | | 140 | | | | |

| Leu | Lys | Gly | Leu | Ala | Asn | Val | Gln | Cys | Ser | Asp | Leu | Leu | Lys | Lys | Trp |
| 145 | | | | | 150 | | | | | 155 | | | | | 160 |

| Leu | Pro | Gln | Arg | Cys | Ala | Thr | Phe | Ala | Ser | Lys | Ile | Gln | Gly | Gln | Val |
| | | | | 165 | | | | | 170 | | | | | 175 | |

| Asp | Lys | Ile | Lys | Gly | Ala | Gly | Gly | Asp | Gly | Pro | Gln | Gly | Gln | Phe | Phe |
| | | | 180 | | | | | 185 | | | | | 190 | | |

| Arg | Glu | Ile | Glu | Asn | Leu | Lys | Glu | Tyr | Phe | Asn | Ala | Ser | Ser | Pro | Asp |
| | 195 | | | | | 200 | | | | | 205 | | | | |

| Val | Ala | Lys | Gly | Gly | Pro | Leu | Phe | Ser | Glu | Ile | Leu | Lys | Asn | Trp | Lys |
| 210 | | | | | 215 | | | | | 220 | | | | | |

| Asp | Glu | Ser | Asp | Lys | Lys | Ile | Ile | Gln | Ser | Gln | Ile | Val | Ser | Phe | Tyr |
| 225 | | | | | 230 | | | | | 235 | | | | | 240 |

| Phe | Lys | Leu | Phe | Glu | Asn | Leu | Lys | Asp | Asn | Gln | Val | Ile | Gln | Arg | Ser |
| | | | | 245 | | | | | 250 | | | | | 255 | |

| Met | Asp | Ile | Ile | Lys | Gln | Asp | Met | Phe | Gln | Lys | Phe | Leu | Asn | Gly | Ser |
| | | | 260 | | | | | 265 | | | | | 270 | | |

| Ser | Glu | Lys | Leu | Glu | Asp | Phe | Lys | Lys | Leu | Ile | Gln | Ile | Pro | Val | Asp |
| | 275 | | | | | 280 | | | | | 285 | | | | |

| Asp | Leu | Gln | Ile | Gln | Arg | Lys | Ala | Ile | Asn | Glu | Leu | Ile | Lys | Val | Met |
| | 290 | | | | | 295 | | | | | 300 | | | | |

| Asn | Asp | Leu | Ser | Pro | Lys | Ser | Asn | Leu | Arg | Lys | Arg | Lys | Arg | Ser | Gln |
| 305 | | | | | 310 | | | | | 315 | | | | | 320 |

| Asn | Leu | Phe | Arg | Gly | Arg | Arg | Ala | Ser | Thr |
| | | | | 325 | | | | | 330 |

<210> SEQ ID NO 79
<211> LENGTH: 501
<212> TYPE: DNA
<213> ORGANISM: Sus scrofa
<220> FEATURE:
<221> NAME/KEY: CDS
<222> LOCATION: (1)..(501)
<223> OTHER INFORMATION: Porcine Interferon Gamma

<400> SEQUENCE: 79 atg agt tat aca act tat ttc tta gct ttt cag ctt tgc gtg act ttg     48

```
Met Ser Tyr Thr Thr Tyr Phe Leu Ala Phe Gln Leu Cys Val Thr Leu
1               5                   10                  15 tgt ttt tct ggc tct tac tgc cag gcg ccc ttt ttt aaa gaa ata acg        96
Cys Phe Ser Gly Ser Tyr Cys Gln Ala Pro Phe Phe Lys Glu Ile Thr
                20                  25                  30 atc cta aag gac tat ttt aat gca agt acc tca gat gta cct aat ggt       144
Ile Leu Lys Asp Tyr Phe Asn Ala Ser Thr Ser Asp Val Pro Asn Gly
                35                  40                  45 gga cct ctt ttc tta gaa att ttg aag aat tgg aaa gag gag agt gac       192
Gly Pro Leu Phe Leu Glu Ile Leu Lys Asn Trp Lys Glu Glu Ser Asp
        50                  55                  60 aaa aaa ata att cag agc caa att gtc tcc ttc tac ttc aaa ttc ttt       240
Lys Lys Ile Ile Gln Ser Gln Ile Val Ser Phe Tyr Phe Lys Phe Phe
65                  70                  75                  80 gaa atc ttc aaa gat aac cag gcc att caa agg agc atg gat gtg atc       288
Glu Ile Phe Lys Asp Asn Gln Ala Ile Gln Arg Ser Met Asp Val Ile
                85                  90                  95 aag caa gac atg ttt cag agg ttc cta aat ggt agc tct ggg aaa ctg       336
Lys Gln Asp Met Phe Gln Arg Phe Leu Asn Gly Ser Ser Gly Lys Leu
                100                 105                 110 aat gac ttc gaa aag ctg att aaa att ccg gta gat aat ctg cag atc       384
Asn Asp Phe Glu Lys Leu Ile Lys Ile Pro Val Asp Asn Leu Gln Ile
                115                 120                 125 cag cgc aaa gcc atc agt gaa ctc atc aaa gtg atg aat gat ctg tca       432
Gln Arg Lys Ala Ile Ser Glu Leu Ile Lys Val Met Asn Asp Leu Ser
        130                 135                 140 cca aga tct aac cta aga aag cgg aag aga agt cag act atg ttc caa       480
Pro Arg Ser Asn Leu Arg Lys Arg Lys Arg Ser Gln Thr Met Phe Gln
145                 150                 155                 160 ggc cag aga gca tca aaa taa                                            501
Gly Gln Arg Ala Ser Lys
                165

<210> SEQ ID NO 80
<211> LENGTH: 166
<212> TYPE: PRT
<213> ORGANISM: Sus scrofa

<400> SEQUENCE: 80

Met Ser Tyr Thr Thr Tyr Phe Leu Ala Phe Gln Leu Cys Val Thr Leu
1               5                   10                  15

Cys Phe Ser Gly Ser Tyr Cys Gln Ala Pro Phe Phe Lys Glu Ile Thr
                20                  25                  30

Ile Leu Lys Asp Tyr Phe Asn Ala Ser Thr Ser Asp Val Pro Asn Gly
                35                  40                  45

Gly Pro Leu Phe Leu Glu Ile Leu Lys Asn Trp Lys Glu Glu Ser Asp
        50                  55                  60

Lys Lys Ile Ile Gln Ser Gln Ile Val Ser Phe Tyr Phe Lys Phe Phe
65                  70                  75                  80

Glu Ile Phe Lys Asp Asn Gln Ala Ile Gln Arg Ser Met Asp Val Ile
                85                  90                  95

Lys Gln Asp Met Phe Gln Arg Phe Leu Asn Gly Ser Ser Gly Lys Leu
                100                 105                 110

Asn Asp Phe Glu Lys Leu Ile Lys Ile Pro Val Asp Asn Leu Gln Ile
                115                 120                 125

Gln Arg Lys Ala Ile Ser Glu Leu Ile Lys Val Met Asn Asp Leu Ser
        130                 135                 140

Pro Arg Ser Asn Leu Arg Lys Arg Lys Arg Ser Gln Thr Met Phe Gln
```

145           150           155           160
Gly Gln Arg Ala Ser Lys
            165

<210> SEQ ID NO 81
<211> LENGTH: 987
<212> TYPE: DNA
<213> ORGANISM: Sus scrofa
<220> FEATURE:
<221> NAME/KEY: CDS
<222> LOCATION: (1)..(987)
<223> OTHER INFORMATION: Porcine GLucON Gamma

<400> SEQUENCE: 81

| | |
|---|---:|
| atg gga gtc aaa gtt ctg ttt gcc ctg atc tgc atc gct gtg gcc gag<br>Met Gly Val Lys Val Leu Phe Ala Leu Ile Cys Ile Ala Val Ala Glu<br>1               5                   10                  15 | 48 |
| gcc aag ccc acc gag aac aac gaa gac ttc aac atc gtg gcc gtg gcc<br>Ala Lys Pro Thr Glu Asn Asn Glu Asp Phe Asn Ile Val Ala Val Ala<br>            20                  25                  30 | 96 |
| agc aac ttc gcg acc acg gat ctc gat gct gac cgc ggg aag ttg ccc<br>Ser Asn Phe Ala Thr Thr Asp Leu Asp Ala Asp Arg Gly Lys Leu Pro<br>        35                  40                  45 | 144 |
| ggc aag aag ctg ccg ctg gag gtg ctc aaa gag atg gaa gcc aat gcc<br>Gly Lys Lys Leu Pro Leu Glu Val Leu Lys Glu Met Glu Ala Asn Ala<br>    50                  55                  60 | 192 |
| cgg aaa gct ggc tgc acc agg ggc tgt ctg atc tgc ctg tcc cac atc<br>Arg Lys Ala Gly Cys Thr Arg Gly Cys Leu Ile Cys Leu Ser His Ile<br>65                  70                  75                  80 | 240 |
| aag tgc acg ccc aag atg aag aag ttc atc cca gga cgc tgc cac acc<br>Lys Cys Thr Pro Lys Met Lys Lys Phe Ile Pro Gly Arg Cys His Thr<br>                85                  90                  95 | 288 |
| tac gaa ggc gac aaa gag tcc gca cag ggc ggc ata ggc gag gcg atc<br>Tyr Glu Gly Asp Lys Glu Ser Ala Gln Gly Gly Ile Gly Glu Ala Ile<br>            100                 105                 110 | 336 |
| gtc gac att cct gag att cct ggg ttc aag gac ttg gag ccc atg gag<br>Val Asp Ile Pro Glu Ile Pro Gly Phe Lys Asp Leu Glu Pro Met Glu<br>        115                 120                 125 | 384 |
| cag ttc atc gca cag gtc gat ctg tgt gtg gac tgc aca act ggc tgc<br>Gln Phe Ile Ala Gln Val Asp Leu Cys Val Asp Cys Thr Thr Gly Cys<br>    130                 135                 140 | 432 |
| ctc aaa ggg ctt gcc aac gtg cag tgt tct gac ctg ctc aag aag tgg<br>Leu Lys Gly Leu Ala Asn Val Gln Cys Ser Asp Leu Leu Lys Lys Trp<br>145                 150                 155                 160 | 480 |
| ctg ccg caa cgc tgt gcg acc ttt gcc agc aag atc cag ggc cag gtg<br>Leu Pro Gln Arg Cys Ala Thr Phe Ala Ser Lys Ile Gln Gly Gln Val<br>                165                 170                 175 | 528 |
| gac aag atc aag ggg gcc ggt ggt gac cag gcg ccc ttt ttt aaa gaa<br>Asp Lys Ile Lys Gly Ala Gly Gly Asp Gln Ala Pro Phe Phe Lys Glu<br>            180                 185                 190 | 576 |
| ata acg atc cta aag gac tat ttt aat gca agt acc tca gat gta cct<br>Ile Thr Ile Leu Lys Asp Tyr Phe Asn Ala Ser Thr Ser Asp Val Pro<br>        195                 200                 205 | 624 |
| aat ggt gga cct ctt ttc tta gaa att ttg aag aat tgg aaa gag gag<br>Asn Gly Gly Pro Leu Phe Leu Glu Ile Leu Lys Asn Trp Lys Glu Glu<br>    210                 215                 220 | 672 |
| agt gac aaa aaa ata att cag agc caa att gtc tcc ttc tac ttc aaa<br>Ser Asp Lys Lys Ile Ile Gln Ser Gln Ile Val Ser Phe Tyr Phe Lys<br>225                 230                 235                 240 | 720 |
| ttc ttt gaa atc ttc aaa gat aac cag gcc att caa agg agc atg gat<br>Phe Phe Glu Ile Phe Lys Asp Asn Gln Ala Ile Gln Arg Ser Met Asp | 768 |

|  |  |  |  |  |  |  |  |  |  |  |  |  |  |  |  |
|---|---|---|---|---|---|---|---|---|---|---|---|---|---|---|---|
|  |  | 245 |  |  |  |  | 250 |  |  |  |  | 255 |  |  |  |
| gtg | atc | aag | caa | gac | atg | ttt | cag | agg | ttc | cta | aat | ggt | agc | tct | ggg | 816 |
| Val | Ile | Lys | Gln | Asp | Met | Phe | Gln | Arg | Phe | Leu | Asn | Gly | Ser | Ser | Gly |
|  |  | 260 |  |  |  |  | 265 |  |  |  |  | 270 |  |  |  |
| aaa | ctg | aat | gac | ttc | gaa | aag | ctg | att | aaa | att | ccg | gta | gat | aat | ctg | 864 |
| Lys | Leu | Asn | Asp | Phe | Glu | Lys | Leu | Ile | Lys | Ile | Pro | Val | Asp | Asn | Leu |
|  |  | 275 |  |  |  |  | 280 |  |  |  |  | 285 |  |  |  |
| cag | atc | cag | cgc | aaa | gcc | atc | agt | gaa | ctc | atc | aaa | gtg | atg | aat | gat | 912 |
| Gln | Ile | Gln | Arg | Lys | Ala | Ile | Ser | Glu | Leu | Ile | Lys | Val | Met | Asn | Asp |
|  | 290 |  |  |  |  | 295 |  |  |  |  | 300 |  |  |  |  |
| ctg | tca | cca | aga | tct | aac | cta | aga | aag | cgg | aag | aga | agt | cag | act | atg | 960 |
| Leu | Ser | Pro | Arg | Ser | Asn | Leu | Arg | Lys | Arg | Lys | Arg | Ser | Gln | Thr | Met |
| 305 |  |  |  |  | 310 |  |  |  |  | 315 |  |  |  |  | 320 |
| ttc | caa | ggc | cag | aga | gca | tca | aaa | taa |  |  |  |  |  |  |  | 987 |
| Phe | Gln | Gly | Gln | Arg | Ala | Ser | Lys |  |  |  |  |  |  |  |  |
|  |  |  |  | 325 |  |  |  |  |  |  |  |  |  |  |  |

<210> SEQ ID NO 82
<211> LENGTH: 328
<212> TYPE: PRT
<213> ORGANISM: Sus scrofa

<400> SEQUENCE: 82

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
                20                  25                  30

Ser Asn Phe Ala Thr Thr Asp Leu Asp Ala Asp Arg Gly Lys Leu Pro
            35                  40                  45

Gly Lys Lys Leu Pro Leu Glu Val Leu Lys Glu Met Glu Ala Asn Ala
        50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
                100                 105                 110

Val Asp Ile Pro Glu Ile Pro Gly Phe Lys Asp Leu Glu Pro Met Glu
            115                 120                 125

Gln Phe Ile Ala Gln Val Asp Leu Cys Val Asp Cys Thr Thr Gly Cys
        130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp Gln Ala Pro Phe Phe Lys Glu
            180                 185                 190

Ile Thr Ile Leu Lys Asp Tyr Phe Asn Ala Ser Thr Ser Asp Val Pro
        195                 200                 205

Asn Gly Gly Pro Leu Phe Leu Glu Ile Leu Lys Asn Trp Lys Glu Glu
    210                 215                 220

Ser Asp Lys Lys Ile Ile Gln Ser Gln Ile Val Ser Phe Tyr Phe Lys
225                 230                 235                 240

Phe Phe Glu Ile Phe Lys Asp Asn Gln Ala Ile Gln Arg Ser Met Asp
                245                 250                 255

Val Ile Lys Gln Asp Met Phe Gln Arg Phe Leu Asn Gly Ser Ser Gly

```
                260                 265                 270
Lys Leu Asn Asp Phe Glu Lys Leu Ile Lys Ile Pro Val Asp Asn Leu
            275                 280                 285

Gln Ile Gln Arg Lys Ala Ile Ser Glu Leu Ile Lys Val Met Asn Asp
            290                 295                 300

Leu Ser Pro Arg Ser Asn Leu Arg Lys Arg Lys Arg Ser Gln Thr Met
305                 310                 315                 320

Phe Gln Gly Gln Arg Ala Ser Lys
                325

<210> SEQ ID NO 83
<211> LENGTH: 588
<212> TYPE: DNA
<213> ORGANISM: Bos taurus
<220> FEATURE:
<221> NAME/KEY: CDS
<222> LOCATION: (1)..(588)
<223> OTHER INFORMATION: Bovine Interferon Lambda IL29

<400> SEQUENCE: 83 atg gcc ccg ggc tgc acg ctg gtg ctg gtg ctg atg ctg acg acc gtg      48
Met Ala Pro Gly Cys Thr Leu Val Leu Val Leu Met Leu Thr Thr Val
1               5                   10                  15 gcg ctg agc agg aca gga gca gtt cct gtg ccc tct gcc ccc agg gcc      96
Ala Leu Ser Arg Thr Gly Ala Val Pro Val Pro Ser Ala Pro Arg Ala
                20                  25                  30 ctc cca cct gcc agg ggc tgc cac gtg gcc cag ttc aag tct ctg tcc     144
Leu Pro Pro Ala Arg Gly Cys His Val Ala Gln Phe Lys Ser Leu Ser
            35                  40                  45 cct caa gag ctg cag gcc ttc aag acg gcc agg gat gcc ttt gaa gac     192
Pro Gln Glu Leu Gln Ala Phe Lys Thr Ala Arg Asp Ala Phe Glu Asp
        50                  55                  60 tcg ttc ttg cca aag gac tgg gac tgc agc acc cac ctt ttc ccc agg     240
Ser Phe Leu Pro Lys Asp Trp Asp Cys Ser Thr His Leu Phe Pro Arg
65                  70                  75                  80 acc cgg gac ctg aag cac ctg cag gtg tgg gag cgc cct gtg gct ctg     288
Thr Arg Asp Leu Lys His Leu Gln Val Trp Glu Arg Pro Val Ala Leu
                85                  90                  95 gag gca gag ctg gcc ctg aca ctg acg gtc ctg gag gcc atg gct aac     336
Glu Ala Glu Leu Ala Leu Thr Leu Thr Val Leu Glu Ala Met Ala Asn
                100                 105                 110 tca tcc ctg ggc cac agc ctg gag cag ccc ctt ctc acg ctg cag aac     384
Ser Ser Leu Gly His Ser Leu Glu Gln Pro Leu Leu Thr Leu Gln Asn
            115                 120                 125 atc cac tcc aag ctc cag gcc tgt gtc cca gct cag ccc aca gca agc     432
Ile His Ser Lys Leu Gln Ala Cys Val Pro Ala Gln Pro Thr Ala Ser
        130                 135                 140 tcc agg ccc cgg ggc cgc ctc cac cac tgg ctg cac cgc ctc cag gag     480
Ser Arg Pro Arg Gly Arg Leu His His Trp Leu His Arg Leu Gln Glu
145                 150                 155                 160 gcc cgg aag gag tcc cag gac tgc ctc gaa gcc tct gtg atg ttc aac     528
Ala Arg Lys Glu Ser Gln Asp Cys Leu Glu Ala Ser Val Met Phe Asn
                165                 170                 175 ctc ctc cgc ctc ctc acc cgg gac ctg aaa tgt gtt gcc agc gga gac     576
Leu Leu Arg Leu Leu Thr Arg Asp Leu Lys Cys Val Ala Ser Gly Asp
                180                 185                 190 cag tgt gtc tga                                                     588
Gln Cys Val
        195
```

<210> SEQ ID NO 84
<211> LENGTH: 195
<212> TYPE: PRT
<213> ORGANISM: Bos taurus

<400> SEQUENCE: 84

```
Met Ala Pro Gly Cys Thr Leu Val Leu Val Leu Met Leu Thr Thr Val
1               5                   10                  15

Ala Leu Ser Arg Thr Gly Ala Val Pro Val Ser Ala Pro Arg Ala
            20                  25                  30

Leu Pro Pro Ala Arg Gly Cys His Val Ala Gln Phe Lys Ser Leu Ser
                35                  40                  45

Pro Gln Glu Leu Gln Ala Phe Lys Thr Ala Arg Asp Ala Phe Glu Asp
    50                  55                  60

Ser Phe Leu Pro Lys Asp Trp Asp Cys Ser Thr His Leu Phe Pro Arg
65                  70                  75                  80

Thr Arg Asp Leu Lys His Leu Gln Val Trp Glu Arg Pro Val Ala Leu
                85                  90                  95

Glu Ala Glu Leu Ala Leu Thr Leu Thr Val Leu Glu Ala Met Ala Asn
                100                 105                 110

Ser Ser Leu Gly His Ser Leu Glu Gln Pro Leu Leu Thr Leu Gln Asn
            115                 120                 125

Ile His Ser Lys Leu Gln Ala Cys Val Pro Ala Gln Pro Thr Ala Ser
130                 135                 140

Ser Arg Pro Arg Gly Arg Leu His His Trp Leu His Arg Leu Gln Glu
145                 150                 155                 160

Ala Arg Lys Glu Ser Gln Asp Cys Leu Glu Ala Ser Val Met Phe Asn
                165                 170                 175

Leu Leu Arg Leu Leu Thr Arg Asp Leu Lys Cys Val Ala Ser Gly Asp
            180                 185                 190

Gln Cys Val
        195
```

<210> SEQ ID NO 85
<211> LENGTH: 1092
<212> TYPE: DNA
<213> ORGANISM: Bos taurus
<220> FEATURE:
<221> NAME/KEY: CDS
<222> LOCATION: (1)..(1092)
<223> OTHER INFORMATION: Bovine GLucON Lambda

<400> SEQUENCE: 85

```
atg gga gtc aaa gtt ctg ttt gcc ctg atc tgc atc gct gtg gcc gag        48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc        96
Ala Lys Pro Thr Glu Asn Asn Glu Asp Phe Asn Ile Val Ala Val Ala
            20                  25                  30 agc aac ttc gcg acc acg gat ctc gat gct gac cgc ggg aag ttg ccc       144
Ser Asn Phe Ala Thr Thr Asp Leu Asp Ala Asp Arg Gly Lys Leu Pro
        35                  40                  45 ggc aag aag ctg ccg ctg gag gtg ctc aaa gag atg gaa gcc aat gcc       192
Gly Lys Lys Leu Pro Leu Glu Val Leu Lys Glu Met Glu Ala Asn Ala
50                  55                  60 cgg aaa gct ggc tgc acc agg ggc tgt ctg atc tgc ctg tcc cac atc       240
Arg Lys Ala Gly Cys Thr Arg Gly Cys Leu Ile Cys Leu Ser His Ile
65                  70                  75                  80 aag tgc acg ccc aag atg aag aag ttc atc cca gga cgc tgc cac acc       288
```

| | | | | | | | | | | | | |
|---|---|---|---|---|---|---|---|---|---|---|---|---|
|Lys|Cys|Thr|Pro|Lys|Met|Lys|Lys|Phe|Ile|Pro|Gly|Arg|Cys|His|Thr|
| | | | |85| | | |90| | | |95| | | |

```
tac gaa ggc gac aaa gag tcc gca cag ggc ggc ata ggc gag gcg atc      336
Tyr Glu Gly Asp Lys Glu Ser Ala Gln Gly Gly Ile Gly Glu Ala Ile
            100                 105                 110 gtt gac att cct gag att cct ggg ttc aag gac ttg gag ccc atg gag      384
Val Asp Ile Pro Glu Ile Pro Gly Phe Lys Asp Leu Glu Pro Met Glu
        115                 120                 125 cag ttc atc gca cag gtc gat ctg tgt gtg gac tgc aca act ggc tgc      432
Gln Phe Ile Ala Gln Val Asp Leu Cys Val Asp Cys Thr Thr Gly Cys
    130                 135                 140 ctc aaa ggg ctt gcc aac gtg cag tgt tct gac ctg ctc aag aag tgg      480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg      528
Leu Pro Gln Arg Cys Ala Thr Phe Ala Ser Lys Ile Gln Gly Gln Val
                165                 170                 175 gac aag atc aag ggg gcc ggt ggt gac ggg ccc agg aca gga gca gtt      576
Asp Lys Ile Lys Gly Ala Gly Gly Asp Gly Pro Arg Thr Gly Ala Val
            180                 185                 190 cct gtg ccc tct gcc ccc agg gca ctc cca cct gcc agg ggc tgc cac      624
Pro Val Pro Ser Ala Pro Arg Ala Leu Pro Pro Ala Arg Gly Cys His
        195                 200                 205 gtg gcc cag ttc aag tct ctg tcc cct caa gag ctg caa gcc ttc aag      672
Val Ala Gln Phe Lys Ser Leu Ser Pro Gln Glu Leu Gln Ala Phe Lys
    210                 215                 220 acg gcc agg gat gcc ttt gaa gac tcg ttc ttg ccg aag gac tgg gac      720
Thr Ala Arg Asp Ala Phe Glu Asp Ser Phe Leu Pro Lys Asp Trp Asp
225                 230                 235                 240 tgt agc acc cac ctt ttc ccc agg aca cga gac ctg aag cac ctg caa      768
Cys Ser Thr His Leu Phe Pro Arg Thr Arg Asp Leu Lys His Leu Gln
                245                 250                 255 gtg tgg gag cgc cct gtg gct ctg gag gca gag ctg gcc ctg aca ctg      816
Val Trp Glu Arg Pro Val Ala Leu Glu Ala Glu Leu Ala Leu Thr Leu
            260                 265                 270 acg gtc ctg gag gca atg gct aac tca tcc ctg ggc cac agc ctg gag      864
Thr Val Leu Glu Ala Met Ala Asn Ser Ser Leu Gly His Ser Leu Glu
        275                 280                 285 cag ccc ctt ctc acg ctg caa aac atc cac tcc aag ctc cag gcc tgt      912
Gln Pro Leu Leu Thr Leu Gln Asn Ile His Ser Lys Leu Gln Ala Cys
    290                 295                 300 gtc cca gct cag ccc aca gca agc tcc aga ccc cga ggc cgc ctc cac      960
Val Pro Ala Gln Pro Thr Ala Ser Ser Arg Pro Arg Gly Arg Leu His
305                 310                 315                 320 cac tgg ctg cac cgc ctc caa gag gcc cgg aag gag tcc cag gac tgc     1008
His Trp Leu His Arg Leu Gln Glu Ala Arg Lys Glu Ser Gln Asp Cys
                325                 330                 335 ctc gaa gcc tct gtg atg ttc aac ctc ctc cgc ctc ctc acc cga gac     1056
Leu Glu Ala Ser Val Met Phe Asn Leu Leu Arg Leu Leu Thr Arg Asp
            340                 345                 350 ctg aaa tgt gtt gcc agc gga gac cag tgt gtc tga                     1092
Leu Lys Cys Val Ala Ser Gly Asp Gln Cys Val
        355                 360

<210> SEQ ID NO 86
<211> LENGTH: 363
<212> TYPE: PRT
<213> ORGANISM: Bos taurus

<400> SEQUENCE: 86
```

```
Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
                100                 105                 110

Val Asp Ile Pro Glu Ile Pro Gly Phe Lys Asp Leu Glu Pro Met Glu
            115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp Gly Pro Arg Thr Gly Ala Val
                180                 185                 190

Pro Val Pro Ser Ala Pro Arg Ala Leu Pro Pro Ala Arg Gly Cys His
                195                 200                 205

Val Ala Gln Phe Lys Ser Leu Ser Pro Gln Glu Leu Gln Ala Phe Lys
    210                 215                 220

Thr Ala Arg Asp Ala Phe Glu Asp Ser Phe Leu Pro Lys Asp Trp Asp
225                 230                 235                 240

Cys Ser Thr His Leu Phe Pro Arg Thr Arg Asp Leu Lys His Leu Gln
                245                 250                 255

Val Trp Glu Arg Pro Val Ala Leu Glu Ala Glu Leu Ala Leu Thr Leu
                260                 265                 270

Thr Val Leu Glu Ala Met Ala Asn Ser Ser Leu Gly His Ser Leu Glu
275                 280                 285

Gln Pro Leu Leu Thr Leu Gln Asn Ile His Ser Lys Leu Gln Ala Cys
    290                 295                 300

Val Pro Ala Gln Pro Thr Ala Ser Ser Arg Pro Arg Gly Arg Leu His
305                 310                 315                 320

His Trp Leu His Arg Leu Gln Glu Ala Arg Lys Glu Ser Gln Asp Cys
                325                 330                 335

Leu Glu Ala Ser Val Met Phe Asn Leu Leu Arg Leu Leu Thr Arg Asp
                340                 345                 350

Leu Lys Cys Val Ala Ser Gly Asp Gln Cys Val
                355                 360

<210> SEQ ID NO 87
<211> LENGTH: 603
<212> TYPE: DNA
<213> ORGANISM: Homo sapiens
<220> FEATURE:
<221> NAME/KEY: CDS
<222> LOCATION: (1)..(603)
<223> OTHER INFORMATION: Human Interferon Lambda 1 (IL29)
```

<400> SEQUENCE: 87

```
atg gct gca gct tgg acc gtg gtg ctg gtg act ttg gtg cta ggc ttg    48
Met Ala Ala Ala Trp Thr Val Val Leu Val Thr Leu Val Leu Gly Leu
1               5                   10                  15 gcc gtg gca ggc cct gtc ccc act tcc aag ccc acc aca act ggg aag    96
Ala Val Ala Gly Pro Val Pro Thr Ser Lys Pro Thr Thr Thr Gly Lys
            20                  25                  30 ggc tgc cac att ggc agg ttc aaa tct ctg tca cca cag gag cta gcg   144
Gly Cys His Ile Gly Arg Phe Lys Ser Leu Ser Pro Gln Glu Leu Ala
        35                  40                  45 agc ttc aag aag gcc agg gac gcc ttg gaa gag tca ctc aag ctg aaa   192
Ser Phe Lys Lys Ala Arg Asp Ala Leu Glu Glu Ser Leu Lys Leu Lys
    50                  55                  60 aac tgg agt tgc agc tct cct gtc ttc ccc ggg aat tgg gac ctg agg   240
Asn Trp Ser Cys Ser Ser Pro Val Phe Pro Gly Asn Trp Asp Leu Arg
65                  70                  75                  80 ctt ctc cag gtg agg gag cgc cct gtg gcc ttg gag gct gag ctg gcc   288
Leu Leu Gln Val Arg Glu Arg Pro Val Ala Leu Glu Ala Glu Leu Ala
                85                  90                  95 ctg acg ctg aag gtc ctg gag gcc gct gct ggc cca gcc ctg gag gac   336
Leu Thr Leu Lys Val Leu Glu Ala Ala Ala Gly Pro Ala Leu Glu Asp
            100                 105                 110 gtc cta gac cag ccc ctt cac acc ctg cac cac atc ctc tcc cag ctc   384
Val Leu Asp Gln Pro Leu His Thr Leu His His Ile Leu Ser Gln Leu
        115                 120                 125 cag gcc tgt atc cag cct cag ccc aca gca ggg ccc agg ccc cgg ggc   432
Gln Ala Cys Ile Gln Pro Gln Pro Thr Ala Gly Pro Arg Pro Arg Gly
    130                 135                 140 cgc ctc cac cac tgg ctg cac cgg ctc cag gag gcc ccc aaa aag gag   480
Arg Leu His His Trp Leu His Arg Leu Gln Glu Ala Pro Lys Lys Glu
145                 150                 155                 160 tcc gct ggc tgc ctg gag gca tct gtc acc ttc aac ctc ttc cgc ctc   528
Ser Ala Gly Cys Leu Glu Ala Ser Val Thr Phe Asn Leu Phe Arg Leu
                165                 170                 175 ctc acg cga gac ctc aaa tat gtg gcc gat ggg aac ctg tgt ctg aga   576
Leu Thr Arg Asp Leu Lys Tyr Val Ala Asp Gly Asn Leu Cys Leu Arg
            180                 185                 190 acg tca acc cac cct gag tcc acc tga                               603
Thr Ser Thr His Pro Glu Ser Thr
        195                 200
```

<210> SEQ ID NO 88
<211> LENGTH: 200
<212> TYPE: PRT
<213> ORGANISM: Homo sapiens

<400> SEQUENCE: 88

```
Met Ala Ala Ala Trp Thr Val Val Leu Val Thr Leu Val Leu Gly Leu
1               5                   10                  15

Ala Val Ala Gly Pro Val Pro Thr Ser Lys Pro Thr Thr Thr Gly Lys
            20                  25                  30

Gly Cys His Ile Gly Arg Phe Lys Ser Leu Ser Pro Gln Glu Leu Ala
        35                  40                  45

Ser Phe Lys Lys Ala Arg Asp Ala Leu Glu Glu Ser Leu Lys Leu Lys
    50                  55                  60

Asn Trp Ser Cys Ser Ser Pro Val Phe Pro Gly Asn Trp Asp Leu Arg
65                  70                  75                  80

Leu Leu Gln Val Arg Glu Arg Pro Val Ala Leu Glu Ala Glu Leu Ala
                85                  90                  95
```

```
Leu Thr Leu Lys Val Leu Glu Ala Ala Gly Pro Ala Leu Glu Asp
            100                 105                 110

Val Leu Asp Gln Pro Leu His Thr Leu His His Ile Leu Ser Gln Leu
        115                 120                 125

Gln Ala Cys Ile Gln Pro Gln Pro Thr Ala Gly Pro Arg Pro Arg Gly
        130                 135                 140

Arg Leu His His Trp Leu His Arg Leu Gln Glu Ala Pro Lys Lys Glu
145                 150                 155                 160

Ser Ala Gly Cys Leu Glu Ala Ser Val Thr Phe Asn Leu Phe Arg Leu
                165                 170                 175

Leu Thr Arg Asp Leu Lys Tyr Val Ala Asp Gly Asn Leu Cys Leu Arg
            180                 185                 190

Thr Ser Thr His Pro Glu Ser Thr
            195                 200

<210> SEQ ID NO 89
<211> LENGTH: 1113
<212> TYPE: DNA
<213> ORGANISM: Homo sapiens
<220> FEATURE:
<221> NAME/KEY: CDS
<222> LOCATION: (1)..(1113)
<223> OTHER INFORMATION: Human GlucON Lambda

<400> SEQUENCE: 89 atg gga gtc aaa gtt ctg ttt gcc ctg atc tgc atc gct gtg gcc gag      48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc      96
Ala Lys Pro Thr Glu Asn Asn Glu Asp Phe Asn Ile Val Ala Val Ala
                20                  25                  30 agc aac ttc gcg acc acg gat ctc gat gct gac cgc ggg aag ttg ccc     144
Ser Asn Phe Ala Thr Thr Asp Leu Asp Ala Asp Arg Gly Lys Leu Pro
            35                  40                  45 ggc aag aag ctg ccg ctg gag gtg ctc aaa gag atg gaa gcc aat gcc     192
Gly Lys Lys Leu Pro Leu Glu Val Leu Lys Glu Met Glu Ala Asn Ala
        50                  55                  60 cgg aaa gct ggc tgc acc agg ggc tgt ctg atc tgc ctg tcc cac atc     240
Arg Lys Ala Gly Cys Thr Arg Gly Cys Leu Ile Cys Leu Ser His Ile
65                  70                  75                  80 aag tgc acg ccc aag atg aag aag ttc atc cca gga cgc tgc cac acc     288
Lys Cys Thr Pro Lys Met Lys Lys Phe Ile Pro Gly Arg Cys His Thr
                85                  90                  95 tac gaa ggc gac aaa gag tcc gca cag ggc ggc ata ggc gag gcg atc     336
Tyr Glu Gly Asp Lys Glu Ser Ala Gln Gly Gly Ile Gly Glu Ala Ile
            100                 105                 110 gtc gac att cct gag att cct ggg ttc aag gac ttg gag ccc atg gag     384
Val Asp Ile Pro Glu Ile Pro Gly Phe Lys Asp Leu Glu Pro Met Glu
        115                 120                 125 cag ttc atc gca cag gtc gat ctg tgt gtg gac tgc aca act ggc tgc     432
Gln Phe Ile Ala Gln Val Asp Leu Cys Val Asp Cys Thr Thr Gly Cys
        130                 135                 140 ctc aaa ggg ctt gcc aac gtg cag tgt tct gac ctg ctc aag aag tgg     480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg     528
Leu Pro Gln Arg Cys Ala Thr Phe Ala Ser Lys Ile Gln Gly Gln Val
                165                 170                 175 gac aag atc aag ggg gcc ggt ggt gac ttg gcc gtg gca ggc cct gtc     576
Asp Lys Ile Lys Gly Ala Gly Gly Asp Leu Ala Val Ala Gly Pro Val
```

```
                Asp Lys Ile Lys Gly Ala Gly Gly Asp Leu Ala Val Ala Gly Pro Val
                                180                 185                 190 ccc act tcc aag ccc acc aca act ggg aag ggc tgc cac att ggc agg        624
Pro Thr Ser Lys Pro Thr Thr Thr Gly Lys Gly Cys His Ile Gly Arg
            195                 200                 205 ttc aaa tct ctg tca cca cag gag cta gcg agc ttc aag aag gcc agg        672
Phe Lys Ser Leu Ser Pro Gln Glu Leu Ala Ser Phe Lys Lys Ala Arg
210                 215                 220 gac gcc ttg gaa gag tca ctc aag ctg aaa aac tgg agt tgc agc tct        720
Asp Ala Leu Glu Glu Ser Leu Lys Leu Lys Asn Trp Ser Cys Ser Ser
225                 230                 235                 240 cct gtc ttc ccc ggg aat tgg gac ctg agg ctt ctc cag gtg agg gag        768
Pro Val Phe Pro Gly Asn Trp Asp Leu Arg Leu Leu Gln Val Arg Glu
                245                 250                 255 cgc cct gtg gcc ttg gag gct gag ctg gcc ctg acg ctg aag gtc ctg        816
Arg Pro Val Ala Leu Glu Ala Glu Leu Ala Leu Thr Leu Lys Val Leu
            260                 265                 270 gag gcc gct gct ggc cca gcc ctg gag gac gtc cta gac cag ccc ctt        864
Glu Ala Ala Ala Gly Pro Ala Leu Glu Asp Val Leu Asp Gln Pro Leu
275                 280                 285 cac acc ctg cac cac atc ctc tcc cag ctc cag gcc tgt atc cag cct        912
His Thr Leu His His Ile Leu Ser Gln Leu Gln Ala Cys Ile Gln Pro
        290                 295                 300 cag ccc aca gca ggg ccc agg ccc cgg ggc cgc ctc cac cac tgg ctg        960
Gln Pro Thr Ala Gly Pro Arg Pro Arg Gly Arg Leu His His Trp Leu
305                 310                 315                 320 cac cgg ctc cag gag gcc ccc aaa aag gag tcc gct ggc tgc ctg gag       1008
His Arg Leu Gln Glu Ala Pro Lys Lys Glu Ser Ala Gly Cys Leu Glu
                325                 330                 335 gca tct gtc acc ttc aac ctc ttc cgc ctc ctc acg cga gac ctc aaa       1056
Ala Ser Val Thr Phe Asn Leu Phe Arg Leu Leu Thr Arg Asp Leu Lys
            340                 345                 350 tat gtg gcc gat ggg aac ctg tgt ctg aga acg tca acc cac cct gag       1104
Tyr Val Ala Asp Gly Asn Leu Cys Leu Arg Thr Ser Thr His Pro Glu
355                 360                 365 tcc acc tga                                                           1113
Ser Thr
    370

<210> SEQ ID NO 90
<211> LENGTH: 370
<212> TYPE: PRT
<213> ORGANISM: Homo sapiens

<400> SEQUENCE: 90

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
                20                  25                  30

Ser Asn Phe Ala Thr Thr Asp Leu Asp Ala Asp Arg Gly Lys Leu Pro
            35                  40                  45

Gly Lys Lys Leu Pro Leu Glu Val Leu Lys Glu Met Glu Ala Asn Ala
        50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110
```

Val Asp Ile Pro Glu Ile Pro Gly Phe Lys Asp Leu Glu Pro Met Glu
    115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Asp Leu Ala Val Ala Gly Pro Val
                180                 185                 190

Pro Thr Ser Lys Pro Thr Thr Gly Lys Gly Cys His Ile Gly Arg
                195                 200                 205

Phe Lys Ser Leu Ser Pro Gln Glu Leu Ala Ser Phe Lys Lys Ala Arg
    210                 215                 220

Asp Ala Leu Glu Glu Ser Leu Lys Leu Lys Asn Trp Ser Cys Ser Ser
225                 230                 235                 240

Pro Val Phe Pro Gly Asn Trp Asp Leu Arg Leu Leu Gln Val Arg Glu
                245                 250                 255

Arg Pro Val Ala Leu Glu Ala Glu Leu Ala Leu Thr Leu Lys Val Leu
                260                 265                 270

Glu Ala Ala Gly Pro Ala Leu Glu Asp Val Leu Asp Gln Pro Leu
    275                 280                 285

His Thr Leu His His Ile Leu Ser Gln Leu Gln Ala Cys Ile Gln Pro
                290                 295                 300

Gln Pro Thr Ala Gly Pro Arg Pro Arg Gly Leu His His Trp Leu
305                 310                 315                 320

His Arg Leu Gln Glu Ala Pro Lys Lys Glu Ser Ala Gly Cys Leu Glu
                325                 330                 335

Ala Ser Val Thr Phe Asn Leu Phe Arg Leu Leu Thr Arg Asp Leu Lys
                340                 345                 350

Tyr Val Ala Asp Gly Asn Leu Cys Leu Arg Thr Ser Thr His Pro Glu
                355                 360                 365

Ser Thr
    370

<210> SEQ ID NO 91
<211> LENGTH: 576
<212> TYPE: DNA
<213> ORGANISM: Sus scrofa
<220> FEATURE:
<221> NAME/KEY: CDS
<222> LOCATION: (1)..(576)
<223> OTHER INFORMATION: Porcine Interferon Lambda 1 (IL29

<400> SEQUENCE: 91 atg gct aca gct tgg atc gtg gtg ctg gcg act gtg atg ctg gac ttg    48
Met Ala Thr Ala Trp Ile Val Val Leu Ala Thr Val Met Leu Asp Leu
1               5                   10                  15 gcc aga gct ggc cct gtc ccc act ttc aag ccc acc aca acc agg aag    96
Ala Arg Ala Gly Pro Val Pro Thr Phe Lys Pro Thr Thr Thr Arg Lys
            20                  25                  30 ggc tgc cac atg ggc cag ttc caa tct ctg tca cca cag gag ctg aag   144
Gly Cys His Met Gly Gln Phe Gln Ser Leu Ser Pro Gln Glu Leu Lys
        35                  40                  45 ggc ttc aag aaa gcc aag gat gct ttg gaa gag tca ctc tca ctg aag   192
Gly Phe Lys Lys Ala Lys Asp Ala Leu Glu Glu Ser Leu Ser Leu Lys
    50                  55                  60

```
aac tgg agc tgc agc tct ccc ctc ttc ccc agg acc cgg gac ctg agg         240
Asn Trp Ser Cys Ser Ser Pro Leu Phe Pro Arg Thr Arg Asp Leu Arg
 65                  70                  75                  80 cag ctg cag gtg tgg gag cgc ctc gtg gcc tta gag gct gag cta gac         288
Gln Leu Gln Val Trp Glu Arg Leu Val Ala Leu Glu Ala Glu Leu Asp
                 85                  90                  95 ttg act ctg aag gtc cta agg gcc gcg gct gac tca tcc ctg ggg gtc         336
Leu Thr Leu Lys Val Leu Arg Ala Ala Ala Asp Ser Ser Leu Gly Val
            100                 105                 110 acc ctg gac cag cca ctt cgc acg ctg cat cac atc cac gtc gaa ctt         384
Thr Leu Asp Gln Pro Leu Arg Thr Leu His His Ile His Val Glu Leu
        115                 120                 125 cag gct tgc atc agg gct cag ccc acg gca gga tcc cgg ctc cag ggc         432
Gln Ala Cys Ile Arg Ala Gln Pro Thr Ala Gly Ser Arg Leu Gln Gly
    130                 135                 140 cgc ctc aac cac tgg ctg cac cgg ctc caa gaa gcc aca aag aaa gag         480
Arg Leu Asn His Trp Leu His Arg Leu Gln Glu Ala Thr Lys Lys Glu
145                 150                 155                 160 tcc caa ggc tgc ctt gag gcc tct gtg aca ttc aac ctc ttc cac ctc         528
Ser Gln Gly Cys Leu Glu Ala Ser Val Thr Phe Asn Leu Phe His Leu
                165                 170                 175 ctc gta agg gac ctg aga agt gtt acc agt gga gac ttg cac atc tga         576
Leu Val Arg Asp Leu Arg Ser Val Thr Ser Gly Asp Leu His Ile
            180                 185                 190

<210> SEQ ID NO 92
<211> LENGTH: 191
<212> TYPE: PRT
<213> ORGANISM: Sus scrofa

<400> SEQUENCE: 92

Met Ala Thr Ala Trp Ile Val Val Leu Ala Thr Val Met Leu Asp Leu
1               5                   10                  15

Ala Arg Ala Gly Pro Val Pro Thr Phe Lys Pro Thr Thr Thr Arg Lys
            20                  25                  30

Gly Cys His Met Gly Gln Phe Gln Ser Leu Ser Pro Gln Glu Leu Lys
        35                  40                  45

Gly Phe Lys Lys Ala Lys Asp Ala Leu Glu Glu Ser Leu Ser Leu Lys
    50                  55                  60

Asn Trp Ser Cys Ser Ser Pro Leu Phe Pro Arg Thr Arg Asp Leu Arg
65                  70                  75                  80

Gln Leu Gln Val Trp Glu Arg Leu Val Ala Leu Glu Ala Glu Leu Asp
                85                  90                  95

Leu Thr Leu Lys Val Leu Arg Ala Ala Ala Asp Ser Ser Leu Gly Val
            100                 105                 110

Thr Leu Asp Gln Pro Leu Arg Thr Leu His His Ile His Val Glu Leu
        115                 120                 125

Gln Ala Cys Ile Arg Ala Gln Pro Thr Ala Gly Ser Arg Leu Gln Gly
    130                 135                 140

Arg Leu Asn His Trp Leu His Arg Leu Gln Glu Ala Thr Lys Lys Glu
145                 150                 155                 160

Ser Gln Gly Cys Leu Glu Ala Ser Val Thr Phe Asn Leu Phe His Leu
                165                 170                 175

Leu Val Arg Asp Leu Arg Ser Val Thr Ser Gly Asp Leu His Ile
            180                 185                 190

<210> SEQ ID NO 93
```

```
<211> LENGTH: 1083
<212> TYPE: DNA
<213> ORGANISM: Sus scrofa
<220> FEATURE:
<221> NAME/KEY: CDS
<222> LOCATION: (1)..(1083)
<223> OTHER INFORMATION: Porcine GLucON Lambda

<400> SEQUENCE: 93
```

| | | | | | | | | | | | | | | | | |
|---|---|---|---|---|---|---|---|---|---|---|---|---|---|---|---|---|
| atg | gga | gtc | aaa | gtt | ctg | ttt | gcc | ctg | atc | tgc | atc | gct | gtg | gcc | gag | 48 |
| Met | Gly | Val | Lys | Val | Leu | Phe | Ala | Leu | Ile | Cys | Ile | Ala | Val | Ala | Glu | |
| 1 | | | | 5 | | | | | 10 | | | | | 15 | | |
| gcc | aag | ccc | acc | gag | aac | aac | gaa | gac | ttc | aac | atc | gtg | gcc | gtg | gcc | 96 |
| Ala | Lys | Pro | Thr | Glu | Asn | Asn | Glu | Asp | Phe | Asn | Ile | Val | Ala | Val | Ala | |
| | | | 20 | | | | | 25 | | | | | 30 | | | |
| agc | aac | ttc | gcg | acc | acg | gat | ctc | gat | gct | gac | cgc | ggg | aag | ttg | ccc | 144 |
| Ser | Asn | Phe | Ala | Thr | Thr | Asp | Leu | Asp | Ala | Asp | Arg | Gly | Lys | Leu | Pro | |
| | | 35 | | | | | 40 | | | | | 45 | | | | |
| ggc | aag | aag | ctg | ccg | ctg | gag | gtg | ctc | aaa | gag | atg | gaa | gcc | aat | gcc | 192 |
| Gly | Lys | Lys | Leu | Pro | Leu | Glu | Val | Leu | Lys | Glu | Met | Glu | Ala | Asn | Ala | |
| | 50 | | | | | 55 | | | | | 60 | | | | | |
| cgg | aaa | gct | ggc | tgc | acc | agg | ggc | tgt | ctg | atc | tgc | ctg | tcc | cac | atc | 240 |
| Arg | Lys | Ala | Gly | Cys | Thr | Arg | Gly | Cys | Leu | Ile | Cys | Leu | Ser | His | Ile | |
| 65 | | | | | 70 | | | | | 75 | | | | | 80 | |
| aag | tgc | acg | ccc | aag | atg | aag | aag | ttc | atc | cca | gga | cgc | tgc | cac | acc | 288 |
| Lys | Cys | Thr | Pro | Lys | Met | Lys | Lys | Phe | Ile | Pro | Gly | Arg | Cys | His | Thr | |
| | | | | 85 | | | | | 90 | | | | | 95 | | |
| tac | gaa | ggc | gac | aaa | gag | tcc | gca | cag | ggc | ggc | ata | ggc | gag | gcg | atc | 336 |
| Tyr | Glu | Gly | Asp | Lys | Glu | Ser | Ala | Gln | Gly | Gly | Ile | Gly | Glu | Ala | Ile | |
| | | | 100 | | | | | 105 | | | | | 110 | | | |
| gtc | gac | att | cct | gag | att | cct | ggg | ttc | aag | gac | ttg | gag | ccc | atg | gag | 384 |
| Val | Asp | Ile | Pro | Glu | Ile | Pro | Gly | Phe | Lys | Asp | Leu | Glu | Pro | Met | Glu | |
| | | 115 | | | | | 120 | | | | | 125 | | | | |
| cag | ttc | atc | gca | cag | gtc | gat | ctg | tgt | gtg | gac | tgc | aca | act | ggc | tgc | 432 |
| Gln | Phe | Ile | Ala | Gln | Val | Asp | Leu | Cys | Val | Asp | Cys | Thr | Thr | Gly | Cys | |
| | 130 | | | | | 135 | | | | | 140 | | | | | |
| ctc | aaa | ggg | ctt | gcc | aac | gtg | cag | tgt | tct | gac | ctg | ctc | aag | aag | tgg | 480 |
| Leu | Lys | Gly | Leu | Ala | Asn | Val | Gln | Cys | Ser | Asp | Leu | Leu | Lys | Lys | Trp | |
| 145 | | | | | 150 | | | | | 155 | | | | | 160 | |
| ctg | ccg | caa | cgc | tgt | gcg | acc | ttt | gcc | agc | aag | atc | cag | ggc | cag | gtg | 528 |
| Leu | Pro | Gln | Arg | Cys | Ala | Thr | Phe | Ala | Ser | Lys | Ile | Gln | Gly | Gln | Val | |
| | | | | 165 | | | | | 170 | | | | | 175 | | |
| gac | aag | atc | aag | ggg | gcc | ggt | ggt | gac | gcc | aga | gct | ggc | cct | gtc | ccc | 576 |
| Asp | Lys | Ile | Lys | Gly | Ala | Gly | Gly | Asp | Ala | Arg | Ala | Gly | Pro | Val | Pro | |
| | | | 180 | | | | | 185 | | | | | 190 | | | |
| act | ttc | aag | ccc | acc | aca | acc | agg | aag | ggc | tgc | cac | atg | ggc | cag | ttc | 624 |
| Thr | Phe | Lys | Pro | Thr | Thr | Thr | Arg | Lys | Gly | Cys | His | Met | Gly | Gln | Phe | |
| | | 195 | | | | | 200 | | | | | 205 | | | | |
| caa | tct | ctg | tca | cca | cag | gag | ctg | aag | ggc | ttc | aag | aaa | gcc | aag | gat | 672 |
| Gln | Ser | Leu | Ser | Pro | Gln | Glu | Leu | Lys | Gly | Phe | Lys | Lys | Ala | Lys | Asp | |
| | 210 | | | | | 215 | | | | | 220 | | | | | |
| gct | ttg | gaa | gag | tca | ctc | tca | ctg | aag | aac | tgg | agc | tgc | agc | tct | ccc | 720 |
| Ala | Leu | Glu | Glu | Ser | Leu | Ser | Leu | Lys | Asn | Trp | Ser | Cys | Ser | Ser | Pro | |
| 225 | | | | | 230 | | | | | 235 | | | | | 240 | |
| ctc | ttc | ccc | agg | acc | cgg | gac | ctg | agg | cag | ctg | cag | gtg | tgg | gag | cgc | 768 |
| Leu | Phe | Pro | Arg | Thr | Arg | Asp | Leu | Arg | Gln | Leu | Gln | Val | Trp | Glu | Arg | |
| | | | | 245 | | | | | 250 | | | | | 255 | | |
| ctc | gtg | gcc | tta | gag | gct | gag | cta | gac | ttg | act | ctg | aag | gtc | cta | agg | 816 |
| Leu | Val | Ala | Leu | Glu | Ala | Glu | Leu | Asp | Leu | Thr | Leu | Lys | Val | Leu | Arg | |
| | | | 260 | | | | | 265 | | | | | 270 | | | |
| gcc | gcg | gct | gac | tca | tcc | ctg | ggg | gtc | acc | ctg | gac | cag | cca | ctt | cgc | 864 |
| Ala | Ala | Ala | Asp | Ser | Ser | Leu | Gly | Val | Thr | Leu | Asp | Gln | Pro | Leu | Arg | |

```
Ala Ala Ala Asp Ser Ser Leu Gly Val Thr Leu Asp Gln Pro Leu Arg
            275                 280                 285 acg ctg cat cac atc cac gtc gaa ctt cag gct tgc atc agg gct cag      912
Thr Leu His His Ile His Val Glu Leu Gln Ala Cys Ile Arg Ala Gln
            290                 295                 300 ccc acg gca gga tcc cgg ctc cag ggc cgc ctc aac cac tgg ctg cac      960
Pro Thr Ala Gly Ser Arg Leu Gln Gly Arg Leu Asn His Trp Leu His
305                 310                 315                 320 cgg ctc caa gaa gcc aca aag aaa gag tcc caa ggc tgc ctt gag gcc     1008
Arg Leu Gln Glu Ala Thr Lys Lys Glu Ser Gln Gly Cys Leu Glu Ala
            325                 330                 335 tct gtg aca ttc aac ctc ttc cac ctc ctc gta agg gac ctg aga agt     1056
Ser Val Thr Phe Asn Leu Phe His Leu Leu Val Arg Asp Leu Arg Ser
            340                 345                 350 gtt acc agt gga gac ttg cac atc tga                                 1083
Val Thr Ser Gly Asp Leu His Ile
            355                 360

<210> SEQ ID NO 94
<211> LENGTH: 360
<212> TYPE: PRT
<213> ORGANISM: Sus scrofa

<400> SEQUENCE: 94

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp Ala Arg Ala Gly Pro Val Pro
            180                 185                 190

Thr Phe Lys Pro Thr Thr Thr Arg Lys Gly Cys His Met Gly Gln Phe
        195                 200                 205

Gln Ser Leu Ser Pro Gln Glu Leu Lys Gly Phe Lys Lys Ala Lys Asp
210                 215                 220

Ala Leu Glu Glu Ser Leu Ser Leu Lys Asn Trp Ser Cys Ser Ser Pro
225                 230                 235                 240

Leu Phe Pro Arg Thr Arg Asp Leu Arg Gln Leu Gln Val Trp Glu Arg
                245                 250                 255
```

```
Leu Val Ala Leu Glu Ala Glu Leu Asp Thr Leu Lys Val Leu Arg
            260                 265                 270

Ala Ala Ala Asp Ser Ser Leu Gly Val Thr Leu Asp Gln Pro Leu Arg
            275                 280                 285

Thr Leu His His Ile His Val Glu Leu Gln Ala Cys Ile Arg Ala Gln
        290                 295                 300

Pro Thr Ala Gly Ser Arg Leu Gln Gly Arg Leu Asn His Trp Leu His
305                 310                 315                 320

Arg Leu Gln Glu Ala Thr Lys Lys Glu Ser Gln Gly Cys Leu Glu Ala
            325                 330                 335

Ser Val Thr Phe Asn Leu Phe His Leu Leu Val Arg Asp Leu Arg Ser
            340                 345                 350

Val Thr Ser Gly Asp Leu His Ile
            355                 360

<210> SEQ ID NO 95
<211> LENGTH: 13
<212> TYPE: DNA
<213> ORGANISM: Artificial Sequence
<220> FEATURE:
<223> OTHER INFORMATION: Kozak Sequence
<220> FEATURE:
<221> NAME/KEY: misc_feature
<222> LOCATION: (7)..(7)
<223> OTHER INFORMATION: R is A or G

<400> SEQUENCE: 95
gccgccrcca tgg                                                          13

<210> SEQ ID NO 96
<211> LENGTH: 5670
<212> TYPE: DNA
<213> ORGANISM: Artificial Sequence
<220> FEATURE:
<223> OTHER INFORMATION: pTarget Empty Vector

<400> SEQUENCE: 96
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg acccccgccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg cccctattg acgtcaatga     420 cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg gggatttcca gtctccaccc ccattgacgt     600
caatgggagt ttgttttggc accaaaatca acgggacttt ccaaaatgtc gtaacaactg     660
cgatcgcccg ccccgttgac gcaaatgggc ggtaggcgtg tacggtggga ggtctatata     720
agcagagctc gtttagtgaa ccgtcagatc actagaagct ttattgcggt agtttatcac     780
agttaaattg ctaacgcagt cagtgcttct gacacaacag tctcgaactt aagctgcagt     840
gactctctta aggtagcctt gcagaagttg gtcgtgaggc actgggcagg taagtatcaa     900
ggttacaaga caggtttaag gagaccaata gaaactgggc ttgtcgagac agagaagact     960
```

```
cttgcgtttc tgataggcac ctattggtct tactgacatc cactttgcct ttctctccac    1020
aggtgtccac tcccagttca attacagctc ttaaaaattg gatctccatt cgccattcag    1080
gctgcgcaac tgctgggaag gacgatcaga gcgggcctct tcgctattac gccagctggc    1140
gaaagggacg tggcaagcaa ggcgattaag ttgagttacg ccaggatttt cccagtcacg    1200
acgttgtaaa acgacggcca gagaattata atacgactca ctatagggcg aattcggatc    1260
cttgctagcc tcgagacgcg tgatatcttt cccgggggta ccgtcgactg cggccgcgaa    1320
ttccaagctt gagtattcta tcgtgtcacc taaataactt ggcgtaatca tggtcatatc    1380
tgtttcctgt gtgaaattgt tatccgctca caattccaca acatacga gccgaagca     1440 taaagtgtaa agcctggggt gcctaatgag tgagctaact cacattaatt gcgttgcgcg    1500
atgcttccat tttgtgaggg ttaatgcttc gagaagacat gataagatac attgatgagt    1560
ttggacaaac cacaacaaga atgcagtgaa aaaaatgctt tatttgtgaa atttgtgatg    1620
ctattgcttt atttgtaacc attataagct gcaataaaca agttaacaac aacaattgca    1680
ttcattttat gtttcaggtt caggggggaga tgtgggaggt ttttttaaagc aagtaaaacc    1740 tctacaaatg tggtaaaatc gataaggat cgattccgga gcctgaatgg cgaatggacg    1800
cgccctgtag cggcgcatta agcgcggcgg gtgtggtggt tacgcgcacg tgaccgctac    1860
acttgccagc gccctagcgc ccgctccttt cgctttcttc ccttcctttc tcgccacgtt    1920
cgccggcttt ccccgtcaag ctctaaatcg ggggctccct ttagggttcc gatttagtgc    1980
tttacggcac ctcgacccca aaaaacttga ttagggtgat ggttcacgta gtgggccatc    2040
gccctgatag acgttttttc gccctttgac gttggagtcc acgttcttta atagtggact    2100
cttgttccaa actggaacaa cactcaaccc tatctcggtc tattcttttg atttataagg    2160
gattttgccg atttcggcct attggttaaa aatgagctg atttaacaaa aatttaacgc    2220
gaattttaac aaaatattaa cgcttacaat ttcgcctgtg taccttctga ggcggaaaga    2280
accagctgtg aatgtgtgt cagttagggt gtggaaagtc cccaggctcc ccagcaggca    2340
gaagtatgca aagcatgcat ctcaattagt cagcaaccag gtgtggaaag tccccaggct    2400
ccccagcagg cagaagtatg caaagcatgc atctcaatta gtcagcaacc atagtcccgc    2460
ccctaactcc gcccatcccg cccctaactc cgcccagttc cgcccattct ccgccccatg    2520
gctgactaat ttttttt tatt tatgcagagg ccgaggccgc ctcggcctct gagctattcc    2580
agaagtagtg aggaggcttt tttggaggcc taggcttttg caaaaagctt gattcttctg    2640
acacaacagt ctcgaactta aggctagagc caccatgatt gaacaagatg gattgcacgc    2700
aggttctccg gccgcttggg tggagaggct attcggctat gactgggcac aacagacaat    2760
cggctgctct gatgccgccg tgttccggct gtcagcgcag gggcgcccgg ttcttttgt    2820 caagaccgac ctgtccggtg ccctgaatga actgcaggac gaggcagcgc ggctatcgtg    2880
gctggccacg acgggcgttc cttgcgcagc tgtgctcgac gttgtcactg aagcgggaag    2940
ggactggctg ctattgggcg aagtgccggg gcaggatctc ctgtcatctc accttgctcc    3000
tgccgagaaa gtatccatca tggctgatgc aatgcggcgg ctgcatacgc ttgatccggc    3060
tacctgccca ttcgaccacc aagcgaaaca tcgcatcgag cgagcacgta ctcggatgga    3120
agccggtctt gtcgatcagg atgatctgga cgaagagcat caggggctcg cgccagccga    3180
actgttcgcc aggctcaagg cgcgcatgcc cgacggcgag gatctcgtcg tgacccatgg    3240
cgatgcctgc ttgccgaata tcatggtgga aaatggccgc ttttctggat tcatcgactg    3300
tggccggctg ggtgtggcgg accgctatca ggacatagcg ttggctaccc gtgatattgc    3360
```

```
tgaagagctt ggcggcgaat gggctgaccg cttcctcgtg ctttacggta tcgccgctcc      3420
cgattcgcag cgcatcgcct tctatcgcct tcttgacgag ttcttctgag cgggactctg      3480
gggttcgaaa tgaccgacca agcgacgccc aacctgccat cacgatggcc gcaataaaat      3540
atctttattt tcattacatc tgtgtgttgg tttttttgtgt gaagatccgc gtatggtgca      3600
ctctcagtac aatctgctct gatgccgcat agttaagcca gccccgacac ccgccaacac      3660
ccgctgacgc gccctgacgg gcttgtctgc tcccggcatc cgcttacaga caagctgtga      3720
ccgtctccgg gagctgcatg tgtcagaggt tttcaccgtc atcaccgaaa cgcgcgagac      3780
gaaagggcct cgtgatacgc ctatttttat aggttaatgt catgataata atggtttctt      3840
agacgtcagg tggcactttt cggggaaatg tgcgcggaac ccctatttgt ttattttttct     3900 aaatacattc aaatatgtat ccgctcatga gacaataacc ctgataaatg cttcaataat      3960
attgaaaaag gaagagtatg agtattcaac atttccgtgt cgcccttatt ccctttttg      4020 cggcattttg ccttcctgtt tttgctcacc cagaaacgct ggtgaaagta aaagatgctg      4080
aagatcagtt gggtgcacga gtgggttaca tcgaactgga tctcaacagc ggtaagatcc      4140
ttgagagttt tcgccccgaa gaacgttttc caatgatgag cacttttaaa gttctgctat      4200
gtggcgcggt attatcccgt attgacgccg ggcaagagca actcggtcgc cgcatacact      4260
attctcagaa tgacttggtt gagtactcac cagtcacaga aaagcatctt acggatggca      4320
tgacagtaag agaattatgc agtgctgcca taaccatgag tgataacact gcggccaact      4380
tacttctgac aacgatcgga ggaccgaagg agctaaccgc ttttttgcac aacatggggg      4440
atcatgtaac tcgccttgat cgttgggaac cggagctgaa tgaagccata ccaaacgacg      4500
agcgtgacac cacgatgcct gtagcaatgg caacaacgtt gcgcaaacta ttaactggcg      4560
aactacttac tctagcttcc cggcaacaat taatagactg gatggaggcg gataaagttg      4620
caggaccact tctgcgctcg gcccttccgg ctggctggtt tattgctgat aaatctggag      4680
ccggtgagcg tgggtctcgc ggtatcattg cagcactggg gccagatggt aagccctccc      4740
gtatcgtagt tatctacacg acggggagtc aggcaactat ggatgaacga atagacaga      4800 tcgctgagat aggtgcctca ctgattaagc attggtaact gtcagaccaa gtttactcat      4860
atatacttta gattgattta aaacttcatt tttaatttaa aaggatctag gtgaagatcc      4920
tttttgataa tctcatgacc aaaatccctt aacgtgagtt ttcgttccac tgagcgtcag      4980
accccgtaga aaagatcaaa ggatcttctt gagatccttt ttttctgcgc gtaatctgct      5040
gcttgcaaac aaaaaaacca ccgctaccag cggtggtttg tttgccggat caagagctac      5100
caactctttt tccgaaggta actggcttca gcagagcgca gataccaaat actgtccttc      5160
tagtgtagcc gtagttaggc caccacttca agaactctgt agcaccgcct acatacctcg      5220
ctctgctaat cctgttacca gtggctgctg ccagtggcga taagtcgtgt cttaccgggt      5280
tggactcaag acgatagtta ccggataagg cgcagcggtc gggctgaacg gggggttcgt      5340
gcacacagcc cagcttggag cgaacgacct acaccgaact gagatacccta cagcgtgagc      5400 tatgagaaag cgccacgctt cccgaaggga gaaaggcgga caggtatccg gtaagcggca      5460
gggtcggaac aggagagcgc acgagggagc ttccaggggg aaacgcctgg tatctttata      5520
gtcctgtcgg gtttcgccac ctctgacttg agcgtcgatt tttgtgatgc tcgtcagggg      5580
ggcggagcct atgaaaaaac gccagcaacg cggcctttttt acggttcctg gccttttgct      5640
ggccttttgc tcacatggct cgacagatct                                       5670
```

<210> SEQ ID NO 97
<211> LENGTH: 6884
<212> TYPE: DNA
<213> ORGANISM: Artificial Sequence
<220> FEATURE:
<223> OTHER INFORMATION: pTarget IFNa-d1D2A-SGluc (-1M)

<400> SEQUENCE: 97

| | | | | | |
|---|---|---|---|---|---|
| tcaatattgg | ccattagcca | tattattcat | tggttatata | gcataaatca | atattggcta | 60 |
| ttggccattg | catacgttgt | atctatatca | taatatgtac | atttatattg | gctcatgtcc | 120 |
| aatatgaccg | ccatgttggc | attgattatt | gactagttat | taatagtaat | caattacggg | 180 |
| gtcattagtt | catagcccat | atatggagtt | ccgcgttaca | taacttacgg | taaatggccc | 240 |
| gcctggctga | ccgcccaacg | acccccgccc | attgacgtca | ataatgacgt | atgttcccat | 300 |
| agtaacgcca | atagggactt | tccattgacg | tcaatgggtg | gagtatttac | ggtaaactgc | 360 |
| ccacttggca | gtacatcaag | tgtatcatat | gccaagtccg | cccctattg | acgtcaatga | 420 |
| cggtaaatgg | cccgcctggc | attatgccca | gtacatgacc | ttacgggact | ttcctacttg | 480 |
| gcagtacatc | tacgtattag | tcatcgctat | taccatggtg | atgcggtttt | ggcagtacac | 540 |
| caatgggcgt | ggatagcggt | ttgactcacg | gggatttcca | agtctccacc | ccattgacgt | 600 |
| caatgggagt | ttgttttggc | accaaaatca | acgggacttt | ccaaaatgtc | gtaacaactg | 660 |
| cgatcgcccg | ccccgttgac | gcaaatgggc | ggtaggcgtg | tacggtggga | ggtctatata | 720 |
| agcagagctc | gtttagtgaa | ccgtcagatc | actagaagct | ttattgcggt | agtttatcac | 780 |
| agttaaattg | ctaacgcagt | cagtgcttct | gacacaacag | tctcgaactt | aagctgcagt | 840 |
| gactctctta | aggtagcctt | gcagaagttg | gtcgtgaggc | actgggcagg | taagtatcaa | 900 |
| ggttacaaga | caggtttaag | gagaccaata | gaaactgggc | ttgtcgagac | agagaagact | 960 |
| cttgcgtttc | tgataggcac | ctattggtct | tactgacatc | cactttgcct | ttctctccac | 1020 |
| aggtgtccac | tcccagttca | attacagctc | ttaaaaattg | gatctccatt | cgccattcag | 1080 |
| gctgcgcaac | tgctgggaag | gacgatcaga | gcgggcctct | tcgctattac | gccagctggc | 1140 |
| gaaagggacg | tggcaagcaa | ggcgattaag | ttgagttacg | ccaggatttt | cccagtcacg | 1200 |
| acgttgtaaa | acgacggcca | gagaattata | atacgactca | ctataggcg | aattcggatc | 1260 |
| cttgctagcg | ccgccaccat | ggccccaacc | tcagccttcc | tcacgccct | ggtgctactc | 1320 |
| agctgcaatg | ccatctgctc | tctgggctgt | gacctgcctc | agacccacag | cctggctcac | 1380 |
| accagagccc | tgaggctcct | ggcacaaatg | aggagaatct | ctcccttctc | ctgcctggac | 1440 |
| cacagaaggg | actttggttc | ccctcatgag | gcttttgggg | gcaaccaggt | ccagaaggct | 1500 |
| caagccatgg | ctctggtgca | tgagatgctc | cagcagacct | tccagctctt | cagcacagag | 1560 |
| ggctcggctg | ctgcctggaa | tgagagcctc | ctgcaccagt | tctgcactgg | actggatcag | 1620 |
| cagctcaggg | acctggaagc | ctgtgtcatg | caggaggcgg | ggctggaagg | accccctg | 1680 |
| ctggaggagg | actccatcct | ggctgtgagg | aaatacttcc | acagactcac | cctctatctg | 1740 |
| caagagaaga | gctacagccc | ctgtgcctgg | gagatcgtca | gggcagaagt | catgagatcc | 1800 |
| ttctctcttcct | ccagaaacct | gcaagacaga | tcaggaaga | aggagctcga | gacgcgtgat | 1860 |
| tgcgccgcca | ccatgagcca | aagcaaaag | atcattgcac | cagcaaagca | gcttctgaat | 1920 |
| tttgacctgc | tcaagttggc | cggagacgtt | gagtccaacc | ctgggccgg | agtcaaagtt | 1980 |
| ctgtttgccc | tgatctgcat | cgctgtggcc | gaggccaagc | ccaccgagaa | caacgaagac | 2040 |
| ttcaacatcg | tggccgtggc | cagcaacttt | gcgaccacgg | atctcgatgc | tgaccgaggg | 2100 |

```
aagttgcccg gcaagaagct gccgctggag gtgctcaaag agatggaagc caatgcccgg   2160
aaagctggct gcaccagggg ctgtctgatc tgcctgtccc acatcaagtg cacgcccaag   2220
atgaagaagt ggctcccagg acgctgccac acctacgaag gcgacaaaga gtccgcacag   2280
ggcggcatag gcgaggcgat cgtcgatatt cctgagattc ctgggttcaa ggacttggag   2340
ccaatggagc agttcatcgc acaggtcgat ctgtgtgtgg actgcacaac tggctgcctc   2400
aaagggcttg ccaacgtgca gtgttcagac ctgctcaaga agtggctgcc gcaacgctgt   2460
gcgacctttg ccagcaagat ccagggccag gtggacaaga tcaagggggc cggtggtgac   2520
taagcggccg cgaattccaa gcttgagtat tctatcgtgt cacctaaata acttggcgta   2580
atcatggtca tatctgtttc ctgtgtgaaa ttgttatccg ctcacaattc cacacaacat   2640
acgagccgga agcataaagt gtaaagcctg gggtgcctaa tgagtgagct aactcacatt   2700
aattgcgttg cgcgatgctt ccatttgtg agggttaatg cttcgagaag acatgataag   2760
atacattgat gagtttggac aaaccacaac aagaatgcag tgaaaaaaat gctttatttg   2820
tgaaatttgt gatgctattg ctttatttgt aaccattata agctgcaata aacaagttaa   2880
caacaacaat tgcattcatt ttatgtttca ggttcagggg gagatgtggg aggttttta   2940
aagcaagtaa aacctctaca aatgtggtaa aatccgataa ggatcgattc cggagcctga   3000
atggcgaatg gacgcgccct gtagcggcgc attaagcgcg gcgggtgtgg tggttacgcg   3060
cacgtgaccg ctacacttgc cagcgcccta gcgcccgctc ctttcgcttt cttcccttcc   3120
tttctcgcca cgttcgccgg ctttccccgt caagctctaa atcggggct ccctttaggg   3180
ttccgattta gtgctttacg gcacctcgac cccaaaaaac ttgattaggg tgatggttca   3240
cgtagtgggc catcgccctg atagacggtt tttcgccctt tgacgttgga gtccacgttc   3300
tttaatagtg gactcttgtt ccaaactgga acaacactca accctatctc ggtctattct   3360
tttgatttat aagggatttt gccgatttcg gcctattggt taaaaaatga gctgatttaa   3420
caaaaattta acgcgaattt taacaaaata ttaacgctta caatttcgcc tgtgtacctt   3480
ctgaggcgga aagaaccagc tgtggaatgt gtgtcagtta gggtgtggaa agtccccagg   3540
ctccccagca ggcagaagta tgcaaagcat gcatctcaat tagtcagcaa ccaggtgtgg   3600
aaagtcccca ggctccccag caggcagaag tatgcaaagc atgcatctca attagtcagc   3660
aaccatagtc ccgcccctaa ctccgcccat cccgccccta ctccgccca gttccgccca   3720
ttctccgccc catggctgac taatttttt tatttatgca gaggccgagg ccgcctcggc   3780
ctctgagcta ttccagaagt agtgaggagg ctttttgga ggcctaggct tttgcaaaaa   3840
gcttgattct tctgacacaa cagtctcgaa cttaaggcta agccaccat gattgaacaa   3900
gatggattgc acgcaggttc tccggccgct tgggtggaga ggctattcgg ctatgactgg   3960
gcacaacaga caatcggctg ctctgatgcc gccgtgttcc ggctgtcagc gcaggggcgc   4020
ccggttcttt ttgtcaagac cgacctgtcc ggtgccctga tgaactgca ggacgaggca   4080
gcgcggctat cgtggctggc cacgacgggc gttccttgcg cagctgtgct cgacgttgtc   4140
actgaagcgg gaagggactg gctgctattg ggcgaagtgc cggggcagga tctcctgtca   4200
tctcaccttg ctcctgccga gaagtatcc atcatggctg atgcaatgcg gcggctgcat   4260
acgcttgatc cggctacctg cccattcgac caccaagcga aacatcgcat cgagcgagca   4320
cgtactcgga tggaagccgg tcttgtcgat caggatgatc tggacgaaga gcatcagggg   4380
ctcgcgccag ccgaactgtt cgccaggctc aaggcgcgca tgcccgacgg cgaggatctc   4440
```

```
gtcgtgaccc atggcgatgc ctgcttgccg aatatcatgg tggaaaatgg ccgcttttct    4500
ggattcatcg actgtggccg gctgggtgtg gcggaccgct atcaggacat agcgttggct    4560
acccgtgata ttgctgaaga gcttggcggc gaatgggctg accgcttcct cgtgctttac    4620
ggtatcgccg ctcccgattc gcagcgcatc gccttctatc gccttcttga cgagttcttc    4680
tgagcgggac tctggggttc gaaatgaccg accaagcgac gcccaacctg ccatcacgat    4740
ggccgcaata aaatatcttt attttcatta catctgtgtg ttggttttt gtgtgaagat    4800 ccgcgtatgg tgcactctca gtacaatctg ctctgatgcc gcatagttaa gccagccccg    4860
acacccgcca cacccgctg acgcgccctg acgggcttgt ctgctcccgg catccgctta    4920
cagacaagct gtgaccgtct ccgggagctg catgtgtcag aggttttcac cgtcatcacc    4980
gaaacgcgcg agacgaaagg gcctcgtgat acgcctattt ttataggtta atgtcatgat    5040
aataatggtt tcttagacgt caggtggcac ttttcgggga atgtgcgcg gaacccctat    5100 ttgtttattt ttctaaatac attcaaatat gtatccgctc atgagacaat aaccctgata    5160
aatgcttcaa taatattgaa aaggaagag tatgagtatt caacatttcc gtgtcgccct    5220
tattcccttt tttgcggcat tttgccttcc tgttttgct cacccagaaa cgctggtgaa    5280
agtaaaagat gctgaagatc agttgggtgc acgagtgggt tacatcgaac tggatctcaa    5340
cagcggtaag atccttgaga gttttcgccc cgaagaacgt tttccaatga tgagcacttt    5400
taaagttctg ctatgtggcg cggtattatc ccgtattgac gccgggcaag agcaactcgg    5460
tcgccgcata cactattctc agaatgactt ggttgagtac tcaccagtca cagaaaagca    5520
tcttacggat ggcatgacag taagagaatt atgcagtgct gccataacca tgagtgataa    5580
cactgcggcc aacttacttc tgacaacgat cggaggaccg aaggagctaa ccgcttttt    5640 gcacaacatg ggggatcatg taactcgcct tgatcgttgg gaaccggagc tgaatgaagc    5700
cataccaaac gacgagcgtg acaccacgat gcctgtagca atggcaacaa cgttgcgcaa    5760
actattaact ggcgaactac ttactctagc ttcccggcaa caattaatag actggatgga    5820
ggcggataaa gttgcaggac cacttctgcg ctcggccctt ccggctggct ggtttattgc    5880
tgataaatct ggagccggtg agcgtgggtc tcgcggtatc attgcagcac tggggccaga    5940
tggtaagccc tcccgtatcg tagttatcta cacgacgggg agtcaggcaa ctatggatga    6000
acgaaataga cagatcgctg agataggtgc ctcactgatt aagcattggt aactgtcaga    6060
ccaagtttac tcatatatac tttagattga tttaaaactt catttttaat ttaaaaggat    6120
ctaggtgaag atcctttttg ataatctcat gaccaaaatc ccttaacgtg agttttcgtt    6180
ccactgagcg tcagaccccg tagaaaagat caaaggatct tcttgagatc ctttttttct    6240
gcgcgtaatc tgctgcttgc aaacaaaaaa accaccgcta ccagcggtgg tttgtttgcc    6300
ggatcaagag ctaccaactc tttttccgaa ggtaactggc ttcagcagag cgcagatacc    6360
aaatactgtc cttctagtgt agccgtagtt aggccaccac ttcaagaact ctgtagcacc    6420
gcctacatac ctcgctctgc taatcctgtt accagtggct gctgccagtg gcgataagtc    6480
gtgtcttacc gggttggact caagacgata gttaccggat aaggcgcagc ggtcgggctg    6540
aacggggggt tcgtgcacac agcccagctt ggagcgaacg acctacaccg aactgagata    6600
cctacagcgt gagctatgag aaagcgccac gcttcccgaa gggagaaagg cggacaggta    6660
tccggtaagc ggcagggtcg gaacaggaga gcgcacgagg gagcttccag ggggaaacgc    6720
ctggtatctt tatagtcctg tcgggtttcg ccacctctga cttgagcgtc gatttttgtg    6780
atgctcgtca gggggggcgga gcctatggaa aaacgccagc aacgcggcct ttttacggtt    6840
```

```
cctggccttt tgctggcctt ttgctcacat ggctcgacag atct              6884
```

<210> SEQ ID NO 98
<211> LENGTH: 6864
<212> TYPE: DNA
<213> ORGANISM: Artificial Sequence
<220> FEATURE:
<223> OTHER INFORMATION: pTarget SGLuc-d1D2A-IFNa

<400> SEQUENCE: 98

```
tcaatattgg ccattagcca tattattcat tggttatata gcataaatca atattggcta    60
ttggccattg catacgttgt atctatatca taatatgtac atttatattg gctcatgtcc   120
aatatgaccg ccatgttggc attgattatt gactagttat taatagtaat caattacggg   180
gtcattagtt catagcccat atatggagtt ccgcgttaca taacttacgg taaatggccc   240
gcctggctga ccgcccaacg acccccgccc attgacgtca ataatgacgt atgttcccat   300
agtaacgcca atagggactt tccattgacg tcaatgggtg gagtatttac ggtaaactgc   360
ccacttggca gtacatcaag tgtatcatat gccaagtccg cccccattg acgtcaatga    420
cggtaaatgg cccgcctggc attatgccca gtacatgacc ttacgggact ttcctacttg   480
gcagtacatc tacgtattag tcatcgctat taccatggtg atgcggtttt ggcagtacac   540
caatgggcgt ggatagcggt ttgactcacg gggatttcca gtctccacc ccattgacgt    600
caatgggagt ttgttttggc accaaaatca acgggacttt ccaaaatgtc gtaacaactg   660
cgatcgcccg ccccgttgac gcaaatgggc ggtaggcgtg tacggtggga ggtctatata   720
agcagagctc gtttagtgaa ccgtcagatc actagaagct ttattgcggt agtttatcac   780
agttaaattg ctaacgcagt cagtgcttct gacacaacag tctcgaactt aagctgcagt   840
gactctctta aggtagcctt gcagaagttg gtcgtgaggc actgggcagg taagtatcaa   900
ggttacaaga caggtttaag gagaccaata gaaactgggc ttgtcgagac agagaagact   960
cttgcgtttc tgataggcac ctattggtct tactgacatc cactttgcct ttctctccac  1020
aggtgtccac tcccagttca attacagctc ttaaaaattg gatctccatt cgccattcag  1080
gctgcgcaac tgctgggaag gacgatcaga gcgggcctct tcgctattac gccagctggc  1140
gaaagggacg tggcaagcaa ggcgattaag ttgagttacg ccaggatttt cccagtcacg  1200
acgttgtaaa acgacggcca gagaattata atacgactca ctatagggcg aattcggatc  1260
cttggcgtgc gccgccacca tgggagtcaa agttctgttt gccctgatct gcatcgctgt  1320
ggccgaggcc aagcccaccg agaacaacga agacttcaac atcgtggccg tggccagcaa  1380
cttcgcgacc acggatctcg atgctgaccg cgggaagttg cccggcaaga agctgccgct  1440
ggaggtgctc aaagagatgg aagccaatgc cggaaagct ggctgcacca ggggctgtct   1500
gatctgcctg tcccacatca gtgcacgcc aagatgaag aagtggctcc aggacgctg     1560
ccacacctac gaaggcgaca agagtccgc acagggcggc ataggcgagg cgatcgtcga   1620
cattcctgag attcctgggt tcaaggactt ggagcccatg gagcagttca tcgcacaggt  1680
cgatctgtgt gtggactgca caactggctg cctcaaaggg cttgccaacg tgcagtgttc  1740
tgacctgctc aagaagtggc tgccgcaacg ctgtgcgacc tttgccagca agatccaggg  1800
ccaggtggac aagatcaagg gggccggtgg tgacgctagc cacaagcaaa agatcattgc  1860
accagcaaag cagcttctga attttgacct gctcaagttg gccggagacg ttgagtccaa  1920
ccctgggccc gggatggccc caacctcagc cttcctcacg gccctggtgc tactcagctg  1980
```

```
caatgccatc tgctctctgg gctgtgacct gcctcagacc cacagcctgg ctcacaccag    2040
agccctgagg ctcctggcac aaatgaggag aatctctccc ttctcctgcc tggaccacag    2100
aagggacttt ggttcccctc atgaggcttt tgggggcaac caggtccaga aggctcaagc    2160
catggctctg gtgcatgaga tgctccagca gaccttccag ctcttcagca cagagggctc    2220
ggctgctgcc tggaatgaga gcctcctgca ccagttctgc actggactgg atcagcagct    2280
cagggacctg gaagcctgtg tcatgcagga ggcgggctg gaagggaccc ccctgctgga    2340
ggaggactcc atcctggctg tgaggaaata cttccacaga ctcaccctct atctgcaaga    2400
gaagagctac agccctgtg cctgggagat cgtcagggca gaagtcatga gatccttctc    2460
ttcctccaga aacctgcaag acagactcag gaagaaggag tgagcggccg cgaattccaa    2520
gcttgagtat tctatcgtgt cacctaaata acttggcgta atcatggtca tatctgtttc    2580
ctgtgtgaaa ttgttatccg ctcacaattc cacacaacat acgagccgga agcataaagt    2640
gtaaagcctg gggtgcctaa tgagtgagct aactcacatt aattgcgttg cgcgatgctt    2700
ccattttgtg agggttaatg cttcgagaag acatgataag atacattgat gagttttggac   2760 aaaccacaac aagaatgcag tgaaaaaaat gctttatttg tgaaatttgt gatgctattg    2820
ctttatttgt aaccattata agctgcaata acaagttaa caacaacaat tgcattcatt     2880
ttatgtttca ggttcagggg gagatgtggg aggttttta aagcaagtaa aacctctaca    2940
aatgtggtaa aatccgataa ggatcgattc cggagcctga atggcgaatg gacgcgccct    3000
gtagcggcgc attaagcgcg gcgggtgtgg tggttacgcg cacgtgaccg ctacacttgc    3060
cagcgcccta gcgcccgctc ctttcgcttt cttcccttcc tttctcgcca cgttcgccgg    3120
ctttccccgt caagctctaa atcgggggct ccctttaggg ttccgattta gtgctttacg    3180
gcacctcgac cccaaaaaac ttgattaggg tgatggttca cgtagtgggc catcgccctg    3240
atagacggtt tttcgccctt tgacgttgga gtccacgttc tttaatagtg gactcttgtt    3300
ccaaactgga caacactca accctatctc ggtctattct tttgatttat aagggatttt     3360
gccgatttcg gcctattggt taaaaatga gctgatttaa caaaaattta acgcgaattt     3420
taacaaaata ttaacgctta caatttcgcc tgtgtaccgt ctgaggcgga aagaaccagc    3480
tgtggaatgt gtgtcagtta gggtgtggaa agtccccagg ctccccagca ggcagaagta    3540
tgcaaagcat gcatctcaat tagtcagcaa ccaggtgtgg aaagtcccca ggctccccag    3600
caggcagaag tatgcaaagc atgcatctca attagtcagc aaccatagtc cgcccctaa    3660 ctccgcccat cccgccccta actccgccca gttccgccca ttctccgccc catggctgac    3720
taattttttt tatttatgca gaggccgagg ccgcctcggc ctctgagcta ttccagaagt    3780
agtgaggagg ctttttgga ggcctaggct tttgcaaaaa gcttgattct tctgacacaa    3840
cagtctcgaa cttaaggcta gagccaccat gattgaacaa gatggattgc acgcaggttc    3900
tccggccgct tgggtggaga ggctattcgg ctatgactgg gcacaacaga caatcggctg    3960
ctctgatgcc gccgtgttcc ggctgtcagc gcagggcgc ccggttcttt ttgtcaagac    4020
cgacctgtcc ggtgccctga atgaactgca ggacgaggca gcgcggctat cgtggctggc    4080
cacgacgggc gttccttgcg cagctgtgct cgacgttgtc actgaagcgg gaagggactg    4140
gctgctattg ggcgaagtgc cggggcagga tctcctgtca tctcaccttg ctcctgccga    4200
gaaagtatcc atcatggctg atgcaatgcg gcggctgcat acgcttgatc cggctacctg    4260
cccattcgac caccaagcga aacatcgcat cgagcgagca cgtactcgga tggaagccgg    4320
tcttgtcgat caggatgatc tggacgaaga gcatcagggg ctcgcgccag ccgaactgtt    4380
```

-continued

```
cgccaggctc aaggcgcgca tgcccgacgg cgaggatctc gtcgtgaccc atggcgatgc    4440
ctgcttgccg aatatcatgg tggaaaatgg ccgcttttct ggattcatcg actgtggccg    4500
gctgggtgtg gcggaccgct atcaggacat agcgttggct acccgtgata ttgctgaaga    4560
gcttggcggc gaatgggctg accgcttcct cgtgctttac ggtatcgccg ctcccgattc    4620
gcagcgcatc gccttctatc gccttcttga cgagttcttc tgagcgggac tctgggttc     4680 gaaatgaccg accaagcgac gcccaacctg ccatcacgat ggccgcaata aaatatcttt    4740
attttcatta catctgtgtg ttggtttttt gtgtgaagat ccgcgtatgg tgcactctca    4800
gtacaatctg ctctgatgcc gcatagttaa gccagcccg acaccgcca acacccgctg       4860 acgcgccctg acgggcttgt ctgctcccgg catccgctta cagacaagct gtgaccgtct    4920
ccgggagctg catgtgtcag aggttttcac cgtcatcacc gaaacgcgcg agacgaaagg    4980
gcctcgtgat acgcctattt ttataggtta atgtcatgat aataatggtt cttagacgt      5040 caggtggcac ttttcgggga atgtgcgcg aacccctat ttgtttattt ttctaaatac       5100
attcaaatat gtatccgctc atgagacaat aaccctgata aatgcttcaa taatattgaa    5160
aaaggaagag tatgagtatt caacatttcc gtgtcgccct tattccctt tttgcggcat      5220 tttgccttcc tgtttttgct cacccagaaa cgctggtgaa agtaaaagat gctgaagatc    5280
agttgggtgc acgagtgggt tacatcgaac tggatctcaa cagcggtaag atccttgaga    5340
gttttcgccc cgaagaacgt tttccaatga tgagcacttt taaagttctg ctatgtggcg    5400
cggtattatc ccgtattgac gccgggcaag agcaactcgg tcgccgcata cactattctc    5460
agaatgactt ggttgagtac tcaccagtca cagaaaagca tcttacggat ggcatgacag    5520
taagagaatt atgcagtgct gccataacca tgagtgataa cactgcggcc aacttacttc    5580
tgacaacgat cggaggaccg aaggagctaa ccgcttttt gcacaacatg ggggatcatg      5640
taactcgcct tgatcgttgg gaaccggagc tgaatgaagc cataccaaac gacgagcgtg    5700
acaccacgat gcctgtagca atggcaacaa cgttgcgcaa actattaact ggcgaactac    5760
ttactctagc ttcccggcaa caattaatag actggatgga ggcggataaa gttgcaggac    5820
cacttctgcg ctcggccctt ccggctggct ggtttattgc tgataaatct ggagccggtg    5880
agcgtgggtc tcgcggtatc attgcagcac tggggccaga tggtaagccc tcccgtatcg    5940
tagttatcta cacgacgggg agtcaggcaa ctatggatga acgaaataga cagatcgctg    6000
agataggtgc ctcactgatt aagcattggt aactgtcaga ccaagtttac tcatatatac    6060
tttagattga tttaaaactt catttttaat ttaaaaggat ctaggtgaag atcctttttg    6120
ataatctcat gaccaaaatc ccttaacgtg agttttcgtt ccactgagcg tcagaccccg    6180
tagaaaagat caaaggatct tcttgagatc cttttttct gcgcgtaatc tgctgcttgc     6240
aaacaaaaaa accaccgcta ccagcggtgg tttgtttgcc ggatcaagag ctaccaactc    6300 ttttccgaa ggtaactggc ttcagcagag cgcagatacc aaatactgtc cttctagtgt      6360
agccgtagtt aggccaccac ttcaagaact ctgtagcacc gcctacatac ctcgctctgc    6420
taatcctgtt accagtggct gctgccagtg gcgataagtc gtgtcttacc gggttggact    6480
caagacgata gttaccggat aaggcgcagc ggtcgggctg aacggggggt tcgtgcacac    6540
agcccagctt ggagcgaacg acctacaccg aactgagata cctacagcgt gagctatgag    6600
aaagcgccac gcttcccgaa gggagaaagg cggacaggta tccggtaagc ggcagggtcg    6660
gaacaggaga gcgcacgagg gagcttccag ggggaaacgc ctggtatctt tatagtcctg    6720
```

```
tcgggtttcg ccacctctga cttgagcgtc gattttttgtg atgctcgtca gggggggcgga    6780 gcctatggaa aaacgccagc aacgcggcct ttttacggtt cctggccttt tgctggcctt    6840
ttgctcacat ggctcgacag atct                                            6864

<210> SEQ ID NO 99
<211> LENGTH: 6106
<212> TYPE: DNA
<213> ORGANISM: Artificial Sequence
<220> FEATURE:
<223> OTHER INFORMATION: pTarget Histone H3

<400> SEQUENCE: 99
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg cccctattg acgtcaatga     420 cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg gggatttcca agtctccacc ccattgacgt     600
caatgggagt ttgttttggc accaaaatca acgggacttt ccaaaatgtc gtaacaactg     660
cgatcgcccg ccccgttgac gcaaatgggc ggtaggcgtg tacggtggga ggtctatata     720
agcagagctc gtttagtgaa ccgtcagatc actagaagct ttattgcggt agtttatcac     780
agttaaattg ctaacgcagt cagtgcttct gacacaacag tctcgaactt aagctgcagt     840
gactctctta aggtagcctt gcagaagttg gtcgtgaggc actgggcagg taagtatcaa     900
ggttacaaga caggtttaag gagaccaata gaaactgggc ttgtcgagac agagaagact     960
cttgcgtttc tgataggcac ctattggtct tactgacatc cactttgcct ttctctccac    1020
aggtgtccac tcccagttca attacagctc ttaaaaattg gatctccatt cgccattcag    1080
gctgcgcaac tgctgggaag gacgatcaga gcgggcctct tcgctattac gccagctggc    1140
gaaagggacg tggcaagcaa ggcgattaag ttgagttacg ccaggatttt cccagtcacg    1200
acgttgtaaa acgacggcca gagaattata atacgactca ctatagggcg aattcggatc    1260
cttgctagcc tcgagacgcg tgataaggag ctcgagccac catggctcgt acaaagcaga    1320
ctgcccgcaa atcgaccggt ggtaaagcac cgaggaagca actcgctaca aaagccgctc    1380
gcaagagtgc gccctctact ggagggggtga agaaacctca tcgttacagg cctggtactg    1440
tggcactccg tgaaattaga cgttatcaga agtccactga acttctgatt cgcaaacttc    1500
ccttccagcg tctggtgcgg gaaattgctc aggacttcaa acagatctg cgcttccaga    1560 gtgcagctat tggtgctttg caggaggcaa gtgaggccta tctggttggc ctttttgaag    1620
acaccaacct gtgtgctatc catgccaaac gtgtaacaat tatgccaaaa gacatccagc    1680
tagcacgccg catacgtgga gaacgtgctt aaggtaacca atctttcccg ggggtaccgt    1740
cgactgcggc cgcgaattcc aagcttgagt attctatcgt gtcacctaaa taacttggcg    1800
taatcatggt catatctgtt tcctgtgtga aattgttatc cgctcacaat tccacacaac    1860
atacgagccg gaagcataaa gtgtaaagcc tggggtgcct aatgagtgag ctaactcaca    1920
```

```
ttaattgcgt tgcgcgatgc ttccattttg tgagggttaa tgcttcgaga agacatgata    1980
agatacattg atgagtttgg acaaaccaca acaagaatgc agtgaaaaaa atgctttatt    2040
tgtgaaattt gtgatgctat tgctttattt gtaaccatta taagctgcaa taaacaagtt    2100
aacaacaaca attgcattca ttttatgttt caggttcagg gggagatgtg ggaggttttt    2160
taaagcaagt aaaacctcta caaatgtggt aaaatccgat aaggatcgat tccggagcct    2220
gaatggcgaa tggacgcgcc ctgtagcggc gcattaagcg cggcgggtgt ggtggttacg    2280
cgcacgtgac cgctacactt gccagcgccc tagcgcccgc tcctttcgct tcttcccctt    2340
cctttctcgc cacgttcgcc ggctttcccc gtcaagctct aaatcggggg ctcccttttag   2400 ggttccgatt tagtgcttta cggcacctcg accccaaaaa acttgattag ggtgatggtt    2460
cacgtagtgg gccatcgccc tgatagacgg ttttcgccc tttgacgttg gagtccacgt     2520
tctttaatag tggactcttg ttccaaactg gaacaacact caaccctatc tcggtctatt    2580
cttttgattt ataagggatt ttgccgattt cggcctattg gttaaaaaat gagctgattt    2640
aacaaaaatt taacgcgaat tttaacaaaa tattaacgct tacaatttcg cctgtgtacc    2700
ttctgaggcg gaaagaacca gctgtggaat gtgtgtcagt tagggtgtgg aaagtcccca    2760
ggctccccag caggcagaag tatgcaaagc atgcatctca attagtcagc aaccaggtgt    2820
ggaaagtccc caggctcccc agcaggcaga agtatgcaaa gcatgcatct caattagtca    2880
gcaaccatag tcccgcccct aactccgccc atcccgcccc taactccgcc cagttccgcc    2940
cattctccgc cccatggctg actaatttt tttatttatg cagaggccga ggccgcctcg     3000
gcctctgagc tattccagaa gtagtgagga ggcttttttg gaggcctagg cttttgcaaa    3060
aagcttgatt cttctgacac aacagtctcg aacttaaggc tagagccacc atgattgaac    3120
aagatggatt gcacgcaggt tctccggccg cttgggtgga gaggctattc ggctatgact    3180
gggcacaaca gacaatcggc tgctctgatg ccgccgtgtt ccggctgtca gcgcaggggc    3240
gcccggttct ttttgtcaag accgacctgt ccggtgccct gaatgaactg caggacgagg    3300
cagcgcggct atcgtggctg gccacgacgg gcgttccttg cgcagctgtg ctcgacgttg    3360
tcactgaagc gggaagggac tggctgctat tgggcgaagt gccggggcag gatctcctgt    3420
catctcacct tgctcctgcc gagaaagtat ccatcatggc tgatgcaatg cggcggctgc    3480
atacgcttga tccggctacc tgcccattcg accaccaagc gaaacatcgc atcgagcgag    3540
cacgtactcg gatggaagcc ggtcttgtcg atcaggatga tctggacgaa gagcatcagg    3600
ggctcgcgcc agccgaactg ttcgccaggc tcaaggcgcg catgcccgac ggcgaggatc    3660
tcgtcgtgac ccatggcgat gcctgcttgc cgaatatcat ggtggaaaat ggccgctttt    3720
ctggattcat cgactgtggc cggctgggtg tggcggaccg ctatcaggac atagcgttgg    3780
ctacccgtga tattgctgaa gagcttggcg gcgaatgggc tgaccgcttc ctcgtgcttt    3840
acggtatcgc cgctcccgat tcgcagcgca tcgccttcta tcgccttctt gacgagttct    3900
tctgagcggg actctggggt tcgaaatgac cgaccaagcg acgcccaacc tgccatcacg    3960
atggccgcaa taaaatatct ttattttcat tacatctgtg tgttggtttt ttgtgtgaag    4020
atccgcgtat ggtgcactct cagtacaatc tgctctgatg ccgcatagtt aagccagccc    4080
cgacacccgc caacacccgc tgacgcgccc tgacgggctt gtctgctccc ggcatccgct    4140
tacagacaag ctgtgaccgt ctccgggagc tgcatgtgtc agaggttttc accgtcatca    4200
ccgaaacgcg cgagacgaaa gggcctcgtg atacgcctat ttttataggt taatgtcatg    4260
```

```
ataataatgg tttcttagac gtcaggtggc acttttcggg gaaatgtgcg cggaacccct    4320
atttgtttat ttttctaaat acattcaaat atgtatccgc tcatgagaca ataaccctga    4380
taaatgcttc aataatattg aaaaggaag agtatgagta ttcaacattt ccgtgtcgcc     4440
cttattccct ttttttgcggc attttgcctt cctgttttg ctcacccaga acgctggtg     4500 aaagtaaaag atgctgaaga tcagttgggt gcacgagtgg gttacatcga actggatctc    4560
aacagcggta agatccttga gagttttcgc cccgaagaac gttttccaat gatgagcact    4620
tttaaagttc tgctatgtgg cgcggtatta tcccgtattg acgccgggca agagcaactc    4680
ggtcgccgca tacactattc tcagaatgac ttggttgagt actcaccagt cacagaaaag    4740
catcttacgg atggcatgac agtaagagaa ttatgcagtg ctgccataac catgagtgat    4800
aacactgcgg ccaacttact tctgacaacg atcggaggac cgaaggagct aaccgctttt    4860
ttgcacaaca tgggggatca tgtaactcgc cttgatcgtt gggaaccgga gctgaatgaa    4920
gccataccaa acgacgagcg tgacaccacg atgcctgtag caatggcaac aacgttgcgc    4980
aaactattaa ctggcgaact acttactcta gcttcccggc aacaattaat agactggatg    5040
gaggcggata agttgcagg accacttctg cgctcggccc ttccggctgg ctggtttatt     5100
gctgataaat ctggagccgg tgagcgtggg tctcgcggta tcattgcagc actggggcca    5160
gatggtaagc cctcccgtat cgtagttatc tacacgacgg ggagtcaggc aactatggat    5220
gaacgaaata gacagatcgc tgagataggt gcctcactga ttaagcattg gtaactgtca    5280
gaccaagttt actcatatat actttagatt gatttaaaac ttcatttta atttaaaagg     5340 atctaggtga agatccttt tgataatctc atgaccaaaa tcccttaacg tgagttttcg     5400
ttccactgag cgtcagaccc cgtagaaaag atcaaaggat cttcttgaga tcctttttt    5460 ctgcgcgtaa tctgctgctt gcaaacaaaa aaaccaccgc taccagcggt ggtttgtttg    5520
ccggatcaag agctaccaac tctttttccg aaggtaactg gcttcagcag agcgcagata    5580
ccaaatactg tccttctagt gtagccgtag ttaggccacc acttcaagaa ctctgtagca    5640
ccgcctacat acctcgctct gctaatcctg ttaccagtgg ctgctgccag tggcgataag    5700
tcgtgtctta ccgggttgga ctcaagacga tagttaccgg ataaggcgca gcggtcgggc    5760
tgaacggggg gttcgtgcac acagcccagc ttggagcgaa cgacctacac cgaactgaga    5820
tacctacagc gtgagctatg agaaagcgcc acgcttcccg aagggagaaa ggcggacagg    5880
tatccggtaa gcggcagggt cggaacagga gagcgcacga gggagcttcc agggggaaac    5940
gcctggtatc tttatagtcc tgtcgggttt cgccacctct gacttgagcg tcgatttttg    6000
tgatgctcgt caggggggcg gagcctatgg aaaaacgcca gcaacgcggc cttttacgg     6060 ttcctggcct tttgctggcc ttttgctcac atggctcgac agatct                   6106
```

<210> SEQ ID NO 100
<211> LENGTH: 6696
<212> TYPE: DNA
<213> ORGANISM: Artificial Sequence
<220> FEATURE:
<223> OTHER INFORMATION: pTarget SGLucON Alpha Porcine

<400> SEQUENCE: 100

```
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
```

```
gcctggctga ccgcccaacg accccegccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg cccectattg acgtcaatga    420
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca gtctccacc ccattgacgt     600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaaaattg gatctccatt cgccattcag   1080
gctgcgcaac tgctgggaag gacgatcaga gcgggcctct tcgctattac gccagctggc   1140
gaaagggacg tggcaagcaa ggcgattaag ttgagttacg ccaggatttt cccagtcacg   1200
acgttgtaaa acgacggcca gagaattata atacgactca ctatagggcg aattcgctag   1260
cgccgccacc atgggagtca agttctgtt tgccctgatc tgcatcgctg tggccgaggc    1320
caagcccacc gagaacaacg aagacttcaa catcgtggcc gtggcagca actttgcgac    1380
cacggatctc gatgctgacc gagggaagtt gcccggcaag aagctgccgc tggaggtgct   1440
caaagagatg gaagccaatg cccggaaagc tggctgcacc aggggctgtc tgatctgcct   1500
gtcccacatc aagtgcacgc ccaagatgaa gaagtggctc ccaggacgct gccacaccta   1560
cgaaggcgac aaagagtccg cacagggcgg cataggcgag gcgatcgtcg atattcctga   1620
gattcctggg ttcaaggact ggagccaat ggagcagttc atcgcacagg tcgatctgtg    1680
tgtggactgc acaactggct gcctcaaagg gcttgccaac gtgcagtgtt ctgacctgct   1740
caagaagtgg ctgccgcaac gctgtgcgac cttgccagc aagatccagg gccaggtgga    1800
caagatcaag ggggccggtg gtgacgggcc cgggtgtgac ctgcctcaga cccacagcct   1860
ggctcacacc agagccctga ggctcctggc acaaatgagg agaatctctc ccttctcctg   1920
cctgaccac agaagggact ttggttcccc tcatgaggct tttgggggca accaggtcca    1980
gaaggctcaa gccatggctc tggtgcatga gatgctccag cagaccttcc agctcttcag   2040
cacagagggc tcggctgctg cctggaatga gagcctcctg caccagttct gcactggact   2100
ggatcagcag ctcagggacc tggaagcctg tgtcatgcag gaggcgggc tggaagggac    2160
cccctgctg gaggaggact ccatcctggc tgtgaggaaa tacttccaca gactcaccct    2220
ctatctgcaa gagaagagct acagccctg tgcctgggag atcgtcaggg cagaagtcat    2280
gagatccttc tcttcctcca gaaacctgca agacagactc aggaagaagg agtgagcggc   2340
cgcgaattcc aagcttgagt attctatcgt gtcacctaaa taacttggcg taatcatggt    2400
catatctgtt tcctgtgtga aattgttatc cgctcacaat tccacacaac atacgagccg    2460
gaagcataaa gtgtaaagcc tggggtgcct aatgagtgag ctaactcaca ttaattgcgt    2520
tgcgcgatgc ttccattttg tgagggttaa tgcttcgaga agacatgata agatacattg    2580
```

```
atgagtttgg acaaaccaca acaagaatgc agtgaaaaaa atgctttatt tgtgaaattt    2640
gtgatgctat tgctttattt gtaaccatta taagctgcaa taaacaagtt aacaacaaca    2700
attgcattca ttttatgttt caggttcagg gggagatgtg ggaggttttt taaagcaagt    2760
aaaacctcta caaatgtggt aaaatccgat aaggatcgat tccggagcct gaatggcgaa    2820
tggacgcgcc ctgtagcggc gcattaagcg cggcgggtgt ggtggttacg cgcacgtgac    2880
cgctacactt gccagcgccc tagcgcccgc tcctttcgct ttcttccctt cctttctcgc    2940
cacgttcgcc ggctttcccc gtcaagctct aaatcggggg ctccctttag ggttccgatt    3000
tagtgcttta cggcacctcg accccaaaaa acttgattag ggtgatggtt cacgtagtgg    3060
gccatcgccc tgatagacgg ttttcgccc tttgacgttg gagtccacgt tctttaatag    3120
tggactcttg ttccaaactg gaacaacact caaccctatc tcggtctatt cttttgattt    3180
ataagggatt ttgccgattt cggcctattg gttaaaaaat gagctgattt aacaaaaatt    3240
taacgcgaat tttaacaaaa tattaacgct tacaatttcg cctgtgtacc ttctgaggcg    3300
gaaagaacca gctgtggaat gtgtgtcagt tagggtgtgg aaagtcccca ggctccccag    3360
caggcagaag tatgcaaagc atgcatctca attagtcagc aaccaggtgt ggaaagtccc    3420
caggctcccc agcaggcaga agtatgcaaa gcatgcatct caattagtca gcaaccatag    3480
tcccgcccct aactccgccc atcccgcccc taactccgcc cagttccgcc cattctccgc    3540
cccatggctg actaattttt tttatttatg cagaggccga ggccgcctcg gcctctgagc    3600
tattccagaa gtagtgagga ggcttttttg gaggcctagg cttttgcaaa aagcttgatt    3660
cttctgacac aacagtctcg aacttaaggc tagagccacc atgattgaac aagatggatt    3720
gcacgcaggt tctccggccg cttgggtgga ggctattc ggctatgact gggcacaaca    3780
gacaatcggc tgctctgatg ccgccgtgtt ccggctgtca gcgcagggc gcccggttct    3840
ttttgtcaag accgacctgt ccggtgccct gaatgaactg caggacgagg cagcgcggct    3900
atcgtggctg gccacgacgg gcgttccttg cgcagctgtg ctcgacgttg tcactgaagc    3960
gggaagggac tggctgctat tgggcgaagt gccggggcag gatctcctgt catctcacct    4020
tgctcctgcc gagaaagtat ccatcatggc tgatgcaatg cggcggctgc atacgcttga    4080
tccggctacc tgcccattcg accaccaagc gaaacatcgc atcgagcgag cacgtactcg    4140
gatgaagccg gtcttgtcg atcaggatga tctggacgaa gagcatcagg gctcgcgcc    4200
agccgaactg ttcgccaggc tcaaggcgcg catgcccgac ggcgaggatc tcgtcgtgac    4260
ccatggcgat gcctgcttgc cgaatatcat ggtggaaaat ggccgctttt ctggattcat    4320
cgactgtggc cggctgggtg tggcggaccg ctatcaggac atagcgttgg ctacccgtga    4380
tattgctgaa gagcttggcg gcgaatgggc tgaccgcttc ctcgtgcttt acggtatcgc    4440
cgctcccgat tcgcagcgca tcgccttcta tcgccttctt gacgagttct tctgagcggg    4500
actctggggt tcgaaatgac cgaccaagcg acgcccaacc tgccatcacg atggccgcaa    4560
taaaatatct ttattttcat tacatctgtg tgttggtttt ttgtgtgaag atccgcgtat    4620
ggtgcactct cagtacaatc tgctctgatg ccgcatagtt aagccagccc cgacacccgc    4680
caacacccgc tgacgcgccc tgacgggctt gtctgctccc ggcatccgct tacagacaag    4740
ctgtgaccgt ctccgggagc tgcatgtgtc agaggttttc accgtcatca ccgaaacgcg    4800
cgagacgaaa gggcctcgtg atacgcctat ttttataggt taatgtcatg ataataatgg    4860
tttcttagac gtcaggtggc acttttcggg gaaatgtgcg cggaacccct atttgtttat    4920
ttttctaaat acattcaaat atgtatccgc tcatgagaca ataaccctga taaatgcttc    4980
```

```
aataatattg aaaaaggaag agtatgagta ttcaacattt ccgtgtcgcc cttattccct    5040
tttttgcggc attttgcctt cctgttttig ctcacccaga aacgctggtg aaagtaaaag    5100
atgctgaaga tcagttgggt gcacgagtgg gttacatcga actggatctc aacagcggta    5160
agatccttga gagttttcgc cccgaagaac gttttccaat gatgagcact tttaaagttc    5220
tgctatgtgg cgcggtatta tcccgtattg acgccgggca agagcaactc ggtcgccgca    5280
tacactattc tcagaatgac ttggttgagt actcaccagt cacagaaaag catcttacgg    5340
atggcatgac agtaagagaa ttatgcagtg ctgccataac catgagtgat aacactgcgg    5400
ccaacttact tctgacaacg atcggaggac cgaaggagct aaccgctttt ttgcacaaca    5460
tgggggatca tgtaactcgc cttgatcgtt gggaaccgga gctgaatgaa gccataccaa    5520
acgacgagcg tgacaccacg atgcctgtag caatggcaac aacgttgcgc aaactattaa    5580
ctggcgaact acttactcta gcttcccggc aacaattaat agactggatg gaggcggata    5640
aagttgcagg accacttctg cgctcggccc ttccggctgg ctggtttatt gctgataaat    5700
ctggagccgg tgagcgtggg tctcgcggta tcattgcagc actggggcca gatggtaagc    5760
cctcccgtat cgtagttatc tacacgacgg ggagtcaggc aactatggat gaacgaaata    5820
gacagatcgc tgagataggt gcctcactga ttaagcattg gtaactgtca gaccaagttt    5880
actcatatat actttagatt gatttaaaac ttcattttta atttaaaagg atctaggtga    5940
agatcctttt tgataatctc atgaccaaaa tcccttaacg tgagttttcg ttccactgag    6000
cgtcagaccc cgtagaaaag atcaaaggat cttcttgaga tcctttttt ctgcgcgtaa    6060 tctgctgctt gcaaacaaaa aaaccaccgc taccagcggt ggtttgtttg ccggatcaag    6120
agctaccaac tcttttccg aaggtaactg gcttcagcag agcgcagata ccaaatactg    6180
tccttctagt gtagccgtag ttaggccacc acttcaagaa ctctgtagca ccgcctacat    6240
acctcgctct gctaatcctg ttaccagtgg ctgctgccag tggcgataag tcgtgtctta    6300
ccgggttgga ctcaagacga tagttaccgg ataaggcgca gcggtcgggc tgaacggggg    6360
gttcgtgcac acagcccagc ttggagcgaa cgacctacac cgaactgaga tacctacagc    6420
gtgagctatg agaaagcgcc acgcttcccg aagggagaaa ggcggacagg tatccggtaa    6480
gcggcagggt cggaacagga gagcgcacga gggagcttcc agggggaaac gcctggtatc    6540
tttatagtcc tgtcgggttt cgccacctct gacttgagcg tcgatttttg tgatgctcgt    6600
caggggggcg gagcctatgg aaaaacgcca gcaacgcggc cttttacgg ttcctggcct    6660 tttgctggcc ttttgctcac atggctcgac agatct                              6696

<210> SEQ ID NO 101
<211> LENGTH: 6693
<212> TYPE: DNA
<213> ORGANISM: Artificial Sequence
<220> FEATURE:
<223> OTHER INFORMATION: pTarget GLucON Beta Porcine

<400> SEQUENCE: 101
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
```

-continued

```
agtaacgcca ataggqactt tccattgacg tcaatgggtg gagtatttac ggtaaactgc      360
ccacttggca gtacatcaag tgtatcatat gccaagtccg cccctattg acgtcaatga      420
cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg gggatttcca agtctccacc ccattgacgt     600
caatgggagt ttgttttggc accaaaatca acgggacttt ccaaaatgtc gtaacaactg     660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaaaattg gatctccatt cgccattcag   1080
gctgcgcaac tgctgggaag gacgatcaga gcgggcctct tcgctattac gccagctggc   1140
gaaagggacg tggcaagcaa ggcgattaag ttgagttacg ccaggatttt cccagtcacg   1200
acgttgtaaa acgacggcca gagaattata atacgactca ctatagggcg aattcgctag   1260
cgccgccacc atgggagtca agttctgtt tgccctgatc tgcatcgctg tggccgaggc    1320
caagcccacc gagaacaacg aagacttcaa catcgtggcc gtggccagca actttgcgac   1380
cacggatctc gatgctgacc gagggaagtt gcccggcaag aagctgccgc tggaggtgct   1440
caaagagatg gaagccaatg cccggaaagc tggctgcacc aggggctgtc tgatctgcct   1500
gtcccacatc aagtgcacgc ccaagatgaa gaagtggctc ccaggacgct gccacaccta   1560
cgaaggcgac aaagagtccg cacagggcgg cataggcgag gcgatcgtcg atattcctga   1620
gattcctggg ttcaaggact ggagccaat ggagcagttc atcgcacagg tcgatctgtg    1680
tgtggactgc acaactggct gcctcaaagg gcttgccaac gtgcagtgtt ctgacctgct   1740
caagaagtgg ctgccgcaac gctgtgcgac ctttgccagc aagatccagg ccaggtgga   1800
caagatcaag ggggccggtg gtgacgggcc cgggatgagc tatgatgtgc ttcgatacca   1860
acaaaggagc agcaatttgg catgtcagaa gctcctggga cagttgcctg ggactcctca   1920
atattgcctc gaagatagga tgaactttga ggtccctgag gagattatgc aaccaccaca   1980
attccagaag gaagatgcag tattgattat ccacgagatg ctccagcaga tcttcggcat   2040
tctcagaaga aatttctcta gcactggctg gaatgaaacc gtcattaaga ctatccttgt   2100
ggaacttgat gggcagatgg atgacctgga gacaatcctg aggaaatca tggaggagga    2160
aaatttcccc aggggagaca tgaccattct tcacctgaag aaatattact tgagcattct   2220
gcagtacctg aagtccaagg agtacagaag ctgtgcctgg acagtcgtcc aagtggaaat   2280
cctcaggaac ttttctttcc ttaacagact tacagattac ctccggaact gagcggccgc   2340
gaattccaag cttgagtatt ctatcgtgtc acctaaataa cttggcgtaa tcatggtcat   2400
atctgttcc tgtgtgaaat tgttatccgc tcacaattcc acacaacata cgagccggaa    2460
gcataaagtg taaagcctgg ggtgcctaat gagtgagcta actcacatta attgcgttgc   2520
gcgatgcttc cattttgtga gggttaatgc ttcgagaaga catgataaga tacattgatg   2580
agtttggaca aaccacaaca agaatgcagt gaaaaaaatg ctttatttgt gaaatttgtg   2640
atgctattgc tttatttgta accattataa gctgcaataa acaagttaac aacaacaatt   2700
```

```
gcattcattt tatgtttcag gttcagggggg agatgtggga ggttttttaa agcaagtaaa    2760
acctctacaa atgtggtaaa atccgataag gatcgattcc ggagcctgaa tggcgaatgg    2820
acgcgccctg tagcggcgca ttaagcgcgg cgggtgtggt ggttacgcgc acgtgaccgc    2880
tacacttgcc agcgccctag cgcccgctcc tttcgctttc ttcccttcct ttctcgccac    2940
gttcgccggc tttccccgtc aagctctaaa tcggggctc cctttagggt tccgatttag     3000
tgctttacgg cacctcgacc ccaaaaaact tgattagggt gatggttcac gtagtgggcc    3060
atcgccctga tagacggttt ttcgcccttt gacgttggag tccacgttct ttaatagtgg    3120
actcttgttc caaactggaa caacactcaa ccctatctcg gtctattctt ttgatttata    3180
agggattttg ccgatttcgg cctattggtt aaaaaatgag ctgatttaac aaaaatttaa    3240
cgcgaatttt aacaaaatat taacgcttac aatttcgcct gtgtaccttc tgaggcggaa    3300
agaaccagct gtggaatgtg tgtcagttag ggtgtggaaa gtccccaggc tccccagcag    3360
gcagaagtat gcaaagcatg catctcaatt agtcagcaac caggtgtgga aagtccccag    3420
gctccccagc aggcagaagt atgcaaagca tgcatctcaa ttagtcagca accatagtcc    3480
cgcccctaac tccgcccatc ccgccccctaa ctccgcccag ttccgcccat tctccgcccc    3540
atggctgact aatttttttt atttatgcag aggccgaggc cgcctcggcc tctgagctat    3600
tccagaagta gtgaggaggc ttttttggag gcctaggctt ttgcaaaaag cttgattctt    3660
ctgacacaac agtctcgaac ttaaggctag agccaccatg attgaacaag atggattgca    3720
cgcaggttct ccggccgctt gggtggagag gctattcggc tatgactggg cacaacagac    3780
aatcggctgc tctgatgccg ccgtgttccg gctgtcagcg caggggcgcc cggttctttt    3840
tgtcaagacc gacctgtccg gtgccctgaa tgaactgcag gacgaggcag cgcggctatc    3900
gtggctggcc acgacgggcg ttccttgcgc agctgtgctc gacgttgtca ctgaagcggg    3960
aagggactgg ctgctattgg gcgaagtgcc ggggcaggat ctcctgtcat ctcaccttgc    4020
tcctgccgag aaagtatcca tcatggctga tgcaatgcgg cggctgcata cgcttgatcc    4080
ggctacctgc ccattcgacc accaagcgaa acatcgcatc gagcgagcac gtactcggat    4140
ggaagccggt cttgtcgatc aggatgatct ggacgaagag catcagggc tcgcgccagc     4200 cgaactgttc gccaggctca aggcgcgcat gcccgacggc gaggatctcg tcgtgaccca    4260
tggcgatgcc tgcttgccga atatcatggt ggaaaatggc cgcttttctg gattcatcga    4320
ctgtggccgg ctgggtgtgg cggaccgcta tcaggacata gcgttggcta cccgtgatat    4380
tgctgaagag cttggcggcg aatgggctga ccgcttcctc gtgctttacg gtatcgccgc    4440
tcccgattcg cagcgcatcg ccttctatcg ccttcttgac gagttcttct gagcgggact    4500
ctggggttcg aaatgaccga ccaagcgacg cccaacctgc catcacgatg gccgcaataa    4560
aatatcttta ttttcattac atctgtgtgt tggttttttg tgtgaagatc gcgtatggt     4620 gcactctcag tacaatctgc tctgatgccg catagttaag ccagcccga cacccgccaa     4680 cacccgctga cgcgccctga cgggcttgtc tgctcccggc atccgcttac agacaagctg    4740
tgaccgtctc cgggagctgc atgtgtcaga ggttttcacc gtcatcaccg aaacgcgcga    4800
gacgaaaggg cctcgtgata cgcctatttt tataggttaa tgtcatgata ataatggttt    4860
cttagacgtc aggtggcact tttcggggaa atgtgcgcgg aacccctatt tgtttatttt    4920
tctaaataca ttcaaatatg tatccgctca tgagacaata accctgataa atgcttcaat    4980
aatattgaaa aaggaagagt atgagtattc aacatttccg tgtcgccctt attcccttt     5040
```

```
ttgcggcatt ttgccttcct gtttttgctc acccagaaac gctggtgaaa gtaaaagatg      5100
ctgaagatca gttgggtgca cgagtgggtt acatcgaact ggatctcaac agcggtaaga      5160
tccttgagag ttttcgcccc gaagaacgtt ttccaatgat gagcactttt aaagttctgc      5220
tatgtggcgc ggtattatcc cgtattgacg ccgggcaaga gcaactcggt cgccgcatac      5280
actattctca gaatgacttg gttgagtact caccagtcac agaaaagcat cttacggatg      5340
gcatgacagt aagagaatta tgcagtgctg ccataaccat gagtgataac actgcggcca      5400
acttacttct gacaacgatc ggaggaccga aggagctaac cgcttttttg cacaacatgg      5460
gggatcatgt aactcgcctt gatcgttggg aaccggagct gaatgaagcc ataccaaacg      5520
acgagcgtga caccacgatg cctgtagcaa tggcaacaac gttgcgcaaa ctattaactg      5580
gcgaactact tactctagct tcccggcaac aattaataga ctggatggag gcggataaag      5640
ttgcaggacc acttctgcgc tcggcccttc cggctggctg gtttattgct gataaatctg      5700
gagccggtga gcgtgggtct cgcggtatca ttgcagcact ggggccagat ggtaagccct      5760
cccgtatcgt agttatctac acgacgggga gtcaggcaac tatggatgaa cgaaatagac      5820
agatcgctga gataggtgcc tcactgatta agcattggta actgtcagac caagtttact      5880
catatatact ttagattgat ttaaaacttc atttttaatt taaaaggatc taggtgaaga      5940
tcctttttga taatctcatg accaaaatcc cttaacgtga gttttcgttc cactgagcgt      6000
cagaccccgt agaaaagatc aaaggatctt cttgagatcc ttttttctg cgcgtaatct      6060 gctgcttgca acaaaaaaa ccaccgctac cagcggtggt ttgtttgccg gatcaagagc      6120
taccaactct ttttccgaag gtaactggct tcagcagagc gcagatacca atactgtcc       6180 ttctagtgta gccgtagtta ggccaccact tcaagaactc tgtagcaccg cctacatacc      6240
tcgctctgct aatcctgtta ccagtggctg ctgccagtgg cgataagtcg tgtcttaccg      6300
ggttggactc aagacgatag ttaccggata aggcgcagcg gtcgggctga acggggggtt      6360
cgtgcacaca gcccagcttg gagcgaacga cctacaccga actgagatac ctacagcgtg      6420
agctatgaga aagcgccacg cttcccgaag ggagaaaggc ggacaggtat ccggtaagcg      6480
gcagggtcgg aacaggagag cgcacgaggg agcttccagg gggaaacgcc tggtatcttt      6540
atagtcctgt cgggtttcgc cacctctgac ttgagcgtcg atttttgtga tgctcgtcag      6600
gggggcggag cctatggaaa aacgccagca acgcggcctt tttacggttc ctggccttt       6660 gctggccttt tgctcacatg gctcgacaga tct                                   6693

<210> SEQ ID NO 102
<211> LENGTH: 6624
<212> TYPE: DNA
<213> ORGANISM: Artificial Sequence
<220> FEATURE:
<223> OTHER INFORMATION: pTarget GLucON Gamma Bovine

<400> SEQUENCE: 102
tcaatattgg ccattagcca tattattcat tggttatata gcataaatca atattggcta        60
ttggccattg catacgttgt atctatatca taatatgtac atttatattg gctcatgtcc       120
aatatgaccg ccatgttggc attgattatt gactagttat taatagtaat caattacggg       180
gtcattagtt catagcccat atatggagtt ccgcgttaca taacttacgg taaatggccc       240
gcctggctga ccgcccaacg acccccgccc attgacgtca ataatgacgt atgttcccat       300
agtaacgcca atagggactt tccattgacg tcaatgggtg gagtatttac ggtaaactgc       360
ccacttggca gtacatcaag tgtatcatat gccaagtccg ccccctattg acgtcaatga       420
```

```
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaaaattg gatctccatt cgccattcag   1080
gctgcgcaac tgctgggaag gacgatcaga gcgggcctct tcgctattac gccagctggc   1140
gaaagggacg tggcaagcaa ggcgattaag ttgagttacg ccaggatttt cccagtcacg   1200
acgttgtaaa acgacggcca gagaattata atacgactca ctatagggcg aattcgctag   1260
cgccgccacc atgggagtca agttctgtt tgccctgatc tgcatcgctg tggccgaggc   1320
caagcccacc gagaacaacg aagacttcaa catcgtggcc gtggccagca actttgcgac   1380
cacggatctc gatgctgacc gagggaagtt gcccggcaag aagctgccgc tggaggtgct   1440
caaagagatg gaagccaatg cccggaaagc tggctgcacc aggggctgtc tgatctgcct   1500
gtcccacatc aagtgcacgc ccaagatgaa gaagtggctc ccaggacgct gccacaccta   1560
cgaaggcgac aaagagtccg cacagggcgg cataggcgag gcgatcgtcg atattcctga   1620
gattcctggg ttcaaggact tggagccaat ggagcagttc atcgcacagg tcgatctgtg   1680
tgtggactgc acaactggct gcctcaaagg gcttgccaac gtgcagtgtt ctgacctgct   1740
caagaagtgg ctgccgcaac gctgtgcgac cttTgccagc aagatccagg gccaggtgga   1800
caagatcaag ggggccggtg gtgacgggcc ccagggccaa ttttttagag aaatagaaaa   1860
cttaaaggag tattttaatg caagtagccc agatgtagct aagggtgggc ctctcttctc   1920
agaaattttg aagaattgga agatgaaaag tgacaaaaaa attattcaga gccaaattgt   1980
ctccttctac ttcaaactct tgaaaacct caaagataac caggtcattc aaaggagcat   2040
ggatataatc aagcaagaca tgtttcagaa gttcttgaat ggcagctctg agaaactgga   2100
ggacttcaaa aagctgattc aaattccggt ggatgatctc cagatccagc gcaaagccat   2160
aaatgaactc atcaaagtga tgaatgacct gtcaccaaaa tctaacctca gaaagcggaa   2220
gagaagtcag aatctctttc gaggccggag agcatcaacg taagcggccg cgaattccaa   2280
gcttgagtat tctatcgtgt cacctaaata acttggcgta atcatggtca tatctgtttc   2340
ctgtgtgaaa ttgttatccg ctcacaattc cacacaacat acgagccgga agcataaagt   2400
gtaaagcctg gggtgcctaa tgagtgagct aactcacatt aattgcgttg cgcgatgctt   2460
ccatttgtg agggttaatg cttcgagaag acatgataag atacattgat gagtttggac   2520
aaaccacaac aagaatgcag tgaaaaaaat gctttatttg tgaaatttgt gatgctattg   2580
ctttatttgt aaccattata agctgcaata acaagttaa caacaacaat tgcattcatt   2640
ttatgtttca ggttcagggg gagatgtggg aggtttttta aagcaagtaa aacctctaca   2700
aatgtggtaa aatccgataa ggatcgattc cggagcctga atggcgaatg gacgcgccct   2760
```

```
gtagcggcgc attaagcgcg gcgggtgtgg tggttacgcg cacgtgaccg ctacacttgc    2820 cagcgccta  gcgcccgctc ctttcgcttt cttcccttcc tttctcgcca cgttcgccgg    2880
cttcccccgt caagctctaa atcgggggct ccctttaggg ttccgattta gtgctttacg    2940
gcacctcgac cccaaaaaac ttgattaggg tgatggttca cgtagtgggc catcgccctg    3000
atagacggtt tttcgccctt tgacgttgga gtccacgttc tttaatagtg gactcttgtt    3060
ccaaactgga acaacactca accctatctc ggtctattct tttgatttat aagggatttt    3120
gccgatttcg gcctattggt taaaaaatga gctgatttaa caaaaattta cgcgaatttt    3180
taacaaaata ttaacgctta caatttcgcc tgtgtacctt ctgaggcgga agaaccagc    3240 tgtggaatgt gtgtcagtta gggtgtggaa agtccccagg ctccccagca ggcagaagta    3300
tgcaaagcat gcatctcaat tagtcagcaa ccaggtgtgg aaagtcccca ggctccccag    3360
caggcagaag tatgcaaagc atgcatctca attagtcagc aaccatagtc ccgcccctaa    3420
ctccgcccat cccgcccta  actccgccca gttccgccca ttctccgccc catggctgac    3480 taatttttt  tatttatgca gaggccgagg ccgcctcggc ctctgagcta ttccagaagt    3540
agtgaggagg cttttttgga ggcctaggct tttgcaaaaa gcttgattct tctgacacaa    3600
cagtctcgaa cttaaggcta gagccaccat gattgaacaa gatggattgc acgcaggttc    3660
tccggccgct tgggtggaga ggctattcgg ctatgactgg gcacaacaga caatcggctg    3720
ctctgatgcc gccgtgttcc ggctgtcagc gcaggggcgc ccggttcttt tgtcaagac    3780 cgacctgtcc ggtgccctga tgaactgca  ggacgaggca gcgcggctat cgtggctggc    3840
cacgacgggc gttccttgcg cagctgtgct cgacgttgtc actgaagcgg gaagggactg    3900
gctgctattg ggcgaagtgc cggggcagga tctcctgtca tctcaccttg ctcctgccga    3960
gaaagtatcc atcatggctg atgcaatgcg gcggctgcat acgcttgatc cggctacctg    4020
cccattcgac caccaagcga acatcgcat  cgagcgagca cgtactcgga tggaagccgg    4080
tcttgtcgat caggatgatc tggacgaaga gcatcagggg ctcgcgccag ccgaactgtt    4140
cgccaggctc aaggcgcgca tgcccgacgg cgaggatctc gtcgtgaccc atggcgatgc    4200
ctgcttgccg aatatcatgg tggaaaatgg ccgcttttct ggattcatcg actgtggccg    4260
gctgggtgtg gcggaccgct atcaggacat agcgttggct acccgtgata ttgctgaaga    4320
gcttggcggc gaatgggctg accgcttcct cgtgctttac ggtatcgccg ctcccgattc    4380
gcagcgcatc gccttctatc gccttcttga cgagttcttc tgagcgggac tctggggttc    4440
gaaatgaccg accaagcgac gcccaacctg ccatcacgat ggccgcaata aaatatcttt    4500
attttcatta catctgtgtg ttggttttt  gtgtgaagat ccgcgtatgg tgcactctca    4560
gtacaatctg ctctgatgcc gcatagttaa gccagccccg acaccgcca  acacccgctg    4620 acgcgccctg acgggcttgt ctgctcccgg catccgctta cagacaagct gtgaccgtct    4680
ccgggagctg catgtgtcag aggttttcac cgtcatcacc gaaacgcgcg agacgaaagg    4740
gcctcgtgat acgcctattt ttataggtta atgtcatgat aataatggtt cttagacgt    4800 caggtggcac ttttcgggga atgtgcgcg  gaacccctat ttgtttattt ttctaaatac    4860
attcaaatat gtatccgctc atgagacaat aaccctgata aatgcttcaa taatattgaa    4920
aaaggaagag tatgagtatt caacatttcc gtgtcgccct tattccctt  tttgcggcat    4980 tttgccttcc tgttttgct  cacccagaaa cgctggtgaa agtaaaagat gctgaagatc    5040
agttgggtgc acgagtgggt tacatcgaac tggatctcaa cagcggtaag atccttgaga    5100
gttttcgccc cgaagaacgt tttccaatga tgagcacttt taaagttctg ctatgtggcg    5160
```

```
cggtattatc ccgtattgac gccgggcaag agcaactcgg tcgccgcata cactattctc    5220
agaatgactt ggttgagtac tcaccagtca cagaaaagca tcttacggat ggcatgacag    5280
taagagaatt atgcagtgct gccataacca tgagtgataa cactgcggcc aacttacttc    5340
tgacaacgat cggaggaccg aaggagctaa ccgcttttt gcacaacatg ggggatcatg    5400
taactcgcct tgatcgttgg aaccggagc tgaatgaagc cataccaaac gacgagcgtg    5460
acaccacgat gcctgtagca atggcaacaa cgttgcgcaa actattaact ggcgaactac    5520
ttactctagc ttcccggcaa caattaatag actggatgga ggcggataaa gttgcaggac    5580
cacttctgcg ctcggccctt ccggctggct ggtttattgc tgataaatct ggagccggtg    5640
agcgtgggtc tcgcggtatc attgcagcac tggggccaga tggtaagccc tcccgtatcg    5700
tagttatcta cacgacgggg agtcaggcaa ctatggatga acgaaataga cagatcgctg    5760
agataggtgc ctcactgatt aagcattggt aactgtcaga ccaagtttac tcatatatac    5820
tttagattga tttaaaactt cattttaat ttaaaaggat ctaggtgaag atcctttttg    5880
ataatctcat gaccaaaatc ccttaacgtg agttttcgtt ccactgagcg tcagaccccg    5940
tagaaaagat caaaggatct tcttgagatc ctttttttct gcgcgtaatc tgctgcttgc    6000
aaacaaaaaa accaccgcta ccagcggtgg tttgtttgcc ggatcaagag ctaccaactc    6060
tttttccgaa ggtaactggc ttcagcagag cgcagatacc aaatactgtc cttctagtgt    6120
agccgtagtt aggccaccac ttcaagaact ctgtagcacc gcctacatac ctcgctctgc    6180
taatcctgtt accagtggct gctgccagtg cgataagtc gtgtcttacc gggttggact    6240
caagacgata gttaccggat aaggcgcagc ggtcgggctg aacggggggt tcgtgcacac    6300
agcccagctt ggagcgaacg acctacaccg aactgagata cctacagcgt gagctatgag    6360
aaagcgccac gcttcccgaa gggagaaagg cggacaggta tccggtaagc ggcagggtcg    6420
gaacaggaga cgcacgagg gagcttccag ggggaaacgc ctggtatctt tatagtcctg    6480
tcgggtttcg ccacctctga cttgagcgtc gatttttgtg atgctcgtca gggggcgga    6540 gcctatggaa aaacgccagc aacgcggcct ttttacggtt cctggccttt tgctggcctt    6600
ttgctcacat ggctcgacag atct                                          6624
```

<210> SEQ ID NO 103
<211> LENGTH: 6723
<212> TYPE: DNA
<213> ORGANISM: Artificial Sequence
<220> FEATURE:
<223> OTHER INFORMATION: pTarget GLucON Lambda Bovine

<400> SEQUENCE: 103

```
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg cccccattg acgtcaatga    420 cggtaaatgg cccgcctggc attatgccca gtacatgacc ttcgggact tcctacttg    480 gcagtacatc tacgtattag tcatcgctat taccatggtg atgcggtttt ggcagtacac    540
```

```
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaaaattg gatctccatt cgccattcag   1080
gctgcgcaac tgctgggaag gacgatcaga gcgggcctct tcgctattac gccagctggc   1140
gaaagggacg tggcaagcaa ggcgattaag ttgagttacg ccaggatttt cccagtcacg   1200
acgttgtaaa acgacggcca gagaattata atacgactca ctatagggcg aattcgctag   1260
cgccgccacc atgggagtca agttctgttt tgccctgatc tgcatcgctg tggccgaggc   1320
caagcccacc gagaacaacg aagacttcaa catcgtggcc gtggcagca actttgcgac   1380 cacggatctc gatgctgacc gagggaagtt gcccggcaag aagctgccgc tggaggtgct   1440
caaagagatg gaagccaatg cccggaaagc tggctgcacc aggggctgtc tgatctgcct   1500
gtcccacatc aagtgcacgc ccaagatgaa gaagtggctc ccaggacgct gccacaccta   1560
cgaaggcgac aaagagtccg cacagggcgg cataggcgag gcgatcgtcg atattcctga   1620
gattcctggg ttcaaggact tggagccaat ggagcagttc atcgcacagg tcgatctgtg   1680
tgtggactgc acaactggct gcctcaaagg gcttgccaac gtgcagtgtt ctgacctgct   1740
caagaagtgg ctgccgcaac gctgtgcgac ctttgccagc aagatccagg ccaggtgga   1800 caagatcaag ggggccggtg gtgacgggcc caggacagga gcagttcctg tgccctctgc   1860
ccccagggcc ctcccacctg ccaggggctg ccacgtggcc cagttcaagt ctctgtcccc   1920
tcaagagctg caggccttca agacggccag ggatgccttt gaagactcgt tcttgccaaa   1980
ggactgggac tgcagcaccc accttttccc caggacccgg gacctgaagc acctgcaggt   2040
gtgggagcgc cctgtggctc tggaggcaga gctggccctg acactgacgg tcctggaggc   2100
catggctaac tcatccctgg ccacagcct ggagcagccc cttctcacgc tgcagaacat   2160
ccactccaag ctccaggcct gtgtcccagc tcagcccaca gcaagctcca ggccccgggg   2220
ccgcctccac cactggctgc accgcctcca ggagcccgg aaggagtccc aggactgcct   2280
cgaagcctct gtgatgttca acctcctccg cctcctcacc cgggacctga atgtgttgc   2340 cagcggagac cagtgtgtct gagcggccgc gaattccaag cttgagtatt ctatcgtgtc   2400
acctaaataa cttggcgtaa tcatggtcat atctgtttcc tgtgtgaaat tgttatccgc   2460
tcacaattcc acacaacata cgagccggaa gcataaagtg taaagcctgg ggtgcctaat   2520
gagtgagcta actcacatta attgcgttgc gcgatgcttc cattttgtga gggttaatgc   2580
ttcgagaaga catgataaga tacattgatg agtttggaca aaccacaaca agaatgcagt   2640
gaaaaaaatg ctttatttgt gaaatttgtg atgctattgc tttatttgta accattataa   2700
gctgcaataa acaagttaac aacaacaatt gcattcattt tatgtttcag gttcaggggg   2760
agatgtggga ggttttttaa agcaagtaaa acctctacaa atgtggtaaa atccgataag   2820
gatcgattcc ggagcctgaa tggcgaatgg acgcgccctg tagcggcgca ttaagcgcgg   2880
cgggtgtggt ggttacgcgc acgtgaccgc tacacttgcc agcgccctag cgcccgctcc   2940
```

```
tttcgctttc ttccctccct ttctcgccac gttcgccggc tttccccgtc aagctctaaa  3000
tcggggcctc cctttagggt tccgatttag tgctttacgg cacctcgacc ccaaaaaact  3060
tgattagggt gatggttcac gtagtgggcc atcgccctga tagacggttt ttcgcccttt  3120
gacgttggag tccacgttct ttaatagtgg actcttgttc caaactggaa caacactcaa  3180
ccctatctcg gtctattctt ttgatttata agggattttg ccgatttcgg cctattggtt  3240
aaaaaatgag ctgatttaac aaaaatttaa cgcgaatttt aacaaaatat taacgcttac  3300
aatttcgcct gtgtaccttc tgaggcggaa agaaccagct gtggaatgtg tgtcagttag  3360
ggtgtggaaa gtccccaggc tccccagcag gcagaagtat gcaaagcatg catctcaatt  3420
agtcagcaac caggtgtgga aagtccccag gctccccagc aggcagaagt atgcaaagca  3480
tgcatctcaa ttagtcagca accatagtcc cgccctaac tccgcccatc cgcccctaa  3540
ctccgcccag ttccgcccat tctccgcccc atggctgact aatttttttt atttatgcag  3600
aggccgaggc cgcctcggcc tctgagctat tccagaagta gtgaggaggc ttttttggag  3660
gcctaggctt ttgcaaaaag cttgattctt ctgacacaac agtctcgaac ttaaggctag  3720
agccaccatg attgaacaag atggattgca cgcaggttct ccggccgctt gggtggagag  3780
gctattcggc tatgactggg cacaacagac aatcggctgc tctgatgccg ccgtgttccg  3840
gctgtcagcg caggggcgcc cggttctttt tgtcaagacc gacctgtccg gtgccctgaa  3900
tgaactgcag gacgaggcag cgcggctatc gtggctggcc acgacgggcg ttccttgcgc  3960
agctgtgctc gacgttgtca ctgaagcggg aagggactgg ctgctattgg gcgaagtgcc  4020
ggggcaggat ctcctgtcat ctcaccttgc tcctgccgag aaagtatcca tcatggctga  4080
tgcaatgcgg cggctgcata cgcttgatcc ggctacctgc ccattcgacc accaagcgaa  4140
acatcgcatc gagcgagcac gtactcggat ggaagccggt cttgtcgatc aggatgatct  4200
ggacgaagag catcagggc tcgcgccagc cgaactgttc gccaggctca aggcgcgcat  4260
gcccgacggc gaggatctcg tcgtgaccca tggcgatgcc tgcttgccga atatcatggt  4320
ggaaaatggc cgcttttctg gattcatcga ctgtggccgg ctgggtgtgg cggaccgcta  4380
tcaggacata gcgttggcta cccgtgatat tgctgaagag cttggcggcg aatgggctga  4440
ccgcttcctc gtgctttacg gtatcgccgc tcccgattcg cagcgcatcg ccttctatcg  4500
ccttcttgac gagttcttct gagcgggact ctggggttcg aaatgaccga ccaagcgacg  4560
cccaacctgc catcacgatg gccgcaataa aatatcttta ttttcattac atctgtgtgt  4620
tggttttttg tgtgaagatc cgcgtatggt gcactctcag tacaatctgc tctgatgccg  4680
catagttaag ccagccccga cacccgccaa cacccgctga cgcgccctga cgggcttgtc  4740
tgctcccggc atccgcttac agacaagctg tgaccgtctc cggagctgc atgtgtcaga  4800
ggttttcacc gtcatcaccg aaacgcgcga gacgaaaggg cctcgtgata cgcctatttt  4860
tataggttaa tgtcatgata taatggttt cttagacgtc aggtggcact tttcggggaa  4920
atgtgcgcgg aacccctatt tgtttatttt tctaaataca ttcaaatatg tatccgctca  4980
tgagacaata accctgataa atgcttcaat aatattgaaa aaggaagagt atgagtattc  5040
aacatttccg tgtcgccctt attcccttt ttgcggcatt ttgccttcct gttttgctc  5100
acccagaaac gctggtgaaa gtaaaagatg ctgaagatca gttgggtgca cgagtgggtt  5160
acatcgaact ggatctcaac agcggtaaga tccttgagag ttttcgcccc gaagaacgtt  5220
ttccaatgat gagcactttt aaagttctgc tatgtggcgc ggtattatcc cgtattgacg  5280
```

| | |
|---|---|
| ccgggcaaga gcaactcggt cgccgcatac actattctca gaatgacttg gttgagtact | 5340 |
| caccagtcac agaaaagcat cttacggatg gcatgacagt aagagaatta tgcagtgctg | 5400 |
| ccataaccat gagtgataac actgcggcca acttacttct gacaacgatc ggaggaccga | 5460 |
| aggagctaac cgcttttttg cacaacatgg gggatcatgt aactcgcctt gatcgttggg | 5520 |
| aaccggagct gaatgaagcc ataccaaacg acgagcgtga ccaccgatg cctgtagcaa | 5580 |
| tggcaacaac gttgcgcaaa ctattaactg gcgaactact tactctagct tcccggcaac | 5640 |
| aattaataga ctggatggag gcggataaag ttgcaggacc acttctgcgc tcggcccttc | 5700 |
| cggctggctg gtttattgct gataaatctg gagccggtga gcgtgggtct cgcggtatca | 5760 |
| ttgcagcact ggggccagat ggtaagccct cccgtatcgt agttatctac acgacgggga | 5820 |
| gtcaggcaac tatggatgaa cgaaatagac agatcgctga gataggtgcc tcactgatta | 5880 |
| agcattggta actgtcagac caagtttact catatatact ttagattgat ttaaaacttc | 5940 |
| atttttaatt taaaaggatc taggtgaaga tcctttttga taatctcatg accaaaatcc | 6000 |
| cttaacgtga gttttcgttc cactgagcgt cagacccgt agaaaagatc aaaggatctt | 6060 |
| cttgagatcc ttttttttctg cgcgtaatct gctgcttgca acaaaaaaa ccaccgctac | 6120 |
| cagcggtggt ttgtttgccg gatcaagagc taccaactct ttttccgaag gtaactggct | 6180 |
| tcagcagagc gcagatacca atactgtcc ttctagtgta gccgtagtta ggccaccact | 6240 |
| tcaagaactc tgtagcaccg cctacatacc tcgctctgct aatcctgtta ccagtggctg | 6300 |
| ctgccagtgg cgataagtcg tgtcttaccg ggttggactc aagacgatag ttaccggata | 6360 |
| aggcgcagcg gtcgggctga cggggggtt cgtgcacaca gcccagcttg gagcgaacga | 6420 |
| cctacaccga actgagatac ctacagcgtg agctatgaga aagcgccacg cttcccgaag | 6480 |
| ggagaaaggc ggacaggtat ccggtaagcg gcagggtcgg aacaggagag cgcacgaggg | 6540 |
| agcttccagg gggaaacgcc tggtatcttt atagtcctgt cgggtttcgc cacctctgac | 6600 |
| ttgagcgtcg atttttgtga tgctcgtcag ggggcggag cctatggaaa aacgccagca | 6660 |
| acgcggcctt tttacggttc ctggccttt gctggccttt tgctcacatg gctcgacaga | 6720 |
| tct | 6723 |

<210> SEQ ID NO 104
<211> LENGTH: 6201
<212> TYPE: DNA
<213> ORGANISM: Artificial Sequence
<220> FEATURE:
<223> OTHER INFORMATION: pTarget porcine interferon alpha

<400> SEQUENCE: 104

| | |
|---|---|
| tcaatattgg ccattagcca tattattcat tggttatata gcataaatca atattggcta | 60 |
| ttggccattg catacgttgt atctatatca taatatgtac atttatattg gctcatgtcc | 120 |
| aatatgaccg ccatgttggc attgattatt gactagttat taatagtaat caattacggg | 180 |
| gtcattagtt catagcccat atatggagtt ccgcgttaca taacttacgg taaatggccc | 240 |
| gcctggctga ccgcccaacg acccccgccc attgacgtca ataatgacgt atgttcccat | 300 |
| agtaacgcca atagggactt tccattgacg tcaatgggtg gagtatttac ggtaaactgc | 360 |
| ccacttggca gtacatcaag tgtatcatat gccaagtccg cccccctattg acgtcaatga | 420 |
| cggtaaatgg cccgcctggc attatgccca gtacatgacc ttcgggact ttcctacttg | 480 |
| gcagtacatc tacgtattag tcatcgctat taccatggtg atgcggtttt ggcagtacac | 540 |
| caatgggcgt ggatagcggt ttgactcacg gggatttcca agtctccacc ccattgacgt | 600 |

```
caatgggagt tgttttggc accaaaatca acgggacttt ccaaaatgtc gtaacaactg      660
cgatcgcccg ccccgttgac gcaaatgggc ggtaggcgtg tacggtggga ggtctatata      720
agcagagctc gtttagtgaa ccgtcagatc actagaagct ttattgcggt agtttatcac      780
agttaaattg ctaacgcagt cagtgcttct gacacaacag tctcgaactt aagctgcagt      840
gactctctta aggtagcctt gcagaagttg gtcgtgaggc actgggcagg taagtatcaa      900
ggttacaaga caggtttaag gagaccaata gaaactgggc ttgtcgagac agagaagact      960
cttgcgtttc tgataggcac ctattggtct tactgacatc cactttgcct ttctctccac     1020
aggtgtccac tcccagttca attacagctc ttaaaaattg gatctccatt cgccattcag     1080
gctgcgcaac tgctgggaag gacgatcaga gcgggcctct tcgctattac gccagctggc     1140
gaaagggacg tggcaagcaa ggcgattaag ttgagttacg ccaggatttt cccagtcacg     1200
acgttgtaaa acgacggcca gagaattata atacgactca ctatagggcg gatccgctag     1260
cgccgccacc atggcccaa cctcagcctt cctcacggcc ctggtgctac tcagctgcaa     1320
tgccatctgc tctctgggct gtgacctgcc tcagacccac agcctggctc acaccagagc     1380
cctgaggctc ctggcacaaa tgaggagaat ctctcccttc cctgcctgg accacagaag     1440 ggactttggt tcccctcatg aggcttttgg gggcaaccag gtccagaagg ctcaagccat     1500
ggctctggtg catgagatgc tccagcagac cttccagctc ttcagcacag agggctcggc     1560
tgctgcctgg aatgagagcc tcctgcacca gttctgcact ggactggatc agcagctcag     1620
ggacctggaa gcctgtgtca tgcaggaggc ggggctggaa gggacccccc tgctggagga     1680
ggactccatc ctggctgtga ggaaatactt ccacagactc acctctatc tgcaagagaa     1740 gagctacagc cctgtgcct gggagatcgt cagggcagaa gtcatgagat ccttctcttc     1800
ctccagaaac ctgcaagaca gactcaggaa gaaggagtga gcggccgcga attccaagct     1860
tgagtattct atcgtgtcac ctaaataact tggcgtaatc atggtcatat ctgtttcctg     1920
tgtgaaattg ttatccgctc acaattccac acaacatacg agccgaagc ataaagtgta     1980 aagcctgggg tgcctaatga gtgagctaac tcacattaat tgcgttcgc gatgcttcca     2040 ttttgtgagg gttaatgctt cgagaagaca tgataagata cattgatgag tttggacaaa     2100
ccacaacaag aatgcagtga aaaaaatgct ttatttgtga aatttgtgat gctattgctt     2160
tatttgtaac cattataagc tgcaataaac aagttaacaa caacaattgc attcatttta     2220
tgtttcaggt tcaggggag atgtgggagg ttttttaaag caagtaaaac ctctacaaat     2280
gtggtaaaat ccgataagga tcgattccgg agcctgaatg gcgaatggac gcgccctgta     2340
gcggcgcatt aagcgcggcg ggtgtggtgg ttacgcgcac gtgaccgcta cacttgccag     2400
cgccctagcg cccgctcctt tcgctttctt cccttccttt ctcgccacgt tcgccggctt     2460
tccccgtcaa gctctaaatc gggggctccc tttagggttc cgatttagtg ctttacggca     2520
cctcgacccc aaaaaacttg attagggtga tggttcacgt agtgggccat cgccctgata     2580
gacggttttt cgccctttga cgttggagtc cacgttcttt aatagtggac tcttgttcca     2640
aactggaaca acactcaacc ctatctcggt ctattctttt gatttataag ggattttgcc     2700
gatttcggcc tattggttaa aaaatgagct gatttaacaa aaatttaacg cgaattttaa     2760
caaaatatta acgcttacaa tttcgcctgt gtaccttctg aggcggaaag aaccagctgt     2820
ggaatgtgtg tcagttaggg tgtggaaagt ccccaggctc cccagcaggc agaagtatgc     2880
aaagcatgca tctcaattag tcagcaacca ggtgtggaaa gtccccaggc tccccagcag     2940
```

```
gcagaagtat gcaaagcatg catctcaatt agtcagcaac catagtcccg cccctaactc      3000
cgcccatccc gccctaact ccgcccagtt ccgcccattc tccgcccat ggctgactaa        3060 tttttttat ttatgcagag gccgaggccg cctcggcctc tgagctattc cagaagtagt       3120
gaggaggctt ttttggaggc ctaggctttt gcaaaaagct tgattcttct gacacaacag     3180
tctcgaactt aaggctagag ccaccatgat tgaacaagat ggattgcacg caggttctcc      3240
ggccgcttgg gtggagaggc tattcggcta tgactgggca caacagacaa tcggctgctc      3300
tgatgccgcc gtgttccggc tgtcagcgca ggggcgcccg gttcttttg tcaagaccga       3360 cctgtccggt gccctgaatg aactgcagga cgaggcagcg cggctatcgt ggctggccac      3420
gacgggcgtt ccttgcgcag ctgtgctcga cgttgtcact gaagcgggaa gggactggct      3480
gctattgggc gaagtgccgg ggcaggatct cctgtcatct caccttgctc ctgccgagaa      3540
agtatccatc atggctgatg caatgcggcg gctgcatacg cttgatccgg ctacctgccc      3600
attcgaccac caagcgaaac atcgcatcga gcgagcacgt actcggatgg aagccggtct      3660
tgtcgatcag gatgatctgg acgaagagca tcagggctc gcgccagccg aactgttcgc       3720
caggctcaag gcgcgcatgc ccgacggcga ggatctcgtc gtgacccatg gcgatgcctg      3780
cttgccgaat atcatggtgg aaaatggccg cttttctgga ttcatcgact gtggccggct      3840
gggtgtggcg gaccgctatc aggacatagc gttggctacc cgtgatattg ctgaagagct      3900
tggcggcgaa tgggctgacc gcttcctcgt gctttacggt atcgccgctc ccgattcgca      3960
gcgcatcgcc ttctatcgcc ttcttgacga gttcttctga gcgggactct ggggttcgaa      4020
atgaccgacc aagcgacgcc caacctgcca tcacgatggc cgcaataaaa tatctttatt     4080
ttcattacat ctgtgtgttg gttttttgtg tgaagatccg cgtatggtgc actctcagta     4140
caatctgctc tgatgccgca tagttaagcc agccccgaca cccgccaaca cccgctgacg     4200
cgccctgacg ggcttgtctg ctcccggcat ccgcttacag acaagctgtg accgtctccg      4260
ggagctgcat gtgtcagagg ttttcaccgt catcaccgaa acgcgcgaga cgaaagggcc      4320
tcgtgatacg cctatttta taggttaatg tcatgataat aatggtttct tagacgtcag     4380
gtggcacttt tcggggaaat gtgcgcggaa cccctatttg tttatttttc taaatacatt     4440
caaatatgta tccgctcatg agacaataac cctgataaat gcttcaataa tattgaaaaa     4500
ggaagagtat gagtattcaa catttccgtg tcgcccttat ccctttttt gcggcatttt      4560 gccttcctgt ttttgctcac ccagaaacgc tggtgaaagt aaaagatgct gaagatcagt     4620
tgggtgcacg agtgggttac atcgaactgg atctcaacag cggtaagatc cttgagagtt     4680
ttcgccccga agaacgtttt ccaatgatga gcacttttaa agttctgcta tgtggcgcgg     4740
tattatcccg tattgacgcc gggcaagagc aactcggtcg ccgcatacac tattctcaga     4800
atgacttggt tgagtactca ccagtcacag aaaagcatct tacggatggc atgacagtaa     4860
gagaattatg cagtgctgcc ataaccatga gtgataacac tgcggccaac ttacttctga     4920
caacgatcgg aggaccgaag gagctaaccg cttttttgca caacatgggg gatcatgtaa     4980
ctcgccttga tcgttgggaa ccggagctga atgaagccat accaaacgac gagcgtgaca     5040
ccacgatgcc tgtagcaatg gcaacaacgt tgcgcaaact attaactggc gaactactta     5100
ctctagcttc ccggcaacaa ttaatagact ggatggaggc ggataaagtt gcaggaccac     5160
ttctgcgctc ggcccttccg gctggctggt ttattgctga taaatctgga gccggtgagc     5220
gtgggtctcg cggtatcatt gcagcactgg ggccagatgg taagccctcc cgtatcgtag     5280
ttatctacac gacggggagt caggcaacta tggatgaacg aaatagacag atcgctgaga     5340
```

```
taggtgcctc actgattaag cattggtaac tgtcagacca agtttactca tatatacttt    5400
agattgattt aaaacttcat ttttaattta aaaggatcta ggtgaagatc cttttttgata   5460 atctcatgac caaaatccct taacgtgagt tttcgttcca ctgagcgtca gaccccgtag    5520
aaaagatcaa aggatcttct tgagatcctt tttttctgcg cgtaatctgc tgcttgcaaa    5580
caaaaaaacc accgctacca gcggtggttt gtttgccgga tcaagagcta ccaactcttt    5640
ttccgaaggt aactggcttc agcagagcgc agataccaaa tactgtcctt ctagtgtagc    5700
cgtagttagg ccaccacttc aagaactctg tagcaccgcc tacatacctc gctctgctaa    5760
tcctgttacc agtggctgct gccagtggcg ataagtcgtg tcttaccggg ttggactcaa    5820
gacgatagtt accggataag cgcagcggt cgggctgaac ggggggttcg tgcacacagc     5880
ccagcttgga gcgaacgacc tacaccgaac tgagatacct acagcgtgag ctatgagaaa    5940
gcgccacgct tcccgaaggg agaaaggcgg acaggtatcc ggtaagcggc agggtcggaa    6000
caggagagcg cacgagggag cttccagggg gaaacgcctg gtatctttat agtcctgtcg    6060
ggtttcgcca cctctgactt gagcgtcgat ttttgtgatg ctcgtcaggg gggcggagcc    6120
tatgaaaaaa cgccagcaac gcggcctttt tacggttcct ggccttttgc tggccttttg    6180
ctcacatggc tcgacagatc t                                              6201

<210> SEQ ID NO 105
<211> LENGTH: 6192
<212> TYPE: DNA
<213> ORGANISM: Artificial Sequence
<220> FEATURE:
<223> OTHER INFORMATION: pTarget Porcine Interferon Beta

<400> SEQUENCE: 105
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg acccccgccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg ccccctattg acgtcaatga     420
cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg ggatttcca gtctccacc ccattgacgt       600 caatgggagt ttgttttggc accaaaatca acgggacttt ccaaaatgtc gtaacaactg     660
cgatcgcccg ccccgttgac gcaaatgggc ggtaggcgtg tacggtggga ggtctatata     720
agcagagctc gtttagtgaa ccgtcagatc actagaagct ttattgcggt agtttatcac     780
agttaaattg ctaacgcagt cagtgcttct gacacaacag tctcgaactt aagctgcagt     840
gactctctta aggtagcctt gcagaagttg gtcgtgaggc actgggcagg taagtatcaa     900
ggttacaaga caggtttaag gagaccaata gaaactgggc ttgtcgagac agagaagact     960
cttgcgtttc tgataggcac ctattggtct tactgacatc cactttgcct ttctctccac    1020
aggtgtccac tcccagttca attacagctc ttaaaaattg gatctccatt cgccattcag    1080
gctgcgcaac tgctgggaag gacgatcaga gcgggcctct tcgctattac gccagctggc    1140
```

```
gaaagggacg tggcaagcaa ggcgattaag ttgagttacg ccaggatttt cccagtcacg    1200
acgttgtaaa acgacggcca gagaattata atacgactca ctatagggcg gatccgctag    1260
cgccgccacc atggctaaca agtgcatcct ccaaatcgct ctcctgatgt gtttctccac    1320
cacagctctt tccatgagct atgatgtgct tcgataccaa caaggagca gcaatttggc     1380 atgtcagaag ctcctgggac agttgcctgg gactcctcaa tattgcctcg aagataggat    1440
gaactttgag gtccctgagg agattatgca accaccacaa ttccagaagg aagatgcagt    1500
attgattatc cacgagatgc tccagcagat cttcggcatt ctcagaagaa atttctctag    1560
cactggctgg aatgaaaccg tcattaagac tatccttgtg gaacttgatg ggcagatgga    1620
tgacctggag acaatcctgg aggaaatcat ggaggaggaa aatttcccca ggggagacat    1680
gaccattctt cacctgaaga aatattactt gagcattctg cagtacctga gtccaaggaa    1740
gtacagaagc tgtgcctgga cagtcgtcca agtggaaatc ctcaggaact tttctttcct    1800
taacagactt acagattacc tccggaactg agcggccgcg aattccaagc ttgagtattc    1860
tatcgtgtca cctaaataac ttggcgtaat catggtcata tctgtttcct gtgtgaaatt    1920
gttatccgct cacaattcca cacaacatac gagccggaag cataaagtgt aaagcctggg    1980
gtgcctaatg agtgagctaa ctcacattaa ttgcgttgcg cgatgcttcc attttgtgag    2040
ggttaatgct tcgagaagac atgataagat acattgatga gtttggacaa accacaacaa    2100
gaatgcagtg aaaaaaatgc tttatttgtg aaatttgtga tgctattgct ttatttgtaa    2160
ccattataag ctgcaataaa caagttaaca acaacaattg cattcatttt atgtttcagg    2220 ttcagggga gatgtgggag gtttttaaa gcaagtaaaa cctctacaaa tgtggtaaaa      2280
tccgataagg atcgattccg gagcctgaat ggcgaatgga cgcgccctgt agcggcgcat    2340
taagcgcggc gggtgtggtg gttacgcgca cgtgaccgct acacttgcca gcgccctagc    2400
gcccgctcct ttcgctttct tcccttcctt tctcgccacg ttcgccggct ttccccgtca    2460
agctctaaat cggggctcc ctttaggggtt ccgatttagt gctttacggc acctcgaccc     2520
caaaaaactt gattagggtg atggttcacg tagtgggcca tcgccctgat agacggtttt    2580
tcgccctttg acgttggagt ccacgttctt taatagtgga ctcttgttcc aaactggaac    2640
aacactcaac cctatctcgg tctattcttt tgatttataa gggattttgc cgatttcggc    2700
ctattggtta aaaaatgagc tgatttaaca aaaatttaac gcgaatttta acaaaatatt    2760
aacgcttaca atttcgcctg tgtaccttct gaggcggaaa gaaccagctg tggaatgtgt    2820
gtcagttagg gtgtggaaag tccccaggct ccccagcagg cagaagtatg caaagcatgc    2880
atctcaatta gtcagcaacc aggtgtggaa agtccccagg ctccccagca ggcagaagta    2940
tgcaaagcat gcatctcaat tagtcagcaa ccatagtccc gcccctaact ccgcccatcc    3000
cgcccctaac tccgcccagt tccgcccatt ctccgcccca tggctgacta attttttta    3060 tttatgcaga ggccgaggcc gcctcggcct ctgagctatt ccagaagtag tgaggaggct    3120
tttttggagg cctaggcttt tgcaaaaagc ttgattcttc tgacacaaca gtctcgaact    3180
taaggctaga gccaccatga ttgaacaaga tggattgcac gcaggttctc cggccgcttg    3240
ggtggagagg ctattcggct atgactggg acaaacagaca atcggctgct ctgatgccgc    3300
cgtgttccgg ctgtcagcgc aggggcgccc ggttcttttt gtcaagaccg acctgtccgg   3360
tgccctgaat gaactgcagg acgaggcagc gcggctatcg tggctggcca cgacgggcgt    3420
tccttgcgca gctgtgctcg acgttgtcac tgaagcggga agggactggc tgctattggg    3480
cgaagtgccg gggcaggatc tcctgtcatc tcaccttgct cctgccgaga aagtatccat    3540
```

```
catggctgat gcaatgcggc ggctgcatac gcttgatccg gctacctgcc cattcgacca   3600
ccaagcgaaa catcgcatcg agcgagcacg tactcggatg gaagccggtc ttgtcgatca   3660
ggatgatctg gacgaagagc atcaggggct cgcgccagcc gaactgttcg ccaggctcaa   3720
ggcgcgcatg cccgacggcg aggatctcgt cgtgacccat ggcgatgcct gcttgccgaa   3780
tatcatggtg gaaaatggcc gcttttctgg attcatcgac tgtggccggc tgggtgtggc   3840
ggaccgctat caggacatag cgttggctac ccgtgatatt gctgaagagc ttggcggcga   3900
atgggctgac cgcttcctcg tgctttacgg tatcgccgct cccgattcgc agcgcatcgc   3960
cttctatcgc cttcttgacg agttcttctg agcgggactc tggggttcga aatgaccgac   4020
caagcgacgc ccaacctgcc atcacgatgg ccgcaataaa atatctttat tttcattaca   4080
tctgtgtgtt ggtttttgt gtgaagatcc gcgtatggtg cactctcagt acaatctgct   4140
ctgatgccgc atagttaagc cagccccgac acccgccaac acccgctgac gcgccctgac   4200
gggcttgtct gctcccggca tccgcttaca gacaagctgt gaccgtctcc gggagctgca   4260
tgtgtcagag gttttcaccg tcatcaccga aacgcgcgag acgaaagggc ctcgtgatac   4320
gcctattttt ataggttaat gtcatgataa taatggtttc ttagacgtca ggtggcactt   4380
ttcggggaaa tgtgcgcgga acccctattt gtttattttt ctaaatacat tcaaatatgt   4440
atccgctcat gagacaataa ccctgataaa tgcttcaata atattgaaaa aggaagagta   4500
tgagtattca acatttccgt gtcgccctta ttcccttttt tgcggcattt tgccttcctg   4560
tttttgctca cccagaaacg ctggtgaaag taaaagatgc tgaagatcag ttgggtgcac   4620
gagtgggtta catcgaactg gatctcaaca gcggtaagat ccttgagagt tttcgccccg   4680
aagaacgttt tccaatgatg agcactttta aagttctgct atgtggcgcg gtattatccc   4740
gtattgacgc cgggcaagag caactcggtc gccgcataca ctattctcag aatgacttgg   4800
ttgagtactc accagtcaca gaaaagcatc ttacggatgg catgacagta agagaattat   4860
gcagtgctgc cataaccatg agtgataaca ctgcggccaa cttacttctg acaacgatcg   4920
gaggaccgaa ggagctaacc gcttttttgc acaacatggg ggatcatgta actcgccttg   4980
atcgttggga accggagctg aatgaagcca taccaaacga cgagcgtgac accacgatgc   5040
ctgtagcaat ggcaacaacg ttgcgcaaac tattaactgg cgaactactt actctagctt   5100
cccggcaaca attaatagac tggatggagg cggataaagt tgcaggacca cttctgcgct   5160
cggcccttcc ggctggctgg tttattgctg ataaatctgg agccggtgag cgtgggtctc   5220
gcggtatcat tgcagcactg gggccagatg gtaagccctc ccgtatcgta gttatctaca   5280
cgacggggag tcaggcaact atggatgaac gaaatagaca gatcgctgag ataggtgcct   5340
cactgattaa gcattggtaa ctgtcagacc aagtttactc atatatactt tagattgatt   5400
taaaacttca ttttttaattt aaaaggatct aggtgaagat cctttttgat aatctcatga   5460
ccaaaatccc ttaacgtgag ttttcgttcc actgagcgtc agaccccgta gaaaagatca   5520
aaggatcttc ttgagatcct ttttttctgc gcgtaatctg ctgcttgcaa acaaaaaaac   5580
caccgctacc agcggtggtt tgtttgccgg atcaagagct accaactctt tttccgaagg   5640
taactggctt cagcagagcg cagataccaa atactgtcct tctagtgtag ccgtagttag   5700
gccaccactt caagaactct gtagcaccgc ctacatacct cgctctgcta atcctgttac   5760
cagtggctgc tgccagtggc gataagtcgt gtcttaccgg gttggactca agacgatagt   5820
taccggataa ggcgcagcgg tcgggctgaa cggggggttc gtgcacacag cccagcttgg   5880
```

| | |
|---|---|
| agcgaacgac ctacaccgaa ctgagatacc tacagcgtga gctatgagaa agcgccacgc | 5940 |
| ttcccgaagg gagaaaggcg gacaggtatc cggtaagcgg cagggtcgga acaggagagc | 6000 |
| gcacgaggga gcttccaggg ggaaacgcct ggtatcttta tagtcctgtc gggtttcgcc | 6060 |
| acctctgact tgagcgtcga ttttttgtgat gctcgtcagg ggggcggagc ctatggaaaa | 6120 |
| acgccagcaa cgcggccttt ttacggttcc tggccttttg ctggcctttt gctcacatgg | 6180 |
| ctcgacagat ct | 6192 |

<210> SEQ ID NO 106
<211> LENGTH: 6124
<212> TYPE: DNA
<213> ORGANISM: Artificial Sequence
<220> FEATURE:
<223> OTHER INFORMATION: pTarget Bovine Interferon Gamma

<400> SEQUENCE: 106

| | |
|---|---|
| tcaatattgg ccattagcca tattattcat tggttatata gcataaatca atattggcta | 60 |
| ttggccattg catacgttgt atctatatca taatatgtac atttatattg gctcatgtcc | 120 |
| aatatgaccg ccatgttggc attgattatt gactagttat taatagtaat caattacggg | 180 |
| gtcattagtt catagcccat atatggagtt ccgcgttaca taacttacgg taaatggccc | 240 |
| gcctggctga ccgcccaacg acccccgccc attgacgtca ataatgacgt atgttcccat | 300 |
| agtaacgcca atagggactt tccattgacg tcaatgggtg gagtatttac ggtaaactgc | 360 |
| ccacttggca gtacatcaag tgtatcatat gccaagtccg cccctattg acgtcaatga | 420 |
| cggtaaatgg cccgcctggc attatgccca gtacatgacc ttacgggact ttcctacttg | 480 |
| gcagtacatc tacgtattag tcatcgctat taccatggtg atgcggtttt ggcagtacac | 540 |
| caatgggcgt ggatagcggt ttgactcacg gggatttcca gtctccacc ccattgacgt | 600 |
| caatgggagt ttgttttggc accaaaatca acgggacttt ccaaaatgtc gtaacaactg | 660 |
| cgatcgcccg ccccgttgac gcaaatgggc ggtaggcgtg tacggtggga ggtctatata | 720 |
| agcagagctc gtttagtgaa ccgtcagatc actagaagct ttattgcggt agtttatcac | 780 |
| agttaaattg ctaacgcagt cagtgcttct gacacaacag tctcgaactt aagctgcagt | 840 |
| gactctctta aggtagcctt gcagaagttg gtcgtgaggc actgggcagg taagtatcaa | 900 |
| ggttacaaga caggtttaag gagaccaata gaaactgggc ttgtcgagac agagaagact | 960 |
| cttgcgtttc tgataggcac ctattggtct tactgacatc cactttgcct ttctctccac | 1020 |
| aggtgtccac tcccagttca attacagctc ttaaaaattg gatctccatt cgccattcag | 1080 |
| gctgcgcaac tgctgggaag gacgatcaga gcgggcctct tcgctattac gccagctggc | 1140 |
| gaaagggacg tggcaagcaa ggcgattaag ttgagttacg ccaggatttt cccagtcacg | 1200 |
| acgttgtaaa acgacggcca gagaattata atacgactca ctatagggcg gatccgctag | 1260 |
| cgccgccacc atgaaatata caagctattt cttagcttta ctgctctgtg gcttttggg | 1320 |
| tttttctggt tcttatggcc agggccaatt ttttagagaa atagaaaact taaggagta | 1380 |
| ttttaatgca agtagcccag atgtagctaa gggtgggcct ctcttctcag aaattttgaa | 1440 |
| gaattggaaa gatgaaagtg acaaaaaaat tattcagagc caaattgtct ccttctactt | 1500 |
| caaactcttt gaaaacctca agataacca ggtcattcaa aggagcatgg atataatcaa | 1560 |
| gcaagacatg tttcagaagt tcttgaatgg cagctctgag aaactggagg acttcaaaaa | 1620 |
| gctgattcaa attccggtgg atgatctcca gatccagcgc aaagccataa atgaactcat | 1680 |
| caaagtgatg aatgacctgt caccaaaatc taaccctcaga aagcggaaga gaagtcagaa | 1740 |

```
tctctttcga ggccggagag catcaacgta agaattccaa gcttgagtat tctatcgtgt    1800
cacctaaata acttggcgta atcatggtca tatctgtttc ctgtgtgaaa ttgttatccg    1860
ctcacaattc cacacaacat acgagccgga agcataaagt gtaaagcctg gggtgcctaa    1920
tgagtgagct aactcacatt aattgcgttg cgcgatgctt ccattttgtg agggttaatg    1980
cttcgagaag acatgataag atacattgat gagtttggac aaaccacaac aagaatgcag    2040
tgaaaaaaat gctttatttg tgaaatttgt gatgctattg ctttatttgt aaccattata    2100
agctgcaata aacaagttaa caacaacaat tgcattcatt ttatgtttca ggttcagggg    2160
gagatgtggg aggttttttta aagcaagtaa aacctctaca aatgtggtaa aatccgataa    2220
ggatcgattc cggagcctga atggcgaatg gacgcgccct gtagcggcgc attaagcgcg    2280
gcgggtgtgg tggttacgcg cacgtgaccg ctacacttgc cagcgcccta gcgcccgctc    2340
ctttcgcttt cttcccttcc tttctcgcca cgttcgccgg ctttccccgt caagctctaa    2400
atcgggggct ccctttaggg ttccgattta gtgctttacg gcacctcgac cccaaaaaac    2460
ttgattaggg tgatggttca cgtagtgggc catcgccctg atagacggtt tttcgccctt    2520
tgacgttgga gtccacgttc tttaatagtg gactcttgtt ccaaactgga acaacactca    2580
accctatctc ggtctattct tttgatttat aagggatttt gccgatttcg gcctattggt    2640
taaaaaatga gctgatttaa caaaaattta acgcgaattt taacaaaata ttaacgctta    2700
caatttcgcc tgtgtacctt ctgaggcgga agaaccagc tgtggaatgt gtgtcagtta    2760
gggtgtggaa agtccccagg ctccccagca ggcagaagta tgcaaagcat gcatctcaat    2820
tagtcagcaa ccaggtgtgg aaagtcccca ggctccccag caggcagaag tatgcaaagc    2880
atgcatctca attagtcagc aaccatagtc ccgcccctaa ctccgcccat cccgccccta    2940
actccgccca gttccgccca ttctccgccc catggctgac taatttttttt tatttatgca    3000 gaggccgagg ccgcctcggc ctctgagcta ttccagaagt agtgaggagg cttttttgga    3060
ggcctaggct tttgcaaaaa gcttgattct tctgacacaa cagtctcgaa cttaaggcta    3120
gagccaccat gattgaacaa gatggattgc acgcaggttc tccggccgct tgggtggaga    3180
ggctattcgg ctatgactgg gcacaacaga caatcggctg ctctgatgcc gccgtgttcc    3240
ggctgtcagc gcaggggcgc ccggttcttt ttgtcaagac cgacctgtcc ggtgccctga    3300
atgaactgca ggacgaggca gcgcggctat cgtggctggc cacgacgggc gttccttgcg    3360
cagctgtgct cgacgttgtc actgaagcgg gaagggactg gctgctattg ggcgaagtgc    3420
cggggcagga tctcctgtca tctcaccttg ctcctgccga aaagtatcc atcatggctg    3480 atgcaatgcg gcggctgcat acgcttgatc cggctacctg cccattcgac caccaagcga    3540
aacatcgcat cgagcgagca cgtactcgga tggaagccgg tcttgtcgat caggatgatc    3600
tggacgaaga gcatcagggg ctcgcgccag ccgaactgtt cgccaggctc aaggcgcgca    3660
tgcccgacgg cgaggatctc gtcgtgaccc atggcgatgc ctgcttgccg aatatcatgg    3720
tggaaaatgg ccgcttttct ggattcatcg actgtggccg gctgggtgtg gcggaccgct    3780
atcaggacat agcgttggct acccgtgata ttgctgaaga gcttggcggc gaatgggctg    3840
accgcttcct cgtgctttac ggtatcgccg ctcccgattc gcagcgcatc gccttctatc    3900
gccttcttga cgagttcttc tgagcgggac tctggggttc gaaatgaccg accaagcgac    3960
gcccaacctg ccatcacgat ggccgcaata aaatatcttt attttcatta catctgtgtg    4020
ttggtttttt gtgtgaagat ccgcgtatgg tgcactctca gtacaatctg ctctgatgcc    4080
```

```
gcatagttaa gccagcccg acacccgcca acaccgctg acgcgccctg acgggcttgt    4140
ctgctcccgg catccgctta cagacaagct gtgaccgtct ccgggagctg catgtgtcag    4200
aggttttcac cgtcatcacc gaaacgcgcg agacgaaagg gcctcgtgat acgcctattt    4260
ttataggtta atgtcatgat aataatggtt tcttagacgt caggtggcac ttttcgggga    4320
aatgtgcgcg gaaccctat ttgttattt ttctaaatac attcaaatat gtatccgctc    4380
atgagacaat aaccctgata aatgcttcaa taatattgaa aaaggaagag tatgagtatt    4440
caacatttcc gtgtcgccct tattccctt tttgcggcat tttgccttcc tgttttgct    4500
cacccagaaa cgctggtgaa agtaaaagat gctgaagatc agttgggtgc acagtgggt    4560
tacatcgaac tggatctcaa cagcggtaag atccttgaga gttttcgccc cgaagaacgt    4620
tttccaatga tgagcacttt taaagttctg ctatgtggcg cggtattatc ccgtattgac    4680
gccgggcaag agcaactcgg tcgccgcata cactattctc agaatgactt ggttgagtac    4740
tcaccagtca cagaaaagca tcttacggat ggcatgacag taagagaatt atgcagtgct    4800
gccataacca tgagtgataa cactgcgcc aacttacttc tgacaacgat cggaggaccg    4860
aaggagctaa ccgcttttt gcacaacatg ggggatcatg taactcgcct tgatcgttgg    4920
gaaccggagc tgaatgaagc cataccaaac gacgagcgtg acaccacgat gcctgtagca    4980
atggcaacaa cgttgcgcaa actattaact ggcgaactac ttactctagc ttcccggcaa    5040
caattaatag actggatgga ggcggataaa gttgcaggac cacttctgcg ctcggccctt    5100
ccggctggct ggtttattgc tgataaatct ggagccggtg agcgtgggtc tcgcggtatc    5160
attgcagcac tggggccaga tggtaagccc tcccgtatcg tagttatcta cacgacgggg    5220
agtcaggcaa ctatggatga acgaaataga cagatcgctg agataggtgc ctcactgatt    5280
aagcattggt aactgtcaga ccaagtttac tcatatatac tttagattga tttaaaactt    5340
catttttaat ttaaaaggat ctaggtgaag atcctttttg ataatctcat gaccaaaatc    5400
ccttaacgtg agttttcgtt ccactgagcg tcagaccccg tagaaaagat caaaggatct    5460
tcttgagatc cttttttct gcgcgtaatc tgctgcttgc aaacaaaaaa accaccgcta    5520
ccagcggtgg tttgtttgcc ggatcaagag ctaccaactc ttttttccgaa ggtaactggc    5580
ttcagcagag cgcagatacc aaatactgtc cttctagtgt agccgtagtt aggccaccac    5640
ttcaagaact ctgtagcacc gcctacatac ctcgctctgc taatcctgtt accagtggct    5700
gctgccagtg gcgataagtc gtgtcttacc gggttggact caagacgata gttaccggat    5760
aaggcgcagc ggtcgggctg aacggggggt tcgtgcacac agcccagctt ggagcgaacg    5820
acctacaccg aactgagata cctacagcgt gagctatgag aaagcgccac gcttcccgaa    5880
gggagaaagg cggacaggta tccggtaagc ggcagggtcg aacaggaga gcgcacgagg    5940
gagcttccag ggggaaacgc ctggtatctt tatagtcctg tcgggtttcg ccacctctga    6000
cttgagcgtc gatttttgtg atgctcgtca ggggggcgga gcctatggaa aaacgccagc    6060
aacgcggcct ttttacggtt cctggccttt tgctggcctt tgctcacat ggctcgacag    6120
atct                                                              6124
```

<210> SEQ ID NO 107
<211> LENGTH: 6210
<212> TYPE: DNA
<213> ORGANISM: Artificial Sequence
<220> FEATURE:
<223> OTHER INFORMATION: pTarget Bovine Interferon Lambda

<400> SEQUENCE: 107

-continued

```
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccccgcc cattgacgtc aataatgacg tatgttccat     300
agtaacgcca atagggactt tccattgacg tcaatgggtg gagtatttac ggtaaactgc     360
ccacttggca gtacatcaag tgtatcatat gccaagtccg cccctattg acgtcaatga      420 cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg gggatttcca gtctccacc ccattgacgt      600 caatgggagt ttgttttggc accaaaatca acgggacttt ccaaaatgtc gtaacaactg     660
cgatcgcccg ccccgttgac gcaaatgggc ggtaggcgtg tacggtggga ggtctatata     720
agcagagctc gtttagtgaa ccgtcagatc actagaagct ttattgcggt agtttatcac     780
agttaaattg ctaacgcagt cagtgcttct gacacaacag tctcgaactt aagctgcagt     840
gactctctta aggtagcctt gcagaagttg gtcgtgaggc actgggcagg taagtatcaa     900
ggttacaaga caggtttaag gagaccaata gaaactgggc ttgtcgagac agagaagact     960
cttgcgtttc tgataggcac ctattggtct tactgacatc cactttgcct ttctctccac    1020
aggtgtccac tcccagttca attacagctc ttaaaaattg gatctccatt cgccattcag    1080
gctgcgcaac tgctgggaag gacgatcaga gcgggcctct tcgctattac gccagctggc    1140
gaaagggacg tggcaagcaa ggcgattaag ttgagttacg ccaggatttt cccagtcacg    1200
acgttgtaaa acgacggcca gagaattata atacgactca ctatagggcg gatccggcgc    1260
gccgccacca tggccccagg ctgcacgctg gtgctggtgc tgatgctgac gaccgtggcg    1320
ctgagcagga caggagcagt cctgtgccc tctgccccca gggcactccc acctgccagg    1380
ggctgccacg tggcccagtt caagtctctg tcccctcaag agctgcaagc cttcaagacg    1440
gccagggatg cctttgaaga ctcgttcttg ccgaaggact gggactgtag cacccacctt    1500
ttccccagga cacgagacct gaagcacctg caagtgtggg agcgccctgt ggctctggag    1560
gcagagctgg ccctgacact gacggtcctg gaggcaatgg ctaactcatc cctgggccac    1620
agcctggagc agcccttct cacgctgcaa acatccact ccaagctcca ggcctgtgtc      1680
ccagctcagc ccacagcaag ctccagaccc cgaggccgcc tccaccactg gctgcaccgc    1740
ctccaagagg cccggaagga gtcccaggac tgcctcgaag cctctgtgat gttcaacctc    1800
ctccgcctcc tcacccgaga cctgaaatgt gttgccagcg agaccagtg tgtctgagaa     1860 ttccaagctt gagtattcta tcgtgtcacc taaataactt ggcgtaatca tggtcatatc    1920
tgtttcctgt gtgaaattgt tatccgctca caattccaca caacatacga gccggaagca    1980
taaagtgtaa agcctggggt gcctaatgag tgagctaact cacattaatt gcgttgcgcg    2040
atgcttccat tttgtgaggg ttaatgcttc gagaagacat gataagatac attgatgagt    2100
ttggacaaac cacaacaaga atgcagtgaa aaaaatgctt tatttgtgaa atttgtgatg    2160
ctattgcttt atttgtaacc attataagct gcaataaaca agttaacaac aacaattgca    2220
ttcattttat gtttcaggtt cagggggaga tgtgggaggt tttttaaagc aagtaaaacc    2280
tctacaaatg tggtaaaatc cgataaggat cgattccgga gcctgaatgg cgaatggacg    2340
```

```
cgccctgtag cggcgcatta agcgcggcgg gtgtggtggt tacgcgcacg tgaccgctac   2400
acttgccagc gccctagcgc ccgctccttt cgctttcttc ccttcctttc tcgccacgtt   2460
cgccggcttt ccccgtcaag ctctaaatcg ggggctccct ttagggttcc gatttagtgc   2520
tttacggcac ctcgaccca aaaaacttga ttagggtgat ggttcacgta gtgggccatc    2580
gccctgatag acggtttttc gcccttttgac gttggagtcc acgttcttta atagtggact  2640
cttgttccaa actggaacaa cactcaaccc tatctcggtc tattcttttg atttataagg   2700
gattttgccg atttcggcct attggttaaa aaatgagctg atttaacaaa aatttaacgc   2760
gaattttaac aaaatattaa cgcttacaat ttcgcctgtg taccttctga ggcgaaaga    2820 accagctgtg aatgtgtgt cagttagggt gtggaaagtc cccaggctcc ccagcaggca    2880
gaagtatgca aagcatgcat ctcaattagt cagcaaccag gtgtggaaag tccccaggct   2940
ccccagcagg cagaagtatg caaagcatgc atctcaatta gtcagcaacc atagtcccgc   3000
ccctaactcc gcccatcccg ccctaactc cgcccagttc cgcccattct ccgccccatg     3060
gctgactaat tttttttatt tatgcagagg ccgaggccgc ctcggcctct gagctattcc    3120
agaagtagtg aggaggcttt tttggaggcc taggcttttg caaaaagctt gattcttctg    3180
acacaacagt ctcgaactta aggctagagc caccatgatt gaacaagatg gattgcacgc    3240
aggttctccg gccgcttggg tggagaggct attcggctat gactgggcac aacagacaat    3300
cggctgctct gatgccgccg tgttccggct gtcagcgcag gggcgcccgg ttcttttttgt   3360 caagaccgac ctgtccggtg ccctgaatga actgcaggac gaggcagcgc ggctatcgtg    3420
gctggccacg acgggcgttc cttgcgcagc tgtgctcgac gttgtcactg aagcgggaag    3480
ggactggctg ctattgggcg aagtgccggg gcaggatctc ctgtcatctc accttgctcc    3540
tgccgagaaa gtatccatca tggctgatgc aatgcggcgg ctgcatacgc ttgatccggc    3600
tacctgccca ttcgaccacc aagcgaaaca tcgcatcgag cgagcacgta ctcggatgga    3660
agccggtctt gtcgatcagg atgatctgga cgaagagcat caggggctcg cgccagccga    3720
actgttcgcc aggctcaagg cgcgcatgcc cgacggcgag gatctcgtcg tgacccatgg    3780
cgatgcctgc ttgccgaata tcatggtgga aaatggccgc ttttctggat tcatcgactg    3840
tggccggctg ggtgtggcgg accgctatca ggacatagcg ttggctaccc gtgatattgc    3900
tgaagagctt ggcggcgaat gggctgaccg cttcctcgtg ctttacggta tcgccgctcc    3960
cgattcgcag cgcatcgcct tctatcgcct tcttgacgag ttcttctgag cgggactctg    4020
gggttcgaaa tgaccgacca agcgacgccc aacctgccat cacgatggcc gcaataaaat    4080
atctttattt tcattacatc tgtgtgttgg ttttttgtgt gaagatccgc gtatggtgca    4140
ctctcagtac aatctgctct gatgccgcat agttaagcca gccccgacac ccgccaacac    4200
ccgctgacgc gccctgacgg gcttgtctgc tcccggcatc cgcttacaga caagctgtga    4260
ccgtctccgg gagctgcatg tgtcagaggt tttcaccgtc atcaccgaaa cgcgcgagac    4320
gaaagggcct cgtgatacgc ctatttttat aggttaatgt catgataata atggtttctt    4380
agacgtcagg tggcactttt cggggaaatg tgcgcggaac ccctatttgt ttatttttct    4440
aaatacattc aaatatgtat ccgctcatga caataaacc ctgataaatg cttcaataat    4500
attgaaaaag gaagagtatg agtattcaac atttccgtgt cgcccttatt cccttttttg    4560
cggcattttg ccttcctgtt tttgctcacc cagaaacgct ggtgaaagta aaagatgctg    4620
aagatcagtt gggtgcacga gtgggttaca tcgaactgga tctcaacagc ggtaagatcc    4680
ttgagagttt tcgccccgaa gaacgttttc caatgatgag cacttttaaa gttctgctat    4740
```

```
gtggcgcggt attatcccgt attgacgccg ggcaagagca actcggtcgc cgcatacact    4800
attctcagaa tgacttggtt gagtactcac cagtcacaga aaagcatctt acggatggca    4860
tgacagtaag agaattatgc agtgctgcca taaccatgag tgataacact gcggccaact    4920
tacttctgac aacgatcgga ggaccgaagg agctaaccgc ttttttgcac aacatggggg    4980
atcatgtaac tcgccttgat cgttgggaac cggagctgaa tgaagccata ccaaacgacg    5040
agcgtgacac cacgatgcct gtagcaatgg caacaacgtt gcgcaaacta ttaactggcg    5100
aactacttac tctagcttcc cggcaacaat taatagactg gatggaggcg gataaagttg    5160
caggaccact tctgcgctcg gcccttccgg ctggctggtt tattgctgat aaatctggag    5220
ccggtgagcg tgggtctcgc ggtatcattg cagcactggg gccagatggt aagccctccc    5280
gtatcgtagt tatctacacg acggggagtc aggcaactat ggatgaacga atagacaga    5340 tcgctgagat aggtgcctca ctgattaagc attggtaact gtcagaccaa gtttactcat    5400
atatacttta gattgattta aaacttcatt tttaatttaa aaggatctag gtgaagatcc    5460
tttttgataa tctcatgacc aaaatccctt aacgtgagtt ttcgttccac tgagcgtcag    5520
accccgtaga aaagatcaaa ggatcttctt gagatccttt ttttctgcgc gtaatctgct    5580
gcttgcaaac aaaaaaacca ccgctaccag cggtggtttg tttgccggat caagagctac    5640
caactctttt tccgaaggta actggcttca gcagagcgca gataccaaat actgtccttc    5700
tagtgtagcc gtagttaggc caccacttca agaactctgt agcaccgcct acatacctcg    5760
ctctgctaat cctgttacca gtggctgctg ccagtggcga taagtcgtgt cttaccgggt    5820
tggactcaag acgatagtta ccggataagg cgcagcggtc gggctgaacg gggggttcgt    5880
gcacacagcc cagcttggag cgaacgacct acaccgaact gagatacta cagcgtgagc    5940 tatgagaaag cgccacgctt cccgaaggga gaaaggcgga caggtatccg gtaagcggca    6000
gggtcggaac aggagagcgc acgagggagc ttccaggggg aaacgcctgg tatctttata    6060
gtcctgtcgg gtttcgccac ctctgacttg agcgtcgatt tttgtgatgc tcgtcagggg    6120
ggcggagcct atggaaaaac gccagcaacg cggccttttt acggttcctg gccttttgct    6180
ggccttttgc tcacatggct cgacagatct                                     6210
```

<210> SEQ ID NO 108
<211> LENGTH: 6314
<212> TYPE: DNA
<213> ORGANISM: Artificial Sequence
<220> FEATURE:
<223> OTHER INFORMATION: pTarget d1D2A-SGluc (-1M)

<400> SEQUENCE: 108

```
tcaatattgg ccattagcca tattattcat tggttatata gcataaatca atattggcta     60
ttggccattg catacgttgt atctatatca taatatgtac atttatattg gctcatgtcc    120
aatatgaccg cctgttggc attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg cccctattg acgtcaatga    420 cggtaaatgg cccgcctggc attatgccca gtacatgacc ttcgggact ttcctacttg    480 gcagtacatc tacgtattag tcatcgctat taccatggtg atgcggtttt ggcagtacac    540
```

-continued

```
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac    1020
aggtgtccac tcccagttca attacagctc ttaaaaattg gatctccatt cgccattcag    1080
gctgcgcaac tgctgggaag gacgatcaga gcgggcctct tcgctattac gccagctggc    1140
gaaagggacg tggcaagcaa ggcgattaag ttgagttacg ccaggatttt cccagtcacg    1200
acgttgtaaa acgacggcca gagaattata atacgactca ctatagggcg aattcggatc    1260
cttgctagcc tcgagctcga gacgcgtgat tgcgccgcca ccatgagcca caagcaaaag    1320
atcattgcac cagcaaagca gcttctgaat tttgacctgc tcaagttggc cggagacgtt    1380
gagtccaacc ctgggcccgg agtcaaagtt ctgtttgccc tgatctgcat cgctgtggcc    1440
gaggccaagc ccaccgagaa caacgaagac ttcaacatcg tggccgtggc cagcaacttt    1500
gcgaccacgg atctcgatgc tgaccgaggg aagttgcccg caagaagct gccgctggag    1560 gtgctcaaag agatggaagc caatgcccgg aaagctggct gcaccagggg ctgtctgatc    1620
tgcctgtccc acatcaagtg cacgcccaag atgaagaagt ggctcccagg acgctgccac    1680
acctacgaag gcgacaaaga gtccgcacag ggcggcatag gcgaggcgat cgtcgatatt    1740
cctgagattc ctgggttcaa ggacttggag ccaatggagc agttcatcgc acaggtcgat    1800
ctgtgtgtgg actgcacaac tggctgcctc aaagggcttg ccaacgtgca gtgttcagac    1860
ctgctcaaga agtggctgcc gcaacgctgt gcgacctttg ccagcaagat ccagggccag    1920
gtggacaaga tcaagggggc cggtggtgac taagcggccg cgaattccaa gcttgagtat    1980
tctatcgtgt cacctaaata acttggcgta atcatggtca tatctgtttc ctgtgtgaaa    2040
ttgttatccg ctcacaattc cacacaacat acgagccgga agcataaagt gtaaagcctg    2100
gggtgcctaa tgagtgagct aactcacatt aattgcgttg cgcgatgctt ccattttgtg    2160
agggttaatg cttcgagaag acatgataag atacattgat gagtttggac aaaccacaac    2220
aagaatgcag tgaaaaaaat gctttatttg tgaaatttgt gatgctattg ctttatttgt    2280
aaccattata agctgcaata acaagttaa caacaacaat tgcattcatt ttatgtttca    2340
ggttcagggg gagatgtggg aggttttta aagcaagtaa aacctctaca aatgtggtaa    2400
aatccgataa ggatcgattc cggagcctga atggcgaatg gacgcgccct gtagcggcgc    2460
attaagcgcg gcgggtgtgg tggttacgcg cacgtgaccg ctacacttgc cagcgcccta    2520
gcgcccgctc ctttcgcttt cttcccttcc tttctcgcca cgttcgccgg ctttccccgt    2580
caagctctaa atcgggggct ccctttaggg ttccgattta gtgctttacg gcacctcgac    2640
cccaaaaaac ttgattaggg tgatggttca cgtagtgggc catcgccctg atagacggtt    2700
tttcgccctt tgacgttgga gtccacgttc tttaatagtg gactcttgtt ccaaactgga    2760
acaacactca accctatctc ggtctattct tttgatttat aagggatttt gccgatttcg    2820
gcctattggt taaaaaatga gctgatttaa caaaaattta acgcgaattt taacaaaata    2880
ttaacgctta caatttcgcc tgtgtacctt ctgaggcgga agaaccagc tgtggaatgt    2940
```

```
gtgtcagtta gggtgtggaa agtccccagg ctcccagca ggcagaagta tgcaaagcat   3000
gcatctcaat tagtcagcaa ccaggtgtgg aaagtcccca ggctcccag caggcagaag   3060 tatgcaaagc atgcatctca attagtcagc aaccatagtc ccgcccctaa ctccgcccat   3120 cccgcccta actccgccca gttccgccca ttctccgccc catggctgac taatttttt   3180 tatttatgca gaggccgagg ccgcctcggc ctctgagcta ttccagaagt agtgaggagg   3240
cttttttgga ggcctaggct tttgcaaaaa gcttgattct tctgacacaa cagtctcgaa   3300
cttaaggcta gagccaccat gattgaacaa gatggattgc acgcaggttc tccggccgct   3360
tgggtggaga ggctattcgg ctatgactgg gcacaacaga caatcggctg ctctgatgcc   3420
gccgtgttcc ggctgtcagc gcaggggcgc ccggttcttt ttgtcaagac cgacctgtcc   3480
ggtgccctga atgaactgca ggacgaggca gcgcggctat cgtggctggc cacgacgggc   3540
gttccttgcg cagctgtgct cgacgttgtc actgaagcgg gaagggactg gctgctattg   3600
ggcgaagtgc cggggcagga tctcctgtca tctcaccttg ctcctgccga gaaagtatcc   3660
atcatggctg atgcaatgcg gcggctgcat acgcttgatc cggctacctg cccattcgac   3720
caccaagcga aacatcgcat cgagcgagca cgtactcgga tggaagccgg tcttgtcgat   3780
caggatgatc tggacgaaga gcatcagggg ctcgcgccag ccgaactgtt cgccaggctc   3840
aaggcgcgca tgcccgacgg cgaggatctc gtcgtgaccc atggcgatgc ctgcttgccg   3900
aatatcatgg tggaaaatgg ccgcttttct ggattcatcg actgtggccg ctgggtgtg   3960 gcggaccgct atcaggacat agcgttggct acccgtgata ttgctgaaga gcttggcggc   4020
gaatgggctg accgcttcct cgtgctttac ggtatcgccg ctcccgattc gcagcgcatc   4080
gccttctatc gccttcttga cgagttcttc tgagcgggac tctggggttc gaaatgaccg   4140
accaagcgac gcccaacctg ccatcacgat ggccgcaata aaatatcttt attttcatta   4200
catctgtgtg ttggttttt gtgtgaagat ccgcgtatgg tgcactctca gtacaatctg   4260
ctctgatgcc gcatagttaa gccagccccg acacccgcca cacccgctg acgcgccctg   4320 acgggcttgt ctgctcccgg catccgctta cagacaagct gtgaccgtct ccggagctg   4380 catgtgtcag aggttttcac cgtcatcacc gaaacgcgcg agacgaaagg gcctcgtgat   4440
acgcctattt ttataggtta atgtcatgat aataatggtt tcttagacgt caggtggcac   4500
ttttcgggga aatgtgcgcg gaaccccat ttgtttatt ttctaaatac attcaaatat   4560
gtatccgctc atgagacaat aaccctgata aatgcttcaa taatattgaa aaaggaagag   4620
tatgagtatt caacatttcc gtgtcgccct tattcccttt tttgcggcat tttgccttcc   4680
tgtttttgct cacccagaaa cgctggtgaa agtaaaagat gctgaagatc agttgggtgc   4740
acgagtgggt tacatcgaac tggatctcaa cagcggtaag atccttgaga gttttcgccc   4800
cgaagaacgt tttccaatga tgagcacttt taaagttctg ctatgtggcg cggtattatc   4860
ccgtattgac gccgggcaag agcaactcgg tcgccgcata cactattctc agaatgactt   4920
ggttgagtac tcaccagtca cagaaaagca tcttacggat ggcatgacag taagagaatt   4980
atgcagtgct gccataacca tgagtgataa cactgcggcc aacttacttc tgacaacgat   5040
cggaggaccg aaggagctaa ccgctttttt gcacaacatg gggatcatg taactcgcct   5100 tgatcgttgg gaaccggagc tgaatgaagc cataccaaac gacgagcgtg acaccacgat   5160
gcctgtagca atggcaacaa cgttgcgcaa actattaact ggcgaactac ttactctagc   5220
ttcccggcaa caattaatag actggatgga ggcggataaa gttgcaggac cacttctgcg   5280
```

```
ctcggccctt ccggctggct ggtttattgc tgataaatct ggagccggtg agcgtgggtc     5340
tcgcggtatc attgcagcac tggggccaga tggtaagccc tcccgtatcg tagttatcta     5400
cacgacgggg agtcaggcaa ctatggatga acgaaataga cagatcgctg agataggtgc     5460
ctcactgatt aagcattggt aactgtcaga ccaagtttac tcatatatac tttagattga     5520
tttaaaactt catttttaat ttaaaaggat ctaggtgaag atcctttttg ataatctcat     5580
gaccaaaatc ccttaacgtg agttttcgtt ccactgagcg tcagaccccg tagaaaagat     5640
caaaggatct tcttgagatc ctttttttct gcgcgtaatc tgctgcttgc aaacaaaaaa     5700
accaccgcta ccagcggtgg tttgtttgcc ggatcaagag ctaccaactc ttttccgaa     5760 ggtaactggc ttcagcagag cgcagatacc aaatactgtc cttctagtgt agccgtagtt     5820
aggccaccac ttcaagaact ctgtagcacc gcctacatac ctcgctctgc taatcctgtt     5880
accagtggct gctgccagtg gcgataagtc gtgtcttacc gggttggact caagacgata     5940
gttaccggat aaggcgcagc ggtcgggctg aacggggggt tcgtgcacac agcccagctt     6000
ggagcgaacg acctacaccg aactgagata cctacagcgt gagctatgag aaagcgccac     6060
gcttcccgaa gggagaaagg cggacaggta tccggtaagc ggcagggtcg gaacaggaga     6120
gcgcacgagg gagcttccag ggggaaacgc ctggtatctt tatagtcctg tcgggtttcg     6180
ccacctctga cttgagcgtc gatttttgtg atgctcgtca ggggggcgga gcctatggaa     6240
aaacgccagc aacgcggcct ttttacggtt cctggccttt tgctggcctt ttgctcacat     6300
ggctcgacag atct                                                      6314

<210> SEQ ID NO 109
<211> LENGTH: 6319
<212> TYPE: DNA
<213> ORGANISM: Artificial Sequence
<220> FEATURE:
<223> OTHER INFORMATION: pTarget SGLuc-d1D2A

<400> SEQUENCE: 109
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg acccccgccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg cccccttattg acgtcaatga     420 cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg gggatttcca gtctccaccc cattgacgt      600 caatgggagt ttgttttggc accaaaatca acgggacttt ccaaaatgtc gtaacaactg     660
cgatcgcccg ccccgttgac gcaaatgggc ggtaggcgtg tacggtggga ggtctatata     720
agcagagctc gtttagtgaa ccgtcagatc actagaagct ttattgcggt agtttatcac     780
agttaaattg ctaacgcagt cagtgcttct gacacaacag tctcgaactt aagctgcagt     840
gactctctta aggtagcctt gcagaagttg gtcgtgaggc actgggcagg taagtatcaa     900
ggttacaaga caggtttaag gagaccaata gaaactgggc ttgtcgagac agagaagact     960
cttgcgtttc tgataggcac ctattggtct tactgacatc cactttgcct ttctctccac    1020
```

```
aggtgtccac tcccagttca attacagctc ttaaaaattg gatctccatt cgccattcag    1080
gctgcgcaac tgctgggaag gacgatcaga gcgggcctct tcgctattac gccagctggc    1140
gaaagggacg tggcaagcaa ggcgattaag ttgagttacg ccaggatttt cccagtcacg    1200
acgttgtaaa acgacggcca gagaattata atacgactca ctatagggcg aattcggatc    1260
cttgctagcc tcgagacgcg tgatatcttt ggcgcgccgc caccatggga gtcaaagttc    1320
tgtttgccct gatctgcatc gctgtggccg aggccaagcc caccgagaac aacgaagact    1380
tcaacatcgt ggccgtggcc agcaacttcg cgaccacgga tctcgatgct gaccgcggga    1440
agttccccgg caagaagctg ccgctggagg tgctcaaaga gatggaagcc aatgcccgga    1500
aagctggctg caccaggggc tgtctgatct gcctgtccca catcaagtgc acgcccaaga    1560
tgaagaagtg gctcccagga cgctgccaca cctacgaagg cgacaaagag tccgcacagg    1620
gcggcatagg cgaggcgatc gtcgacattc ctgagattcc tgggttcaag gacttggagc    1680
ccatggagca gttcatcgca caggtcgatc tgtgtgtgga ctgcacaact ggctgcctca    1740
aagggcttgc caacgtgcag tgttctgacc tgctcaagaa gtggctgccg caacgctgtg    1800
cgacctttgc cagcaagatc cagggccagg tggacaagat caaggggggcc ggtggtgacg    1860 ctagccacaa gcaaaagatc attgcaccag caaagcagct tctgaatttt gacctgctca    1920
agttggccgg agacgttgag tccaaccctg gacccggggc ggccgcgaat tccaagcttg    1980
agtattctat cgtgtcacct aaataacttg gcgtaatcat ggtcatatct gtttcctgtg    2040
tgaaattgtt atccgctcac aattccacac aacatacgag ccggaagcat aaagtgtaaa    2100
gcctggggtg cctaatgagt gagctaactc acattaattg cgttgcgcga tgcttccatt    2160
ttgtgagggt taatgcttcg agaagacatg ataagataca ttgatgagtt tggacaaacc    2220
acaacaagaa tgcagtgaaa aaaatgcttt atttgtgaaa tttgtgatgc tattgcttta    2280
tttgtaacca ttataagctg caataaacaa gttaacaaca acaattgcat tcattttatg    2340
tttcaggttc agggggagat gtgggaggtt ttttaaagca agtaaaacct ctacaaatgt    2400
ggtaaaatcc gataaggatc gattccggag cctgaatggc gaatgacgc gccctgtagc    2460 ggcgcattaa gcgcggcggg tgtggtggtt acgcgcacgt gaccgctaca cttgccagcg    2520
ccctagcgcc cgctcctttc gctttcttcc cttcctttct cgccacgttc gccggctttc    2580
cccgtcaagc tctaaatcgg gggctccctt tagggttccg atttagtgct ttacggcacc    2640
tcgaccccaa aaaacttgat tagggtgatg gttcacgtag tgggccatcg ccctgataga    2700 cggttttcg ccctttgacg ttggagtcca cgttctttaa tagtggactc ttgttccaaa     2760
ctggaacaac actcaaccct atctcggtct attcttttga tttataaggg attttgccga    2820
tttcggccta ttggttaaaa aatgagctga tttaacaaaa atttaacgcg aattttaaca    2880
aaatattaac gcttacaatt tgcctgtgt accttctgag gcggaaagaa ccagctgtgg     2940
aatgtgtgtc agttagggtg tggaaagtcc ccaggctccc cagcaggcag aagtatgcaa    3000
agcatgcatc tcaattagtc agcaaccagg tgtggaaagt ccccaggctc cccagcaggc    3060
agaagtatgc aaagcatgca tctcaattag tcagcaacca tagtcccgcc cctaactccg    3120
cccatcccgc ccctaactcc gcccagttcc gcccattctc cgccccatgg ctgactaatt    3180
ttttttattt atgcagaggc cgaggccgcc tcggcctctg agctattcca gaagtagtga    3240
ggaggctttt ttggaggcct aggcttttgc aaaaagcttg attcttctga cacaacagtc    3300
tcgaacttaa ggctagagcc accatgattg aacaagatgg attgcacgca ggttctccgg    3360
```

```
ccgcttgggt ggagaggcta ttcggctatg actgggcaca acagacaatc ggctgctctg    3420
atgccgccgt gttccggctg tcagcgcagg ggcgcccggt tcttttttgtc aagaccgacc    3480 tgtccggtgc cctgaatgaa ctgcaggacg aggcagcgcg gctatcgtgg ctggccacga    3540
cgggcgttcc ttgcgcagct gtgctcgacg ttgtcactga agcgggaagg gactggctgc    3600
tattgggcga agtgccgggg caggatctcc tgtcatctca ccttgctcct gccgagaaag    3660
tatccatcat ggctgatgca atgcggcggc tgcatacgct tgatccggct acctgcccat    3720
tcgaccacca agcgaaacat cgcatcgagc gagcacgtac tcggatggaa gccggtcttg    3780
tcgatcagga tgatctggac gaagagcatc agggctcgc gccagccgaa ctgttcgcca    3840
ggctcaaggc gcgcatgccc gacggcgagg atctcgtcgt gacccatggc gatgcctgct    3900
tgccgaatat catggtggaa aatggccgct tttctggatt catcgactgt ggccggctgg    3960
gtgtggcgga ccgctatcag gacatagcgt tggctacccg tgatattgct gaagagcttg    4020
gcggcgaatg ggctgaccgc ttcctcgtgc tttacggtat cgccgctccc gattcgcagc    4080
gcatcgcctt ctatcgcctt cttgacgagt tcttctgagc gggactctgg ggttcgaaat    4140
gaccgaccaa gcgacgccca acctgccatc acgatggccg caataaaata tctttatttt    4200
cattacatct gtgtgttggt tttttgtgtg aagatccgcg tatggtgcac tctcagtaca    4260
atctgctctg atgccgcata gttaagccag ccccgacacc cgccaacacc cgctgacgcg    4320
ccctgacggg cttgtctgct cccggcatcc gcttacagac aagctgtgac cgtctccggg    4380
agctgcatgt gtcagaggtt ttcaccgtca tcaccgaaac gcgcgagacg aaagggcctc    4440
gtgatacgcc tatttttata ggttaatgtc atgataataa tggtttctta cgtcaggt     4500 ggcactttc ggggaaatgt gcgcggaacc cctatttgtt tatttttcta aatacattca    4560
aatatgtatc cgctcatgag acaataaccc tgataaatgc ttcaataata ttgaaaaagg    4620
aagagtatga gtattcaaca tttccgtgtc gcccttattc ccttttttgc ggcattttgc    4680
cttcctgttt ttgctcaccc agaaacgctg gtgaaagtaa aagatgctga agatcagttg    4740
ggtgcacgag tgggttacat cgaactggat ctcaacagcg gtaagatcct tgagagtttt    4800
cgccccgaag aacgttttcc aatgatgagc acttttaaag ttctgctatg tggcgcggta    4860
ttatcccgta ttgacgccgg gcaagagcaa ctcggtcgcc gcatacacta ttctcagaat    4920
gacttggttg agtactcacc agtcacagaa aagcatctta cggatggcat gacagtaaga    4980
gaattatgca gtgctgccat aaccatgagt gataacactg cggccaactt acttctgaca    5040
acgatcggag gaccgaagga gctaaccgct ttttttgcaca acatggggga tcatgtaact    5100
cgccttgatc gttgggaacc ggagctgaat gaagccatac caaacgacga gcgtgacacc    5160
acgatgcctg tagcaatggc aacaacgttg cgcaaactat taactggcga actacttact    5220
ctagcttccc ggcaacaatt aatagactgg atggaggcgg ataaagttgc aggaccactt    5280
ctgcgctcgg cccttccggc tggctggttt attgctgata atctggagc cggtgagcgt    5340 gggtctcgcg gtatcattgc agcactgggg ccagatggta agccctcccg tatcgtagtt    5400
atctacacga cggggagtca ggcaactatg gatgaacgaa atagacagat cgctgagata    5460
ggtgcctcac tgattaagca ttggtaactg tcagaccaag tttactcata tatactttag    5520
attgatttaa aacttcattt ttaatttaaa aggatctagg tgaagatcct ttttgataat    5580
ctcatgacca aaatccctta acgtgagttt tcgttccact gagcgtcaga ccccgtagaa    5640
aagatcaaag gatcttcttg agatcctttt tttctgcgcg taatctgctg cttgcaaaca    5700
aaaaaaccac cgctaccagc ggtggtttgt ttgccggatc aagagctacc aactctttt    5760
```

```
ccgaaggtaa ctggcttcag cagagcgcag ataccaaata ctgtccttct agtgtagccg    5820
tagttaggcc accacttcaa gaactctgta gcaccgccta catacctcgc tctgctaatc    5880
ctgttaccag tggctgctgc cagtggcgat aagtcgtgtc ttaccgggtt ggactcaaga    5940
cgatagttac cggataaggc gcagcggtcg ggctgaacgg ggggttcgtg cacacagccc    6000
agcttggagc gaacgaccta caccgaactg agatacctac agcgtgagct atgagaaagc    6060
gccacgcttc ccgaagggag aaaggcggac aggtatccgg taagcggcag ggtcggaaca    6120
ggagagcgca cgagggagct tccaggggga aacgcctggt atctttatag tcctgtcggg    6180
tttcgccacc tctgacttga gcgtcgattt ttgtgatgct cgtcaggggg gcggagccta    6240
tggaaaaacg ccagcaacgc ggcctttta cggttcctgg ccttttgctg gccttttgct     6300
cacatggctc gacagatct                                                 6319
```

<210> SEQ ID NO 110
<211> LENGTH: 993
<212> TYPE: DNA
<213> ORGANISM: Bos taurus
<220> FEATURE:
<221> NAME/KEY: CDS
<222> LOCATION: (1)..(993)
<223> OTHER INFORMATION: SGlucON Bovine gamma

<400> SEQUENCE: 110

```
atg gga gtc aaa gtt ctg ttt gcc ctg atc tgc atc gct gtg gcc gag    48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc    96
Ala Lys Pro Thr Glu Asn Asn Glu Asp Phe Asn Ile Val Ala Val Ala
                20                  25                  30 agc aac ttt gcg acc acg gat ctc gat gct gac cga ggg aag ttg ccc   144
Ser Asn Phe Ala Thr Thr Asp Leu Asp Ala Asp Arg Gly Lys Leu Pro
            35                  40                  45 ggc aag aag ctg ccg ctg gag gtg ctc aaa gag atg gaa gcc aat gcc   192
Gly Lys Lys Leu Pro Leu Glu Val Leu Lys Glu Met Glu Ala Asn Ala
        50                  55                  60 cgg aaa gct ggc tgc acc agg ggc tgt ctg atc tgc ctg tcc cac atc   240
Arg Lys Ala Gly Cys Thr Arg Gly Cys Leu Ile Cys Leu Ser His Ile
65                  70                  75                  80 aag tgc acg ccc aag atg aag aag tgg ctc cca gga cgc tgc cac acc   288
Lys Cys Thr Pro Lys Met Lys Lys Trp Leu Pro Gly Arg Cys His Thr
                85                  90                  95 tac gaa ggc gac aaa gag tcc gca cag ggc ggc ata ggc gag gcg atc   336
Tyr Glu Gly Asp Lys Glu Ser Ala Gln Gly Gly Ile Gly Glu Ala Ile
                100                 105                 110 gtc gat att cct gag att cct ggg ttc aag gac ttg gag cca atg gag   384
Val Asp Ile Pro Glu Ile Pro Gly Phe Lys Asp Leu Glu Pro Met Glu
            115                 120                 125 cag ttc atc gca cag gtc gat ctg tgt gtg gac tgc aca act ggc tgc   432
Gln Phe Ile Ala Gln Val Asp Leu Cys Val Asp Cys Thr Thr Gly Cys
        130                 135                 140 ctc aaa ggg ctt gcc aac gtg cag tgt tct gac ctg ctc aag aag tgg   480
Leu Lys Gly Leu Ala Asn Val Gln Cys Ser Asp Leu Leu Lys Lys Trp
145                 150                 155                 160 ctg ccg caa cgc tgt gcg acc ttt gcc agc aag atc cag ggc cag gtg   528
Leu Pro Gln Arg Cys Ala Thr Phe Ala Ser Lys Ile Gln Gly Gln Val
                165                 170                 175 gac aag atc aag ggg gcc ggt ggt gac ggg ccc cag ggc caa ttt ttt   576
Asp Lys Ile Lys Gly Ala Gly Gly Asp Gly Pro Gln Gly Gln Phe Phe
```

```
              180                 185                 190
aga gaa ata gaa aac tta aag gag tat ttt aat gca agt agc cca gat      624
Arg Glu Ile Glu Asn Leu Lys Glu Tyr Phe Asn Ala Ser Ser Pro Asp
            195                 200                 205 gta gct aag ggt ggg cct ctc ttc tca gaa att ttg aag aat tgg aaa      672
Val Ala Lys Gly Gly Pro Leu Phe Ser Glu Ile Leu Lys Asn Trp Lys
210                 215                 220 gat gaa agt gac aaa aaa att att cag agc caa att gtc tcc ttc tac      720
Asp Glu Ser Asp Lys Lys Ile Ile Gln Ser Gln Ile Val Ser Phe Tyr
225                 230                 235                 240 ttc aaa ctc ttt gaa aac ctc aaa gat aac cag gtc att caa agg agc      768
Phe Lys Leu Phe Glu Asn Leu Lys Asp Asn Gln Val Ile Gln Arg Ser
                245                 250                 255 atg gat atc atc aag caa gac atg ttt cag aag ttc ttg aat ggc agc      816
Met Asp Ile Ile Lys Gln Asp Met Phe Gln Lys Phe Leu Asn Gly Ser
            260                 265                 270 tct gag aaa ctg gag gac ttc aaa aag ctg att caa att ccg gtg gat      864
Ser Glu Lys Leu Glu Asp Phe Lys Lys Leu Ile Gln Ile Pro Val Asp
        275                 280                 285 gat ctg cag atc cag cgc aaa gcc ata aat gaa ctc atc aaa gtg atg      912
Asp Leu Gln Ile Gln Arg Lys Ala Ile Asn Glu Leu Ile Lys Val Met
    290                 295                 300 aat gac ctg tca cca aaa tct aac ctc aga aag cgg aag aga agt cag      960
Asn Asp Leu Ser Pro Lys Ser Asn Leu Arg Lys Arg Lys Arg Ser Gln
305                 310                 315                 320 aat ctc ttt cga ggc cgg aga gca tca acg taa                          993
Asn Leu Phe Arg Gly Arg Arg Ala Ser Thr
                325                 330

<210> SEQ ID NO 111
<211> LENGTH: 330
<212> TYPE: PRT
<213> ORGANISM: Bos taurus

<400> SEQUENCE: 111

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Trp Leu Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175
```

-continued

```
Asp Lys Ile Lys Gly Ala Gly Gly Asp Gly Pro Gln Gly Gln Phe Phe
            180                 185                 190

Arg Glu Ile Glu Asn Leu Lys Glu Tyr Phe Asn Ala Ser Ser Pro Asp
        195                 200                 205

Val Ala Lys Gly Gly Pro Leu Phe Ser Glu Ile Leu Lys Asn Trp Lys
    210                 215                 220

Asp Glu Ser Asp Lys Lys Ile Ile Gln Ser Gln Ile Val Ser Phe Tyr
225                 230                 235                 240

Phe Lys Leu Phe Glu Asn Leu Lys Asp Asn Gln Val Ile Gln Arg Ser
                245                 250                 255

Met Asp Ile Ile Lys Gln Asp Met Phe Gln Lys Phe Leu Asn Gly Ser
            260                 265                 270

Ser Glu Lys Leu Glu Asp Phe Lys Lys Leu Ile Gln Ile Pro Val Asp
        275                 280                 285

Asp Leu Gln Ile Gln Arg Lys Ala Ile Asn Glu Leu Ile Lys Val Met
    290                 295                 300

Asn Asp Leu Ser Pro Lys Ser Asn Leu Arg Lys Arg Lys Arg Ser Gln
305                 310                 315                 320

Asn Leu Phe Arg Gly Arg Arg Ala Ser Thr
                325                 330
```

<210> SEQ ID NO 112
<211> LENGTH: 1092
<212> TYPE: DNA
<213> ORGANISM: Bos taurus
<220> FEATURE:
<221> NAME/KEY: CDS
<222> LOCATION: (1)..(1092)
<223> OTHER INFORMATION: SGlucON Lambda bovine

<400> SEQUENCE: 112

```
atg gga gtc aaa gtt ctg ttt gcc ctg atc tgc atc gct gtg gcc gag     48
Met Gly Val Lys Val Leu Phe Ala Leu Ile Cys Ile Ala Val Ala Glu
1               5                   10                  15 gcc aag ccc acc gag aac aac gaa gac ttc aac atc gtg gcc gtg gcc     96
Ala Lys Pro Thr Glu Asn Asn Glu Asp Phe Asn Ile Val Ala Val Ala
                20                  25                  30 agc aac ttt gcg acc acg gat ctc gat gct gac cga ggg aag ttg ccc    144
Ser Asn Phe Ala Thr Thr Asp Leu Asp Ala Asp Arg Gly Lys Leu Pro
            35                  40                  45 ggc aag aag ctg ccg ctg gag gtg ctc aaa gag atg gaa gcc aat gcc    192
Gly Lys Lys Leu Pro Leu Glu Val Leu Lys Glu Met Glu Ala Asn Ala
        50                  55                  60 cgg aaa gct ggc tgc acc agg ggc tgt ctg atc tgc ctg tcc cac atc    240
Arg Lys Ala Gly Cys Thr Arg Gly Cys Leu Ile Cys Leu Ser His Ile
65                  70                  75                  80 aag tgc acg ccc aag atg aag aag tgg ctc cca gga cgc tgc cac acc    288
Lys Cys Thr Pro Lys Met Lys Lys Trp Leu Pro Gly Arg Cys His Thr
                85                  90                  95 tac gaa ggc gac aaa gag tcc gca cag ggc ggc ata ggc gag gcg atc    336
Tyr Glu Gly Asp Lys Glu Ser Ala Gln Gly Gly Ile Gly Glu Ala Ile
            100                 105                 110 gtc gat att cct gag att cct ggg ttc aag gac ttg gag cca atg gag    384
Val Asp Ile Pro Glu Ile Pro Gly Phe Lys Asp Leu Glu Pro Met Glu
        115                 120                 125 cag ttc atc gca cag gtc gat ctg tgt gtg gac tgc aca act ggc tgc    432
Gln Phe Ile Ala Gln Val Asp Leu Cys Val Asp Cys Thr Thr Gly Cys
    130                 135                 140 ctc aaa ggg ctt gcc aac gtg cag tgt tct gac ctg ctc aag aag tgg    480
```

| | | |
|---|---|---|
| Leu Lys Gly Leu Ala Asn Val Gln Cys Ser Asp Leu Leu Lys Lys Trp<br>145                            150                        155                       160 | | |
| ctg ccg caa cgc tgt gcg acc ttt gcc agc aag atc cag ggc cag gtg<br>Leu Pro Gln Arg Cys Ala Thr Phe Ala Ser Lys Ile Gln Gly Gln Val<br>                        165                        170                       175 | 528 |
| gac aag atc aag ggg gcc ggt ggt gac ggg ccc agg aca gga gca gtt<br>Asp Lys Ile Lys Gly Ala Gly Gly Asp Gly Pro Arg Thr Gly Ala Val<br>          180                        185                       190 | 576 |
| cct gtg ccc tct gcc ccc agg gcc ctc cca cct gcc agg ggc tgc cac<br>Pro Val Pro Ser Ala Pro Arg Ala Leu Pro Pro Ala Arg Gly Cys His<br>195                          200                       205 | 624 |
| gtg gcc cag ttc aag tct ctg tcc cct caa gag ctg cag gcc ttc aag<br>Val Ala Gln Phe Lys Ser Leu Ser Pro Gln Glu Leu Gln Ala Phe Lys<br>    210                        215                       220 | 672 |
| acg gcc agg gat gcc ttt gaa gac tcg ttc ttg cca aag gac tgg gac<br>Thr Ala Arg Asp Ala Phe Glu Asp Ser Phe Leu Pro Lys Asp Trp Asp<br>225                          230                       235                       240 | 720 |
| tgc agc acc cac ctt ttc ccc agg acc cgg gac ctg aag cac ctg cag<br>Cys Ser Thr His Leu Phe Pro Arg Thr Arg Asp Leu Lys His Leu Gln<br>                        245                        250                       255 | 768 |
| gtg tgg gag cgc cct gtg gct ctg gag gca gag ctg gcc ctg aca ctg<br>Val Trp Glu Arg Pro Val Ala Leu Glu Ala Glu Leu Ala Leu Thr Leu<br>          260                        265                       270 | 816 |
| acg gtc ctg gag gcc atg gct aac tca tcc ctg ggc cac agc ctg gag<br>Thr Val Leu Glu Ala Met Ala Asn Ser Ser Leu Gly His Ser Leu Glu<br>275                          280                       285 | 864 |
| cag ccc ctt ctc acg ctg cag aac atc cac tcc aag ctc cag gcc tgt<br>Gln Pro Leu Leu Thr Leu Gln Asn Ile His Ser Lys Leu Gln Ala Cys<br>    290                        295                       300 | 912 |
| gtc cca gct cag ccc aca gca agc tcc agg ccc cgg ggc cgc ctc cac<br>Val Pro Ala Gln Pro Thr Ala Ser Ser Arg Pro Arg Gly Arg Leu His<br>305                          310                       315                       320 | 960 |
| cac tgg ctg cac cgc ctc cag gag gcc cgg aag gag tcc cag gac tgc<br>His Trp Leu His Arg Leu Gln Glu Ala Arg Lys Glu Ser Gln Asp Cys<br>                        325                        330                       335 | 1008 |
| ctc gaa gcc tct gtg atg ttc aac ctc ctc cgc ctc ctc acc cgg gac<br>Leu Glu Ala Ser Val Met Phe Asn Leu Leu Arg Leu Leu Thr Arg Asp<br>          340                        345                       350 | 1056 |
| ctg aaa tgt gtt gcc agc gga gac cag tgt gtc tga<br>Leu Lys Cys Val Ala Ser Gly Asp Gln Cys Val<br>355                          360 | 1092 |

<210> SEQ ID NO 113
<211> LENGTH: 363
<212> TYPE: PRT
<213> ORGANISM: Bos taurus

<400> SEQUENCE: 113

Met Gly Val Lys Val Leu Phe Ala Leu Ile Cys Ile Ala Val Ala Glu
1                 5                     10                     15

Ala Lys Pro Thr Glu Asn Asn Glu Asp Phe Asn Ile Val Ala Val Ala
                 20                     25                     30

Ser Asn Phe Ala Thr Thr Asp Leu Asp Ala Asp Arg Gly Lys Leu Pro
        35                     40                     45

Gly Lys Lys Leu Pro Leu Glu Val Leu Lys Glu Met Glu Ala Asn Ala
50                        55                     60

Arg Lys Ala Gly Cys Thr Arg Gly Cys Leu Ile Cys Leu Ser His Ile
65                70                     75                     80

Lys Cys Thr Pro Lys Met Lys Lys Trp Leu Pro Gly Arg Cys His Thr

-continued

```
                         85                  90                  95
Tyr Glu Gly Asp Lys Glu Ser Ala Gln Gly Gly Ile Gly Glu Ala Ile
                100                 105                 110

Val Asp Ile Pro Glu Ile Pro Gly Phe Lys Asp Leu Glu Pro Met Glu
            115                 120                 125

Gln Phe Ile Ala Gln Val Asp Leu Cys Val Asp Cys Thr Thr Gly Cys
        130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp Gly Pro Arg Thr Gly Ala Val
            180                 185                 190

Pro Val Pro Ser Ala Pro Arg Ala Leu Pro Pro Ala Arg Gly Cys His
        195                 200                 205

Val Ala Gln Phe Lys Ser Leu Ser Pro Gln Glu Leu Gln Ala Phe Lys
    210                 215                 220

Thr Ala Arg Asp Ala Phe Glu Asp Ser Phe Leu Pro Lys Asp Trp Asp
225                 230                 235                 240

Cys Ser Thr His Leu Phe Pro Arg Thr Arg Asp Leu Lys His Leu Gln
                245                 250                 255

Val Trp Glu Arg Pro Val Ala Leu Glu Ala Glu Leu Ala Leu Thr Leu
            260                 265                 270

Thr Val Leu Glu Ala Met Ala Asn Ser Ser Leu Gly His Ser Leu Glu
        275                 280                 285

Gln Pro Leu Leu Thr Leu Gln Asn Ile His Ser Lys Leu Gln Ala Cys
    290                 295                 300

Val Pro Ala Gln Pro Thr Ala Ser Ser Arg Pro Arg Gly Arg Leu His
305                 310                 315                 320

His Trp Leu His Arg Leu Gln Glu Ala Arg Lys Glu Ser Gln Asp Cys
                325                 330                 335

Leu Glu Ala Ser Val Met Phe Asn Leu Leu Arg Leu Leu Thr Arg Asp
            340                 345                 350

Leu Lys Cys Val Ala Ser Gly Asp Gln Cys Val
355                 360
```

FUSION PROTEINS CONTAINING LUCIFERASE AND A POLYPEPTIDE OF INTEREST

CROSS-REFERENCE TO RELATED APPLICATIONS

This continuation application claims priority to U.S. application Ser. No. 15/583,459, filed May 1, 2017, which is a continuation in part (CIP) application that claims priority to U.S. application Ser. No. 15/259,409 filed Sep. 8, 2016, now U.S. Pat. No. 10,385,319, each of which is incorporated by reference in its entirety.

REFERENCE TO A SEQUENCE LISTING

In accordance with 37 CFR § 1.52(e)(5), the present specification references a Sequence Listing submitted electronically as a .txt file named "SEQ_LST DHS-0128US01.txt". The Sequence Listing file was generated on Sep. 9, 2019 and is 325 kb in size. The entire contents of the Sequence Listing are herein incorporated by reference.

BACKGROUND OF THE INVENTION

Field of the Invention

The present disclosure generally relates to fusion polynucleotides encoding fusion proteins comprising interferons and luciferases which have biotherapeutic, diagnostic, and quality control uses in both the medical and veterinary fields.

Description of the Related Art

Interferons (IFN) are a class of cytokines that interfere with viral replication. Interferons are divided into three classes, type I, type II, and type III. Type I interferons utilize the IFNAR1-IFNAR2 receptor complex and include IFNα and IFN β. Type II interferons consist of IFN γ and utilize the IFNGR1-IFNGR2 receptor complex. Type III interferons consist of IFN λ, also called interleukin-28A, interleukin-28B, and interleukin-29, the most recently discovered interferon type. Type III interferons utilize the IFNLR1-IL10Rβ receptor complex.

Type I interferons are used to treat a number of medical conditions in humans. Commercially available IFN alpha is used for the treatment of hairy cell leukemia, malignant melanoma, and AIDS-related Kaposi's sarcoma while IFN beta has been used as a treatment for relapsing-remitting and secondary-progressive forms of multiple sclerosis. In a veterinary setting IFN alpha can be used to treat Feline Herpesvirus 1, Feline infectious peritonitis, Feline Immunodeficiency Virus, Feline Leukemia Virus, and Canine papilloma virus in companion animals while in livestock both IFN α and IFN β have been found to inhibit Foot-and-Mouth Disease Virus (FMDV). Type III interferon, IFN λ, is also capable of inhibiting FMDV in cattle.

Interferons are naturally secreted, often by specialized cell types, and are comprised of a secretion peptide sequence along with an activity domain. The secretion domain is not essential for protective activity. Protective activity of interferons, and in particular IFN α, is often evaluated using Vesicular Stomatitis Virus (VSV). VSV is a member of the Rhabdoviridea family and is capable of infecting insects, cattle, horses, pigs, and under the right circumstances humans.

Hybrid peptides comprised of interferons and various molecules have been constructed and evaluated for a number of reasons. Previous work has made hybrid molecules comprised of IFN α and portions of placental growth factor-2 to enhance the anti-tumor properties of IFN α. Chimeras of interferons with different reporter molecules such as DsRed2 and GFP as well as with antibodies for immunotherapy have also been previously reported in literature.

Quantification of interferon concentrations is typically dependent upon either an activity assay or antibody based methods such as an ELISA. Measurements obtained by interferon activity assays are related to interferon concentration but not definitively related. For example, addition of placental growth factor-2 can enhance interferon activity resulting in detection of a higher interferon activity. However, this higher interferon activity is not directly related to the absolute concentration of interferon. This raises the potential that undesired and/or unknown contaminations during production can artificially influence determination of a final product concentration.

Antibody-based detection assays, such as ELISA, can be inaccurate because antibodies used to detect interferon can bind to more than one type of interferon or can exhibit different affinities for interferon under different conditions. Antibody binding affinities are dependent upon recognition of structural elements such as linear and conformational epitopes in the target substrate such as interferon. Amino acid sequence differences or conformation differences between or among interferon molecules in a sample can cause antibodies to exhibit different binding affinities. This leads to inaccuracies in determining the absolute concentration of an interferon, or a particular interferon, in a sample. As a result the usage of ELISA to determine the absolute concentrations of molecules with different amino acid sequences is not always a reliable option. Antibody-based detection assays also carry a high cost associated with the need to produce a consistent antibody amongst different production batches. The usage of antibodies also contributes to a limited shelf life.

In view of these problems, the inventors developed novel chimeric proteins that fuse a luciferase reporter with an interferon or enzyme of interest. The resulting chimeric proteins allow for easy and accurate determination of absolute concentrations for interferons and other biologically active molecules.

BRIEF SUMMARY OF THE INVENTION

The inventors disclose herein chimeric proteins fusing a *Gaussia* Luciferase (GLuc) or Super-luminescent *Gaussia* Luciferase (SGLuc) reporter to different kinds of interferons.

GLuc is a 185 amino acid naturally secreted luciferase isolated from *Gaussia princeps*. Mutations to GLuc which enhance luciferase output may include, but are not limited to, the 8990 mutant also identified as SGLuc.

GLuc and SGLuc constructs with 2A or 2A-like protein sequences such as, for example, a Δ1D2A translational interrupter, retained both luciferase activity and secretion, which make them viable biomarkers for expression in a single open reading frame.

Several types of such chimeric fusion proteins are exemplified. In one or more embodiments, three different chimeric molecules were created using IFN α sequence, as exemplified in FIG. 1. As a first example, SGLuc-Δ1D2A-IFNα is a SGLuc-Δ1D2A fused to a complete IFN α sequence on the C-terminus. This translated construct expresses two separate proteins—SGLuc-Δ1D2A and IFN α. As a second example, IFNα-Δ1D2A-SGLuc Δ1M, is a complete IFN α sequence with a Δ1D2A-SGLuc Δ1M fused on the C-terminus. This translated construct expresses two separate proteins IFNα-Δ1D2A and SGLuc Δ1M. As a third example, SGLucON α is a SGLuc sequence with just the activity domain of IFN α fused to the C-terminus. This translated construct expresses a single protein SGLucON α which is comprised of both SGLuc and just the activity domain of IFNα.

SGLucON α was used as a template to create three additional chimeric molecules based off of porcine IFN β, bovine IFN γ, and bovine IFN λ. For the creation of these constructs each IFN sequence was examined and the secretion domains identified, FIG. 3. Chimeric molecules were constructed by making chimeras only of SGLuc with the resulting non-secretion related amino acid sequences, FIG. 4. The resulting chimeras are identified as SGLucON β, SGLucON γ, and SGLucON λ.

Utilization of chimeric molecules of GLuc or SGLuc with interferons or a protein of interest provides a simple and fast method to substantially quantify an absolute concentration of a particular kind of interferon or protein of interest. When utilizing a construct containing the Δ1D2A translational interrupter the resulting product is two proteins and concentration is determined of the luciferase as a correlate to concentration of interferon or a protein of interest. When utilizing fused protein like SGLucON α, the concentration can be measured directly using the resulting luciferase activities of the chimeric protein.

BRIEF DESCRIPTION OF THE DRAWINGS

FIG. 1 depicts the layout of the three interferon α containing construct open reading frames.

FIG. 2A describes luciferase readings of constructs separated by the Δ1D2A translational interrupter and corresponding controls.

FIG. 2B depicts Western blots of media harvested off of cells transfected with constructs separated by the Δ1D2A translational interrupter and corresponding controls.

FIG. 3 describes amino acid sequences for Porcine Interferon α (SEQ ID NO: 24), Porcine Interferon β (SEQ ID NO: 66), Bovine Interferon γ (SEQ ID NO: 75), and Bovine Interferon λ (SEQ ID NO: 84). Underlined residues represent the secretion domains of each interferon sequence.

FIG. 4 describes amino acid sequences for SGLucON α (SEQ ID NO: 48), SGLucON β (SEQ ID NO: 70), SGLucON γ (SEQ ID NO: 111), and SGLucON λ (SEQ ID NO: 113). Underlined residues represent the *Gaussia* Luciferase amino acids.

FIG. 5A depicts Western blots of media harvested from transfected cells using anti-GLuc, Anti-IFN α, Anti-IFN β, and Anti-IFN λ, antibodies.

FIG. 5B describes relative Luciferase Units per half second for IFN and SGLucON α, β, γ, and λ, media samples.

FIG. 6 depicts a plaque assay of IFN α, SGLuc-Δ1D2A-IFN α, IFN α-Δ1D2A-SGLuc (Δ1M), and SGLucON α activity against Vesicular Stomatitis Virus-NJ.

FIG. 7 depicts concentration of IFNα in harvested media from cells transfected with pTarget IFNα, pTarget SGLuc-Δ1D2A-IFNα, pTarget IFNα-Δ1D2A-SGLucΔ1M, pTarget Δ1D2A-SGLuc Δ1M, and pTarget SGLuc-Δ1D2A. There were 3 replicates per each of 4 dilutions for each sample.

FIG. 8 depicts effects of IFNα on growth of VSV-NJ. IFNα levels produced in growth media harvested from HEK293-T cells transfected with pTarget IFNα, pTarget SGLuc-Δ1D2A-IFNα, pTarget IFNα-Δ1D2A-SGLuc Δ1M, mpTarget SGLucONα, or pTarget SGLuc-Δ1D2A (negative control) were measured and adjusted to concentrations listed before samples were exposed to MDBK cells. VSV-NJ was added to the MDBK cells and Plaque Forming Units (PFU) were counted after the growth period; average of 2 replicates are reported. ND, not determined.

DETAILED DESCRIPTION OF THE INVENTION

Definitions

The term "fusion protein" or "chimeric protein" refers to a polypeptide containing polypeptides or segments of polypeptides from different sources, such as a segment of a luciferase from *Gaussia princeps* and a biologically active segment of an interferon. A fusion protein may be produced by joining two or more polynucleotides that originally coded for the separate proteins or protein segments into a single fusion polynucleotide. Besides the polynucleotide sequences encoding for the separate proteins, a fusion polynucleotide may comprise other polynucleotide sequences such as those encoding translation interrupter sequences or those encoding amino acid sequences which otherwise traffic or process an expressed protein. In some embodiments, the term "fusion protein" will refer to an intact fusion protein, such as a fusion between a luciferase and interferon sequence. In other embodiments, this term may refer to separate polypeptides derived from translation of a fusion polynucleotide, for example, can encompass separate polypeptides produced from a fusion construct containing a translation interrupter sequence.

Translation of the fusion polynucleotide results in a single or multiple polypeptides with functional properties derived from each of the original proteins. A single fusion protein may be expressed from a fusion polynucleotide. Such a single fusion protein may be processed into one, two or more polypeptides depending on the design of the fusion polynucleotide and the host cell expressing it. A fusion polynucleotide can express more than one polypeptide depending on its design, for example, depending on the presence of translation interrupters, stop codons, or other regulatory elements.

A polypeptide encoded by a fusion polynucleotide need not exactly correspond to all the residues of the original protein, for example, it may contain fewer or more amino acid residues than a full-length source protein, but contain an active site or functional domain of the source protein, for example, it may be a fragment of interferon that retains at least one interferon activity. A fusion polynucleotide may also be engineered to encode modified forms of a source protein, such as those having at least 70, 80, 90, 95 or 99% sequence identity or similarly with a source protein or with a functional segment thereof.

The term "fragment thereof," as applied to a polypeptide component of a fusion polypeptide described herein, refers to a polypeptide comprising any portion of the amino acid sequence of the polypeptide, wherein the fragment substantially retains at least one function of the full-length polypeptide from which it was derived. For example, a fragment of a luciferase may emit light or be processed and/or secreted in a manner similar to the full-length luciferase; a fragment of a translation interruption or interrupter sequence can retain the ability to interrupt translation, and a fragment of a biologically active molecule, such as interferon, can retain at least one physiological, pharmacodynamics, pharmacokinetic or immunological activity of the full-length molecule and/or an ability to be processed, trafficked or secreted in a way similar to the native biologically active molecule from which it was derived.

The term "derivative thereof" or "modified sequence" as applied to the polypeptide components disclosed herein, refers to a polypeptide consisting of an amino acid sequence that is at least 70, 80, 90, 95, or 99% identical or similar to the amino acid sequence of a biologically active molecule such as a luciferase, translation interruption or interrupter sequence, or interferon, wherein the polypeptide derivative substantially retains the ability to induce the secretion of a target polypeptide to which it is fused. In some embodiments, the derivative comprises an amino acid sequence that is at least 75%, 80%, 85%, 86%, 87%, 88%, 89%, 90%, 91%, 92%, 93%, 94%, 95%, 96%, 97%, 98%, or 99% identical to the amino acid sequence of a native or previously engineered sequence. The derivative may comprise additions, deletions, substitutions, post-translational modifications, chemical modifications, or a combination thereof to the amino acid sequence of a native or previously engineered molecule. A derivative may include a mutant polypeptide with 1, 2, 3, 4, 5, 6, 7, 8, 9, 10, 11-15, 16-20, 21-25, or 26-30 additions, substitutions, post-translational modifications, chemical modifications, or deletions. Additions or substitutions also include the use of non-naturally occurring amino acids or modified amino acids.

BLASTN may be used to identify a polynucleotide sequence having at least 70%, 75%, 80%, 85%, 87.5%, 90%, 92.5%, 95%, 97.5%, 98%, 99% sequence identity to a reference polynucleotide. A representative BLASTN setting optimized to find highly similar sequences uses an Expect Threshold of 10 and a Wordsize of 28, max matches in query range of 0, match/mismatch scores of 1/−2, and linear gap cost. Low complexity regions may be filtered or masked. Default settings of a Standard Nucleotide BLAST are described by and incorporated by reference to blast.ncbi.nlm.nih.gov/_ Blast.cgi?PROGRAM=blastn&BLAST_PROGRAMS=megaBlast&PA GE_TYPE=BlastSearch&SHOW_ DEFAULTS=on&LINK_LOC=blasthome (last accessed Feb. 4, 2016).

BLASTP can be used to identify an amino acid sequence having at least 70%, 75%, 80%, 85%, 87.5%, 90%, 92.5%, 95%, 97.5%, 98%, 99% sequence identity, or similarity to a reference amino acid using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Other default settings for BLASTP are described by and incorporated by reference to the disclosure available at: blast.ncbi.nlm.nih.gov/_Blast.cgi?PROGRAM=blastp&PAGE_TYPE=BlastSearch&LINK_LOC=blasthome (last accessed Jun. 29, 2016). Derivatives, analogs or modified versions of any of the polynucleotide or amino acid sequences specifically described herein or in the sequence listing having the above-mentioned ranges of sequence identity or similarly are specifically contemplated.

A "biologically active" or "active" interferon or other polypeptide of interest will exhibit at least one activity of the native molecule, such as an ability to modulate the immune system, treat an autoimmune disease, induce humoral or cellular immunity, interfere with virus replication, treat a tumor or microbial infection, contain diagnostically or immunologically useful epitopes, or any other function of the native molecule. These functions will depend on the nature of the native polypeptide of interest.

A "biotherapeutic" or a composition containing a fusion protein or cleavage product(s) of such a fusion protein, as described herein, including living cells which express or contain such a fusion protein or fusion protein fragments, may be formulated by any of the methods known in the art.

It can be typically prepared as an injectable (e.g. subcutaneous, intradermal and intramuscular injection, jet injections) or as a formulation for oral administration, intranasal administration (e.g. aerosol inhalation or instillation), topical administration to the eye, electroporation, gene gun, transfection, liposome-mediated delivery or combinations thereof, either as liquid solutions or suspensions. Solid forms suitable for solution in, or suspension in, liquid prior to injection or other administration may also be prepared. The preparation may also be emulsified or encapsulated in liposomes. Suitable excipients include but are not limited to water, saline, dextrose, glycerol, ethanol, or the like and combinations thereof. In a further embodiment, example diluents include, but are not limited to, water, physiological saline solution, human serum albumin, oils, polyethylene glycols, glycerin, propylene glycol or other synthetic solvents, antibacterial agents such as benzyl alcohol, antioxidants such as ascorbic acid or sodium bisulfite, chelating agents, such as ethylene diamine-tetra-acetic acid, buffers such as acetates, citrates or phosphates and agents for adjusting osmolarity, such as sodium chloride or dextrose. In a further embodiment, example carriers include, but are not limited to, liquid carriers (e.g., water, saline, culture medium, saline, aqueous dextrose, aqueous glycols) and solid carriers (e.g., carbohydrates such as starch, glucose, lactose, sucrose, dextrans; anti-oxidants such as ascorbic acid and glutathione, hydrolyzed proteins). In a further embodiment, pharmaceutically acceptable salts, include but are not limited to, the acid addition salts (formed with free amino groups of the peptide) which are formed with inorganic acids (e.g., hydrochloric acid or phosphoric acids) and organic acids (e.g., acetic, oxalic, tartaric, or maleic acid). Salts formed with the free carboxyl groups may also be derived from inorganic bases (e.g., sodium, potassium, ammonium, calcium, or ferric hydroxides), and organic bases (e.g., isopropylamine, trimethylamine, 2-ethylaminoethanol, histidine, and procaine). In a further embodiment, the biotherapeutic or other compositions according to the invention may contain minor amounts of auxiliary substances such as wetting or emulsifying agents, pH buffering agents, and/or other agents, which enhance the effectiveness of the vaccine. Examples of agents which may be effective include, but are not limited to: aluminum hydroxide;

N-acetyl-muramyl-L-threonyl-D-isoglutamine (thr-MDP); N-acetyl-nor-muramyl-L-alanyl-D-isoglutamine (CGP 11637, referred to as nor-MDP); N-acetyl muramyl-L-alanyl-D-isoglutaminy 1-L-alanine-2-(1'-2'-dipalmitoyl-sn-glycero-3-hydroxyphosphoryloxy)-ethyl amine (CGP 19835A, referred to as MTP-PE); and RIBI, which contains three components extracted from bacteria: monophosphoryl lipid A, trehalose dimycolate and cell wall skeleton (MPL+ TDM+CWS) in a 2% squalene/Tween 80 emulsion.

In one or more embodiments, the biotherapeutics and compositions described herein may be administered prophylactically (e.g., to prevent or ameliorate the effects of a future infection), therapeutically (e.g., to treat or to empower the immune system of an infected subject) or both, in a manner compatible with the dosage formulation, and in such an amount and manner as will be prophylactically and/or therapeutically effective.

In an alternative embodiment, polynucleotides encoding a fusion protein according to the invention may be administered as a DNA composition which can be administered at dosages such as in the range of 0.05-3 µg/µl. Other factors that can form the basis of what dosage range to implement include but are not limited the size of the subject, the particular pathogen or disease being treated and the particular type of interferon or other biologically active molecule encoded.

A polynucleotide-based composition may be given in a single dose; two dose schedule, for example two to eight weeks apart; or a multiple dose schedule. A multiple dose schedule is one in which a primary course of administration may include 1 to 10 or more separate doses, followed by other doses administered at subsequent time intervals as required to maintain and/or reinforce the desired response on a subject's immune system.

"*Gaussia* luciferase" or "GLuc" describes luciferases produced by members of the genus *Gaussia*, amino acid sequence variants of native *Gaussia* luciferases, such as those having at least 70, 80, 90, 95, 99% sequence identity or homology to a native or previously engineered *Gaussia* luciferase or that contain 1, 2, 3, 4, 5, 6, 7, 8, 9, 10 or more amino acid deletions, substitutions or insertions to a native *Gaussia* luciferase amino acid sequence, and truncated native or variant *Gaussia* luciferases that retain luciferase activity. *Gaussia* luciferase or GLuc from *G. princeps* is commercially available (SEQ ID NO: 2). GLuc is a 185 amino acid naturally secreted luciferase isolated from *Gaussia princeps* and has a higher luminescence intensity than firefly or *Renilla* luciferases. It has been used to monitor tumor growth in vivo.

"Super-luminescent *Gaussia* luciferase" or "SGLuc" describes amino acid sequence variants of *Gaussia* luciferase containing an amino acid substitution at residues 89 and 90 of GLuc (SEQ ID NO:4) and which exhibit a higher stability than unmodified *G. princeps* luciferase in certain cell lysis buffers. This term encompasses other luciferase variants that are at least 70, 80, 90, 95, or 99% identical or similar to the GLuc or SGLuc of SEQ ID NO: 2 or 4, respectively, which exhibit substantially the same properties. The addition of 30 amino acid sequence comprising the FMDV 2A translational interrupter sequence, Δ1D2A, to the C-terminus of GLuc or the 8990 GLuc mutant (SGLuc) did not prevent either secretion or luminescence.

The luciferases described herein may be expressed in a form, or processed and expressed in a form that is capable of secretion from a host cell expressing a fusion polypeptide expressing them.

The term "interferon" includes native or previously-engineered mammalian Type I (IFN-α, IFN-β, IFN-ε, -κ, -τ, -δ, and -ζ, IFN-ω and IFN-ν), and non-mammalian interferons, such as those from birds, reptiles, amphibians, fish and other vertebrates. It also includes Type II interferon (IFN-γ) and Type III interferon (IFN-λ). Representative interferon polynucleotide or amino acids sequences are described by SEQ ID NOS: 23/24, 49/50, 53/54, 57/58, 61/62, 65/66, 71/72, 75/76, 79/80, 83/84, 87/88, or 91/92.

This term includes IFN α, β, and γ interferons, amino acid sequence variants of native interferons, such as those having at least 70, 80, 90, 95, 99% sequence identity or homology to a native or previously engineered interferon or that contain 1, 2, 3, 4, 5, 6, 7, 8, 9, 10 or more deletions, substitutions or insertions to a native or previously engineered interferon amino acid sequence, and truncated native or variant interferons that retain at least one functional activity of the native or previously-engineered interferon.

An interferon may be obtained or derived from a human or other mammal, avian, or vertebrate, including but not limited to monkeys and other primates, mice, rats, rabbits, horses, domestic dogs and other *Canidae*, domestic cats and other *Felidae*, pigs and other *Suidae*, cows and other *Bovinae*, cattle, sheep, goats, water buffalos, yaks, reindeer, deer, elk, llamas, alpacas, bison, moose, camels, chamois, giraffes, hogs, warthogs, kudus, antelopes, gazelles, and wildebeests.

The term "interferon secretion sequence" includes, but is not limited to, native amino acid sequences that facilitate secretion of interferons, such as those described by the amino acid sequences of SEQ ID NOS: 26, 28, 30, 32, 34, 36, 38, 40, 42, 44 and 46. Other interferon secretion sequences include those that are at least 70, 80, 90, 95, 99% identical or similar to a native interferon secretion sequence which facilitate secretion of interferon or other biologically active proteins. Modified interferon secretion sequences also include those with 1, 2, 3, 4, 5, 6, 7, 8, 9, 10 or more amino acid deletions, substitutions or insertions to a native sequence. Representative polynucleotides encoding these secretion sequences are described by SEQ ID NOS: 25, 27, 29, 31, 33, 35, 37, 39, 41, 43 and 45 as well as by degenerate versions of these sequences and by modified polynucleotide sequences that encode an interferon secretion sequence that is at least 70, 80, 90, 95, 99% identical or similar to a native interferon secretion sequence as described herein.

The term "biologically active" or "active" molecule includes members of the interferon family described herein, as well as other cytokines such as members of the IL-2 family (including IL-4, IL-7, IL-9, IL-15, IL-21, EPO, TPO and other molecules having a four alpha helix bundle), IL-10 family (including L-19, IL-20, IL-22, IL-24 and IL-26), IL-1 family (including IL-1 and IL-18), IL-17 family (including IL17A-IL17F) and cysteine-knot family (TNF-β1, TNF-⊕2, TNF-β3). It includes lymphokines, interleukins and chemokines as well as peptide hormones such as amyline, anti-mullerian hormone, adiponectin, adrenocorticotropic hormone, angiotensinogen, angiotensin, antidiuretic hormone, atrial-natriuretic peptide, brain natriuretic peptide, calcitonin, cholecystokinin, corticotropin-releasing hormone, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, insulin like growth factor, leptin, lipotropin, luteinizing hormone, melanocyte stimulating hormone, motilin, orexin, oxytocin, pancreatic polypeptide, parathyroid hormone, pituitary adenylate cyclase-activating peptide, prolactin, prolactin releasing hormone, relaxin, renin, secretin, somatostatin, thrombopoietin, thyroid-stimulating hormone, thyrotropin-releasing hormone, vasoactive intestinal peptide, guanylin, and uroguanylin. Modified versions of these native molecules are included, such as those that are at least 70, 80, 90, 95, 99% identical or similar to a native biologically active molecule and which retain at least one activity thereof as well as those having 1, 2, 3, 4, 5, 6, 7, 8, 9, 10 or more amino acid deletions, substitutions or insertions to a native sequence.

A "translation interrupter" includes 2A, Δ1D2A, or other 2A-like translational interrupters. The 2A translation interrupter is well known in the art pertaining to Foot-and-mouth Disease Virus (FMDV). Other such translational interrupters from other viruses are known. Variants of such interrupters with 1, 2, 3, 4, 5, 6, 7, 8, 9 or 10 insertions, deletions or substitutions of an amino acid residues that retain the ability to interrupt translation also may be used to process fusion proteins described herein. Non-limiting examples of translation interrupter sequences or polynucleotides encoding them are described by SEQ ID NOS: 5-14.

A "pharmaceutically acceptable carrier", "adjuvant", or "excipient" is known in the art, including, but not limited to, physiological saline, mineral oil, vegetable oils, aqueous carboxymethyl cellulose or polyvinylpyrrolidone. The skilled practitioner will recognize that such carriers should be compatible with the fusion proteins or nucleic acid constructs. Phosphate buffered saline (PBS) is one example of an acceptable carrier. The concentration and amount of the proteins or nucleic acid constructs in the final composition may vary depending upon the desired use and type of response needed, and the host animal. The fusion proteins or nucleic acid constructs should be provided in an amount effective to induce the preferred response as determined by routine testing. Appropriate adjuvants as known in the art may also be included in the formulation. Without being limited thereto, suitable adjuvants include but are not limited to mineral oil, vegetable oils, alum, Freund's incomplete adjuvant, and microparticles or nanoparticles or beads of biocompatible matrix materials such as agar or polyacrylate. Other known immunogenic agents used in conventional vaccines for a subject may also be included in the formulation as well as other therapeutic agents, such as antibacterial or antiviral drugs.

Additional non-limiting aspects and embodiments of the disclosure are described in the following enumerated paragraphs. Some embodiments are directed to compositions containing polynucleotides, these include, without limitation, the following:

1. A polynucleotide that encodes at least one fusion protein comprising at least one of *Gaussia* Luciferase (GLuc), super-luminescent *Gaussia* luciferase (SGLuc) or other luciferase which, preferably, when expressed can be secreted, and at least one interferon, cytokine, enzyme, or other polypeptide of interest. Examples of polynucleotides encoding GLuc and SGLuc include those comprising the sequences of SEQ ID NO: 1 and SEQ ID NO: 3. Representative luciferase sequences are described by SEQ ID NO: 2 and SEQ ID NO: 4, respectively. The polynucleotides encoding the luciferase may be directly adjoined to those encoding the interferon or other polypeptide of interest or may be separated from the sequences encoding the interferon or other polypeptide of interest, for example, by an intervening translation interruption or interrupter sequence. A polynucleotide sequence encoding a luciferase may replace a polynucleotide sequence encoding the N-terminal portion of an interferon or other polypeptide of interest, for example, it may replace a native secretion sequence or sequence not essential for the biological activity (or immunogenicity) of an interferon or other polypeptide of interest.

The above-mentioned polynucleotide sequence may encode fusion proteins having their various components in any order. For example, it may encode a fusion protein comprising in order from the N-terminal: a luciferase amino acid sequence (such as GLuc or SGLuc), a translation interrupter amino acid sequence (such as 2A or Δ1D2A) and a biologically active molecule amino acid sequence (such as IFN α). In this embodiment the fusion polynucleotide, upon translation, can produce two separate proteins: the first comprising the luciferase-translation interrupter and the second comprising the biologically active amino acid sequence, e.g., (SGLuc-Δ1D2A and IFN α).

This embodiment may encode a fusion protein comprising in order from the N-terminal: a biologically active molecule amino acid sequence (such as IFN α), a translation interrupter amino acid sequence (such as 2A or Δ1D2A), and a luciferase amino acid sequence (such as GLuc or SGLuc). In this embodiment, upon translation, the fusion polynucleotide can produce two separate proteins: the first comprising the luciferase and the second comprising the translation interrupter sequence and the biologically active amino acid sequence which may be expressed without an N-terminal Met residue (e.g., IFNα-Δ1D2A and SGLuc Δ1M).

This embodiment it may encode a GLucON or SGLucON sequence comprising in order from the N-terminal a luciferase amino acid sequence (such as GLuc or SGLuc) fused to an active domain of a biologically active protein, such as IFN α with its native secretion domain replaced with GLuc or SGLuc secretion sequence. No translation interrupter sequence is required for this fusion protein construct which can be transported out of a host cell intact.

2. The polynucleotide of embodiment 1, wherein the at least one fusion protein further comprises at least one promoter or other transcription regulatory element, at least one prokaryotic or eukaryotic translation initiation sequence or other translation regulatory element, at least one translational interrupter sequence, or at least one reporter gene operatively linked to, or embedded within the polynucleotide sequence encoding the at least one fusion protein.

3. The polynucleotide of embodiment 1, wherein the at least one fusion protein further comprises at least one of a 2A, Δ1D2A, or other translational interrupter sequence.

4. The polynucleotide of embodiment 1, wherein the at least one fusion protein further comprises at least one an Aphthovirus 2A, Δ1D2A, or other Aphthovirus translational interrupter sequence. Representative examples of polynucleotides encoding translation interrupter sequences include those comprising SEQ ID NOS: 5, 7, 9, 11, 13, 15, 17, 19, and 21. Representative encoded amino acid sequences are respectively described by SEQ ID NOS: 6, 8, 10, 12, 14, 16, 18, 20 and 22.

5. The polynucleotide of embodiment 1, wherein the at least one fusion protein further comprises at least one of a foot and mouth disease virus (FMDV) 2A, FMDV Δ1D2A, or other FMDV translational interrupter sequence.

6. The polynucleotide of embodiment 1, wherein the at least one fusion protein further comprises a Δ1D2A sequence engineered at the C-terminus of the at least one of *Gaussia* Luciferase (GLuc), super-luminescent *Gaussia* luciferase (SGLuc) or other luciferase.

7. The polynucleotide of embodiment 1, wherein the at least one fusion protein further comprises a Δ1D2A sequence engineered at the N-terminus of the at least one of *Gaussia* Luciferase (GLuc), super-luminescent *Gaussia* luciferase (SGLuc) or other luciferase.

8. The polynucleotide of embodiment 1, wherein the at least one fusion protein further comprises a translational interrupter sequence engineered at the C-terminus of at least one of *Gaussia* Luciferase (GLuc), super-luminescent *Gaussia* luciferase (SGLuc) or other luciferase.

9. The polynucleotide of embodiment 1, wherein the at least one fusion protein further comprises a translational interrupter sequence engineered at the N-terminus of the at least one of *Gaussia* Luciferase (GLuc), super-luminescent *Gaussia* luciferase (SGLuc) or other luciferase.

10. The polynucleotide of embodiment 1, wherein the at least one fusion protein further comprises an FMDV 2A sequence engineered at the C-terminus of at least one of *Gaussia* Luciferase (GLuc), super-luminescent *Gaussia* luciferase (SGLuc) or other luciferase.

11. The polynucleotide of embodiment 1, wherein the at least one fusion protein further comprises an FMDV 2A sequence engineered at the N-terminus of the at least one of *Gaussia* Luciferase (GLuc), super-luminescent *Gaussia* luciferase (SGLuc) or other luciferase.

12. The polynucleotide of embodiment 1, wherein the at least one of *Gaussia* Luciferase (GLuc), super-luminescent *Gaussia* luciferase (SGLuc) or other luciferase which can be secreted does not have an N-terminal methionine residue.

13. The polynucleotide of embodiment 1 that encodes at least one fusion protein comprising at least one of *Gaussia* Luciferase (GLuc), super-luminescent *Gaussia* luciferase (SGLuc) or other luciferase, and at least one interferon, cytokine, enzyme, or other polypeptide of interest. Representative, but not limited, polynucleotides may comprise one or more polynucleotide subsequences (e.g., encoding a luciferase, a secretion polypeptide, interferon or other biologically active molecule, translation terminator, translation interrupter sequence, etc.) described in the sequence listing or may comprise a fusion polynucleotide such as those described by SEQ ID NOS: 97-103 and 108-109. Modified polynucleotides, which retain the functional properties of those described herein are included, such as polynucleotides that are at least 70, 80, 90, 95, or 99% identical or similar to those of SEQ ID NOS: 97-109 and which encode functional luciferases, translational terminators, or interferons or fusions or secretable fusions thereof. The polynucleotides described herein may be incorporated into a vector, including transposons, or into a host chromosome.

Other embodiments of the invention are directed to vectors these include, without limitation, the following:

14. A vector comprising the polynucleotide of embodiment 1 which encodes at least one fusion protein comprising at least one of *Gaussia* Luciferase (GLuc), super-luminescent *Gaussia* luciferase (SGLuc) or other luciferase, preferably, in a form which can be secreted, and at least one interferon, cytokine, enzyme, or other polypeptide of interest.

15. The vector of embodiment 14, wherein the polynucleotide encoding the at least one fusion protein further comprises at least one promoter or other transcription regulatory element, at least one prokaryotic or eukaryotic translation initiation sequence or other translation regulatory element, at least one translational interrupter sequence, or at least one reporter gene operatively linked to, or embedded within, the polynucleotide sequence encoding the at least one fusion protein.

16. The vector of embodiment 14, wherein the at least one fusion protein further comprises at least one of a 2A, Δ1D2A, or other translational interrupter sequence.

17. The vector of embodiment 14, wherein the at least one fusion protein further comprises at least one an Aphthovirus 2A, Δ1D2A, or other Aphthovirus translational interrupter sequence.

18. The vector of embodiment 14, wherein the at least one fusion protein further comprises at least one of a foot and mouth disease virus (FMDV) 2A, FMDV Δ1D2A, or other FMDV translational interrupter sequence.

19. The vector of embodiment 14, wherein the at least one fusion protein further comprises a Δ1D2A sequence engineered at the C-terminus of the at least one of *Gaussia* Luciferase (GLuc), super-luminescent *Gaussia* luciferase (SGLuc) or other luciferase which can be secreted.

20. The vector of embodiment 14, wherein the at least one fusion protein further comprises a Δ1D2A sequence engineered at the N-terminus of the at least one of *Gaussia* Luciferase (GLuc), super-luminescent *Gaussia* luciferase (SGLuc) or other luciferase which can be secreted.

21. The vector of embodiment 14, wherein the at least one fusion protein further comprises a translational interrupter sequence engineered at the C-terminus of the at least one of *Gaussia* Luciferase (GLuc), super-luminescent *Gaussia* luciferase (SGLuc) or other luciferase which can be secreted.

22. The vector of embodiment 14, wherein the at least one fusion protein further comprises a translational interrupter sequence engineered at the N-terminus of the at least one of *Gaussia* Luciferase (GLuc), super-luminescent *Gaussia* luciferase (SGLuc) or other luciferase which can be secreted.

23. The vector of embodiment 14, wherein the at least one fusion protein further comprises an FMDV 2A sequence engineered at the C-terminus of at least one of *Gaussia* Luciferase (GLuc), super-luminescent *Gaussia* luciferase (SGLuc) or other luciferase which can be secreted.

24. The vector of embodiment 14, wherein the at least one fusion protein further comprises an FMDV 2A sequence engineered at the N-terminus of the at least one of *Gaussia* Luciferase (GLuc), super-luminescent *Gaussia* luciferase (SGLuc) or other luciferase which can be secreted.

25. The vector of embodiment 14, wherein the at least one of *Gaussia* Luciferase (GLuc), super-luminescent *Gaussia* luciferase (SGLuc) or other luciferase which can be secreted does not have an N-terminal methionine residue.

26. The vector of embodiment 14 that expresses the at least one engineered polypeptide of interest in a eukaryotic cell.

27. The vector of embodiment 14 that expresses the at least one engineered polypeptide of interest in a yeast cell.

28. The vector of embodiment 14 that expresses the at least one engineered polypeptide of interest in a fungus cell.

29. The vector of embodiment 14 that expresses the at least one engineered polypeptide of interest in an insect cell.

30. The vector of embodiment 14 that expresses the at least one engineered polypeptide of interest in a vertebrate cell.

31. The vector of embodiment 14 that expresses the at least one engineered polypeptide of interest in a mammalian cell.

32. The vector of embodiment 14 that expresses the at least one engineered polypeptide of interest in a prokaryotic cell.

33. The vector of embodiment 14 that expresses the at least one engineered polypeptide of interest in a gram-positive prokaryote.

34. The vector of embodiment 14 that expresses the at least one engineered polypeptide of interest in a gram-negative prokaryote.

35. The vector of embodiment 14 that is a minicircle vector, a replication deficient adenovirus vector, a vaccinia virus vector, or other viral vector that expresses the at least one fusion protein comprising at least one of *Gaussia* Luciferase (GLuc), super-luminescent *Gaussia* luciferase (SGLuc) or other luciferase which can be secreted, and at least one interferon, cytokine, enzyme or other polypeptide of interest.

36. The vector of embodiment 14, further comprising a polynucleotide described by any of embodiments 1-13. A vector includes episomes, plasmids, phage sequences, viral sequences, transposons, and other polynucleotide constructs that can transform a host cell or be expressed by a host cell.

Other embodiments of the invention are directed to host cells, these include, without limitation, the following:

37. A host cell comprising a vector of embodiment 14, wherein the host cell expresses the at least one fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest.

38. The host cell of embodiment 37, wherein the vector comprises at least one promoter or other transcription regulatory element, at least one prokaryotic or eukaryotic translation initiation sequence or other translation regulatory element, at least one translational interrupter sequence, or at least one reporter gene operatively linked to, or embedded within, the polynucleotide sequence encoding the at least one fusion protein.

39. The host cell of embodiment 37, wherein the at least one fusion protein further comprises at least one of a 2A, Δ1D2A, or other translational interrupter sequence.

40. The host cell of embodiment 37, wherein the at least one fusion protein further comprises at least one of an Aphthovirus 2A, Δ1D2A, or other Aphthovirus translational interrupter sequence.

41. The host cell of embodiment 37 wherein the at least one fusion protein further comprises at least one of a foot and mouth disease virus (FMDV) 2A, FMDV Δ1D2A, or other FMDV translational interrupter sequence.

42. The host cell of embodiment 37, wherein the at least one fusion protein further comprises a Δ1D2A sequence engineered at the C-terminus of the at least one of *Gaussia* Luciferase (GLuc), super-luminescent *Gaussia* luciferase (SGLuc) or other luciferase which can be secreted.

43. The host cell of embodiment 37, wherein the at least one fusion protein further comprises a Δ1D2A sequence engineered at the N-terminus of the at least one of *Gaussia* Luciferase (GLuc), super-luminescent *Gaussia* luciferase (SGLuc) or other luciferase which can be secreted.

44. The host cell of embodiment 37, wherein the at least one fusion protein further comprises a translational interrupter sequence engineered at the C-terminus of the at least one of *Gaussia* Luciferase (GLuc), super-luminescent *Gaussia* luciferase (SGLuc) or other luciferase which can be secreted.

45. The host cell of embodiment 37, wherein the at least one fusion protein further comprises a translational interrupter sequence engineered at the N-terminus of the at least one of *Gaussia* Luciferase (GLuc), super-luminescent *Gaussia* luciferase (SGLuc) or other luciferase which can be secreted.

46. The host cell of embodiment 37, wherein the at least one fusion protein further comprises an FMDV 2A sequence engineered at the C-terminus of the at least one of *Gaussia* Luciferase (GLuc), super-luminescent *Gaussia* luciferase (SGLuc) or other luciferase which can be secreted.

47. The host cell of embodiment 37, wherein the at least one fusion protein further comprises an FMDV 2A sequence engineered at the N-terminus of the at least one of *Gaussia* Luciferase (GLuc), super-luminescent *Gaussia* luciferase (SGLuc) or other luciferase which can be secreted.

48. The host cell of embodiment 37, wherein the at least one of *Gaussia* Luciferase (GLuc), super-luminescent *Gaussia* luciferase (SGLuc) or other luciferase which can be secreted does not have an N-terminal methionine residue.

49. The host cell of embodiment 37 that is a eukaryotic cell.

50. The host cell of embodiment 37 that is a yeast cell.

51. The host cell of embodiment 37 that is a fungus cell.

52. The host cell of embodiment 37 that is an insect cell.

53. The host cell of embodiment 37 that is a vertebrate cell.

54. The host cell of embodiment 37 that is mammalian cell.

55. The host cell of embodiment 37 that is a prokaryotic cell.

56. The host cell of embodiment 37 that is a gram-positive prokaryote.

57. The host cell of embodiment 37 that is a gram-negative prokaryote.

58. The host cell of embodiment 37, wherein the vector is a minicircle vector, a replication deficient adenovirus vector, a vaccinia virus vector, or other viral vector that expresses the at least one fusion protein comprising at least one of *Gaussia* Luciferase (GLuc), super-luminescent *Gaussia* luciferase (SGLuc) or other luciferase which can be secreted, and at least one interferon, cytokine, enzyme or other polypeptide of interest.

59. The host cell of embodiment 37, wherein the vector further comprises a polynucleotide selected from the group of polynucleotide sequences or vectors described by embodiments 1-36.

Other embodiments of the invention are directed to polypeptides or fusion proteins these include, without limitation, the following:

60. A fusion protein comprising at least one of *Gaussia* Luciferase (GLuc), super-luminescent *Gaussia* luciferase (SGLuc) or other luciferase, preferably in a form which can be secreted, and at least one interferon, cytokine, enzyme or other polypeptide of interest. The fusion protein may be expressed intact with the luciferase and polypeptide of interest fused together, or may be expressed, for example, via translation interruption, where the fusion protein is separated into at least two polypeptide components.

61. The fusion protein of embodiment 60, which is encoded by a polynucleotide or vector further comprising at least one promoter or other transcription regulatory element, at least one prokaryotic or eukaryotic translation initiation sequence or other translation regulatory element, at least one translational interrupter sequence, or at least one reporter gene operatively linked to, or embedded within, the polynucleotide sequence encoding the fusion protein.

62. The fusion protein of embodiment 60, further comprising at least one of a 2A, Δ1D2A, or other translational interrupter sequence.

63. The fusion protein of embodiment 60, further comprising at least one of an Aphthovirus 2A, Δ1D2A, or other Aphthovirus translational interrupter sequence.

64. The fusion protein of embodiment 60, further comprising at least one of a foot and mouth disease virus (FMDV) 2A, FMDV Δ1D2A, or other FMDV translational interrupter sequence.

65. The fusion protein of embodiment 60, further comprising a Δ1D2A sequence engineered at the C-terminus of the at least one of *Gaussia* Luciferase (GLuc), super-luminescent *Gaussia* luciferase (SGLuc) or other luciferase which can be secreted.

66. The fusion protein of embodiment 60, further comprising a Δ1D2A sequence engineered at the N-terminus of the at least one of *Gaussia* Luciferase (GLuc), super-luminescent *Gaussia* luciferase (SGLuc) or other luciferase which can be secreted.

67. The fusion protein of embodiment 60, further comprising a translator interrupter sequence engineered at the N-terminus of the at least one of *Gaussia* Luciferase (GLuc), super-luminescent *Gaussia* luciferase (SGLuc) or other luciferase which can be secreted.

68. The fusion protein of embodiment 60, further comprising a translator interrupter sequence engineered at the C-terminus of the at least one of *Gaussia* Luciferase (GLuc), super-luminescent *Gaussia* luciferase (SGLuc) or other luciferase which can be secreted.

69. The fusion protein of embodiment 60, further comprising an FMDV 2A sequence engineered at the N-terminus of the at least one of *Gaussia* Luciferase (GLuc), super-luminescent *Gaussia* luciferase (SGLuc) or other luciferase which can be secreted.

70. The fusion protein of embodiment 60, further comprising an FMDV 2A sequence engineered at the C-terminus of the at least one of *Gaussia* Luciferase (GLuc), super-luminescent *Gaussia* luciferase (SGLuc) or other luciferase which can be secreted.

71. The fusion protein of embodiment 60, wherein the at least one of *Gaussia* Luciferase (GLuc), super-luminescent *Gaussia* luciferase (SGLuc) or other luciferase which can be secreted does not have an N-terminal methionine residue.

72. The fusion protein of embodiment 60 that encoded by any of the polynucleotide or vector embodiments 1-36 or which expressed by the host cells of any of embodiments 37-59.

Other embodiments of the invention are directed to vaccines, these include, without limitation, the following:

73. An antigen, immunogen, or vaccine comprising the fusion protein of embodiment 60 and a suitable carrier, excipient or adjuvant.

74. An antigen, immunogen, or vaccine comprising the fusion protein of embodiment 61 and a suitable carrier, excipient or adjuvant.

75. An antigen, immunogen, or vaccine comprising the fusion protein of embodiment 62 and a suitable carrier, excipient or adjuvant.

76. An antigen, immunogen, or vaccine comprising the fusion protein of embodiment 63 and a suitable carrier, excipient or adjuvant.

77. An antigen, immunogen, or vaccine comprising the fusion protein of embodiment 64 and a suitable carrier, excipient or adjuvant.

78. An antigen, immunogen, or vaccine comprising the fusion protein of embodiment 65 and a suitable carrier, excipient or adjuvant.

79. An antigen, immunogen, or vaccine comprising the fusion protein of embodiment 66 and a suitable carrier, excipient or adjuvant.

80. An antigen, immunogen, or vaccine comprising the fusion protein of embodiment 67 and a suitable carrier, excipient or adjuvant.

81. An antigen, immunogen, or vaccine comprising the fusion protein of embodiment 68 and a suitable carrier, excipient or adjuvant.

82. An antigen, immunogen, or vaccine comprising the fusion protein of embodiment 69 and a suitable carrier, excipient or adjuvant.

83. An antigen, immunogen, or vaccine comprising the fusion protein of embodiment 70 and a suitable carrier, excipient or adjuvant.

84. An antigen, immunogen, or vaccine comprising the fusion protein of embodiment 71 and a suitable carrier, excipient or adjuvant.

85. An antigen, immunogen, or vaccine comprising the fusion protein of embodiment 72 and a suitable carrier, excipient or adjuvant.

The antigen, immunogen or vaccine described above may comprise an intact fusion protein or may be in the form of one or more immunologically active fragments of such a fusion protein. Suitable carriers, excipients or adjuvants are known in the art and are described elsewhere herein.

Other embodiments of the invention include a method of making fusion protein and include, without limitation, the following:

86. A method for making, expressing and/or processing a fusion protein comprising at least one of *Gaussia* Luciferase (GLuc), super-luminescent *Gaussia* luciferase (SGLuc) or other luciferase, preferably in a form which can be secreted, and at least one interferon, cytokine, enzyme or other polypeptide of interest, comprising culturing the host cell according to embodiment 37 in a suitable medium and recovering the fusion protein.

87. A method for expressing and processing a fusion protein comprising at least one of *Gaussia* Luciferase (GLuc), super-luminescent *Gaussia* luciferase (SGLuc) or other luciferase, preferably in a form which can be secreted, and at least one interferon, cytokine, enzyme or other polypeptide of interest, comprising culturing the host cell according to embodiment 38 in a suitable medium and recovering the fusion protein.

88. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 39 in a suitable medium and recovering the fusion protein.

89. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 40 in a suitable medium and recovering the fusion protein.

90. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 41 in a suitable medium and recovering the fusion protein.

91. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 42 in a suitable medium and recovering the fusion protein.

92. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 43 in a suitable medium and recovering the fusion protein.

93. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 44 in a suitable medium and recovering the fusion protein.

94. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 45 in a suitable medium and recovering the fusion protein.

95. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 46 in a suitable medium and recovering the fusion protein.

96. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 47 in a suitable medium and recovering the fusion protein.

97. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to any of embodiments 48-57 in a suitable medium and recovering the fusion protein.

98. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 58 in a suitable medium and recovering the fusion protein.

99. A method for expressing and processing a fusion protein comprising at least one of *Gaussia* Luciferase (GLuc), super-luminescent *Gaussia* luciferase (SGLuc) or other luciferase preferably in a form which can be secreted, and at least one interferon, cytokine, enzyme or other polypeptide of interest, comprising culturing the host cell according to embodiment 59 in a suitable medium and recovering the fusion protein.

In preferred embodiments of the method described above, the luciferase will be one that can be expressed and exported from the cell. Prior to export or secretion from the cell, it may be processed, for example, by action of a translation interruption sequence, to separate it from other sequences encoded by a fusion polynucleotide. Alternatively, if may be exported or secreted as part of a fusion polypeptide.

Other embodiments of the invention include a method for quantifying an amount of interferon, cytokine, enzyme or other polypeptide of interest and include, without limitation, the following:

100. A method for quantifying an amount of an interferon, cytokine, enzyme or other polypeptide of interest produced in an expression system comprising:
    providing the vector according to embodiment 14;
    transforming the vector into a host cell;
    culturing the cells in a medium;
    harvesting the medium; and
    quantifying the intensity of luminescent output in the harvested medium, thus quantifying the amount of the interferon, cytokine, enzyme or other polypeptide of interest produced in an expression system.

101. A method for quantifying an amount of an interferon, cytokine, enzyme or other polypeptide of interest produced in an expression system comprising:
    providing the vector according to embodiment 15;
    transforming the vector into a host cell;
    culturing the cells in a medium;
    harvesting the medium; and
    quantifying the intensity of luminescent output in the harvested medium, thus quantifying the amount of the interferon, cytokine, enzyme or other polypeptide of interest produced in an expression system.

102. A method for quantifying an amount of an interferon, cytokine, enzyme or other polypeptide of interest produced in an expression system comprising:
    providing the vector according to embodiment 16;
    transforming the vector into a host cell;
    culturing the cells in a medium;
    harvesting the medium; and
    quantifying the intensity of luminescent output in the harvested medium, thus quantifying the amount of the interferon, cytokine, enzyme or other polypeptide of interest produced in an expression system.

103. A method for quantifying an amount of an interferon, cytokine, enzyme or other polypeptide of interest produced in an expression system comprising:
    providing the vector according to embodiment 17;
    transforming the vector into a host cell;
    culturing the cells in a medium;
    harvesting the medium; and
    quantifying the intensity of luminescent output in the harvested medium, thus quantifying the amount of the interferon, cytokine, enzyme or other polypeptide of interest produced in an expression system.

104. A method for quantifying an amount of an interferon, cytokine, enzyme or other polypeptide of interest produced in an expression system comprising:

providing the vector according to embodiment 18;
transforming the vector into a host cell;
culturing the cells in a medium;
harvesting the medium; and
quantifying the intensity of luminescent output in the harvested medium, thus quantifying the amount of the interferon, cytokine, enzyme or other polypeptide of interest produced in an expression system.

105. A method for quantifying an amount of an interferon, cytokine, enzyme or other polypeptide of interest produced in an expression system comprising:
providing the vector according to embodiment 19;
transforming the vector into a host cell;
culturing the cells in a medium;
harvesting the medium; and
quantifying the intensity of luminescent output in the harvested medium, thus quantifying the amount of the interferon, cytokine, enzyme or other polypeptide of interest produced in an expression system.

106. A method for quantifying an amount of an interferon, cytokine, enzyme or other polypeptide of interest produced in an expression system comprising:
providing the vector according to embodiment 20;
transforming the vector into a host cell;
culturing the cells in a medium;
harvesting the medium; and
quantifying the intensity of luminescent output in the harvested medium, thus quantifying the amount of the interferon, cytokine, enzyme or other polypeptide of interest produced in an expression system.

107. A method for quantifying an amount of an interferon, cytokine, enzyme or other polypeptide of interest produced in an expression system comprising:
providing the vector according to embodiment 21;
transforming the vector into a host cell;
culturing the cells in a medium;
harvesting the medium; and
quantifying the intensity of luminescent output in the harvested medium, thus quantifying the amount of the interferon, cytokine, enzyme or other polypeptide of interest produced in an expression system.

108. A method for quantifying an amount of an interferon, cytokine, enzyme or other polypeptide of interest produced in an expression system comprising:
providing the vector according to embodiment 22;
transforming the vector into a host cell;
culturing the cells in a medium;
harvesting the medium; and
quantifying the intensity of luminescent output.

109. A method for quantifying an amount of an interferon, cytokine, enzyme or other polypeptide of interest produced in an expression system comprising:
providing the vector according to embodiment 23;
transforming the vector into a host cell;
culturing the cells in a medium;
harvesting the medium; and
quantifying the intensity of luminescent output in the harvested medium, thus quantifying the amount of the interferon, cytokine, enzyme or other polypeptide of interest produced in an expression system.

110. A method for quantifying an amount of an interferon, cytokine, enzyme or other polypeptide of interest produced in an expression system comprising:
providing the vector according to embodiment 24;
transforming the vector into a host cell;
culturing the cells in a medium;
harvesting the medium; and
quantifying the intensity of luminescent output in the harvested medium, thus quantifying the amount of the interferon, cytokine, enzyme or other polypeptide of interest produced in an expression system.

111. A method for quantifying an amount of an interferon, cytokine, enzyme or other polypeptide of interest produced in an expression system comprising:
providing the vector according to embodiment 25;
transforming the vector into a host cell;
culturing the cells in a medium;
harvesting the medium; and
quantifying the intensity of luminescent output in the harvested medium, thus quantifying the amount of the interferon, cytokine, enzyme or other polypeptide of interest produced in an expression system.

112. A method for quantifying an amount of an interferon, cytokine, enzyme or other polypeptide of interest produced in an expression system comprising:
providing the vector according to embodiment 35;
transforming the vector into a host cell;
culturing the cells in a medium;
harvesting the medium; and
quantifying the intensity of luminescent output in the harvested medium, thus quantifying the amount of the interferon, cytokine, enzyme or other polypeptide of interest produced in an expression system.

113. A method for quantifying an amount of an interferon, cytokine, enzyme or other polypeptide of interest produced in an expression system comprising:
providing the vector according to embodiment 36;
transforming the vector into a host cell;
culturing the cells in a medium;
harvesting the medium; and
quantifying the intensity of luminescent output in the harvested medium, thus quantifying the amount of the interferon, cytokine, enzyme or other polypeptide of interest produced in an expression system.

In the methods described above the intensity of the luminescent output in the harvested medium is usually measured. This luminescent output may be correlated to the amount of luciferase or fusion protein containing luciferase in the medium and used to quantify expression or activity of a biological molecule. However, in some embodiments, the luminescent intensity of cells separated from the harvested medium may be measured, or measurements may be taken for a combination of both cells and medium or for each separately. In other embodiments, the harvested medium or cells may be further processed, diluted, or purified prior to detection of luminescence. This method may be practiced in conjunction with conventional methods for determining the presence, activity or quantity of a biologically active molecule, such as antibody-based methods, as described herein. Luminescence may be detected or quantified by equipment or methods known in the art, for example, spectrophotometrically.

Other embodiments of the invention include a method for quantifying a concentration of interferon, cytokine, enzyme or other polypeptide of interest and include, without limitation, the following:

114. A method for quantifying a concentration of an interferon, cytokine, enzyme or other polypeptide of interest produced in an expression system comprising:
providing the vector according to embodiment 14;
transforming the vector into a host cell;
culturing the cells in a medium;
harvesting the medium; and quantifying the intensity of luminescent output in the harvested medium, thus quantifying the concentration of the interferon, cytokine, enzyme or other polypeptide of interest produced in an expression system.

115. A method for quantifying a concentration of an interferon, cytokine, enzyme or other polypeptide of interest produced in an expression system comprising:
providing the vector according to embodiment 15,
transforming the vector into a host cell;
culturing the cells in a medium;
harvesting the medium; and
quantifying the intensity of luminescent output in the harvested medium, thus quantifying the concentration of the interferon, cytokine, enzyme or other polypeptide of interest produced in an expression system.

116. A method for quantifying a concentration of an interferon, cytokine, enzyme produced in an expression system comprising:
providing the vector according to embodiment 16,
transforming the vector into a host cell;
culturing the cells in a medium;
harvesting the medium; and
quantifying the intensity of luminescent output in the harvested medium, thus quantifying the concentration of the interferon, cytokine, enzyme or other polypeptide of interest produced in an expression system.

117. A method for quantifying a concentration of an interferon, cytokine, enzyme or other polypeptide of interest produced in an expression system comprising:
providing the vector according to any one embodiments 17-36;
transforming the vector into a host cell;
culturing the cells in a medium;
harvesting the medium; and
quantifying the intensity of luminescent output.

In the methods described above the intensity of the luminescent output in the harvested medium is usually measured. This luminescent output may be correlated to the concentration of luciferase or fusion protein containing luciferase in the medium and used to quantify expression or activity of a biological molecule. However, in some embodiments, the luminescent intensity of cells separated from the harvested medium may be measured, or measurements may be taken for a combination of both cells and medium or for each separately. In other embodiments, the harvested medium or cells may be further processed, diluted, or purified prior to detection of luminescence. This method may be practiced in conjunction with conventional methods for determining the presence, activity or quantity of a biologically active molecule, such as antibody-based methods, as described herein. Luminescence may be detected or quantified by equipment or methods known in the art, for example, spectrophotometrically.

Other embodiments of the invention include a method for facilitating secretion of a fusion protein and include, without limitation, the following:

118. A method for facilitating secretion of a fusion protein from a host cell comprising:
providing the vector according to embodiment 14;
transforming the vector into a host cell;
culturing the cells in a medium; and
recovering the secretable fusion protein from the medium.

119. A method for facilitating secretion of a fusion protein from a host cell comprising:
providing the vector according to embodiment 15;
transforming the vector into a host cell;
culturing the cells in a medium; and
recovering the secretable fusion protein from the medium.

120. A method for facilitating secretion of a fusion protein from a host cell comprising:
providing the vector according to embodiment 16;
transforming the vector into a host cell;
culturing the cells in a medium; and
recovering the secretable fusion protein from the medium.

121. A method for facilitating secretion of a fusion protein from a host cell comprising:
providing the vector according to embodiment 17;
transforming the vector into a host cell;
culturing the cells in a medium; and
recovering the secretable fusion protein from the medium.

122. A method for facilitating secretion of a fusion protein from a host cell comprising:
providing the vector according to embodiment 18;
transforming the vector into a host cell;
culturing the cells in a medium; and
recovering the secretable fusion protein from the medium.

123. A method for facilitating secretion of a fusion protein from a host cell comprising:
providing the vector according to embodiment 19;
transforming the vector into a host cell;
culturing the cells in a medium; and
recovering the secretable fusion protein from the medium.

124. A method for facilitating secretion of a fusion protein from a host cell comprising:
providing the vector according to embodiment 20;
transforming the vector into a host cell;
culturing the cells in a medium; and
recovering the secretable fusion protein from the medium.

125. A method for facilitating secretion of a fusion protein from a host cell comprising:
providing the vector according to embodiment 21;
transforming the vector into a host cell;
culturing the cells in a medium; and
recovering the secretable fusion protein from the medium.

126. A method for facilitating secretion of a fusion protein from a host cell comprising:
providing the vector according to embodiment 22;
transforming the vector into a host cell;
culturing the cells in a medium; and
recovering the secretable fusion protein from the medium.

127. A method for facilitating secretion of a fusion protein from a host cell comprising:
providing the vector according to embodiment 23;
transforming the vector into a host cell;
culturing the cells in a medium; and
recovering the secretable fusion protein from the medium.

128. A method for facilitating secretion of a fusion protein from a host cell comprising:
providing the vector according to embodiment 24;
transforming the vector into a host cell;
culturing the cells in a medium; and
recovering the secretable fusion protein from the medium.

129. A method for facilitating secretion of a fusion protein from a host cell comprising:
providing the vector according to any one of embodiments 25-34;
transforming the vector into a host cell;
culturing the cells in a medium; and
recovering the secretable fusion protein from the medium.

130. A method for facilitating secretion of a fusion protein from a host cell comprising:
providing the vector according to embodiment 35;
transforming the vector into a host cell;

culturing the cells in a medium; and recovering the secretable fusion protein from the medium.

131. A method for facilitating secretion of a fusion protein from a host cell comprising:

providing the vector according to embodiment 36;

transforming the vector into a host cell;

culturing the cells in a medium; and recovering the secretable fusion protein from the medium.

Recovery of a fusion protein includes concentration, purification, and/or isolation from other polypeptide components or nonpolypeptide components of a medium, cells or cell lysate. Examples of recovery methods include chromatographic isolation or separation of a fusion protein, affinity purification using antibodies or ligands that bind to epitopes of tags in a target fusion protein, PAGE, isoelectric focusing, or dialysis and concentration. A recovered fusion protein may be purified to homogeneity or to represent 10, 20, 30, 40, 50, 60, 70, 80, 90, 95, 99% by mass of the protein content (or the solid, nonaqueous content) in a recovered fusion protein composition.

Other embodiments of the invention include a method for measuring an amount of a biotherapeutic peptide in a subject and include, without limitation, the following:

132. A method for measuring an amount of a biotherapeutic peptide (or biotherapeutic polypeptide) in a subject in need thereof comprising:

providing the vector according to embodiment 14;

transforming the vector into the subject;

recovering from the subject a sample of biological material, such as blood, serum, plasma, CSF, or urine, containing a fusion protein comprising a biotherapeutic peptide and a luciferase, or a luciferase expressed by the vector; and detecting or quantifying the intensity of luminescent output in the sample thereby determining an amount of a biotherapeutic peptide in the subject.

133. A method for measuring an amount of a biotherapeutic peptide in a subject in need thereof comprising:

providing the vector according to embodiment 15;

transforming the vector into the subject;

recovering from the subject a sample of biological material, such as blood, serum, plasma, CSF, or urine, containing a fusion protein comprising a biotherapeutic peptide and a luciferase, or a luciferase expressed by the vector; and detecting or quantifying the intensity of luminescent output in the sample thereby determining an amount of a biotherapeutic peptide in the subject.

134. A method for measuring an amount of a biotherapeutic peptide in a subject in need thereof comprising:

providing the vector according to embodiment 16;

transforming the vector into the subject;

recovering from the subject a sample of biological material, such as blood, serum, plasma, CSF, or urine, containing a fusion protein comprising a biotherapeutic peptide and a luciferase, or a luciferase expressed by the vector; and detecting or quantifying the intensity of luminescent output in the sample thereby determining an amount of a biotherapeutic peptide in the subject.

135. A method for measuring an amount of a biotherapeutic peptide in a subject in need thereof comprising:

providing the vector according to embodiment 17;

transforming the vector into the subject;

recovering from the subject a sample of biological material, such as blood, serum, plasma, CSF, or urine, containing a fusion protein comprising a biotherapeutic peptide and a luciferase, or a luciferase expressed by the vector; and detecting or quantifying the intensity of luminescent output in the sample thereby determining an amount of a biotherapeutic peptide in the subject.

136. A method for measuring an amount of a biotherapeutic peptide in a subject in need thereof comprising:

providing the vector according to embodiment 18;

transforming the vector into the subject;

recovering from the subject a sample of biological material, such as blood, serum, plasma, CSF, or urine, containing a fusion protein comprising a biotherapeutic peptide and a luciferase, or a luciferase expressed by the vector; and detecting or quantifying the intensity of luminescent output in the sample thereby determining an amount of a biotherapeutic peptide in the subject.

137. A method for measuring an amount of a biotherapeutic peptide in a subject in need thereof comprising:

providing the vector according to embodiment 19;

transforming the vector into the subject;

recovering from the subject a sample of biological material, such as blood, serum, plasma, CSF, or urine, containing a fusion protein comprising a biotherapeutic peptide and a luciferase, or a luciferase expressed by the vector; and detecting or quantifying the intensity of luminescent output in the sample thereby determining an amount of a biotherapeutic peptide in the subject.

138. A method for measuring an amount of a biotherapeutic peptide in a subject in need thereof comprising:

providing the vector according to embodiment 20;

transforming the vector into the subject;

recovering from the subject a sample of biological material, such as blood, serum, plasma, CSF, or urine, containing a fusion protein comprising a biotherapeutic peptide and a luciferase, or a luciferase expressed by the vector; and detecting or quantifying the intensity of luminescent output in the sample thereby determining an amount of a biotherapeutic peptide in the subject.

139. A method for measuring an amount of a biotherapeutic peptide in a subject in need thereof comprising:

providing the vector according to embodiment 21;

transforming the vector into the subject;

recovering from the subject a sample of biological material, such as blood, serum, plasma, CSF, or urine, containing a fusion protein comprising a biotherapeutic peptide and a luciferase, or a luciferase expressed by the vector; and detecting or quantifying the intensity of luminescent output in the sample thereby determining an amount of a biotherapeutic peptide in the subject.

140. A method for measuring an amount of a biotherapeutic peptide in a subject in need thereof comprising:

providing the vector according to embodiment 22;

transforming the vector into the subject;

recovering from the subject a sample of biological material, such as blood, serum, plasma, CSF, or urine, containing a fusion protein comprising a biotherapeutic peptide and a luciferase, or a luciferase expressed by the vector; and detecting or quantifying the intensity of luminescent output in the sample thereby determining an amount of a biotherapeutic peptide in the subject.

141. A method for measuring an amount of a biotherapeutic peptide in a subject in need thereof comprising:

providing the vector according to embodiment 23;

transforming the vector into the subject;

recovering from the subject a sample of biological material, such as blood, serum, plasma, CSF, or urine, containing a fusion protein comprising a biotherapeutic peptide and a luciferase, or a luciferase expressed by the vector; and detecting or quantifying the intensity of luminescent output in the sample thereby determining an amount of a biotherapeutic peptide in the subject.

142. A method for measuring an amount of a biotherapeutic peptide in a subject in need thereof comprising:
providing the vector according to embodiment 24;
transforming the vector into the subject;
recovering from the subject a sample of biological material, such as blood, serum, plasma, CSF, or urine, containing a fusion protein comprising a biotherapeutic peptide and a luciferase, or a luciferase expressed by the vector; and
detecting or quantifying the intensity of luminescent output in the sample thereby determining an amount of a biotherapeutic peptide in the subject.

143. A method for measuring an amount of a biotherapeutic peptide in a subject in need thereof comprising:
providing the vector according to any of embodiments 25-34;
transforming the vector into the subject;
recovering from the subject a sample of biological material, such as blood, serum, plasma, CSF, or urine, containing a fusion protein comprising a biotherapeutic peptide and a luciferase, or a luciferase expressed by the vector; and
detecting or quantifying the intensity of luminescent output in the sample thereby determining an amount of a biotherapeutic peptide in the subject.

144. A method for measuring an amount of a biotherapeutic peptide in a subject in need thereof comprising:
providing the vector according to embodiment 35;
transforming the vector into the subject;
recovering from the subject a sample of biological material, such as blood, serum, plasma, CSF, or urine, containing a fusion protein comprising a biotherapeutic peptide and a luciferase, or a luciferase expressed by the vector; and
detecting or quantifying the intensity of luminescent output in the sample thereby determining an amount of a biotherapeutic peptide in the subject.

145. A method for measuring an amount of a biotherapeutic peptide in a subject in need thereof comprising:
providing the vector according to embodiment 36;
transforming the vector into the subject;
recovering from the subject a sample of biological material, such as blood, serum, plasma, CSF, or urine, containing a fusion protein comprising a biotherapeutic peptide and a luciferase, or a luciferase expressed by the vector; and
detecting or quantifying the intensity of luminescent output in the sample thereby determining an amount of a biotherapeutic peptide in the subject.

Recovery of a fusion protein comprising a biotherapeutic peptide or polypeptide includes concentration, dilution, purification, and/or isolation from other polypeptide components or nonpolypeptide components of a medium, cells or cell lysate. Examples of recovery methods include chromatographic isolation or separation of a fusion protein, affinity purification using antibodies or ligands that bind to epitopes of tags in a target fusion protein, PAGE, isoelectric focusing, or dialysis and concentration. In some embodiments luminescence may be determined directly from a biological sample or a diluted biological sample. A recovered biotherapeutic peptide or polypeptide may be purified to homogeneity or to represent 10, 20, 30, 40, 50, 60, 70, 80, 90, 95, 99% by mass of the protein content (or the solid, nonaqueous content) in a recovered fusion protein composition.

Other embodiments of the invention include a method for certifying expression of a polypeptide vaccine in a subject and include, without limitation, the following:

146. A method for certifying vaccine expression in vivo comprising:
providing the vector according to embodiment 14;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

147. A method for certifying vaccine expression in vivo comprising:
providing the vector according to embodiment 15;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

148. A method for certifying vaccine expression in vivo comprising:
providing the vector according to embodiment 16;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

149. A method for certifying vaccine expression in vivo comprising:
providing the vector according to embodiment 17;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

150. A method for certifying vaccine expression in vivo comprising:
providing the vector according to embodiment 18;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

151. A method for certifying vaccine expression in vivo comprising:
providing the vector according to embodiment 19;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and detecting or quantifying the intensity of luminescent output in the sample thereby certifying expression of the vaccine peptide or polypeptide in the host organism.

152. A method for certifying vaccine expression in vivo comprising:
providing the vector according to embodiment 20;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

153. A method for certifying vaccine expression in vivo comprising:
providing the vector according to embodiment 21;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

154. A method for certifying vaccine expression in vivo comprising:
providing the vector according to embodiment 22;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

155. A method for certifying vaccine expression in vivo comprising:
providing the vector according to embodiment 23;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

156. A method for certifying vaccine expression in vivo comprising:
providing the vector according to embodiment 24;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

157. A method for certifying vaccine expression in vivo comprising:
providing the vector according to embodiment 25-34;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

158. A method for certifying vaccine expression in vivo comprising:
providing the vector according to embodiment 35;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

159. A method for certifying vaccine expression in vivo comprising:
providing the vector according to embodiment 36;
transforming the vector into a host organism;
recovering from the host organism a sample of biological material, such as blood, serum, plasma, CSF, or urine, containing a fusion protein comprising a vaccine peptide (or polypeptide) and a luciferase, or a luciferase expressed by the vector; and
detecting or quantifying the intensity of luminescent output in the sample thereby certifying expression of the vaccine peptide or polypeptide in the host organism.

Recovery of a fusion protein comprising a vaccine peptide or polypeptide includes concentration, dilution, purification, and/or isolation from other polypeptide components or non-polypeptide components of a medium, cells or cell lysate. Examples of recovery methods include chromatographic isolation or separation of a fusion protein, affinity purification using antibodies or ligands that bind to epitopes of tags in a target fusion protein, PAGE, isoelectric focusing, or dialysis and concentration. In some embodiments luminescence may be determined directly from a biological sample or a diluted biological sample. In the methods above, vaccine expression may be formally certified such as by a formal medical or scientific statement, attestation, logs or other records or less formally detected, determined, or recorded, for example in a laboratory notebook or workbook, photo, audio/visual recording, or other record.

Other embodiments of the invention include a pharmaceutical composition containing a fusion protein and include, without limitation, the following:

160. A pharmaceutical composition comprising the fusion protein of embodiment 60 and at least one pharmaceutically acceptable carrier, adjuvant, or excipient.

161. A pharmaceutical composition comprising the fusion protein of embodiment 61 and at least one pharmaceutically acceptable carrier, adjuvant, or excipient.

162. A pharmaceutical composition comprising the fusion protein of embodiment 62 and at least one pharmaceutically acceptable carrier, adjuvant, or excipient.

163. A pharmaceutical composition comprising the fusion protein of embodiment 63 and at least one pharmaceutically acceptable carrier, adjuvant, or excipient.

164. A pharmaceutical composition comprising the fusion protein of embodiment 64 and at least one pharmaceutically acceptable carrier, adjuvant, or excipient.

165. A pharmaceutical composition comprising the fusion protein of embodiment 65 and at least one pharmaceutically acceptable carrier, adjuvant, or excipient.

166. A pharmaceutical composition comprising the fusion protein of embodiment 66 and at least one pharmaceutically acceptable carrier, adjuvant, or excipient.

167. A pharmaceutical composition comprising the fusion protein of embodiment 67 and at least one pharmaceutically acceptable carrier, adjuvant, or excipient.

168. A pharmaceutical composition comprising the fusion protein of embodiment 68 and at least one pharmaceutically acceptable carrier, adjuvant, or excipient.

169. A pharmaceutical composition comprising the fusion protein of embodiment 69 and at least one pharmaceutically acceptable carrier, adjuvant, or excipient.

170. A pharmaceutical composition comprising the fusion protein of embodiment 70 and at least one pharmaceutically acceptable carrier, adjuvant, or excipient.

171. A pharmaceutical composition comprising the fusion protein of embodiment 71 and at least one pharmaceutically acceptable carrier, adjuvant, or excipient.

172. A pharmaceutical composition comprising the fusion protein of embodiment 72 and at least one pharmaceutically acceptable carrier, adjuvant, or excipient Other embodiments of the invention include a biotherapeutic comprising a fusion protein and include, without limitation, the following:

173. A biotherapeutic comprising the fusion protein of embodiment 60 and a suitable carrier, excipient or adjuvant.

174. A biotherapeutic comprising the fusion protein of embodiment 61 and a suitable carrier, excipient or adjuvant.

175. A biotherapeutic comprising the fusion protein of embodiment 62 and a suitable carrier, excipient or adjuvant.

176. A biotherapeutic comprising the fusion protein of embodiment 63 and a suitable carrier, excipient or adjuvant.

177. A biotherapeutic comprising the fusion protein of embodiment 64 and a suitable carrier, excipient or adjuvant.

178. A biotherapeutic comprising the fusion protein of embodiment 65 and a suitable carrier, excipient or adjuvant.

179. A biotherapeutic comprising the fusion protein of embodiment 66 and a suitable carrier, excipient or adjuvant.

180. A biotherapeutic comprising the fusion protein of embodiment 67 and a suitable carrier, excipient or adjuvant.

181. A biotherapeutic comprising the fusion protein of embodiment 68 and a suitable carrier, excipient or adjuvant.

182. A biotherapeutic comprising the fusion protein of embodiment 69 and a suitable carrier, excipient or adjuvant.

183. A biotherapeutic comprising the fusion protein of embodiment 70 and a suitable carrier, excipient or adjuvant.

184. A biotherapeutic comprising the fusion protein of embodiment 71 and a suitable carrier, excipient or adjuvant.

185. A biotherapeutic comprising the fusion protein of embodiment 72 and a suitable carrier, excipient or adjuvant.

In the biotherapeutics described above, the fusion protein preferably comprises a biologically active polypeptide, such as an interferon (e.g., interferon-alpha or interferon-beta or modified versions thereof) or an immunogenic polypeptide. These biotherapeutics may constitute a fusion protein according to the invention or a polynucleotide encoding such a fusion protein. The fusion protein may be intact or processed, for example, into separate fusion protein fragments by action of a translation interruption sequence. The fusion protein may be in a purified form isolated from other cellular components of a host cell expressing it, or may be contained within a host cell or transformed cell, such as a cell obtained from a subject being treated for a particular disease, disorder or condition. A biotherapeutic may comprise a living cell, such as a leukocyte, bone marrow, muscle, endothelial, or stem cell, that expresses interferon or other polypeptide of interest that produced by transformation of a subject's or patient's cells with a vector as described herein. It may be homologous to the subject or patient or obtained from a suitable donor.

Other embodiments of the invention include a method of treating a subject and include, without limitation, the following:

186. A method for treating Foot-and-Mouth Disease comprising administering the composition according to embodiment 160 to a subject in need thereof.

187. A method for treating Foot-and-Mouth Disease comprising administering the composition according to embodiment 161 to a subject in need thereof.

188. A method for treating Foot-and-Mouth Disease comprising administering the composition according to embodiment 162 to a subject in need thereof.

189. A method for treating Foot-and-Mouth Disease comprising administering the composition according to embodiment 163 to a subject in need thereof.

190. A method for treating Foot-and-Mouth Disease comprising administering the composition according to embodiment 164 to a subject in need thereof.

191. A method for treating Foot-and-Mouth Disease comprising administering the composition according to embodiment 165 to a subject in need thereof.

192. A method for treating Foot-and-Mouth Disease comprising administering the composition according to embodiment 166 to a subject in need thereof.

193. A method for treating Foot-and-Mouth Disease comprising administering the composition according to embodiment 167 to a subject in need thereof.

194. A method for treating Foot-and-Mouth Disease comprising administering the composition according to embodiment 168 to a subject in need thereof.

195. A method for treating Foot-and-Mouth Disease comprising administering the composition according to embodiment 169 to a subject in need thereof.

196. A method for treating Foot-and-Mouth Disease comprising administering the composition according to embodiment 170 to a subject in need thereof.

197. A method for treating Foot-and-Mouth Disease comprising administering the composition according to embodiment 171 to a subject in need thereof.

198. A method for treating Foot-and-Mouth Disease comprising administering the composition according to embodiment 172 to a subject in need thereof.

199. A method for treating malignant melanoma comprising administering the composition according to embodiment 160 to a subject in need thereof.

200. A method for treating malignant melanoma comprising administering the composition according to embodiment 161 to a subject in need thereof.

201. A method for treating malignant melanoma comprising administering the composition according to embodiment 162 to a subject in need thereof.

202. A method for treating malignant melanoma comprising administering the composition according to embodiment 163 to a subject in need thereof.

203. A method for treating malignant melanoma comprising administering the composition according to embodiment 164 to a subject in need thereof.

204. A method for treating malignant melanoma comprising administering the composition according to embodiment 165 to a subject in need thereof.

205. A method for treating malignant melanoma comprising administering the composition according to embodiment 166 to a subject in need thereof.

206. A method for treating malignant melanoma comprising administering the composition according to embodiment 167 to a subject in need thereof.

207. A method for treating malignant melanoma comprising administering the composition according to embodiment 168 to a subject in need thereof.

208. A method for treating malignant melanoma comprising administering the composition according to embodiment 169 to a subject in need thereof.

209. A method for treating malignant melanoma comprising administering the composition according to embodiment 170 to a subject in need thereof.

210. A method for treating malignant melanoma comprising administering the composition according to embodiment 171 to a subject in need thereof.

211. A method for treating malignant melanoma comprising administering the composition according to embodiment 172 to a subject in need thereof.

212. A method for treating hepatitis B, hepatitis C, or other viral infection comprising administering the composition according to embodiment 160 to a subject in need thereof.

213. A method for treating hepatitis B, hepatitis C or other viral infection comprising administering the composition according to embodiment 161 to a subject in need thereof.

214. A method for treating hepatitis B, hepatitis C, or other viral infection comprising administering the composition according to embodiment 162 to a subject in need thereof.

215. A method for treating hepatitis B, hepatitis C, or other viral infection comprising administering the composition according to embodiment 163 to a subject in need thereof.

216. A method for treating hepatitis B, hepatitis C, or other viral infection comprising administering the composition according to embodiment 164 to a subject in need thereof.

217. A method for treating hepatitis B, hepatitis C, or other viral infection comprising administering the composition according to embodiment 165 to a subject in need thereof.

218. A method for treating hepatitis B, hepatitis C, or other viral infection comprising administering the composition according to embodiment 166 to a subject in need thereof.

219. A method for treating hepatitis B, hepatitis C, or other viral infection comprising administering the composition according to embodiment 167 to a subject in need thereof.

220. A method for treating hepatitis B, hepatitis C, or other viral infection comprising administering the composition according to embodiment 168 to a subject in need thereof.

221. A method for treating hepatitis B, hepatitis C, or other viral infection comprising administering the composition according to embodiment 169 to a subject in need thereof.

222. A method for treating hepatitis B, hepatitis C, or other viral infection comprising administering the composition according to embodiment 170 to a subject in need thereof.

223. A method for treating hepatitis B, hepatitis C, or other viral infection comprising administering the composition according to embodiment 171 to a subject in need thereof.

224. A method for treating hepatitis B, hepatitis C, or other viral infection comprising administering the composition according to embodiment 172 to a subject in need thereof.

In the methods described above, the fusion protein preferably comprises a biologically active polypeptide that induces a protective effect against the particular pathological condition or pathogens mentioned, such as an interferon (e.g., interferon-alpha or interferon-beta or modified versions thereof) that enhances immune responses to FMDV, melanoma or other tumors or cancers, or hepatitis B or C infection, or such as an immunogen that induces cellular or humoral immunity against tumors or viral pathogens. This method may be performed by administering a fusion protein according to the invention or a polynucleotide encoding such a fusion protein, for example, by transformation of a cell with a vector encoding a fusion protein, and administration of the transformed cells to a subject or patient in need treatment for a particular disease, disorder or condition.

Other embodiments of the invention include a method of treating a subject and include, without limitation, the following:

225. A method for cytokine therapy comprising administering the composition according to embodiment 160 to a subject in need thereof.

226. A method for cytokine therapy comprising administering the composition according to embodiment 161 to a subject in need thereof.

227. A method for cytokine therapy comprising administering the composition according to embodiment 162 to a subject in need thereof.

228. A method for cytokine therapy comprising administering the composition according to embodiment 163 to a subject in need thereof.

229. A method for cytokine therapy comprising administering the composition according to embodiment 164 to a subject in need thereof.

230. A method for cytokine therapy comprising administering the composition according to embodiment 165 to a subject in need thereof.

231. A method for cytokine therapy comprising administering the composition according to embodiment 166 to a subject in need thereof.

232. A method for cytokine therapy comprising administering the composition according to embodiment 167 to a subject in need thereof.

233. A method for cytokine therapy comprising administering the composition according to embodiment 168 to a subject in need thereof.

234. A method for cytokine therapy comprising administering the composition according to embodiment 169 to a subject in need thereof.

235. A method for cytokine therapy comprising administering the composition according to embodiment 170 to a subject in need thereof.

236. A method for cytokine therapy comprising administering the composition according to embodiment 171 to a subject in need thereof.

237. A method for cytokine therapy comprising administering the composition according to embodiment 172 to a subject in need thereof.

In the method described above, the fusion protein preferably comprises a biologically active cytokine that modulates or enhances a subject's immune system. This method may be performed by administering a fusion protein according to the invention or a polynucleotide encoding such a fusion protein. It may be practiced with cells transformed to express a fusion protein or fusion protein fragments having cytokine activity, for example, by transformation of a cell with a vector encoding a fusion protein, and administration of the transformed cells to a subject or patient in need of cytokine activity.

Other embodiments of the invention include a method of treating a subject and include, without limitation, the following:

238. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 160 to the animal in need thereof.

239. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 161 to the animal in need thereof.

240. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 162 to the animal in need thereof.

241. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 163 to the animal in need thereof.

242. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 164 to the animal in need thereof.

243. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 165 to the animal in need thereof.

244. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 166 to the animal in need thereof.

245. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 167 to the animal in need thereof.

246. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 168 to the animal in need thereof.

247. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 169 to the animal in need thereof.

248. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 170 to the animal in need thereof.

249. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 171 to the animal in need thereof.

250. A method for treating Feline Herpesvirus 1, Feline infectious peritonitis, Feline Immunodeficiency Virus, Feline Leukemia Virus, Canine papilloma virus or other viral infection in domestic or wild animals comprising administering the composition according to embodiment 172 to the animal in need thereof.

In the methods described above, the fusion protein preferably comprises a biologically active cytokine that modulates or enhances a subject's immune system response to the above-mentioned viruses or that comprises protective antigens or epitopes of said viruses. This method may be performed by administering a fusion protein according to the invention or a polynucleotide encoding such a fusion protein.

The methods described above for treating feline diseases or disorders may be practiced with *Felis catus* α, β and/or γ interferon(s) such as those encoded by Accession numbers: NM_001031830.1 or GI:73611927 (α interferon); NM_001009297.1 or GI:57163828 ((β interferon); or NM_001009873.1 or GI:57619124 (γ interferon); or analogs, derivatives or modified forms thereof as described herein. These accession numbers are incorporated by reference.

The methods described above for treating canine diseases or disorders may be practiced with *Canis lupus familiaris* α, β and/or γ interferon(s) such as those encoded by Accession numbers: M28624.1 or GI:163973 (α), GenBank: E11229.1 (β) and EF095772.1 or GI: 118505119 (γ); or analogs, derivatives or modified forms thereof as described herein. These accession numbers are incorporated by reference.

Example 1

Δ1D2A Constructs Retain Luciferase and Interferon Secretion

Two constructs comprising interferon and luciferase sequences were made utilizing the translation interrupter Δ1D2A to separate SGLuc and IFN α, see FIG. 1.

These constructs expressed two polypeptides which differed as to which polypeptide retained the Δ1D2A sequence, see FIG. 1. The addition of the Δ1D2A sequence to either the N-terminus or C-terminus of SGLuc was found to not inhibit either secretion or luminescence of the SGLuc and as shown by FIG. 2A top two bars (media luminescence) and FIG. 2B (Western blot of harvested media). To confirm that the addition of an IFN α sequence to either the N-terminus, in the case of IFNα-Δ1D2A-SGLuc Δ1M, or to the C-terminus, in the case of SGLuc-Δ1D2A-IFNα, did not alter critical luminescence properties, media from HEK293-T cells transfected with constructs pTarget IFNα-Δ1D2A-SGLuc Δ1M and pTarget SGLuc-Δ1D2A-IFNα was evaluated for luciferase activity, see FIG. 2A. HEK293-T cells transfected with constructs pTarget SGLuc-Δ1D2A and pTarget Δ1D2A-SGLuc Δ1M were used as controls, see FIG. 2A. Confirmation of the presence of GLuc in the media and of separation of the fusion protein by Δ1D2A was performed by western blotting using a polyclonal anti-GLuc antibody, see FIG. 2B, which shows efficient separation of GLuc from fusion polypeptides. Only a small amount of unseparated fused peptide was present in the media, FIG. 2B.

To confirm that the addition of an IFN α sequence to either the N-terminus, in the case of IFNα-Δ1D2A-SGLuc Δ1M, or to the C-terminus, in the case of SGLuc-Δ1D2A-IFNα, did not alter critical secretion properties the presence of IFNα and IFNα-Δ1D2A in cell culture media was determined using a commercially available ELISA assay. A standard curve of IFN α concentration was determined using nine different concentrations of an IFN α standard Four different dilutions of media from cells transfected with pTarget IFN α, pTarget IFNα-Δ1D2A-SGLuc Δ1M, pTarget SGLuc-Δ1D2A-IFNα, pTarget SGLuc-Δ1D2A, and pTarget Δ1D2A-SGLuc Δ1M were assayed using the same ELISA assay, see FIG. 7. The ELISA results of media show in FIG. 7 demonstrate that IFNα is present in the media of cells transfected with plasmids pTarget IFN α, pTarget IFNα-Δ1D2A-SGLuc Δ1M, and pTarget SGLuc-Δ1D2A-IFNα but not in cells transfected with the control plasmids pTarget SGLuc-Δ1D2A, and pTarget Δ1D2A-SGLuc Δ1M. This confirms that the addition of the Δ1D2A peptide to either the N- or C-terminus of IFNα does not prevent secretion.

This example demonstrates that the Δ1D2A sequence can be successfully used to separate SGLuc and IFN α components of a fusion polypeptide and that both the SGLuc and IFN α components retain the ability to be secreted.

These results provide a new way to design a luciferase assay that can be used to quantify the amount of IFN produced in an expression system without the drawbacks of an antibody-based system. Such an assay provides a fast and reliable way to substantially determine the absolute concentration of a molecule in an expression system. The amount of GLuc or SGLuc moieties secreted into culture medium measured by luminescence, after these are released from a longer precursor fusion polypeptide by translational interruption, provides a proportionate way to substantially determine the absolute amount of interferon expressed. The amount of interferon expressed by the expression system will directly correlate with the amount of luminescence appearing in the culture medium. No interferon-binding antibodies are necessary.

This new method provides a more reliable way to standardize samples and avoid the unpredictability and problems associated with antibody-based systems like ELISA. As described above, many of these problems are attributable to the variation of antibody binding affinities for different interferon mutants, different kinds of interferons, or interferons in different kinds of samples.

While constructs using the Δ1D2A sequence can be conveniently used to monitor interferon expression, they do not directly quantify interferon concentrations. That is because they detect extracellular luminescence produced by the luciferase, not a direct and dependent property of interferon. Indirect methods using Δ1D2A may be biased by differential expression, degradation or trafficking of soluble GLuc moieties into the extracellular medium. For example, differential rates of GLuc or SGLuc moiety degradation for a mutant compared to a non-mutant IFN might bias results. To address these problems the inventors tested interferon-luciferase constructs that did not contain the Δ1D2A translation interruption sequence, see FIG. 4. The luminescent moieties in such constructs are directly attached to interferon and thus luminescence detected extracellularly indicates the amount of interferon present.

Example 2

Comparison of Secretion of Interferon to GLucON Constructs

Native interferons contain an N-terminal secretion domain to facilitate their secretion into the extracellular medium. Examples of the secretion domains for interferons are described by SEQ ID NOS: 25-46. This secretion sequence is not necessary to elicit a desired immune stimulatory response. To this end the inventors constructed fusion peptides that contain the SGLuc luciferase and the non-secretion domain of four different interferons, α, β, γ, and λ, collectively identified as SGLucONs and depicted by FIG. 4.

The secretion of two types of porcine interferons, α and β, and two types of bovine interferons, γ and λ, were compared to SGLucON constructs containing the same interferon types. The SGLucON constructs take advantage of the naturally secretable properties of SGLuc to facilitate the secretion of the fusion peptide.

All four interferons and all four SGLucON constructs were demonstrated to be secreted into the extracellular medium as shown in FIGS. 5A and 5B. This confirms that the creation of these fusion peptides does not prevent the secretion of the peptide from the cell. Since all SGLucONs (α, β, γ, λ) showed retention of secretion, FIG. 5A, we tested media samples harvested from transfected HEK293-T cells for luciferase activity, FIG. 5B. Media harvested from cells expressing Interferon (α, β, γ, λ) samples was also tested for luciferase activity to ensure that any luciferase activity observed was the result of the presence of the SGLuc component. All four SGLucON samples (α, β, γ, λ) and only the SGLucON samples showed luciferase activity, FIG. 5B. This confirms that the addition of the interferon sequence to SGLuc does not prevent luminescence.

The SGLucON λ sample showed a more than two-fold higher luciferase readings than the other three other SGLucON samples, FIG. 5B, but did not appear to have a proportionally greater concentration when examined by western blotting with the anti-GLuc antibody, FIG. 5A. This result suggests that in the case of SGLucON λ the addition of the IFN λ sequence may either enhance luminescence or hinder luminescence less than the other IFN sequences, π, β, γ, when comparing amongst the SGLucON constructs.

Control constructs of IFN α, β, and λ were also shown to be secreted by usage of antibodies specific to each one. There was no reliable available antibody to bovine IFN γ limiting the ability to confirm its presence. Western blots using anti-GLuc, anti-IFN α, anti-IFN β, and anti-IFN λ show that the SGLucON chimeras retain both luciferase and interferon components fused together and are not post-translationally processed, FIG. 5A. In the case of Interferon β there was a notable difference in post-translational modifications between IFN β and SGLucON β, FIG. 5A. IFN β shows substantial post-translational modifications, possibly through glycosylation or differential processing, resulting in multiple bands being present in the anti-IFN β western blot FIG. 5A. SGLucON β is predominantly in a single band as shown by FIG. 5A, suggesting that SGLucON β is not subject to the same degree of post-translational modifications as IFN β.

These results demonstrate that direct fusion of SGLuc to an interferon can be successfully secreted by a cell and then detected by luminescence. These constructs do not rely on separation of SGLuc from the interferon and thus are not subject to the same risks associated with the utilization of a Δ1D2A translation interruption sequence to produce two separate molecules.

Quantifying luciferase activity with SGLucON samples is a direct quantification of the concentration in the sample rather than an indirect quantification as is the case when utilizing the Δ1D2A sequence. This removes variables that may alter concentrations of either SGLuc or IFN after translation such as differential secretion rates and the potential for preferential protein degradation.

Example 3

Δ1D2A IFN Constructs Retain Biological Activity

An IFN α ELISA assay was performed to quantify the concentrations of IFN α in the cell culture media of HEK293-T cells transfected with plasmids pTarget IFN α, pTarget SGLuc-Δ1D2A-IFNα, pTarget IFNα-Δ1D2A-SGLuc Δ1M, and pTarget SGLuc-Δ1D2A. These concentrations were used to set up a dilution series to test for retention of antiviral activity against VSV and to compare this activity to an established commercially available porcine IFNα, FIG. 6 and FIG. 8.

The results show that IFN α produced from constructs pTarget SGLuc-Δ1D2A-IFNα and pTarget IFNα-Δ1D2A-SGLuc Δ1M retains anti-viral activity, FIG. 6 and FIG. 8. This was particularly novel as the IFN α produced from these constructs contains additional amino acids compared to a native IFN α sequence. The IFN α produced from the pTarget SGLuc-Δ1D2A-IFNα construct contains an addition N-terminal proline while the IFN α produced from the pTarget IFNα-Δ1D2A-SGLuc Δ1M construct contains an additional 40 amino acids, containing the Δ1D2A sequence, on the C-terminus, FIG. 1. For the pTarget IFNα-Δ1D2A-SGLuc Δ1M construct the 40 additional amino acids represent a 20% increase in length for the resulting molecule. The substantial increase in the size of the molecule makes the result that it retained anti-viral activity all the more unexpected.

IFN α produced from the pTarget IFN α serves as a control to compare effectiveness to an unmodified protein produced in a similar manner. The IFN α samples only showed plaques at 0.625 ng/mL suggesting that a protective concentration was 1.25 ng/mL or less. Both the IFN α produced from the pTarget SGLuc-Δ1D2A-IFNα construct and that from the pTarget IFNα-Δ1D2A-SGLuc Δ1M construct provided complete protection at 2.5 ng/mL with plaques present at 1.25 ng/mL, FIG. 6. Even at the lowest doses tested, 0.1265 ng/mL, the plaques present in samples were noticeably smaller than those present in the SGLuc-Δ1D2A negative control.

Example 4

GLucON α Construct Retains Biological Activity

An IFN α ELISA assay was performed to quantify the concentrations of both IFN α and SGLucON α in harvested media. Equivalent concentrations of each were determined and used in a plaque assay for interferon anti-viral activity against Vesicular Stomatitis Virus (VSV). The results are shown by FIG. 6 and FIG. 8.

The results show that SGLucON α retained anti-viral activity against VSV. A concentration of less than or equal to 1.25 ng/mL but greater than 0.625 ng/mL of SGLucON α was sufficient to completely inhibit VSV and concentrations as low as 0.1265 ng/mL were shown to partially inhibit VSV when compared to the negative control SGLuc-Δ1D2A.

IFN α produced by the same means was also able to provide complete protection at a concentration of less than or equal to 1.25 ng/mL but greater than 0.3125 ng/mL. This suggests that SGLucON α has at least equivalent anti-viral activity than IFN α, FIG. 6 and FIG. 8. Interestingly SGLucON α gives consistently lower PFUs than IFN α alone at equivalent concentrations FIG. 8. While complete protection from VSV was obtained at the same concentration for both IFN α and SGLucON α consistently lower PFU numbers at susceptible dilutions suggest that SGLucON α offers better protection than IFN α, FIG. 8.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "substantially", "about" or "approximately," even if the term does not expressly appear. The terms "substantially", "substantially no", "substantially free", "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

---

What is claimed is:

1. A polynucleotide comprising a single open reading frame (ORF) that encodes a fusion protein comprising a luciferase, an interferon, and an Aphthovirus 2A.

2. The polynucleotide of claim 1, wherein the fusion protein comprises, in order from the N-terminal, the luciferase, the Aphthovirus 2A and the interferon.

3. The polynucleotide of claim 1, wherein the fusion protein comprises, in order from the N-terminal, the interferon, the Aphthovirus 2A and the luciferase.

4. The polynucleotide of claim 3, wherein the amino acid sequence of the luciferase is modified to remove its N-terminal methionine initiation site.

5. The polynucleotide of claim 1, wherein the Aphthovirus 2A comprises the amino acid sequence of SEQ ID NO: 5, SEQ ID NO: 6, SEQ ID NO: 7, SEQ ID NO: 8, SEQ ID NO: 16 or SEQ ID NO: 18.

6. The polynucleotide of claim 1, comprising the nucleotide sequence of SEQ ID NO: 97, SEQ ID NO: 98, SEQ ID NO: 108 or SEQ ID NO: 109.

7. The polynucleotide of claim 1, wherein the Aphthovirus 2A is FMDV Δ1D2A.

8. The polynucleotide of claim 1, wherein the Aphthovirus 2A comprises at least one selected from the group consisting of: SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, and SEQ ID NO: 22.

9. A polynucleotide comprising a single open reading frame (ORF) that encodes a fusion protein comprising, in order from the N-terminal, a secretable luciferase fused to a modified polypeptide of interest, wherein:
 the modified polypeptide of interest has been modified to remove a native N-terminal secretion peptide sequence;
 the removed N-terminal secretion peptide sequence has been replaced by the secretable luciferase; and
 the polynucleotide encoding the secretable luciferase is directly adjoined at the 3' end to the 5' end of the polynucleotide encoding the modified polypeptide of interest.

10. The polynucleotide of claim 9, further comprising at least one promoter or other transcription regulatory element.

11. The polynucleotide of claim 9, wherein the polypeptide of interest is an interferon.

12. The polynucleotide of claim 9, encoding for the polypeptide of at least one selected from the group consisting of: SEQ ID NO: 48, SEQ ID NO: 52, SEQ ID NO: 56, SEQ ID NO: 60, SEQ ID NO: 64, SEQ ID NO: 68, SEQ ID NO: 70, SEQ ID NO:74, SEQ ID NO: 78, SEQ ID NO: 82, SEQ ID NO: 86, SEQ ID NO: 90, SEQ ID NO: 94, SEQ ID NO: 111, and SEQ ID NO: 113.

13. A fusion protein comprising, in order from the N-terminal, a secretable luciferase and a modified polypeptide of interest, wherein:
 the modified polypeptide of interest has been modified to remove a native N-terminal secretion peptide sequence;
 the removed N-terminal secretion peptide domain has been replaced by the secretable luciferase; and
 the secretable luciferase is directly adjoined at the C-terminus to the N-terminus of the modified polypeptide of interest.

14. The fusion protein of claim 13, wherein the polypeptide of interest is an interferon.

15. The fusion protein of claim 13, comprising at least one selected from the group consisting of: SEQ ID NO: 48, SEQ ID NO: 52, SEQ ID NO: 56, SEQ ID NO: 60, SEQ ID NO: 64, SEQ ID NO: 68, SEQ ID NO: 70, SEQ ID NO:74, SEQ ID NO: 78, SEQ ID NO: 82, SEQ ID NO: 86, SEQ ID NO: 90, SEQ ID NO: 94, SEQ ID NO: 111, and SEQ ID NO: 113.

16. A method for producing a secretable fusion protein, comprising:
 providing a host cell expressing a polynucleotide comprising a single open reading frame encoding the fusion protein;
 culturing the host cell in a suitable medium, wherein the secretable fusion protein is expressed and secreted by the host cell into the medium; and
 recovering the secreted fusion protein from the medium, wherein:
  the fusion protein comprises, in order from the N-terminal, a secretable luciferase and a modified polypeptide of interest;
  the modified polypeptide of interest has been modified to remove a native N-terminal secretion peptide domain;
  the native N-terminal secretion peptide domain has been replaced by the secretable luciferase; and
  the luciferase is directly adjoined at the C-terminus to the N-terminus of the modified polypeptide of interest.

17. The method of claim 16, wherein the host cell is a eukaryotic cell.

18. The method of claim 16, wherein the polypeptide of interest is an interferon.

19. The method of claim 16, wherein the polynucleotide comprises at least one promoter or other transcription regulatory element.

* * * * *